(12) United States Patent
McCurdy et al.

(10) Patent No.: US 9,724,435 B2
(45) Date of Patent: Aug. 8, 2017

(54) HIGHLY SELECTIVE SIGMA RECEPTOR LIGANDS AND RADIOLIGANDS AS PROBES IN NOCICEPTIVE PROCESSING AND THE PATHPHYSIOLOGICAL STUDY OF MEMORY DEFICITS AND COGNITIVE DISORDERS

(71) Applicants: The University of Mississippi, University, MS (US); The Board of Trustees of the Leland Stanford Junior University, Palo Alto, CA (US)

(72) Inventors: Christopher R. McCurdy, Oxford, MS (US); Christophe Mesangeau, Hellemmes (FR); Frederick T. Chin, Sunnyvale, CA (US); Michelle L. James, Menlo Park, CA (US); Bin Shen, Mountain View, CA (US); Sanjiv Gambhir, Portola Valley, CA (US); Sandip Biswal, Stanford, CA (US); Deepak Behera, Fremont, CA (US)

(73) Assignees: THE UNIVERSITY OF MISSISSIPPI, University, MS (US); THE BOARD OF TRUSTEES OF THE LELAND STANFORD JUNIOR UNIVERSITY, Palo Alto, CA (US)

( * ) Notice: Subject to any disclaimer, the term of this patent is extended or adjusted under 35 U.S.C. 154(b) by 168 days.

(21) Appl. No.: 14/196,483

(22) Filed: Mar. 4, 2014

(65) Prior Publication Data
US 2014/0328755 A1 Nov. 6, 2014

Related U.S. Application Data

(63) Continuation-in-part of application No. 13/151,084, filed on Jun. 1, 2011, now Pat. No. 9,604,926, which
(Continued)

(51) Int. Cl.
*A61K 31/428* (2006.01)
*C07D 209/48* (2006.01)
(Continued)

(52) U.S. Cl.
CPC ........ *A61K 51/0468* (2013.01); *A61K 31/428* (2013.01); *A61K 51/0453* (2013.01); *A61K 51/0455* (2013.01); *A61K 51/0459* (2013.01); *C07D 209/08* (2013.01); *C07D 209/10* (2013.01); *C07D 209/48* (2013.01); *C07D 235/26* (2013.01); *C07D 263/58* (2013.01); *C07D 265/36* (2013.01); *C07D 277/68* (2013.01); *C07D 277/70* (2013.01); *C07D 277/74* (2013.01); *C07D 279/16* (2013.01); *C07D 295/13* (2013.01); *C07D 403/06* (2013.01); *C07D 405/04* (2013.01);
(Continued)

(58) Field of Classification Search
CPC .. A61K 31/428; A61K 51/453; A61K 51/455; A61K 51/459; A61K 51/468; C07D 209/48; C07D 235/26; C07D 263/58; C07D 277/68; C07D 277/70; C07D 299/13; C07D 403/06; C07D 405/04; C07D 413/06; C07D 413/12; C07D 417/06; C07D 491/107; C07D 491/20
See application file for complete search history.

(56) References Cited

PUBLICATIONS

Bars, D.L "Florine-18 and medical imaging: Radiopharmaceuticals for positron emission tomography" Journal of Florine Chemistry, 2006 vol. 127, pp. 1488-1493.*
Maestrup et al. "Evaluation of Spirocyclic 3-(3-Fluoropropyl)-2-benzofurnas as sigma-1 Receptor Ligands for Neuroimaging with Positron Emission Tomography" J. Med. Chem., 2009, vol. 52, pp. 6062-6072.*
Waterhouse et al. "In vivo Evaluation of 18F 1-(3-Fluoropropyl)-4-(4-cyanophenoxymethyl)piperidine: A Selective Sigma-1 Receptor Radioligand for PET", Nuclear Medicine & Biology, 1997, vol. 24, pp. 127-134.*
Ucar et al. "2(3H)-benzoxazolone and 2(3H)-benzothiazolone derivatives: Novel, potent and selective sigma-1 receptor ligands" European Journal of Pharmacology, 1997, vol. 355, pp. 267-273.*
(Continued)

*Primary Examiner* — Kendra D Carter
(74) *Attorney, Agent, or Firm* — Hershkovitz & Associates, PLLC; Abraham Hershkovitz; Eugene C. Rzucidlo

(57) ABSTRACT

A method for localizing and quantifying S1R role in nociceptive processing; for providing a guide to providing an analgesic therapy; of using an S1R selective ligand as a biomarker for pathphysiological study of memory deficits and cognitive disorders; or of detecting increased S1R density at the site of nerve injury arising from neuropathic pain comprising using as a probe at least one SR1 selective compound or radioligand of the general formula III', or IV':

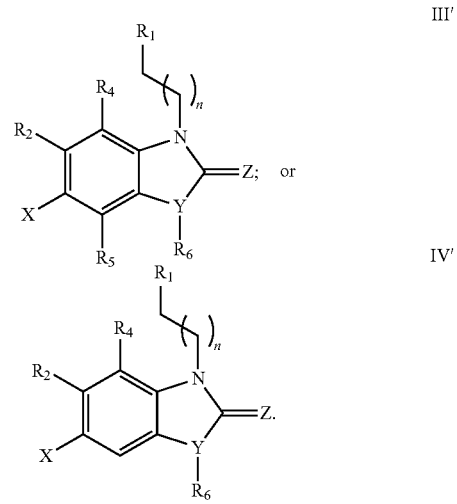

5 Claims, 16 Drawing Sheets

Related U.S. Application Data is a continuation-in-part of application No. 12/785,217, filed on May 21, 2010, now Pat. No. 8,686,008, which is a continuation-in-part of application No. 12/673,486, filed as application No. PCT/US2008/073478 on Aug. 18, 2008, now Pat. No. 8,809,381.

(60) Provisional application No. 60/956,249, filed on Aug. 16, 2007.

(51) Int. Cl.
| | |
|---|---|
| *C07D 235/26* | (2006.01) |
| *C07D 263/58* | (2006.01) |
| *C07D 277/68* | (2006.01) |
| *C07D 403/06* | (2006.01) |
| *C07D 405/04* | (2006.01) |
| *C07D 413/06* | (2006.01) |
| *C07D 413/12* | (2006.01) |
| *C07D 417/06* | (2006.01) |
| *C07D 491/107* | (2006.01) |
| *C07D 491/20* | (2006.01) |
| *A61K 51/04* | (2006.01) |
| *C07D 265/36* | (2006.01) |
| *C07D 209/08* | (2006.01) |
| *C07D 209/10* | (2006.01) |
| *C07D 277/70* | (2006.01) |
| *C07D 279/16* | (2006.01) |
| *C07D 295/13* | (2006.01) |
| *C07D 277/74* | (2006.01) |

(52) U.S. Cl.
CPC ......... *C07D 413/06* (2013.01); *C07D 413/12* (2013.01); *C07D 417/06* (2013.01); *C07D 491/107* (2013.01); *C07D 491/20* (2013.01)

(56) References Cited

PUBLICATIONS

Yous et al. Novel 2(3H)-Benzothiazolones as Highly Potent and Selective Sigma-1-Receptor Ligands, 2005, Med Chem Res, vol. 14, pp. 158-168.*

De la Puente et al. "Sigma-1 receptors regulate activity-induced spinal sensitization and neuropathic pain after peripheral nerve injury" Pain, 2009, vol. 145, pp. 294-303.*

* cited by examiner

Figure 1. Selected sigma-1 receptor (σ-1 receptor) ligands and radioligands.
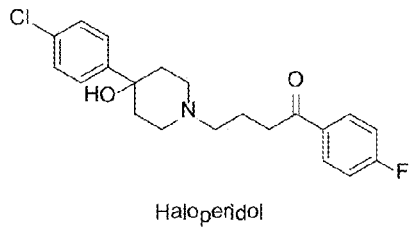
Haloperidol
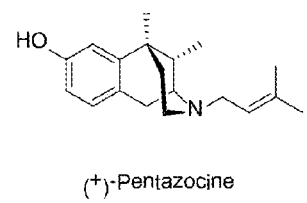
(+)-Pentazocine
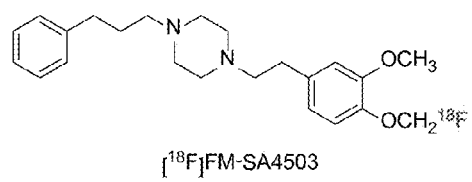
[$^{18}$F]FM-SA4503
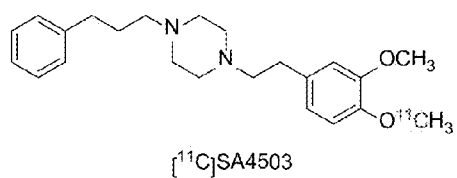
[$^{11}$C]SA4503
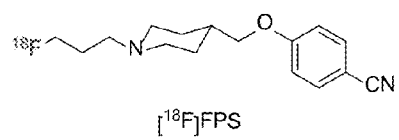
[$^{18}$F]FPS
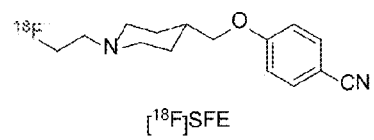
[$^{18}$F]SFE
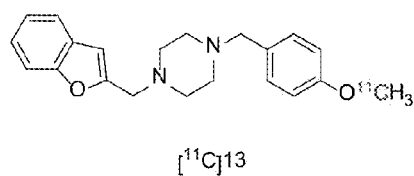
[$^{11}$C]13
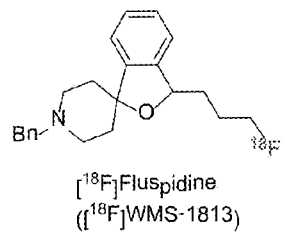
[$^{18}$F]Fluspidine
([$^{18}$F]WMS-1813)
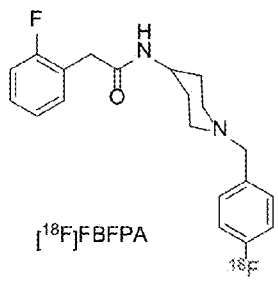
[$^{18}$F]FBFPA
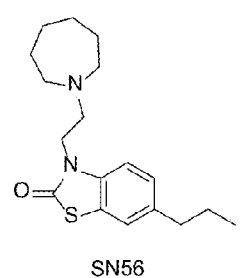
SN56
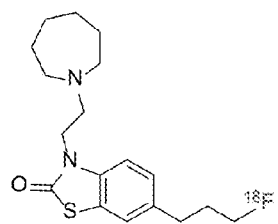
[$^{18}$F]FTC-146
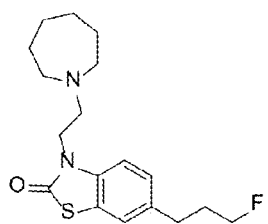
CM304

Metabolic stability of AZ_66 by Rat liver microsomes (1mg/ml)

| Time(min) | Percent Remaining | Percent Loss |
|---|---|---|
| 0 | 100 | 0 |
| 5 | 95.51694 | 4.48306 |
| 15 | 88.64231 | 11.35845 |
| 30 | 82.70131 | 17.29879 |
| 60 | 75.09347 | 24.3653 |

*In vitro* Half-life and Intrinsic clearance

| k(min$^{-1}$) | t$_{1/2}$(min) | CLint(ml/min/mg) | CLint (whole liver) (L/min) |
|---|---|---|---|
| 0.006 | 115.56±15 | 0.006 | 0.002434 |

Incubation of CM_156 (10μM) with rat liver microsomes (1mg/ml)

| Time (min) | Percent Remaining |
|---|---|
| 0 | 100 |
| 15 | 16.4605 |
| 30 | 9.2356 |

Fig, 21 A, B, C, and D

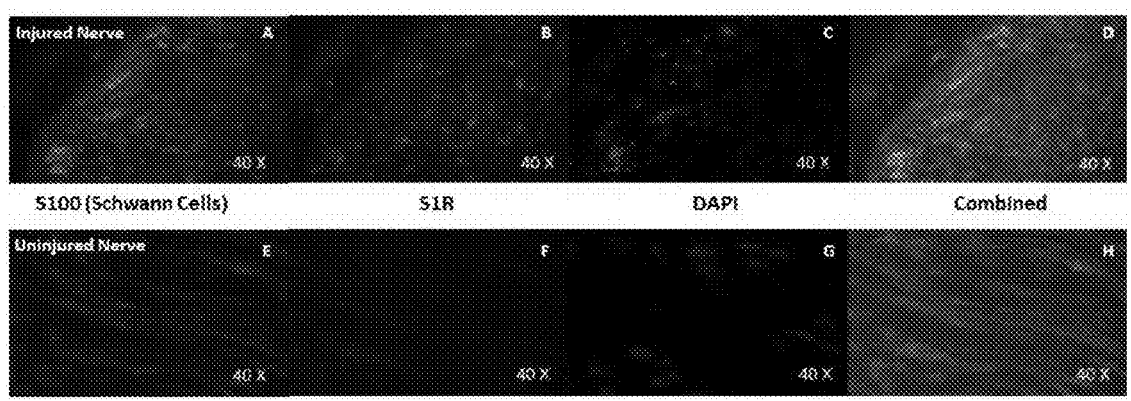
Fig. 23 A, B, C, D, E, F, G and H

HIGHLY SELECTIVE SIGMA RECEPTOR LIGANDS AND RADIOLIGANDS AS PROBES IN NOCICEPTIVE PROCESSING AND THE PATHPHYSIOLOGICAL STUDY OF MEMORY DEFICITS AND COGNITIVE DISORDERS

CROSS-REFERENCE TO RELATED APPLICATIONS

This is a Continuation-in-Part application of U.S. application Ser. No. 13/151,084, filed on Jun. 1, 2011 entitled "HIGHLY SELECTIVE SIGMA RECEPTOR LIGANDS," which is a Continuation-in-Part application of U.S. application Ser. No. 12/785,217, filed on May 21, 2010 entitled "HIGHLY SELECTIVE SIGMA RECEPTOR LIGANDS," which is a Continuation-in-part application of U.S. application Ser. No. 12/673,486, filed on May 12, 2010, entitled "HIGHLY SELECTIVE SIGMA RECEPTOR LIGANDS," which claims priority of PCT/US08/73478 filed Aug. 18, 2008 which claims priority to U.S. Provisional Application No. 60/956,249 filed Aug. 16, 2007, the disclosure of all of which is expressly incorporated by reference herein in its entirety.

The subject invention was made with government support under a research project supported by the United States Government in NIDA Grant Number NIGMS Grant Number GM194932 and NCI ICMIC P50 CA114747 and the government has certain rights in this invention.

FIELD OF INVENTION

The present invention relates to localizing and quantifying the role of S1R in nociceptive processing comprising using as a probe at least one SR1 selective compound or SR1 selective radioligand and to the use of an S1R selective ligand or a S1R selective radioligand as a biomarker for the pathphysiological study of memory deficits and cognitive disorders.

BACKGROUND OF THE INVENTION

Sigma receptors (σ) have received much attention from the drug discovery field due to their possible involvement in schizophrenia, regulation of motor behavior, convulsions, anxiety, and the psychostimulant effects of drugs of abuse including cocaine, methamphetamine and 3,4-methylenedioxymethamphetamine (MDMA).[1,2] In addition to a host of neurological and psychiatric areas of interest, sigma receptors are promising drug development targets for, oncological, immunological, cardiovascular, opthalmological, developmental, gastrointestinal and metabolic disorders as well as those affecting the endocrine system. They are structurally unique proteins that are distinct from classical G protein-coupled receptors, ionotropic receptors, or receptor tyrosine kinases. With two subtypes currently known, they modulate cell survival and excitability, and subserve many critical functions in the body. Endogenous ligands for these receptors are unknown, though current clues point to neurosteroids.[3]

The two subtypes, σ-1 and σ-2, were delineated by studies examining their respective molecular weights, distribution in tissue and drug selectivity profiles. The 223 amino acid σ-1 protein with two transmembrane spanning regions has been purified and cloned from several animal species including mouse, rat, guinea pig, and human.[4-8] To date, the σ-1 receptor is well studied and known because of the receptor sequence information and availability of selective σ-1 ligands. But, the protein corresponding to σ-2 sites has not yet been cloned. Also, σ-2 receptor-selective ligands are less common, with tritiated DTG (1,3-di(2-tolyl)guanidine) being accepted as a radioligand in the presence of (+)-pentazocine (to block binding to σ-1 sites). Due to the lack of availability of detailed protein structural information and truly selective σ-2 ligands, the pharmacological characterization of the σ-2 subtype has been very limited. There is clearly a need for a selective σ-2 ligand which can not only act as a probe to explore unknown biochemical mechanisms, but also be used as a radioligand in σ-2 receptor binding assays.

The abuse of drugs is a serious social, economic and health problem worldwide. Some of the opiates, cocaine, amphetamines and phencyclidine (PCP) are the drugs of abuse with significant affinities for σ receptors. Current treatments for drugs of abuse are limited and there is a need to develop novel and effective agents to combat this problem.

Cocaine use and abuse have been reported as early as the late 1500s.[9] The historical use has been associated with the chewing of leaves from the *Erythroxylon coca* bush, from which cocaine was isolated in 1860,[10] to eliminate fatigue in workers. Indeed, cocaine is a powerful and addictive psychostimulant. Cocaine abuse is widespread and is responsible for more serious intoxications and deaths than any other illicit drug. However, the invigorating effects of cocaine have caused it to become a major recreational drug of abuse throughout the world with an estimated 13 million people using the drug. In 2004, 34.2 million Americans aged 12 and over reported lifetime use of cocaine with approximately 5.6 million reporting annual use and an estimated 2 million reporting current use of the drug. In 2004 alone, there were an estimated 1 million new users of cocaine amounting to ~2,700 per day. Despite a decline between 2002 and 2003 which is thought to potentially be due to increases in usage of other stimulants such as methamphetamine, data from the National Survey on Drug Use and Health showed near a 70% increase in the number of people receiving treatment for cocaine addiction from 276,000 in 2003 to 466,000 in 2004.[11]

Currently, there are no approved medications to treat cocaine abuse or addiction. An effective strategy used to develop an anti-cocaine agent was the development of antagonists that compete with cocaine for its target proteins. For years, treatment approaches have targeted the dopaminergic system which is known to be involved in the actions and rewards of cocaine use. Many compounds were generated and tested that targeted the dopamine transporter which was identified as a primary site of action of cocaine. These compounds were met with very limited success as many of them just substituted for cocaine.[12] After many years of investigation at the dopamine transporter as well as the dopamine receptors, researchers have been challenged to envision novel mechanisms that may afford new therapeutic interventions for cocaine addiction.

Although many other mechanisms are under investigation, the σ receptor system has been demonstrated and validated as a legitimate target for the attenuation of cocaine effects. The ability of cocaine to bind to the sigma receptors was discovered and first documented in 1988.[13] It was reported that cocaine had a micromolar affinity for the sigma receptor, and this interaction corresponded to micromolar levels that were achievable by cocaine in the body.[14] Additional studies have indicated that reducing brain sigma receptor levels with antisense oligonucleotides attenuates the convulsive and locomotor stimulant actions of cocaine. Synthetic small molecule antagonists of sigma receptors have also been shown to mitigate the actions of cocaine in animal models. From prior work, the role of the σ-1 subtype has been clearly linked to the actions of cocaine. However, the role of the σ-2 receptor has been suggested, but is less clear due to the lack of truly selective ligands for this subtype.

Radioligands selective for σ-1 receptors have the potential to non-invasively detect and monitor various pathologies, including neurodegenerative diseases and cancer.

Applicant herein reports the synthesis, radiofluorination and evaluation of a new $^{18}F$ fluorinated σ-1 receptor ligands including 6-(3-fluoropropyl)-3-(2-(azapan-1-yl)ethyl)benzo[d]thiazol-2(3H)-one (18, [$^{18}F$] FTC-146). [$^{18}F$] FTC-146 displays superior in vitro affinity and selectivity compared to other reported σ-1 receptor compounds. The new $^{18}F$ fluorinated σ-1 receptor ligands, including [$^{18}F$] FTC-146, can be synthesized by nucleophilic fluorination using an automated module. [$^{18}F$] FTC-146 afforded a product with >99% radiochemical purity (RCP) and specific activity (SA) of 3.9±1.9 Ci/μmol (n=13). Cell uptake studies revealed that [$^{18}F$] FTC-146 accumulation correlated with levels of σ-1 receptor protein. Furthermore, the binding profile of [$^{18}F$] FTC-146 was comparable to that of known high affinity σ-1 receptor ligand (+)-[$^{3}H$] pentazocine in the same cell uptake assay. PET images of [$^{18}F$] FTC-146 in normal mice showed high uptake of the radioligand in the brain which is known to contain high levels of σ-1 receptors. Time activity curves (TACs) showed rapid, high initial uptake of [$^{18}F$] FTC-146 in the mouse brain. Pre-treatment with non-radioactive CM304 (1 mg/kg) reduced the binding of [$^{18}F$]FTC-146 in the brain at 60 min by 83% denoting that [$^{18}F$] FTC-146 accumulation in mouse brain represents a specific binding to σ-1 receptors. These results indicate that [$^{18}F$] FTC-146 is a good candidate radiotracer for studying σ-1 receptors in living subjects.

Initially the sigma receptor was thought to belong to the opioid class of receptors;[15] however, further studies classified it as a distinct molecular entity, resulting in its recognition as a separate family of receptors.[16] There are at least two σ receptor subtypes, the σ-1 and σ-2 receptors.[17] The σ-1 receptor is the best characterized of the two at present.[18, 19]

Despite initial controversy and conflicting ideas, recent key discoveries concerning the σ receptor have helped elucidate various biological aspects about this molecular chaperone and its putative functional roles.[20,21] Mainly located at the endoplasmic reticulum of cells, σ-1 receptors have been implicated in a host of biochemical processes and pathological conditions including neurodegenerative diseases, psychiatric disorders, drug addiction, digestive function, regulation of smooth muscle contraction and ischemia.[20, 22-24] σ-1 receptors are also highly expressed in most known human cancers (e.g., breast, lung, colon, ovarian, prostate, brain).[24,25] Agonists for σ-1 receptors influence intracellular and extracellular Ca2+ levels and thus have a broad range of neuromodulatory effects.[26,27] Certain σ-1 receptor agonists have been shown to regulate endothelial cell proliferation,[28] improve cognition,[29,30] provide neuroprotection,[31] and act as anti-depressant agents,[18,32] while antagonists inhibit/attenuate cocaine-induced seizures,[33] highlighting the potential of σ-1 receptors as both a diagnostic and therapeutic target.

There are a multitude of compounds that target σ receptors, including three specific classes of compounds; 1) benzomorphans, such as (+)-pentazocine (FIG. 1) and (+)—N-allylnormetazocine (NANM) that preferentially bind σ-1 receptors (compared to their (−)-enantiomers), 2) endogenous neurosteroids like progesterone (an antagonist of the σ-1 receptor) and 3) butyrophenones, such as the antipsychotic agent haloperidol that displays high affinity for both a receptor subtypes.[19,34] Over the last two decades numerous groups have reported the development of high affinity σ-1 receptor ligands[34-42]—and of these, some have been labeled with radioisotopes (FIG. 1) for use in positron emission tomography (PET) studies.

Examining σ-1 receptors in living subjects with PET is an important step towards understanding the receptor's functional role and involvement in disease. PET radioligands specific for σ-1 receptors could potentially provide a non-invasive means of 1) visualizing and investigating the machinery of these sites, 2) assessing receptor occupancy (to help determine optimal doses of therapeutic drugs), 3) early detection and staging of σ-1 receptor-related disease(s), and 4) monitoring therapeutic response. Some existing σ-1 receptor radioligands include: [$^{11}C$] SA4503,[43] [$^{18}F$] FM-SA4503,[44] [$^{18}F$] FPS,[45] [$^{18}F$] SFE,[46,47]-[$^{18}F$] FBFPA,[48] [$^{18}G$] fluspidine[49] and [$^{11}C$]13[39] (FIG. 1). The high affinity σ-1 receptor radioligand [$^{11}C$] SA4503 has demonstrated promising results in rodents,[43] felines[50] and non-human primates,[51] and is currently the only σ-1 receptor radioligand being routinely used in clinical research;[52, 53] however, it is far from ideal for several reasons including its high non-specific binding, affinity for other sites such as emopamil binding protein (EBP),[54] and suboptimal kinetic profile (indicative of irreversible binding). The fluorinated derivative of [$^{11}C$]SA4503 (known as [$^{18}F$]FM-SA4503) has demonstrated similar disadvantages in rodents and non-human primates, and is yet to be evaluated in humans. The piperidine [$^{18}F$] FPS reported by Waterhouse and colleagues was evaluated in human subjects in 2003,[46, 55, 56] however it displayed unfavorable kinetics (due to its inability to reach transient equilibrium at 4 h p.i.). Following these results, a lower affinity fluoromethyl derivative of [$^{18}F$]FPS (known as [$^{18}F$]SFE) was developed in hope of rectifying the issue of irreversible binding.[46] Whilst [$^{18}F$]SFE exhibited a superior kinetic profile (cleared from rat brain with a 40% reduction in peak uptake over a 90 min period), it was found to have a lower selectivity ratio, and in fact blocking studies in rats using a selective σ-2 receptor compound resulted in a small yet noticeable reduction in [$^{18}F$]SFE uptake.[46] In 2005 Mach and colleagues reported the radiosynthesis of another piperidine derivative [$^{18}F$]FBFPA (affinity for σ-2 receptor/σ-1 receptor=44) and demonstrated its ability to bind σ-1 receptors in both rodent and rhesus monkey brain.[48] In 2010 the synthesis of a spirocyclic piperidine σ-1 receptor radioligand, [$^{18}F$]fluspidine, and its evaluation in mice was reported.[37, 49] Biodistribution results showed 40% reduction in brain [$^{18}F$]fluspidine uptake over 2 hours, indicating that it may display reversible binding; however, it is still in the early stages of evaluation. Moussa and colleagues published the radiosynthesis of a carbon-11 labeled N-benzyl piperazine σ-1 receptor ligand, [$^{11}C$] 13, and its in vivo evaluation in Papio hamadryas baboons using PET imaging. Whilst [$^{11}C$] 13 accumulated in sigma-1 rich regions of the brain and peripheral organs, it was found to display a low selectivity ratio (affinity for σ-2 receptor/σ-1 receptor=38) and also a nanomolar affinity for 5-HT2B receptors.[39]

Until the present patent application, there was no highly selective σ-1 receptor radioligand labeled with fluorine-18 or carbon-11 available for clinical research.

Alzheimer's Disease (AD) is a progressive degenerative brain disorder that destroys brain cells, causing memory loss and problems with thinking and behavior severe enough to affect work, lifestyles, or social life. Sigma-1 receptors (S1Rs) have been shown to be critical target in the treatment of memory deficits and cognitive disorders including AD. S1R is implicated in cellular differentiation [37,40], neuroplasticity [145,149], neuroprotection [71,89], and cognitive functioning of the brain [85] [Waarde Reference]. Previous studies showed a decrease of sigma receptor density in aging and neurodegenerative disease by autoradiography in monkeys (e.g., [3H] DTG) and positron emission tomography (PET) in human (e.g., [11C] SA4503).

PET imaging of S1Rs has the potential to non-invasively detect and monitor the numerous pathologies in which this receptor plays a role, building upon the established ability of PET to quantify specific ligand-receptor binding in the brain." Although several S1R-binding compounds 3-10 have been made, [11C] SA4503 is currently the only radiotracer used for imaging S1R in the clinic, 11 despite its moderate selectivity for other targets including the sigma-2 receptor. Thus, the goal of this proposal is to develop and apply a more selective PET imaging S1R-selective ligand as a biomarker for therapeutic drug discovery and for the pathophysiological study of Alzheimer's disease.

It is an object of the present invention to develop a highly selective novel ligand or radioligand to image the action of these proteins in vivo in order to facilitate the understanding of various biological aspects about this molecular chaperone and its putative functional roles, and to accelerate the design and evaluation of novel molecular targeted therapies against AD.

Thus, the goal of this proposal is to develop and apply a more selective PET imaging S1R-selective ligand as a biomarker for therapeutic drug discovery and for the pathophysiological study of Alzheimer's disease.

Peripheral nerve injury, as a consequence of trauma, surgery, inflammation, degenerative changes, diabetes, and a variety of other causes, is a major clinical problem resulting in significant morbidity such as chronic pain, weakness, and other sensorimotor disabilities. Consequently, peripheral nerve injury and neuroinflammation are an overwhelming public health problem, and often require significant resources for the diagnosis and treatment of patients with chronic pain, nerve regeneration, and other related conditions.

Current methods to diagnose nerve injury include computed tomography (CT), ultrasound imaging (US), magnetic resonance imaging (MRI) and electrophysiologic (EP) (i.e., Electrodiagnostic or electroneurography) tests, namely, electromyography, quantitative neurosensory testing, and nerve conduction studies. In particular, the EP tests can be helpful in identifying conduction abnormalities and grading the extent of nerve injury in the interrogated regions, but the results of these studies are susceptible to a variety of limitations. For example, EP tests are invasive often requiring multiple passes of the needle in regions of interest to derive a diagnosis. Additionally, the results of these tests provide limited information about the cause and the location of the injury and are temporally-dependent relative to the timing and extent of nerve injury. EP results are also open to technical and operator-dependent errors, including the interpretation of the waveform results, which is a relatively subjective experience that can potentially lead to inaccurate conclusions (77).

By comparison, currently employed clinical imaging methods used to diagnose peripheral nerve injury, such as MRI, may be able to provide better insight as to the cause and the location of the nerve injury itself and secondary consequences of muscle denervation (78). However, the correlation between MRI and EP tests in detecting such lesions remains suboptimal. For example, investigators have found that only half of those individuals presenting with carpal tunnel syndrome with confirmed electrophysiologic abnormalities of the median nerve show an abnormality on MRI (79). Others have also found no correlation between EP studies and MR findings of the peripheral nerve (80) and in some cases there are no specific EP findings or imaging findings in certain patients (80, 81).

Even the challenges of current clinical methods, the identification of molecular imaging approaches that exploit molecular markers of nerve injury or neuroinflammation, and thus highlight the location and extent of nerve injury, is of paramount importance to advancing the management of nerve injury, neuroinflammation, and the ensuing clinical manifestations of these entities. While MRI has unparalleled soft tissue contrast and ultra-high spatial resolution, it suffers from poor sensitivity, and is limited in terms of its currently available clinical molecular imaging applications. Positron emission tomography (PET) is a molecular imaging technique, which is ideally suited for monitoring cellular and biochemical events early in the course of a disease due to its high sensitivity, unlimited depth of penetration, non-invasive nature, and quantitative capabilities. The combination of PET with MRI is an exciting prospect; as one can leverage the advantages of each imaging technique—i.e., high sensitivity and spatial resolution—to simultaneously visualize biochemical and anatomical alterations. While the use of PET-MRI has not yet been reported for clinical imaging of chronic pain and/or nerve injury, it holds great promise for improving the way we identify regions of nerve injury and pain generators, and thus the diagnosis and treatment of chronic pain and related conditions.

A potential biomarker associated with nerve injury and neuroinflammation is the sigma-1 receptor (S1R), which was initially believed to be a subtype of opioid receptor (15), but is now known to be a distinct class of receptors with unique biological functions (20,18, 83). S1R antagonists, for example, are known to modulate opioid analgesia (84), and drugs such as haloperidol, which bind S1Rs, can augment the anti-nociceptive effect of opioids (85). In addition, S1Rs can modulate various ion channels and receptors, including potassium channels, calcium channels, dopamine and gamma-amino butyric acid (GABA) receptors (86-88), thereby significantly impacting neural excitability and transmission by affecting the release of several neurotransmitters including serotonin, dopamine, noradrenaline, glutamate, and GABA.

With respect to pain, it has been known for quite some time that S1R agonists inhibit opioid analgesia, whereas antagonists enhance analgesic effects (84, 90). Furthermore, S1R knockout mice showed decreased response to pain in various pain models (31, 60, 92). Treatment with S1R antagonists such as haloperidol and its metabolites I and II also produces similar results (93, 94). Further, spinal S1R activation can result in mechanical and thermal hypersensitivity (95) and increased N-methyl-D-Aspartate (NMDA) receptor-induced pain (96, 97) while spinal S1R inhibition alleviates pain behavior (60, 94, 98). S1R is involved in synaptic plasticity and central sensitization, which are implicated in the "memorizing" of pain responsible for making it chronic and self-perpetuating (60, 92). It is not surprising that S1R antagonists are quickly becoming popular as potential candidates for the next generation analgesics (99). BD1047 is a selective S1R antagonist with high affinity that has recently been successfully tested as an analgesic in animal neuropathic pain models (100).

Since S1Rs are involved in nociception, it would be extremely valuable to have a tool which could help us better understand the role of these receptors in vivo in pain/nerve injury, potentially leading to better approaches to diagnose and treat pain. Applicant has recently developed a highly selective radiotracer, [$^{18}$F] FTC-146, for imaging S1Rs with PET, and have demonstrated its specificity in mice, rats, and monkeys (Scheme 1) [ref, James et al submitted, JNM]. Here applicant aims to employ [$^{18}$F]FTC-146 as a tool for visualizing S1Rs in a rat model of nerve injury so that applicant might gain information about S1R levels during nerve injury and whether the S1R might be a useful in vivo imaging biomarker of nerve injury.

BRIEF DESCRIPTION OF THE INVENTION

The present invention relates to compounds useful as sigma receptors of the following formula I:

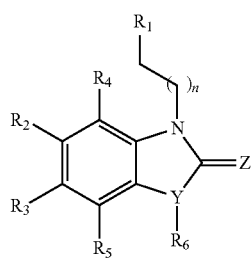

I $R_1$ can be an optionally substituted nitrogen-containing heterocycle radical such as, for example, radicals of optionally substituted piperidines, optionally substituted piperazines, optionally substituted tetrahydropyridines, optionally substituted azepanes, tertiary amines (cyclic or acyclic), isoindoline-1,3-dione, or optionally substituted tetrahydroisoquinolones (aromatically substituted): $R_{2,3,4,5,6}$ can each independently be any one or combinations of the following moieties, such as, for example, hydrogen, cyano, nitro, acyl, alkyl, amido, azido, isothiocyanate, isocyanate anilino (unsubstituted or substituted), halogens (such as fluorine, chlorine, bromine and iodine), ethers, sulfonamides, thioacyl, nitro, aromatic, heterocyclic, olefinic, acetylenic, deuterium, or tritium; Y can be either CH, CH$_2$, O, S, OCH$_2$, N—R, N—Ar, C—R, C—Ar where Ar is an optionally substituted aryl. Z can be either H, O, S, S—R or NR. R groups can be either H, aryls, alkyls, or cycloalkyls. "n" can be 1 to 5 carbons in length and stereoisomers, analogs, and pharmaceutically acceptable salts thereof as well as compositions comprising said compounds. The moiety bridging $R_1$ and N in the formula I can be an optionally substituted C$_1$-C$_6$ alkylene, C$_1$-C$_6$ alkenylene or C$_1$-C$_6$ alkynylene group wherein the alkylene group can have inserted into its chain a C$_3$-C$_5$ cycloalkyl group, aromatic, and heterocyclic group.

The present invention further relates to compounds useful as sigma receptors of the following formula II:

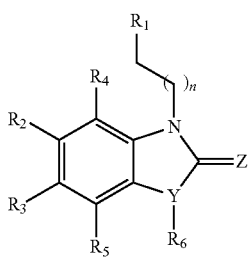

II $R_1$ can be an optionally substituted nitrogen-containing heterocycle radical such as, for example, radicals of optionally substituted piperidines, optionally substituted piperazines, optionally substituted tetrahydropyridines, optionally substituted azepanes, tertiary amines (cyclic or acyclic), isoindoline-1,3-dione, or optionally substituted tetrahydroisoquinolones (aromatically substituted): $R_{2,4,5,6}$ can each independently be any one or combinations of the following moieties, such as, for example, hydrogen, cyano, nitro, acyl, alkyl, amido, azido, isothiocyanate, isocyanate anilino (unsubstituted or substituted), halogens (such as fluorine, chlorine, bromine and iodine), ethers, sulfonamides, thioacyl, nitro, aromatic, heterocyclic, olefinic, acetylenic, deuterium, or tritium; Y can be either CH, CH$_2$, O, S, OCH$_2$, N—R, N—Ar, C—R, C—Ar where Ar is an optionally substituted aryl. Z can be either H, O, S, S—R or NR. R groups can be either H, aryls, alkyls, or cycloalkyls. "n" can be 1 to 5 carbons in length and stereoisomers, analogs, and pharmaceutically acceptable salts thereof as well as compositions comprising said compounds. The moiety bridging $R_1$ and N in the formula II can be a substituted C$_1$-C$_6$ alkylene, C$_1$-C$_6$ alkenylene wherein the alkylene group can have inserted into its chain a C$_3$-C$_5$ cycloalkyl group, aromatic, and heterocyclic group.

The present invention relates to still yet further compounds useful as sigma receptors of the following formula III:

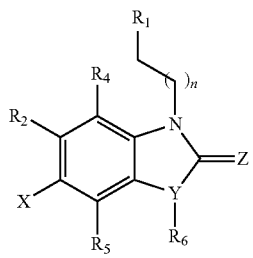

III $R_1$, $R_{2,4,5,6}$ and "n" can be the options provided for formula II, above and wherein $X_1$ is halogen, or C$_1$-C$_4$ haloalkyl.

The present invention relates to a still yet further series of compounds useful as sigma receptors of the following formula IV:

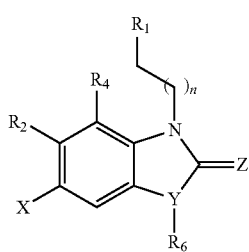

IV

Wherein $R_1$ can be an optionally substituted nitrogen-containing heterocycle radical such as, for example, radicals of optionally substituted piperidines, optionally substituted piperazines, optionally substituted tetrahydropyridines, optionally substituted azepanes, tertiary amines (cyclic or acyclic), isoindoline-1,3-dione, or optionally substituted tetrahydroisoquinolones (aromatically substituted): $R_{2,4,6}$ can each independently be any one or combinations of the following moieties, such as, for example, hydrogen, cyano, nitro, acyl, alkyl, amido, azido, isothiocyanate, isocyanate anilino (unsubstituted or substituted), halogens (such as fluorine, chlorine, bromine and iodine), ethers, sulfonamides, thioacyl, nitro, aromatic, heterocyclic, olefinic, acetylenic, deuterium, or tritium; Y can be either CH, $CH_2$, O, S, $OCH_2$, N—R, N—Ar, C—R, C—Ar where Ar is an optionally substituted aryl. Z can be either H, O, S, S—R or NR. R groups can be either H, aryls, alkyls, or cycloalkyls. "n" can be 1 to 5 carbons in length and stereoisomers, analogs, and pharmaceutically acceptable salts thereof as well as compositions comprising said compounds. The moiety bridging $R_1$ and N in the formula IV can be a substituted $C_1$-$C_6$ alkylene having the formula —$(CHR_x$—$(CH_2)$—$CH_2)$— wherein the —$CHR_x$— moiety is attached to $R_1$ and the alkylene group can have inserted into its chain a $C_3$-$C_5$ cycloalkyl group, aromatic, and heterocyclic group and wherein the $R_x$ is a $C_1$-$C_5$ straight chain or branched chain alkyl or a $C_1$-$C_4$ straight chain or branched chain haloalkyl.

The present invention further relates to compounds useful as sigma receptors of the following formula V:

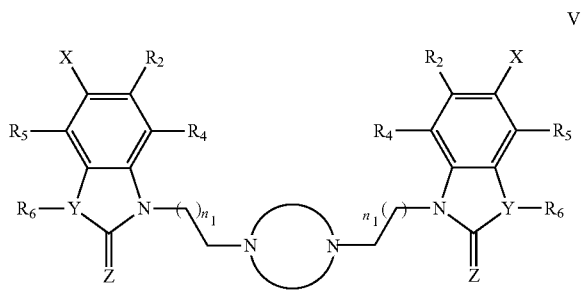

V $R_{2,3,4,5,6}$ can each independently be any one or combinations of the following moieties, such as, for example, hydrogen, cyano, nitro, acyl, alkyl, amido, azido, isothiocyanate, isocyanate anilino (unsubstituted or substituted), halogens (such as fluorine, chlorine, bromine and iodine), ethers, sulfonamides, thioacyl, nitro, aromatic, heterocyclic, olefinic, acetylenic, deuterium, or tritium; Y can be either CH, $CH_2$, O, S, $OCH_2$, N—R, N—Ar, C—R, C—Ar where Ar is an optionally substituted aryl. Z can be either H, O, S, S—R or NR. R groups can be either H, aryls, alkyls, or cycloalkyls. "n" can be 1 to 5 carbons in length and stereoisomers, analogs, and pharmaceutically acceptable salts thereof as well as compositions comprising said compounds. The $R_1$ bridging moiety in the formula V can be an optionally substituted $C_1$-$C_6$ alkylene, $C_1$-$C_6$ alkenylene or $C_1$-$C_6$ alkynylene group wherein the alkylene group can have inserted into its chain a $C_3$-$C_5$ cycloalkyl group, aromatic, and heterocyclic group.

With the aim of synthesizing a new, selective PET radioligand for studying σ-1 receptors in living subjects, the present invention comprising another embodiment which relates to 18F fluorinated σ-1 receptor ligands from the benzothiazolone class of compounds as possible σ-1 receptor ligands. A lead compound from the benzothiazolone class of compounds originally reported by Yous and colleagues in 2005[42], SN56 (FIG. 1) from this class was reported to have high affinity (Ki=0.56 nM) and extremely high selectivity for the σ-1 receptor (Selectivity Ratio>1000). More recently, a tritiated version of SN56 ([$^3$H]-SN56) was produced and assessed in vitro.[50] Results suggested [$^3$H]-SN56 may be a favorable alternative to the σ-1 receptor radioligand [$^3$H](+)-pentazocine. Applicant devised a strategy for modifying SN56 in a way that would allow incorporation of a fluorine-18 radiolabel without greatly altering the structure of the molecule in the hope of maintaining its high affinity and selectivity for the σ-1 receptor. The target molecule, 6-(3-fluoropropyl)-3-(2-(piperidin-1-yl)ethyl)benzo[d]thiazol-2(3H)-one 30)

(CM304) (FIG. 1) contains a fluoropropyl, in place of the propyl group on SN56. This is the only structural difference.

To the best of applicant's knowledge, no compounds from the benzothiazolone class have been evaluated as radioligands for σ-1 receptors. Since CM304 has an entirely different scaffold from other known σ-1 receptor radiotracers, and was born out of a class of highly selective σ-1 receptor compounds, applicant believes studies using this probe may generate valuable and novel information about the σ-1 receptor.

In this application, applicant reports new $^{18}$F fluorinated σ-1 receptor ligands from the benzothiazolone class of compounds as possible σ-1 receptor ligands. Specifically, the applicant reports the synthesis of CM304, the radiosynthesis of [$^{18}$F] FTC-146 and the preliminary evaluation of [$^{18}$F] FTC-146 σ-1 receptor radioligand through the use of cellular uptake assays (using cells transfected with σ-1 receptor cDNA), mouse serum stability studies, and PET imaging of mice.

The present invention further comprises a method for localizing and quantifying the role of S1R in nociceptive processing comprising using as a probe at least one SR1 selective compound or SR1 selective radioligand. The invention further comprises a method for providing a guide to providing an analgesic therapy wherein said therapy comprises the treatment of conditions involving nociceptive processing, said method comprising using as a probe at least one SR1 selective ligand or SR1 selective ligand radioligand.

The instant method localizes and quantifies the role of S1R in nociceptive processing and provides a guide to new analgesic therapies to target S1Rs. A specific embodiment of the present method is the use of the previously described radioligand [$^{18}$F]FTC-146, a highly S1R-selective radioligand, for PET-MRI imaging and autoradiography (ARG). Immunohistochemistry (IHC) was also performed to correlate imaging data with S1R levels.

The present invention also further comprises a method of using an S1R selective ligand or a S1R selective radioligand as a biomarker for the pathphysiological study of memory deficits and cognitive disorders comprising quantifying S1R binding in a brain using as an S1R specific legend or S1R specific radioligand.

The present invention relates to a method for localizing and quantifying S1R role in nociceptive processing comprising using as a probe at least one SR1 selective compound or radioligand of the general formula III', or IV':

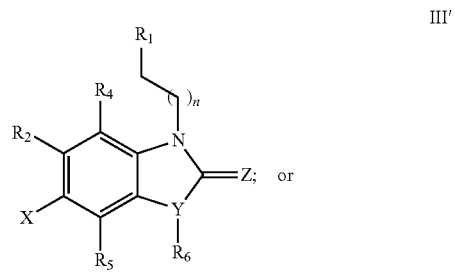

III'

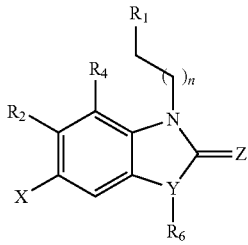

wherein $R_1$ can be a radical of an optionally substituted C4 to C7 N-containing heterocycle or a radical of an optionally substituted cyclic or acyclic tertiary amine or isoindoline-1,3-dione: $R_{2,4,5,6}$ can each independently be any one or combinations of the following moieties, hydrogen, cyano, nitro, acyl, alkyl, amido, azido, isothiocyanato, isocyanato, optionally substituted anilino, halogens, ethers, sulfonamides, thioacyl, nitro, aromatic, heterocyclic, olefinic, acetylene, deuterium, or tritium; Y is S; Z can be either H, O, S, S—R or NR where R groups can be either H, aryls, alkyls, or cycloalkyls; "n" can be 1 to 5 carbons in length and stereoisomers, functional analogs, and pharmaceutically acceptable salts thereof and wherein the moiety bridging $R_1$ and N can be a substituted alkylene, optionally substituted alkenylene or optionally substituted alkynylene and where the alkylene group can include an inserted $C_3$-$C_5$ cycloalkyl group, aromatic, and heterocyclic group; and wherein X is $R_2$ or $C_1$-$C_4$ radiohaloalkyl.

The present invention further relates to a method for providing a guide to providing an analgesic therapy wherein said therapy comprises the treatment of conditions involving nociceptive processing, said method comprising using as a probe at least one SR1 selective ligand or radioligand having the general formula III', or IV'

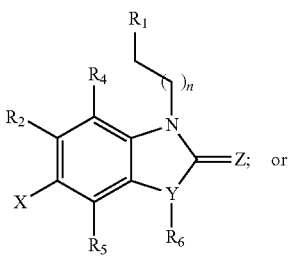

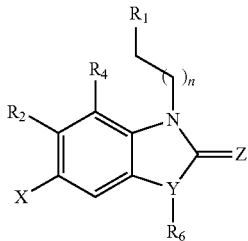

wherein $R_1$ can be a radical of an optionally substituted C4 to C7 N-containing heterocycle or a radical of an optionally substituted cyclic or acyclic tertiary amine or isoindoline-1,3-dione: $R_{2,4,5,6}$ can each independently be any one or combinations of the following moieties, hydrogen, cyano, nitro, acyl, alkyl, amido, azido, isothiocyanato, isocyanato, optionally substituted anilino, halogens, ethers, sulfonamides, thioacyl, nitro, aromatic, heterocyclic, olefinic, acetylene, deuterium, or tritium; Y is S; Z can be either H, O, S, S—R or NR where R groups can be either H, aryls, alkyls, or cycloalkyls; "n" can be 1 to 5 carbons in length and stereoisomers, functional analogs, and pharmaceutically acceptable salts thereof and wherein the moiety bridging $R_1$ and N can be a substituted alkylene, optionally substituted alkenylene or optionally substituted alkynylene and where the alkylene group can include an inserted $C_3$-$C_5$ cycloalkyl group, aromatic, and heterocyclic group; and wherein X is $R_2$ or $C_1$-$C_4$ radiohaloalkyl.

The present invention yet further relates to a method of using an S1R selective ligand as a biomarker for pathphysiological study of memory deficits and cognitive disorders comprising quantifying S1R binding in a brain using as the S1R specific ligand having the general formula III', or IV' wherein $R_1$ can be a radical of an optionally substituted C4 to C7 N-containing heterocycle or a radical of an optionally substituted cyclic or acyclic tertiary amine or isoindoline-1,3-dione: $R_{2,4,5,6}$ can each independently be any one or combinations of the following moieties, hydrogen, cyano, nitro, acyl, alkyl, amido, azido, isothiocyanato, isocyanato, optionally substituted anilino, halogens, ethers, sulfonamides, thioacyl, nitro, aromatic, heterocyclic, olefinic, acetylene, deuterium, or tritium; Y is S; Z can be either H, O, S, S—R or NR where R groups can be either H, aryls, alkyls, or cycloalkyls; "n" can be 1 to 5 carbons in length and stereoisomers, functional analogs, and pharmaceutically acceptable salts thereof and wherein the moiety bridging $R_1$ and N can be a substituted alkylene, optionally substituted alkenylene or optionally substituted alkynylene and where the alkylene group can include an inserted $C_3$-$C_5$ cycloalkyl group, aromatic, and heterocyclic group; and wherein X is $R_2$ or $C_1$-$C_4$ radiohaloalkyl.

The present invention relates to a still further invention comprising a method of detecting increased S1R density at the site of nerve injury arising from neuropathic pain comprising S1R-PET imaging a tissue with an imaging agent to determine a non-invasive biomarker of nerve injury and inflammation wherein the imaging agent comprises at least one SR1 selective compound or radioligand of the general formula III', or IV':

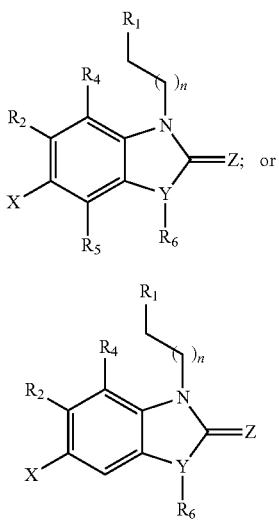

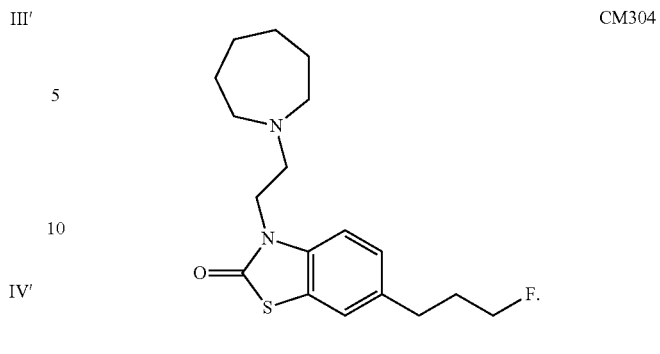

wherein R₁ can be a radical of an optionally substituted C4 to C7 N-containing heterocycle or a radical of an optionally substituted cyclic or acyclic tertiary amine or isoindoline-1,3-dione; $R_{2,4,5,6}$ can each independently be any one or combinations of the following moieties, hydrogen, cyano, nitro, acyl, alkyl, amido, azido, isothiocyanato, isocyanato, optionally substituted anilino, halogens, ethers, sulfonamides, thioacyl, nitro, aromatic, heterocyclic, olefinic, acetylene, deuterium, or tritium; Y is S; Z can be either H, O, S, S—R or NR where R groups can be either H, aryls, alkyls, or cycloalkyls; "n" can be 1 to 5 carbons in length and stereoisomers, functional analogs, and pharmaceutically acceptable salts thereof and wherein the moiety bridging R₁ and N can be a substituted alkylene, optionally substituted alkenylene or optionally substituted alkynylene and where the alkylene group can include an inserted $C_3$-$C_5$ cycloalkyl group, aromatic, and heterocyclic group; and wherein X is R₂ or $C_1$-$C_4$ radiohaloalkyl.

In preferred embodiments of the present methods, the S1R selective imaging agent has the formula XII′

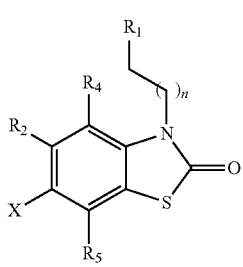

wherein n=1-5.

A still yet preferred embodiment uses as the S1R imaging agent wherein X is F¹⁸ C1-C4 alkyl. A most preferred embodiment uses as the S1R imaging agent of the formula:

BRIEF DESCRIPTION OF THE FIGURES

FIG. 1—Selected sigma-1 receptor ligands and radioligands

positive control cell lysate for σ-1 receptor as supplied by Santa Cruz Biotech (JAR cells). Blot was also stained for α-tubulin as a protein loading control.

Figure 17:
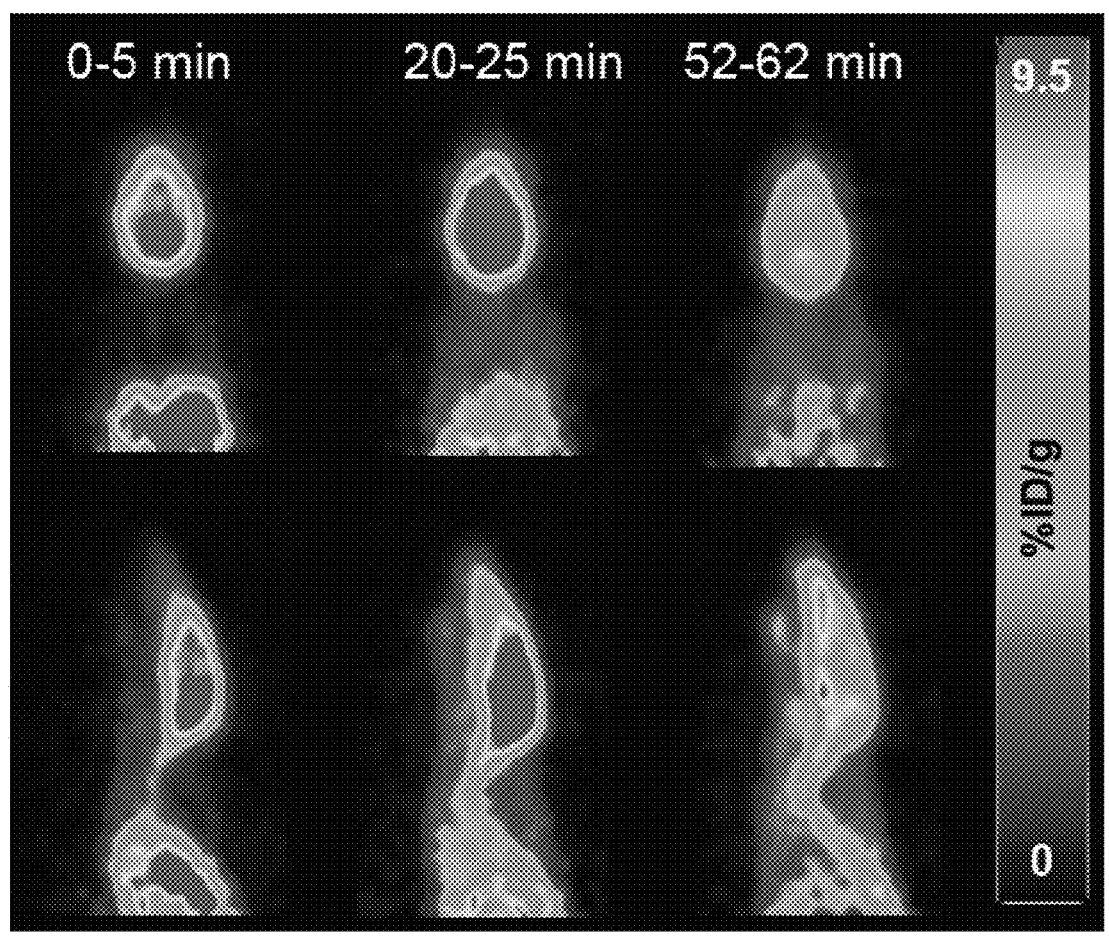

FIG. 17—[$^{18}$F]FTC-146 PET study in mice. Images from a selected baseline mouse PET study summed over different times. Dynamic imaging was commenced 1 minute prior to i.v. administration of [$^{18}$F]FTC-146 (102 µCi) and continued for a total of 62 minutes.

Figure 18:
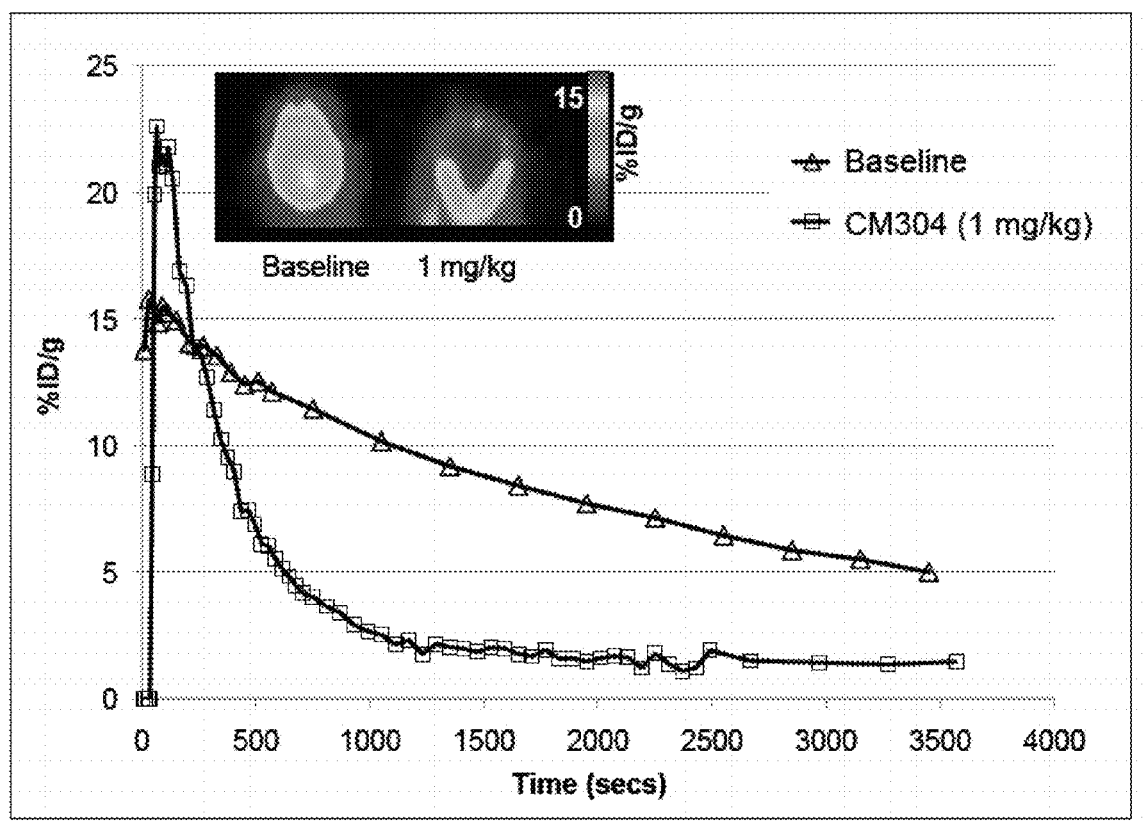

FIG. 18—[$^{18}$F]FTC-146 time activity curves. Time activity curves (TACs) representing accumulation of [$^{18}$F]FTC-146 in whole mouse brain as a function of time for both baseline (n=3) and blocking (n=3) PET imaging studies. Baseline studies involved i.v. administration of [$^{18}$F]FTC-146 (95-125 µCi), whereas blocking studies involved pre-treatment of mice with CM304 (1 mg/kg) 10 minutes prior to i.v. administration of [$^{18}$F]FTC-146 (95-125 µCi). Representative brain PET images (one baseline and one blocking) summed over the last 30 minutes are also shown.

Figure 19A:
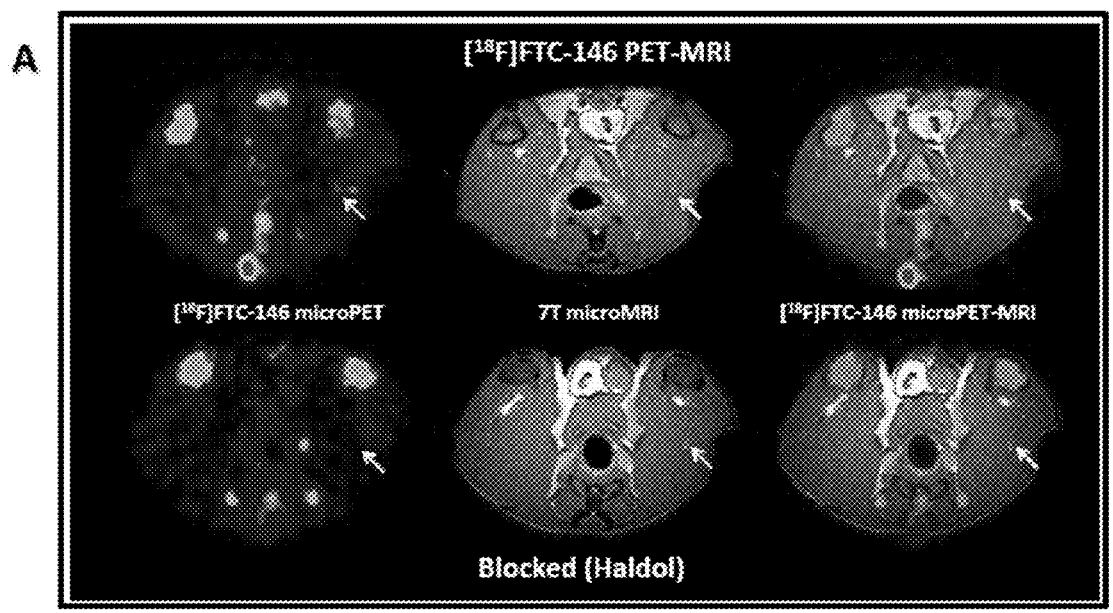

FIG. 19A shows representative transaxial PET, MRI and PET-MRI showing injured sciatic nerves (arrows). Top row: Increased [$^{18}$F]FTC-146 uptake is seen on the side with spared-nerve injury (left), compared with the uninjured side (right). Bottom row: When blocked with Haloperidol, no increase in [$^{18}$F]FTC-146 uptake is seen in the left side over the right side. Representative transaxial PET, MRI and PET-MRI showing injured sciatic nerves (arrows). Top row: Increased [$^{18}$F]FTC-146 uptake is seen on the side with spared-nerve injury (left), compared with the uninjured side (right). Bottom row: When blocked with Haloperidol, no increase in [$^{18}$F]FTC-146 uptake is seen in the left side over the right side.

Figure 19B:
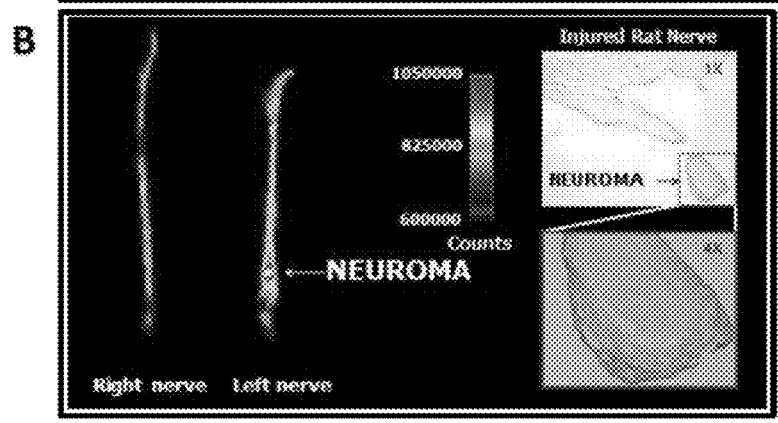

FIG. 19B is an autoradiograph of sciatic nerve specimens from spared-nerve injury model showed that [$^{18}$F]FTC-146 uptake is higher in injured left sciatic nerve than in the uninjured right sciatic nerve.

Figure 19C:
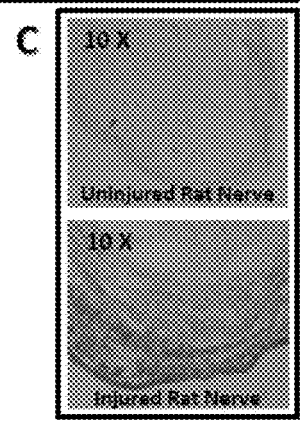

FIG. 19C shows immunohistochemistry results indicate qualitatively increased presence of sigma-1 receptors in SNI group comparing to the control group.

Figure 20:
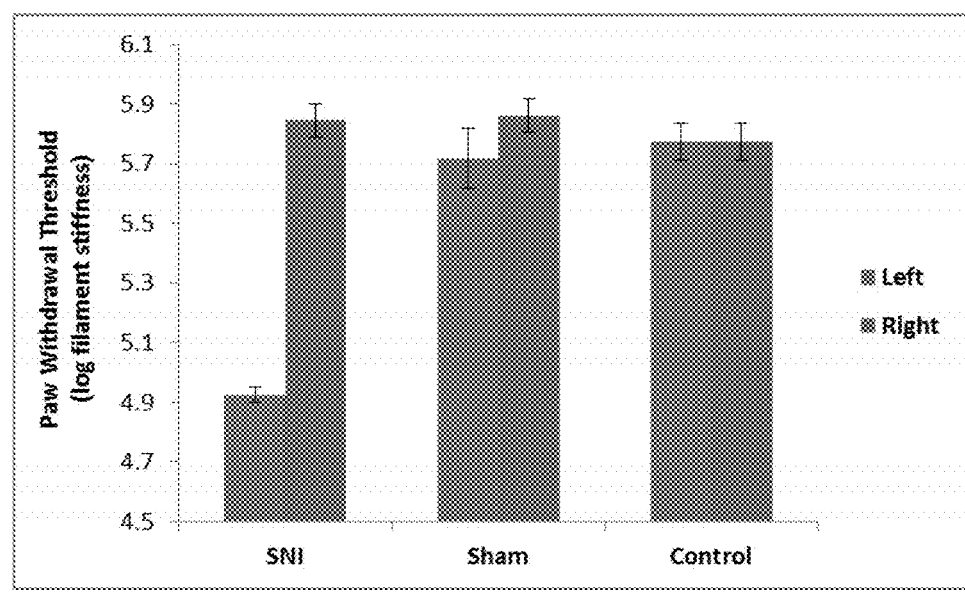

FIG. 20 is a Von Frey test for pain behavior: Lower threshold for paw withdrawal to mechanical stimulation is seen only in injured (Left) hindlimbs of SNI rats, indicating presence of pain (allodynia). The uninjured (Right) hindlimbs of SNI rats and both hindlimbs of Sham and Control rats show normal thresholds for paw withdrawal response. Error bars represent standard errors. (*p<0.001; n=4). SNI=spared nerve injury of left sciatic nerve; Sham=sham surgery with no nerve injury; Control=no surgery.

Figure 21:
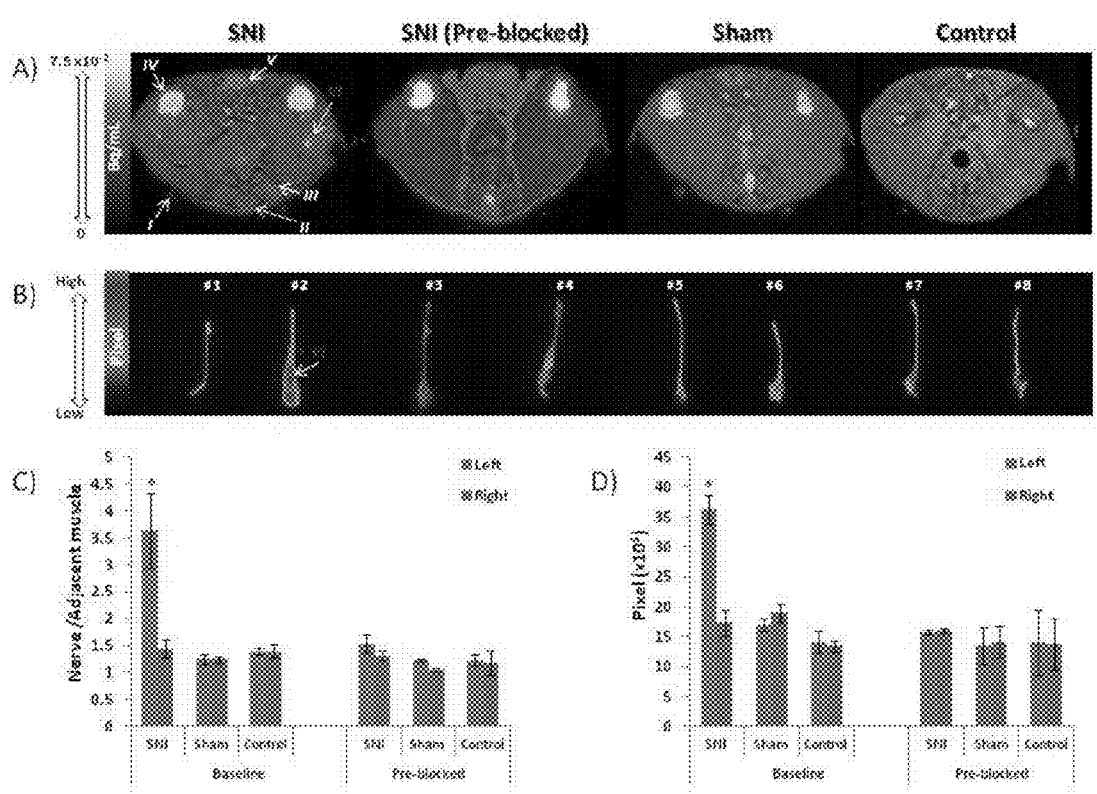

FIGS. 21 A, B, and C show (A) Representative axial PET-MR images through the thighs of SNI, SNI (pre-blocked), sham and control rats (I=fiducial; II=vein&tail; III=lymphatic's; IV=joint; V=penile urethra; VI=neuroma), (B) Autoradiography of representative excised nerves from SNI, SNI (pre-blocked), sham and control rats (#1, #3, #5, #7, #8 are uninjured sciatic nerve without surgery; #6 is are uninjured sciatic nerve with Sham surgery; #2, #4 are injured sciatic nerve), (C) Average normalized maximum signal in sciatic nerves on PET-MRI (n=4), (D) Signal intensity in sciatic nerves on autoradiography (n=2). Error bars represent standard errors. On both PET-MRI and auto-radiography, greater [$^{18}$F]FTC-146 uptake is seen in left nerve of SNI group than in the right or in either nerve of sham and control groups. Pre-blocking with haloperidol reduces tracer uptake in injured nerves to uninjured levels. (*p<0.001). SNI=spared nerve injury of left sciatic nerve; SNI (Pre-blocked)=SNI rats pre-blocked with haloperidol (1.6 mg/kg); Sham=sham surgery with no nerve injury; Control=no surgery.

Figure 22:
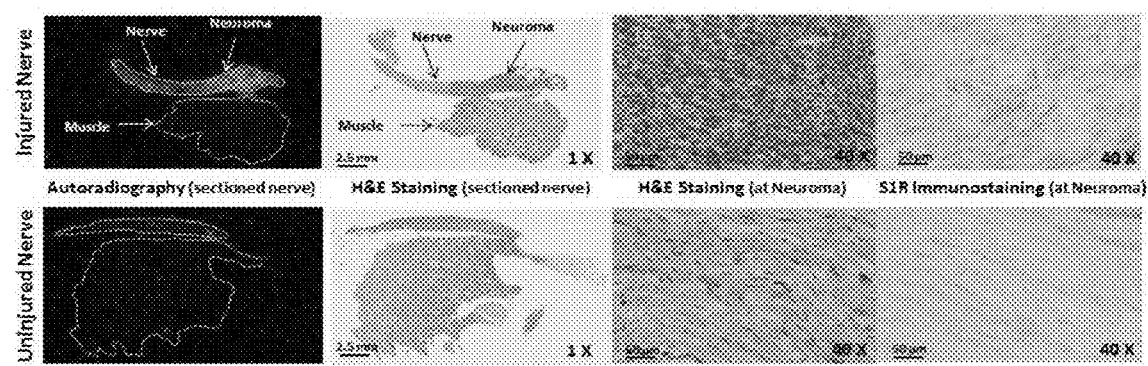

FIG. 22 shows autoradiography and immunohistochemical staining of dissected injured nerve (upper panel) and uninjured nerve (lower panel). Increased [$^{18}$F]FTC-146 uptake is seen in the neuroma, which also shows increased cellularity on H&E staining and increased S1R immunostaining compared to the uninjured nerve. Of note, adjacent muscular tissue in the sections did not contain significant radiotracer material. H&E=Hematoxylin and Eosin; S1R=Sigma 1 receptor.

FIGS. 23 A, B, C, D, E, F, G and H show the double immunofluorescence staining of injured (upper panel) and uninjured (lower panel) sciatic nerve: (A, E) Immunostain of Schwann cell body/myelin (S100 antibody, green). (B, F) S1R immunostaining (S1R specific primary antibody, red). (C, G) Cell nucleus staining of nucleic acids (DAPI, blue); (D, H) shows co-localization of Schwann cell and S1R. S1R density correlates with Schwann cell proliferation. S1R=Sigma 1 receptor; DAPI=4',6-diamidino-2-phenylindole.

DETAILED DESCRIPTION OF THE INVENTION

The generic structures of Formulae I, II, III, IV and V encompass a diverse range of heterocycles. Embodiments within this genus, for example, include 2(3H)-benzoxazolone (Y=O, Z=O) and 2(3H)-benzothiazolone (Y=S, Z=O) compounds and the sigma receptor affinity shown by these heterocycles. The 2(3H)-benzoxazolone (BOA) and its bioisosteric surrogate 2(3H)-benzothiazolone (BTA) heterocycle is a bicyclic ring system which promotes high versatility in organic synthesis involving N-substitution (either N-alkylation or N-acylation) and aromatic ring electrophilic substitution reactions.

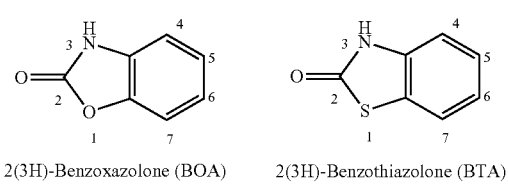

2(3H)-Benzoxazolone (BOA)　　2(3H)-Benzothiazolone (BTA)

Chemical Structures of BOA and BTA

The present invention relates to compounds having the general formula I

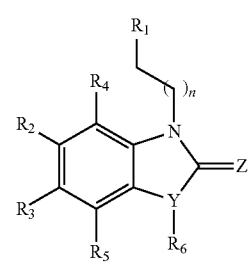

wherein $R_1$ can be a radical of an optionally substituted C-4 to C-7 N-containing heterocycle or a radical of an optionally substituted cyclic or acyclic tertiary amine, or isoindoline-1,3-dione $R_{2,3,4,5,6}$ can each independently be any one or combinations of the following moieties, hydrogen, cyano, nitro, acyl, alkyl, amido, azido, isothiocyanates, isocyanates, optionally substituted anilino, halogens, ethers, sulfonamides, thioacyl, nitro, aromatic, heterocyclic, olefinic, acetylene, deuterium, or tritium; Y can be either CH, $CH_2$, O, S, $OCH_2$, N—R, N—Ar, C—R, C—Ar; Z can be either H, O, S, S—R or NR. R groups can be either H, aryls, alkyls, or cycloalkyls; "n" can be 1 to 5 carbons in length and stereoisomers, functional analogs, and pharmaceutically acceptable salts thereof and wherein the moiety bridging $R_1$ and N can be optionally substituted alkylene, optionally substituted alkenylene or optionally substituted alkynylene and where the alkylene group can include an inserted $C_3$-$C_5$ cycloalkyl group, aromatic and heterocycle group.

The optionally substituted N-containing heterocyclic radical can be for example optionally substituted piperidine, optionally substituted tetrahydropiperidine, optionally substituted piperazine, optionally substituted tetrahydropyridine, optionally substituted azepanes or optionally substituted tetrahydroisoquinoline in which the optional substituents are on the aromatic moiety.

The present invention further relates to compounds useful as sigma receptors of the following formula II:

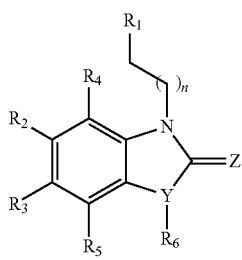

wherein $R_1$ can be an optionally substituted nitrogen-containing heterocycle radical such as, for example, radicals of optionally substituted piperidines, optionally substituted piperazines, optionally substituted tetrahydropyridines, optionally substituted azepanes, tertiary amines (cyclic or acyclic), isoindoline-1,3-dione, or optionally substituted tetrahydroisoquinolones (aromatically substituted): $R_{2,4,5,6}$ can each independently be any one or combinations of the following moieties, such as, for example, hydrogen, cyano, nitro, acyl, alkyl, amido, azido, isothiocyanate, isocyanate anilino (unsubstituted or substituted), halogens (such as fluorine, chlorine, bromine and iodine), ethers, sulfonamides, thioacyl, nitro, aromatic, heterocyclic, olefinic, acetylenic, deuterium, or tritium; Y can be either CH, $CH_2$, O, S, $OCH_2$, N—R, N—Ar, C—R, C—Ar where Ar is an optionally substituted aryl. Z can be either H, O, S, S—or NR. R groups can be either H, aryls, alkyls, or cycloalkyls. "n" can be 1 to 5 carbons in length and stereoisomers, analogs, and pharmaceutically acceptable salts thereof as well as compositions comprising said compounds. The moiety bridging $R_1$ and N in the formula II can be a substituted $C_1$-$C_6$ alkylene, $C_1$-$C_5$ alkenylene wherein the alkylene group can have inserted into its chain a $C_3$-$C_5$ cycloalkyl group, aromatic, and heterocyclic group.

Formulae I and II differ from each other only in the definition of the moiety bridging R1 and N.

The present invention relates to still yet further compounds useful as sigma receptors of the following formula III:

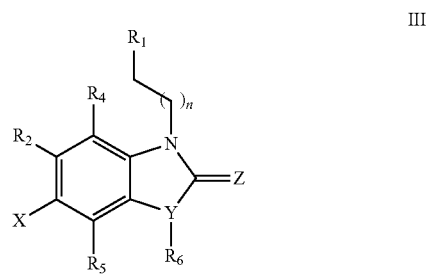

wherein $R_1$, $R_{2,4,5,6}$ and "n" can be the options provided for formula II, above and wherein $X_1$ is halogen, or $C_1$-$C_4$ haloalkyl.

The present invention relates to a still yet further series of compounds useful as sigma receptors of the following formula IV:

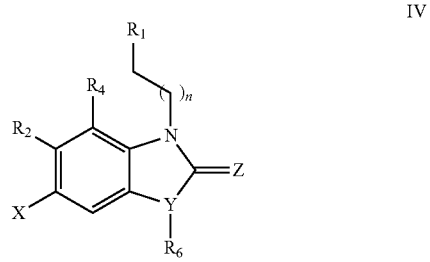

wherein $R_1$ can be an optionally substituted nitrogen-containing heterocycle radical such as, for example, radicals of optionally substituted piperidines, optionally substituted piperazines, optionally substituted tetrahydropyridines, optionally substituted azepanes, tertiary amines (cyclic or acyclic), isoindoline-1,3-dione, or optionally substituted tetrahydroisoquinolones (aromatically substituted): $R_{2,4,6}$ can each independently be any one or combinations of the following moieties, such as, for example, hydrogen, cyano, nitro, acyl, alkyl, amido, azido, isothiocyanate, isocyanate anilino (unsubstituted or substituted), halogens (such as fluorine, chlorine, bromine and iodine), ethers, sulfonamides, thioacyl, nitro, aromatic, heterocyclic, olefinic, acetylenic, deuterium, or tritium; Y can be either CH, $CH_2$, O, S, $OCH_2$, N—R, N—Ar, C—R, C—Ar where Ar is an optionally substituted aryl. Z can be either H, O, S, S—or NR. R groups can be either H, aryls, alkyls, or cycloalkyls. "n" can be 1 to 5 carbons in length and stereoisomers, analogs, and pharmaceutically acceptable salts thereof as well as compositions comprising said compounds. The moiety bridging $R_1$ and N in the formula IV can be a substituted $C_1$-$C_6$ alkylene having the formula —(CHR$_x$—(CH$_2$)—CH$_2$)— wherein the —CHR$_x$— moiety is attached to $R_1$ and the alkylene group can have inserted into its chain a $C_3$-$C_5$ cycloalkyl group, aromatic, and heterocyclic group and wherein the R$_x$ is a $C_1$-$C_4$ straight chain or branched chain alkyl or a $C_1$-$C_4$ straight chain or branched chain haloalkyl.

The present invention relates to compounds useful as sigma receptors of the following formula V:

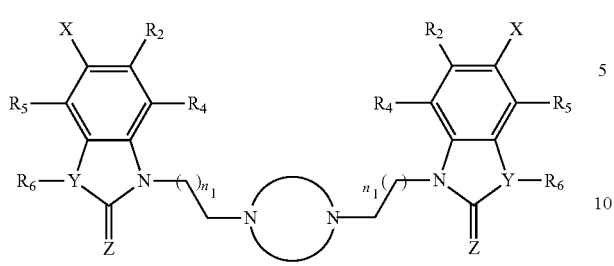

V wherein $R_{2,3,4,5,6}$ can each independently be any one or combinations of the following moieties, such as, for example, hydrogen, cyano, nitro, acyl, alkyl, amido, azido, isothiocyanate, isocyanate anilino (unsubstituted or substituted), halogens (such as fluorine, chlorine, bromine and iodine), ethers, sulfonamides, thioacyl, nitro, aromatic, heterocyclic, olefinic, acetylenic, deuterium, or tritium; Y can be either CH, $CH_2$, O, S, $OCH_2$, N—R, N—Ar, C—R, C—Ar where Ar is an optionally substituted aryl. Z can be either H, O, S, S— or NR. R groups can be either H, aryls, alkyls, or cycloalkyls. "n" can be 1 to 5 carbons in length and stereoisomers, analogs, and pharmaceutically acceptable salts thereof as well as compositions comprising said compounds. The $R_1$ bridging moiety in the formula V can be an optionally substituted $C_1$-$C_5$ alkylene, $C_1$-$C_6$ alkenylene or $C_1$-$C_6$ alkynylene group wherein the alkylene group can have inserted into its chain a $C_3$-$C_5$ cycloalkyl group, aromatic, and heterocyclic group.

Exemplary compounds of the invention can be of the general formulae shown below in which n=1-5:

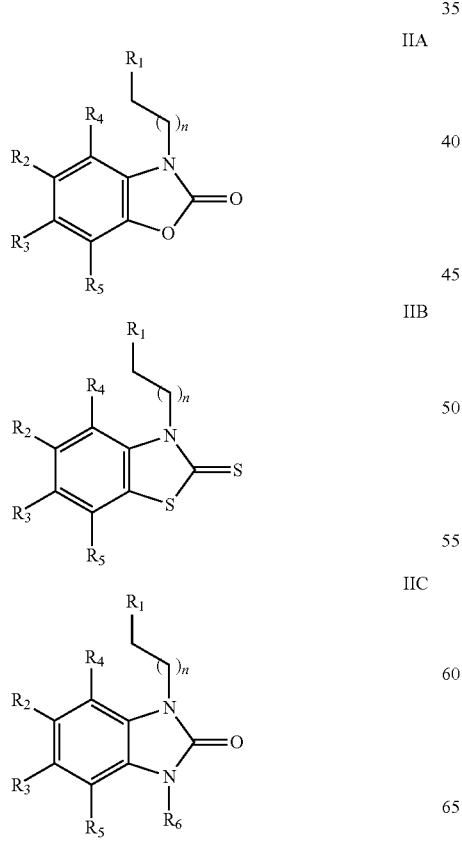

IIA

IIB

IIC

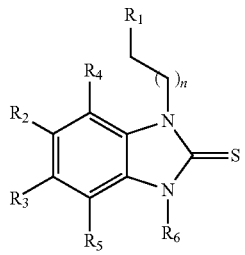

IID

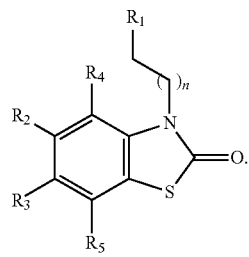

IIE

Further exemplary compounds of the invention can be of the general formulae shown below in which n=1-5:

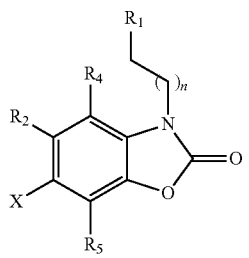

IIIA

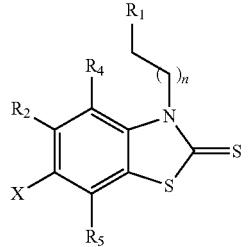

IIIB

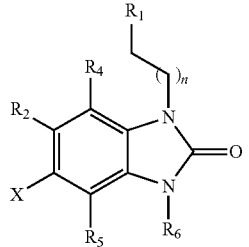

IIIC

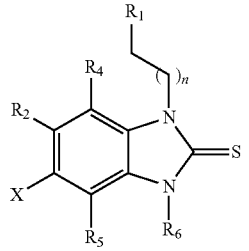

IIID

IIIE
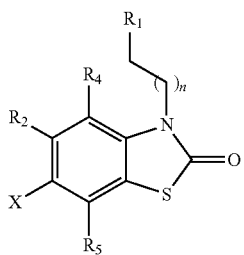
IVA
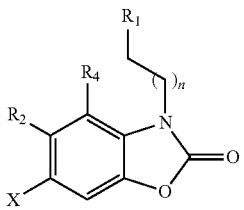
IVB
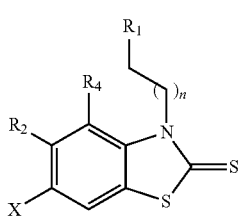
IVC
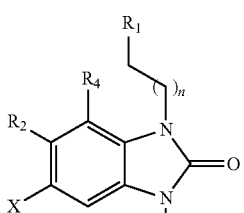
IVD
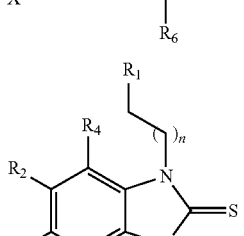
IVE
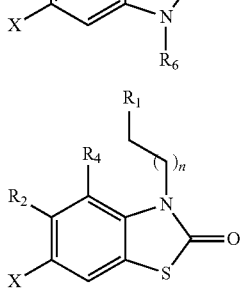
VA
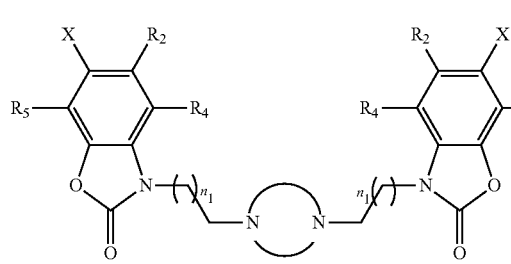
VB
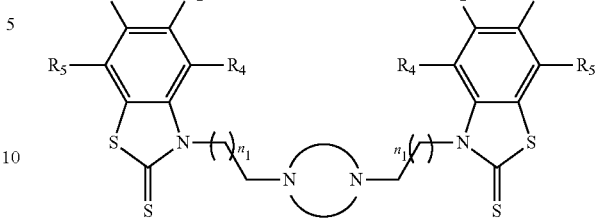
VC
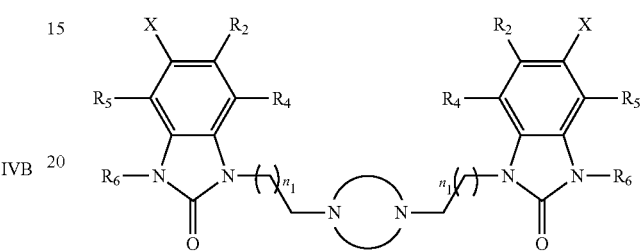
VD
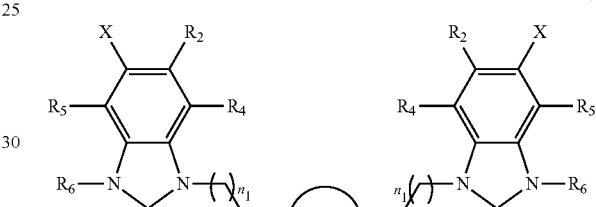
VE
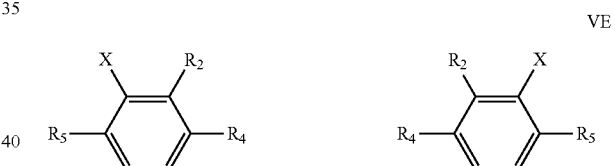
Other exemplary compounds of the invention are compounds where Y=O and Z=O; or Y=S and Z=S; or where Y=CH₂ or Y=CH.
R₁ for example is optionally substituted
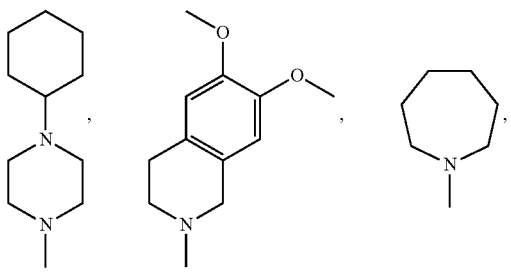

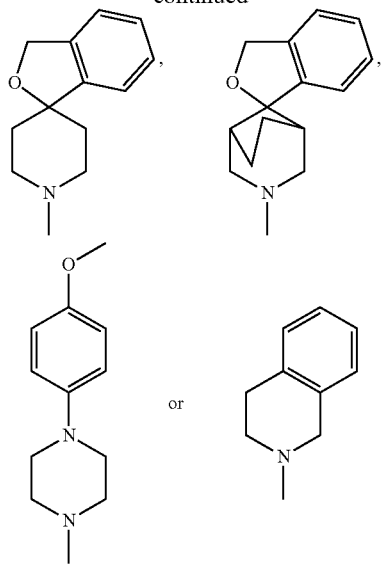

DEFINITIONS OF TERMS

As used herein, the term "lower" refers to a group having between one and six carbons.

As used herein, the term "alkyl" refers to a straight or branched chain hydrocarbon having from one to ten carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, azido, isothiocyanate, isocyanate, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkyl" group may contain one or more O, S, S(O), or S(O)$_2$ atoms. Examples of "alkyl" as used herein include, but are not limited to, methyl, n-butyl, t-butyl, n-pentyl, isobutyl, and isopropyl, and the like.

As used herein, the term haloalkyl refers to a straight or branched chain alkyl having one to four carbon atoms in which at least one H up to all of the H's of the alkyl is substituted with a halo moiety wherein halo includes fluoro, chloro, bromo or iodo.

As used herein, the term "alkylene" refers to a straight or branched chain divalent hydrocarbon radical having from one to ten carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkylene" group may contain one or more O, S, S(O), or S(O)$_2$ atoms. Examples of "alkylene" as used herein include, but are not limited to, methylene, ethylene, and the like.

As used herein, the term "alkenyl" refers to a hydrocarbon radical having from two to ten carbons and at least one carbon-carbon double bond, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkenyl" group may contain one or more O, S, S(O), or S(O)$_2$ atoms.

As used herein, the term "alkenylene" refers to a straight or branched chain divalent hydrocarbon radical having from two to ten carbon atoms and one or more carbon-carbon double bonds, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkenylene" group may contain one or more O, S, S(O), or S(O)$_2$ atoms. Examples of "alkenylene" as used herein include, but are not limited to, ethene-1,2-diyl, propene-1,3-diyl, methylene-1,1-diyl, and the like.

As used herein, the term "alkynyl" refers to a hydrocarbon radical having from two to ten carbons and at least one carbon-carbon triple bond, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkynyl" group may contain one or more O, S, S(O), or S(O)$_2$ atoms.

As used herein, the term "alkynylene" refers to a straight or branched chain 5 divalent hydrocarbon radical having from two to ten carbon atoms and one or more carbon-carbon triple bonds, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkynylene" group may contain one or more O, S, S(O), or S(O)$_2$ atoms. Examples of "alkynylene" as used herein include, but are not limited to, ethyne-1,2-diyl, propyne-1,3-diyl, and the like.

As used herein, "cycloalkyl" refers to an alicyclic hydrocarbon group optionally possessing one or more degrees of unsaturation, having from three to twelve carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. "Cycloalkyl" includes by way of example cyclopropyl, cyclobutyl, cyclopentyl, cyclohexyl, cycloheptyl, or cyclooctyl, and the like.

As used herein, the term "cycloalkylene" refers to a non-aromatic alicyclic divalent hydrocarbon radical having from three to twelve carbon atoms and optionally possessing one or more degrees of unsaturation, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "cycloalkylene" as used herein include, but are not limited to, cyclopropyl-1,1-diyl, cyclopropyl-1,2-diyl, cyclobutyl-1,2-diyl, cyclopentyl-1,3-diyl, cyclohexyl-1,4-diyl, cycloheptyl-1,4-diyl, or cyclooctyl-1,5-diyl, and the like.

As used herein, the term 'heterocyclic" or the term "heterocyclyl" refers to a three to twelve-membered heterocyclic ring optionally possessing one or more degrees of unsaturation, containing one or more heteroatomic substitutions selected from S, SO, $SO_2$, O, or N, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more of another "heterocyclic" ring(s) or cycloalkyl ring(s). Examples of "heterocyclic" include, but are not limited to, tetrahydrofuran, 1,4-dioxane, 1,3-dioxane, piperidine, pyrrolidine, morpholine, piperazine, tetrahydropyridine, hexahydroazepine and the like.

As used herein, the term 'heterocyclyl containing at least one basic nitrogen atom" refers to a "heterocyclic" or "heterocyclyl" group as defined above, wherein said heterocyclyl group contains at least one nitrogen atom flanked by 20 hydrogen, alkyl, alkylene, or alkylyne groups, wherein said alkyl and/or alkylene groups are not substituted by oxo. Examples of "heterocyclyl containing at least one basic nitrogen atom" include, but are not limited to, piperazine-2-yl, pyrrolidine-2-yl, azepine-4-yl,

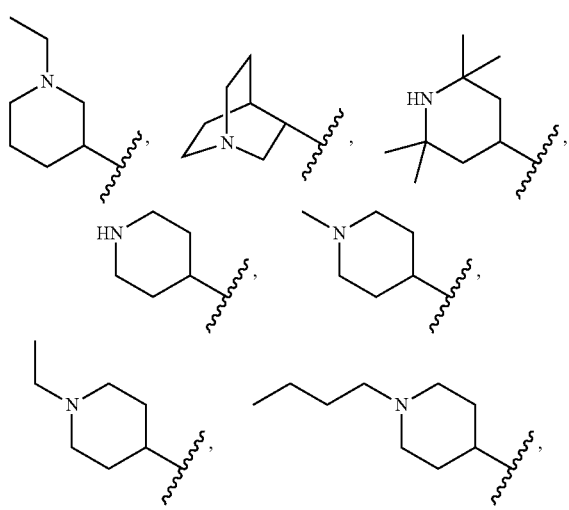

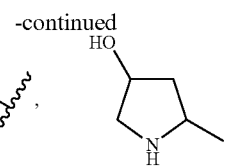

and the like.

As used herein, the term "heterocyclylene" refers to a three to twelve-membered heterocyclic ring diradical optionally having one or more degrees of unsaturation containing one or more heteroatoms selected from S, SO, $SO_2$, O, or N, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more benzene rings or to one or more of another "heterocyclic" rings or cycloalkyl rings. Examples of "heterocyclylene" include, but are not limited to, tetrahydrofuran-2,5-diyl, morpholine-2, pyran-2,4-diyl, 1,4-dioxane-2,3-diyl, 1,3-dioxane-2,4-diyl, piperidine-2,4-diyl, piperidine-1,4-diyl, pyrrolidine-1 morpholine-2,4-diyl, piperazine-1,4-diyl, and the like.

As used herein, the term "aryl" refers to a benzene ring or to an optionally substituted benzene ring system fused to one or more optionally substituted benzene rings, optionally substituted with substituents selected from the group consisting of lower alkyl, lower alkoxy, lower alkylsulfanyl, lower alkylsulfenyl, lower alkylsulfonyl, oxo, hydroxy optionally substituted by acyl, mercapto, azido, isothiocyanate, isocyanate, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of aryl include, but are not limited to, phenyl, 2-naphthyl, 1-naphthyl, 1-anthracenyl, and the like.

As used herein, the term "arylene" refers to a benzene ring diradical or to a benzene ring system diradical fused to one or more optionally substituted benzene rings, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of "arylene" include, but are not limited to, benzene-1,4-diyl, naphthalene-1,8-diyl, and the like.

As used herein, the term "heteroaryl" refers to a five- to seven-membered aromatic ring, or to a polycyclic heterocyclic aromatic ring, containing one or more nitrogen, oxygen, or sulfur heteroatoms, where N-oxides and sulfur monoxides and sulfur dioxides are permissible heteroaromatic substitutions, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. For polycyclic aromatic ring systems, one or more of the rings may contain one or more heteroatoms. Examples of "heteroaryl" used herein are furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, quinazoline, benzofuran, benzothiophene, indole, and indazole, and the like.

As used herein, the term "heteroarylene" refers to a five- to seven-membered aromatic ring diradical, or to a polycyclic heterocyclic aromatic ring diradical, containing one or more nitrogen, oxygen, or sulfur heteroatoms, where N-oxides and sulfur monoxides and sulfur dioxides are permissible heteroaromatic substitutions, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. For polycyclic aromatic ring system diradicals, one or more of the rings may contain one or more heteroatoms. Examples of "heteroarylene" used herein are furan-2,5-diyl, thiophene-2,4-diyl, 1,3,4-oxadiazole-2,5-diyl, 1,3,4-thiadiazole-2,5-diyl, 1,3-thiazole-2,4-diyl, 1,3-thiazole-2,5-diyl, pyridine-2,4-diyl, pyridine-2,3-diyl, pyridine-2,5-diyl, pyrimidine-2,4-diyl, quinoline-2,3-diyl, and the like.

As used herein, halo includes fluoro, bromo and iodo.

Initial efforts were focused on incorporating a good directionality by implying side-chains on a rigid template using conventional simple synthetic methodology. Exploring the effects of linker length between two hydrophobic regions for sigma receptor affinity led to the synthesis of 2 to 6 carbon linkers of 2(3H)-benzoxazolones ligands and 2(3H)-benzothiazolones compounds.

The in vitro receptor binding affinities of the initial series of compounds of formulae II and III investigated in rat brain homogenates at σ-1 and σ-2 subtypes are summarized in tables 1 and 2.

TABLE 1

Initial series 2 (3H)-benzoxazolones to explore the effects of linker length on sigma receptor affinity

| Compd. | R₁ | R₂-R₅ | n | σ-1 (K$_i$, nM) | σ-2 (K$_i$, nM) | σ-1/σ-2 |
|---|---|---|---|---|---|---|
| CM-129 | —N(piperazine)N—cyclohexyl | H | 2 | 6.90 ± 0.37 | 5.43 ± 0.78 | 1.3 |
| CM-124 | —N(piperazine)N—cyclohexyl | H | 3 | 5.22 ± 1.11 | 8.74 ± 2.30 | 0.6 |
| CM-121 | —N(piperazine)N—cyclohexyl | H | 4 | 11.3 ± 1.25 | 1.83 ± 0.17 | 6.2 |
| CM-126 | —N(piperazine)N—cyclohexyl | H | 5 | 10.6 ± 2.52 | 5.89 ± 1.31 | 1.8 |
| SN-48 | —N(piperazine)N—cyclohexyl | H | 6 | 4.60 ± 1.08 | 3.06 ± 0.45 | 1.5 |

TABLE 2

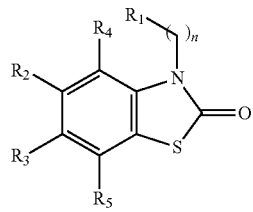

Initial series 2 (3H)-benzothiazolones to explore the effects of linker length on sigma receptor affinity

| Compd. | R₁ | R₂-R₅ | n | σ-1 ($K_i$, nM) | σ-2 ($K_i$, nM) | σ-1/σ-2 |
|---|---|---|---|---|---|---|
| SN-97 | —N(piperazine)N-cyclohexyl | H | 2 | 4.66 ± 0.74 | 2.25 ± 0.37 | 2.1 |
| SN-98 | —N(piperazine)N-cyclohexyl | H | 3 | 5.61 ± 0.74 | 3.05 ± 0.41 | 1.84 |
| CM-145 | —N(piperazine)N-cyclohexyl | H | 4 | 4.17 ± 0.62 | 0.39 ± 0.06 | 10.69 |
| SN-99 | —N(piperazine)N-cyclohexyl | H | 5 | 4.98 ± 0.42 | 2.44 ± 0.26 | 2.04 |
| SN-102 | —N(piperazine)N-cyclohexyl | H | 6 | 6.55 ± 0.25 | 1.49 ± 0.18 | 4.40 |

CM121 showed a six fold preference for the σ-2 subtype, suggesting that a four methylene spacer between the piperazine ring and the heterocycle may favor σ-2 affinity (Table 1, Scheme 1). During further SAR studies, compound CM170 was found to have an 11 fold preference for the σ-2 subtype, suggesting a 4-fluoropiperazine moiety may favor σ-2 affinity (Scheme 1). Additionally, CM142 having a 6-acetyl group in the 2 (3H)-benzoxazolone heterocycle increased the preference for G-2 receptors by 7 fold (Scheme 1).

Scheme 1: Sigma-2 selective ligands

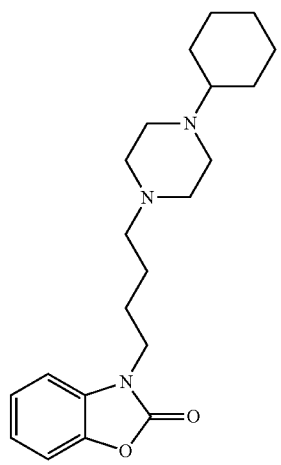

CM121, σ-1 = 11.26 ± 1.25 nM
σ-2 = 1.83 ± 0.17 nM
(6-fold σ-2 selective)

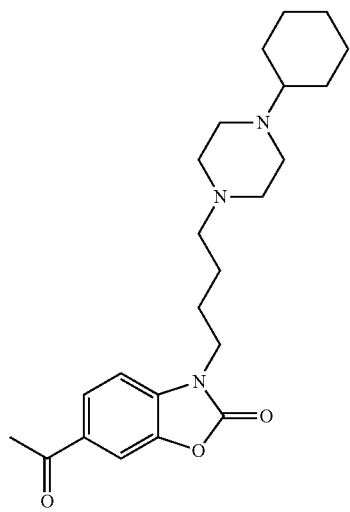

CM142, σ-1 = 46.37 ± 8.06 nM
σ-2 = 7.04 ± 0.79 nM
(7-fold σ-2 selective)

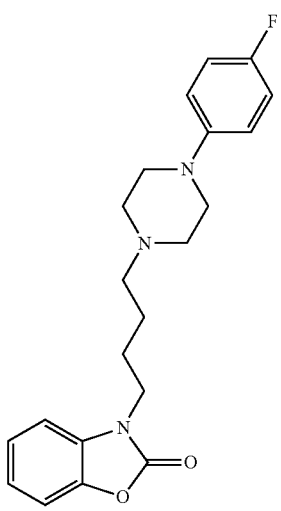

CM170, σ-1 = 7.59 ± 0.08 nM
σ-2 = 0.70 ± 0.11 nM
(11-fold σ-2 selective)

Interestingly, SN79 (Scheme 2) showed the high selectivity (>16,500 fold) for the σ-2 subtype suggesting that a four methylene linker, a 6-acetyl group in the 2(3H)-benzoxazolone heterocycle and a 4-fluoropiperazine moiety favor σ-2 affinity over the σ-1 subtype.

Scheme 2:

Compound SN79

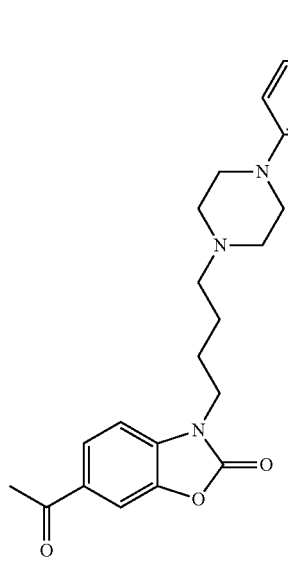

SN79, σ-1 = >100,000 nM
σ-2 = 6.06 ± 0.74 nM
(>16500 fold σ-2 selective)

When tested on select non-sigma binding sites in rat brain homogenates (Table 3), compound SN79 exhibited weaker interactions, confirming preferential affinity for sigma receptors.

TABLE 3

| Non-sigma binding affinity of SN79 | | | |
|---|---|---|---|
| Monoamine transporters | $K_i$, nM | Other Receptors | $K_i$, nM |
| DAT | 2615 ± 62 | Opioid | >10,000 |
| SERT | 159 ± 15 | NMDA | >10,000 |
| NET | 177 ± 14 | Dopamine ($D_2$) | >10,000 |
| | | 5-HT$_2$ | 320 ± 16 |

Compound SN79 was investigated for in vivo antagonizing effects in cocaine treated mice. Pretreatment of mice with SN79 led to a significant attenuation of cocaine-induced convulsions, locomotor activity and behavioral sensitization as seen in FIGS. 2-5. These data further demonstrate that compound SN79, acting through σ-2 receptors is able to significantly attenuate both the acute effects of cocaine as well as its chronic effects.

In addition to compounds exhibiting selectivity for the σ-2 receptor, compounds from this same series have demonstrated high affinity for both subtypes. Compound CM156 (Scheme 3), where the 2-oxo is replaced with a sulfur, demonstrated the highest affinity for both subtypes and was therefore examined in several non-sigma binding assays as shown in table 4. CM156 had a much weaker affinity for other proteins of interest, confirming preferential affinity for sigma receptors.

Scheme 3:

Compound CM156

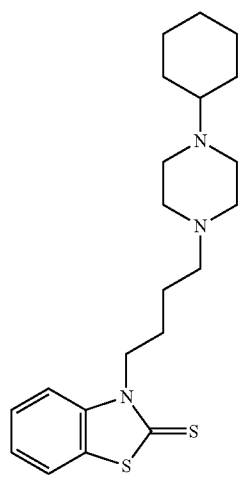

CM 156, σ-1 = 1.28 ± 0.38 nM
σ-2 = 0.55 ± 0.08 nM

TABLE 4

Non-sigma binding affinity of CM156

| Monoamine transporters | $K_i$, nM | Other Receptors | $K_i$, nM |
|---|---|---|---|
| DAT | 1175 ± 10 | Opioid | >10,000 |
| SERT | 1402 ± 152 | NMDA | >10,000 |
| NET | >10,000 | Dopamine ($D_2$) | 1041 ± 9 |
|  |  | 5-$HT_2$ | 1326 ± 159 |

Figure 6:
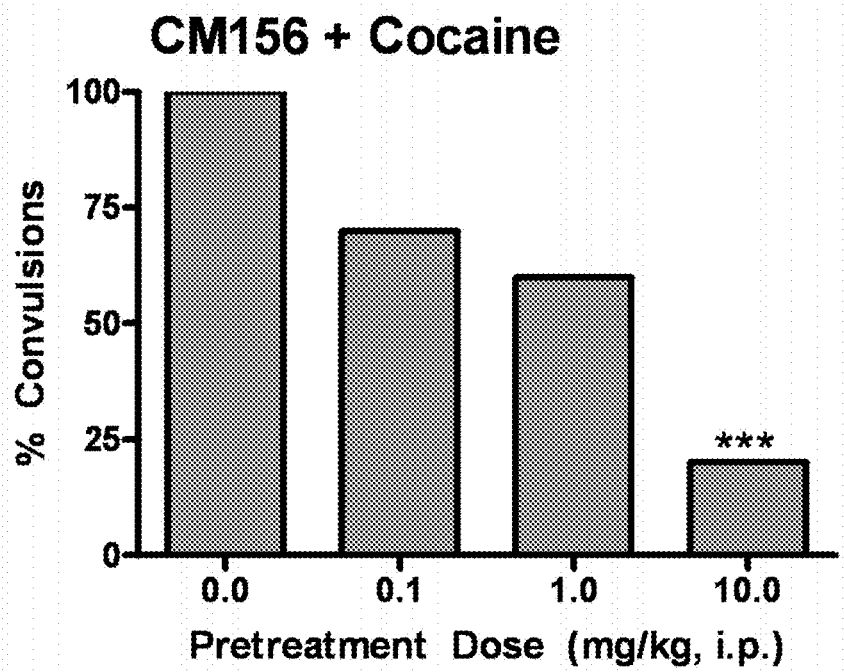
FIG. 6—CM156 attenuates the convulsive effects of cocaine (***P<0.005)
Figure 7:
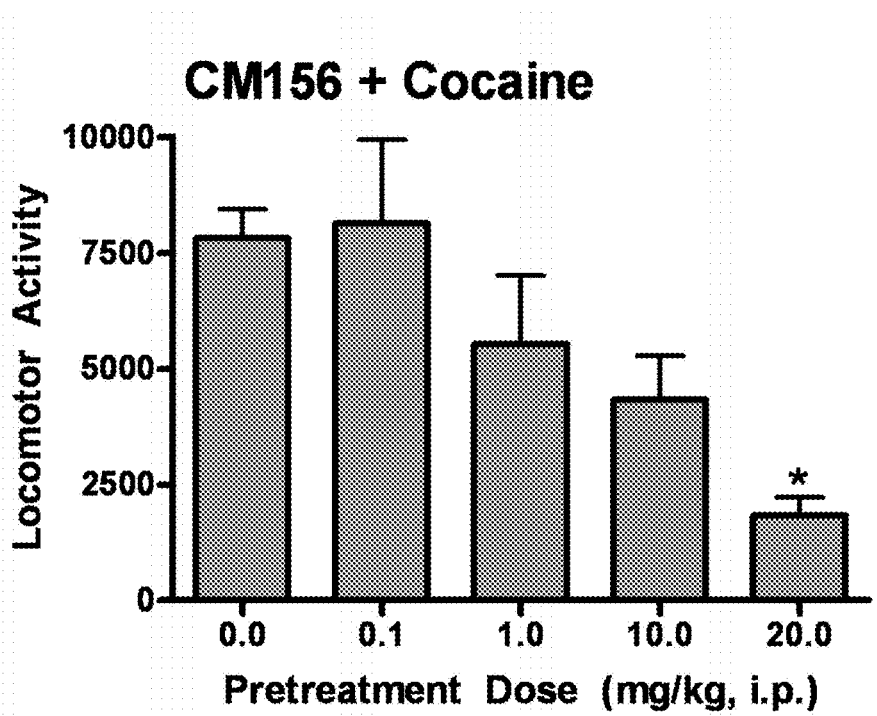
FIG. 7—CM156 pretreatment attenuates cocaine-induced locomotor activity (*P<0.05)
Figure 8:
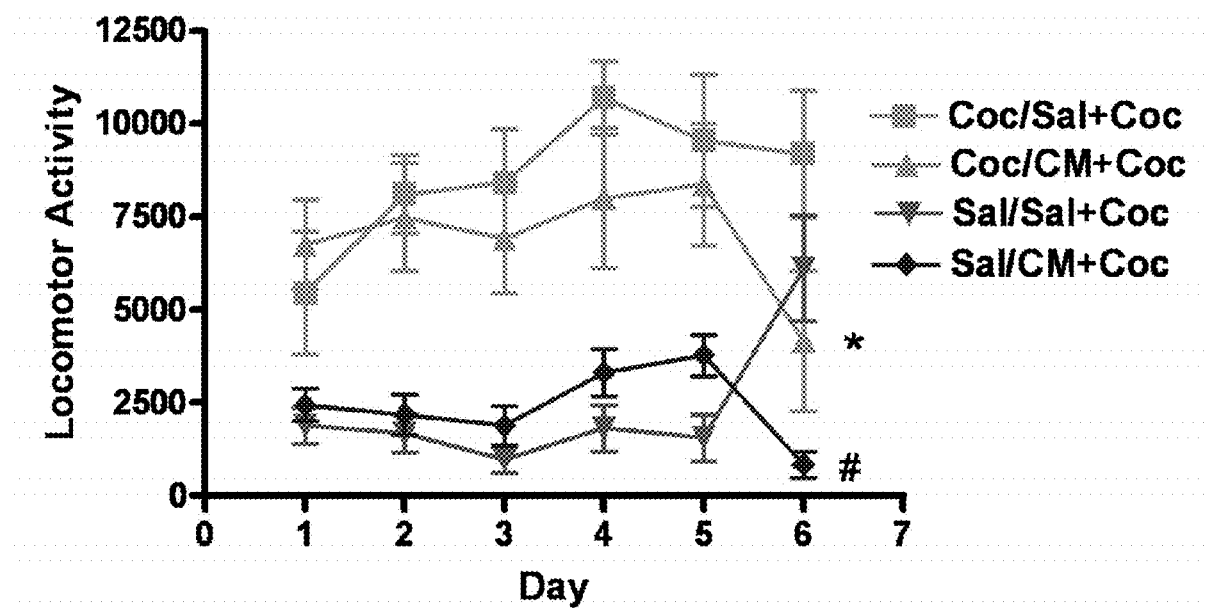
FIG. 8—CM156 pretreatment attenuates the expression of cocaine-induced sensitization (*P<0.05 vs sensitized, #P<0.05 vs acute cocaine)
Figure 9:
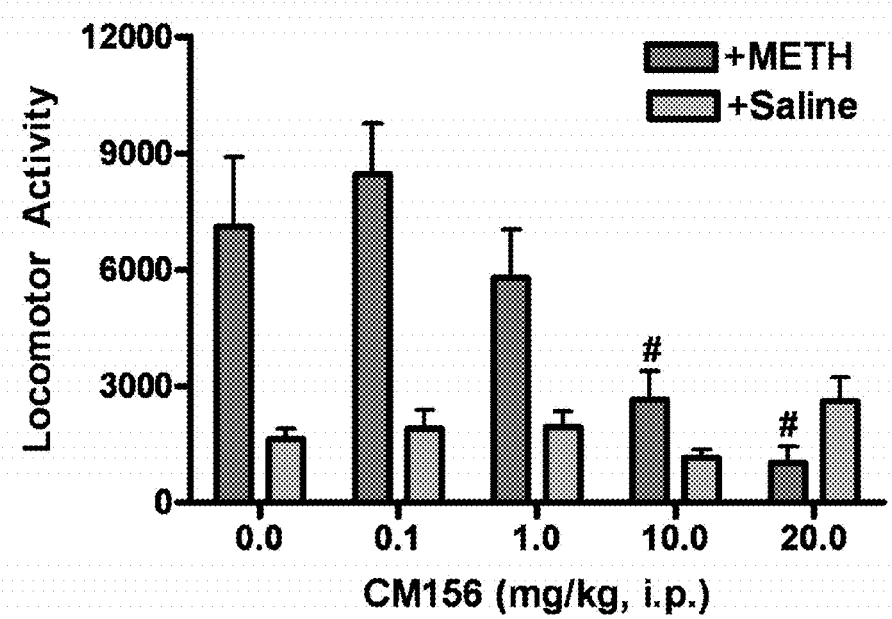
FIG. 9—CM156 pretreatment attenuates methamphetamine-induced locomotor activity (#P<0.05)
Figures 10, 11:
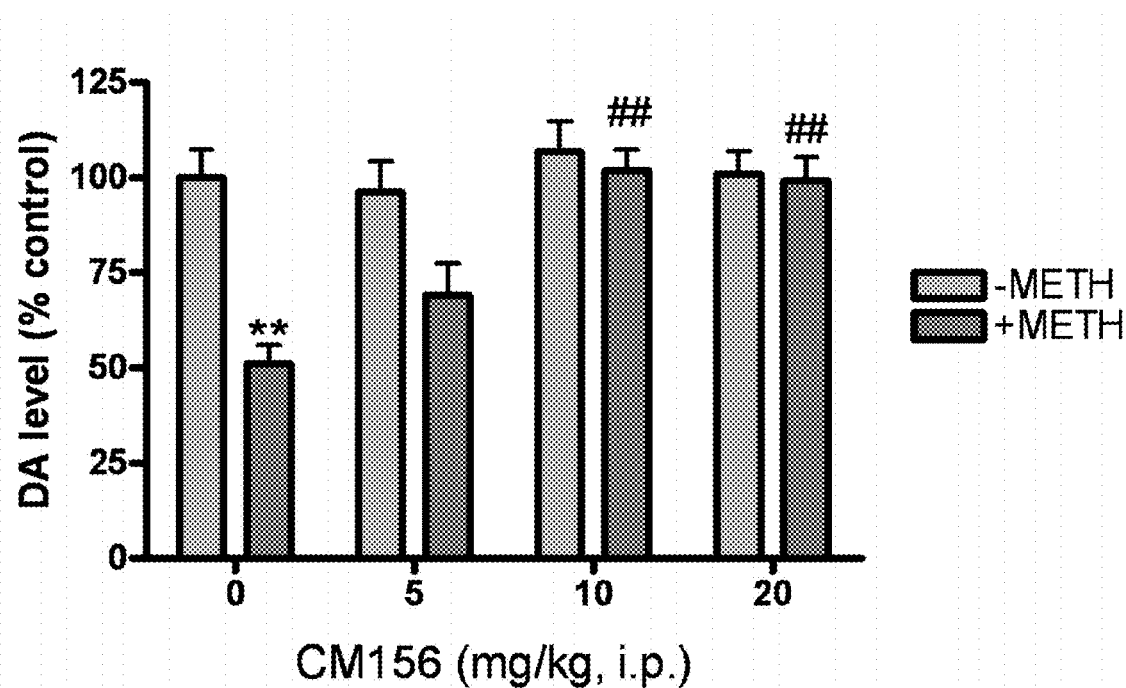
FIG. 10—CM156 pretreatment attenuates methamphetamine-induced dopamine depletions (**P<0.05, #4P<0.05)
FIG. 11—Table 1: Metabolic stability of AZ_66 by Rat liver microsomes (1 mg/ml)
Figures 12, 13:
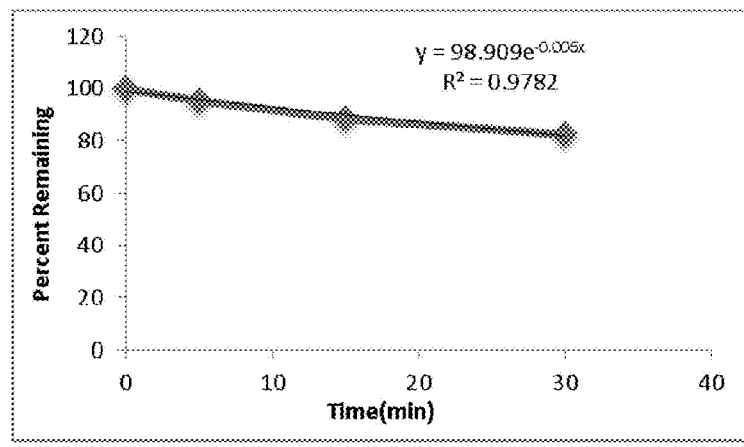
FIG. 12—Metabolic stability of AZ_66 by Rat liver microsomes (1 mg/ml)
FIG. 13—Table 2: In vitro Half-life and Intrinsic clearance
Figures 14, 15:
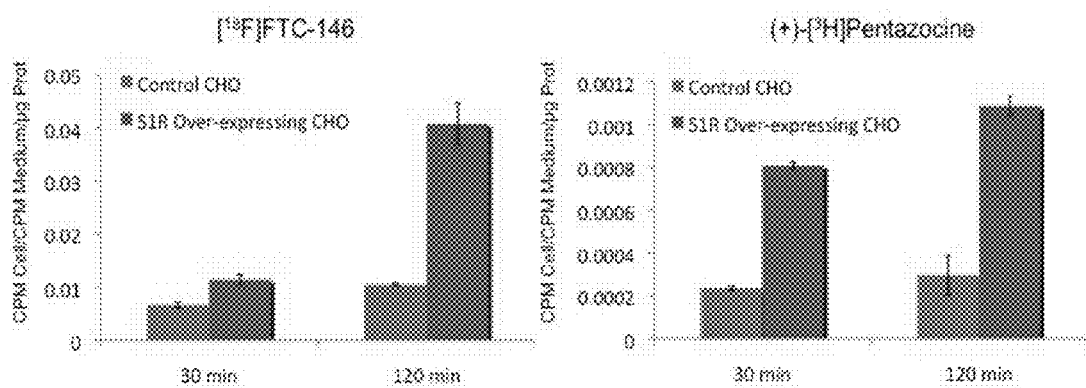
FIG. 14—Table 3: Incubation of CM_156 (10 μM) with rat liver microsomes (1 mg/ml)
FIG. 15—[¹⁸F]FTC-146 uptake in CHO cells. Uptake of either [¹⁸F]FTC-146 (left) or (+)-[³H]pentazocine (right) in control CHO cells and CHO cells transfected with sigma-1 receptor (σ-1 receptor) cDNA following incubation for either 30 or 120 minutes. Results are expressed as counts per minute (CPM) recorded in a sample from a particular well/CPM recorded in medium/amount of protein (μg) present in a sample from that well.

Compound CM156 was further investigated in vivo for antagonizing effects in cocaine treated mice. Pretreatment of mice with CM156 led to a significant attenuation of cocaine-induced convulsions, locomotor activity and behavioral sensitization as seen in FIGS. 6-8. Compound CM156 was additionally investigated for its ability to attenuate methamphetamine-induced locomotor stimulation and neurotoxicity in mice. As seen in FIGS. 9 and 10, CM156 attenuated the locomotor stimulant effects of methamphetamine as well as the neurotoxic effects resulting from methamphetamine exposures. Together, these data demonstrate that CM156 with high affinity for both σ subtypes can mitagate a variety of drug-induced effects, both from cocaine and methamphetamine, in vivo.

Metabolic Stability of AZ_66 in Rat Liver Microsomes

AIM: To study the metabolic stability of AZ_66 in Rat liver microsomes.
Analytical Method Set Up
For the metabolism studies of AZ_66, an isocratic method was developed using UPLC/MS/MS.
Chromatographic Conditions
Mobile phase A: 0.3% Formic acid in water, 10 mM Ammonium Formate (50%)
Mobile phase B: 0.1% Formic acid in Methanol (50%)
Column: Atlantis dC18 (2.1×50 mm, 5 μm)
Flow rate: 0.2 mL/min
Injection volume: 10 μl
Mass Parameters
The detection of the analyte was carried out using ESI+ve mode. The MS conditions were as follows: Capillary voltage 4.88V, Cone voltage 46V, Extractor voltage 3V, RF lens voltage 0.5V. The source and desolvation temperatures were 120° C. and 250° C. respectively, and the desolvation and cone gas flows were 500 and 60 L/hr., respectively. The selected mass-to-charge (m/z) ratio transition of AZ-66 ions $[M+H]^+$ used in the single ion reaction (SIR) was m/z: 406.2
Method
Metabolic stability of AZ_66 (1 μM) was performed in Ammonium acetate buffer (50 mM, pH 7.4) with Rat liver microsomes (0.5 mg) at 37° C. in 0.5 ml of incubation mixture. The incubation mixture composed of Ammonium acetate buffer (50 mM, pH 7.4), Magnesium chloride (3 mM), a NADPH regenerating system consisting of NADP (1 mM), glucose-6-phosphate (5 mM), and glucose-6-phosphate dehydrogenase (1 Unit/mL). The Substrate and microsomes were pre incubated at 37° C. for 5 min before starting the reaction. The reactions were started by the addition of regenerating system and carried out at 37° C. in a shaking water bath for 60 min. The incubations were stopped by adding an equal volume of ice cold acetonitrile at predetermined time points (0, 5, 15, 30, 60 min). The samples were centrifuged for 10 min at 4° C. and the supernatant was injected into UPLC/MS/MS. Control incubation without NADPH was also performed and these served as 100% value. All microsomal incubations were conducted using the same lot of microsomes.
Additional Controls
Additional incubations were performed using rat liver microsomes at same experimental conditions with CM_156 (10 μM). This served as a positive control to determine if the test system used in this study were metabolically competent.
In vitro half-life and CLint: The percent of the parent compound remaining is plotted versus time. The slope of the line gives the rate constant k for the disappearance of parent compound, from which an in vitro $t_{1/2}$ can be calculated. CLint can be calculated using the following formula $$CLint = k(\text{min}^{-1}) \times \frac{[V](L)}{[P](\text{mg})} = (L/\text{mg} \times \text{min})$$

[V] is the incubation volume in μl and [P] is the amount of microsomal protein in the incubation.
Results
The metabolism of AZ_66 was investigated in vitro using rat liver microsomes for 60-min. The estimated $t_{1/2}$ for disappearance of AZ_66 in rat liver microsomes was 115.56±15 min. Linear part of the Concentration vs Time graph was selected for the half-life calculations i.e. from 0-30 min. The estimated CLint from microsomes was 0.006 ml/min/mg. The CLint whole liver of AZ_66 1 μM was 0.002434 L/min. There is no loss of substrate in the absence of cofactor indicating that the loss of AZ_66 is through metabolism by NADPH-dependent enzymes.
AZ_66 was found to be stable in rat liver microsomes even after 60 min of incubation. Microsomes metabolized about 25% of the added substrate by 60 min. The results revealed that the metabolism was slow and continued at a linear rate for 30 min with an apparent departure from linearity after 30 min. The deviation from linearity may be due to limiting amounts of substrate or known organic and inorganic cofactors.
The substantial stability of the compound may be attributed to the C—F bond and oxygen in the thiazole ring. The other possible reason for higher stability could be the presence of methyl group preventing the N-dealkylation.
It may be concluded that the rate of metabolism could be decreased by incorporation of appropriate substituents at the primary sites of metabolism. See FIGS. 11, 12, 13, and 14.

The compounds of the present invention are for use as novel radioligands and agents for the treatment of drugs of abuse including cocaine- and methamphetamine-induced abuse and toxicities.

EXPERIMENTAL

Chemical Synthesis of Novel α Antagonists

Compounds can be modified in several positions to investigate the effects around the core structure on σ-1 and σ-2 affinities and activities. It has been demonstrated that one can substitute the template molecule through several synthetic routes. These routes which can be easily performed utilizing parallel synthesis methodology, can be easily varied to obtain multiple novel ligands. Initial studies focused on exploring the following changes to the molecules through parallel methodologies: 1) varying the methylene spacer between the tertiary amine and heterocycle; 2) modifying substituents to the piperazine nitrogen above the template; 3) modifying the piperazine ring to substitute piperidines, tetrahydropyridines, azepanes and diazepines; 4) modifying the order of heteroatoms in the heterocycle portion of the molecule as well as the connectivity pattern; and 5) substitution on the benzo portion of the heterocycle to probe the space and physicochemical requirements of the □ receptors.

Compounds were analyzed after purification using standard techniques (NMR, IR, LC/MS, HPLC) and converted into hydrochloride salts for water solubility. Final purity of compounds was achieved through melting points and elemental analysis. When necessary, X-ray crystallography was performed.

Syntheses of 2(3H)-benzoxazolones and 2(3H)-benzothiazolones were accomplished by multi-step solution phase synthesis as shown Scheme 4. Synthesis involved simple base-mediated alkylation and Friedel-Craft's alkylation reactions.

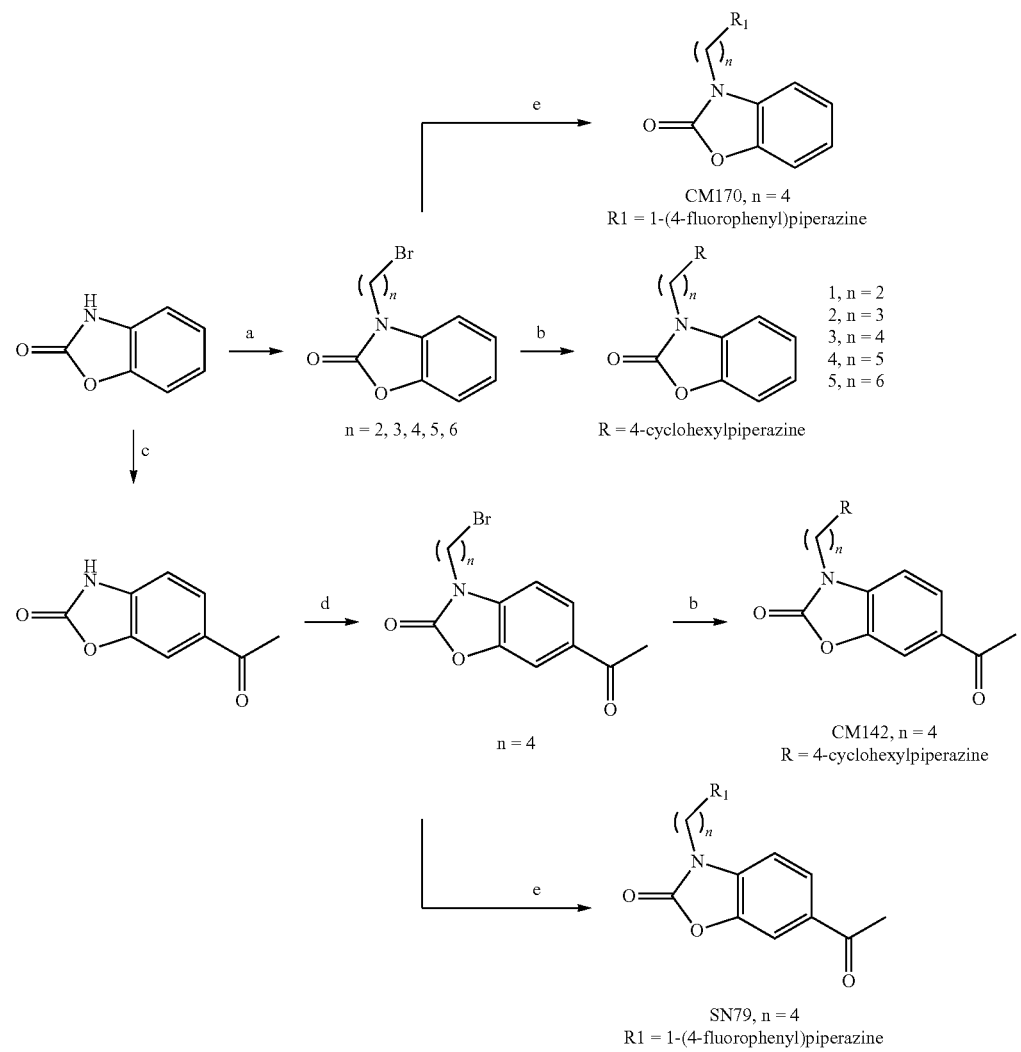

Scheme 4.

Reagents and conditions: a) Dibromoalkane, K₂CO₃, DMF, 60° C., 2 h; b) 1-cyclohexylpiperazine, K₂CO₃, DMF, 60° C., 3 h; c) (CH₃CO)₂O, AlCl₃, 75° C., 4 h; d) 1,4-dibromobutane, K₂CO₃, DMF, 60° C., 2 h; e) 1-(4-fluorophenyl)piperazine, K₂CO₃, DMF, 60° C., 4 h Sigma Compounds—Synthetic Scheme

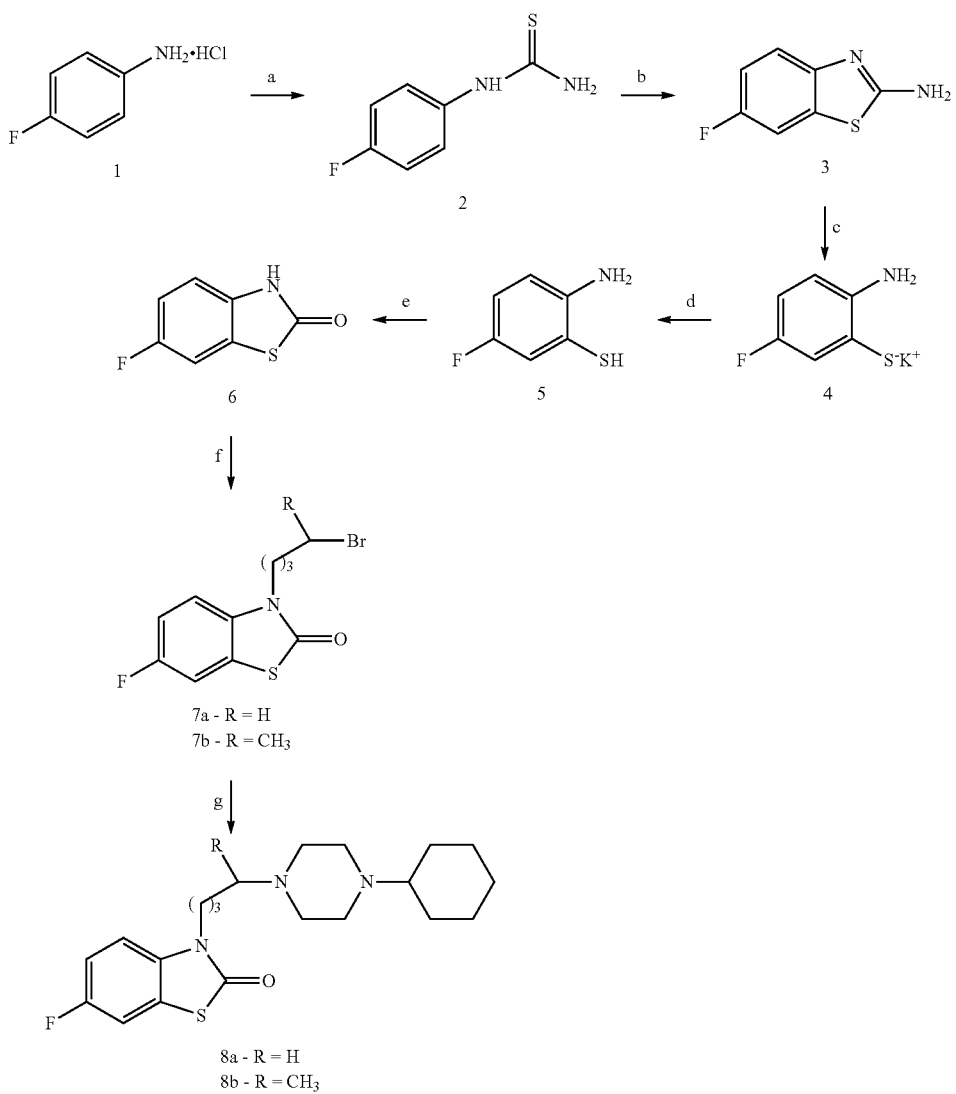

Reagents and conditions: (a) NH₄SCN, H₂O, reflux, 4 h; (b) Br₂, CHCl₃, 1 h. at 0° C., reflux 2 h; (c) KOH (d) Gl. acetic acid (e) Carbonyl 1,1' diimidazole, THF, reflux, 3 h; (f) 1,4 dibromoalkane, K₂CO₃, DMF, 60° C., 3 h; (g) cyclohexyl piperazine, K₂CO₃, TBAI, ACN, reflux 6 h σ Receptor Assays Compounds were evaluated for σ-1 and σ-2 binding in rat brain homogenates. Twelve concentrations of each test ligand (0.001-1,000 nM) were incubated for 120 min at 25° C. in 50 mM Tris-HCl, pH 8.0 with 500 μg membrane protein, and 5 nM [³H](+)-pentazocine (for $\sigma_1$ assays) or 3 nM [³H]DTG plus 300 nM (+)-pentazocine (for $\sigma_2$ assays); non-specific binding was determined in the presence of 10 μM haloperidol. The assays were terminated with ice-cold 10 mM Tris-HCl, pH 8.0, followed by two washes through glass fiber filters that were pre-soaked for at least 30 min in 0.5% polyethyleneimine.

Non-σ Assays

Compounds were tested at various non-σ target sites to evaluate selectivity because cocaine interacts with these sites (dopamine, serotonin and norepinephrine transporters) or historic "sigma" ligands interact with them (opioid, NMDA, dopamine $D_2$, 5-HT$_2$ receptors).

The compounds were tested in competition binding assays using rat brain homogenates as previously published. Briefly, the radioligands to label the sites of interest and compounds to define non-specific binding were as follows: dopamine transporters (0.5 nM [³H]WIN35,428, 50 μM cocaine), serotonin transporters (0.2 nM [³H]paroxetine, 1.5 μM imipramine), norepinephrine transporters (0.5 nM [³H] nisoxetine, 4 μM desipramine), opioid receptors (2 nM [³H]bremazocine, 10 μM levollorphan), NMDA receptors (5 nM [³H]TCP, 10 μM cyclazocine), dopamine $D_2$ receptors (5 nM [³H](−)-sulpiride, 1 μM haloperidol), and 5-HT$_2$ receptors (2 nM [³H]ketanserin, 1 μM mianserin). The results were reported as $K_i$ in nM. If after three independent replications of the assay, the 10,000 nM concentration of the compound did not display at least 30% inhibition of the radioligand, the affinity of the compound was reported as >10,000 nM.

Cocaine-Induced Convulsions

Male, Swiss Webster mice were pretreated (i.p.) with saline or compound (0.1-10 mg/kg), then challenged 15 min later with a convulsive dose of cocaine (70 mg/kg, i.p.). Mice were observed for the next 30 min for convulsions, which were defined as a loss of righting reflexes for at least 5 sec. combined with the presence of clonic limb movements or popcorn jumping. Fisher's exact test was used to determine whether the effect produced by pretreatment with a particular drug dose differed significantly from pretreatment with the saline control.

Cocaine-Induced Locomotor Activity

Male, Swiss Webster mice were acclimated to the treatment room and then to the chambers of the automated activity monitoring system (San Diego Instruments, San Diego, Calif.). They were injected (i.p.) with saline or compound (0.1-20 mg/kg), then challenged 15 min later with cocaine (20 mg/kg, i.p.) or saline (i.p.). The total locomotor activity (ambulatory, fine and rearing movements) of the mice was recorded for the next 30 min as the number of disruptions made by them in the 16×16 photobeam grid of their testing chamber.

Development of Sensitization

Male, Swiss Webster mice were acclimated as detailed above. For five consecutive days (Days 1-5), the mice were pretreated (i.p.) with saline or compound (0.1-20 mg/kg), then challenged 15 min later with cocaine (10 mg/kg, i.p.) or saline (i.p.). The total locomotor activity (ambulatory, fine and rearing movements) of the mice was recorded for the next 30 min as the number of disruptions made by them in the 16×16 photobeam grids of their testing chamber on each of the five days. A 10 day drug-free period followed. On Day 15, all of the mice were pre-administered (i.p.) saline followed by cocaine (10 mg/kg, i.p.), and locomotor activity quantified for the next 30 min.

Expression of Sensitization

Male, Swiss Webster mice were acclimated as detailed above. For five consecutive days (Days 1-5), the mice were pretreated (i.p.) with saline, then challenged 15 min later with cocaine (10 mg/kg, i.p.). The total locomotor activity (ambulatory, fine and rearing movements) of the mice was recorded for the next 30 min. A 10 day drug free period followed and on Day 15, the mice were administered saline (i.p.) or compound (0.1-20 mg/kg), followed 15 min later with cocaine (10 mg/kg, i.p.). Locomotor activity was then recorded for the next 30 min.

Methamphetamine-Induced Locomotor Activity

Male, Swiss Webster mice were acclimated as detailed above. They were injected (i.p.) with saline or compound (0.1-20 mg/kg), then challenged 15 min later with methamphetamine (1 mg/kg, i.p.) or saline (i.p.). The total locomotor activity (ambulatory, fine and rearing movements) of the mice was recorded for the next 30 min as the number of disruptions made by them in the 16×16 photobeam grids surrounding their testing chambers.

Methamphetamine-Induced Dopamine Depletions

Male, Swiss Webster mice were injected (i.p.) with saline or compound (0-20 mg/kg), followed 15 min later with either saline (-METH) or methamphetamine (5 mg/kg) at 2 hr intervals, a total of four times. Striatal dopamine levels were measured one week later.

The following represents compounds which are within the scope of the invention and which were prepared and tested for activity. Also included are compounds which were prepared but not tested but which are expected to have activity similar to the prepared and tested compounds. Also included in the listing are compounds which can be prepared and which would be expected to have activities similar to those compounds which were prepared and tested.

| Compd. | Structure | Ki (nM) |
|---|---|---|
| SN-48 | 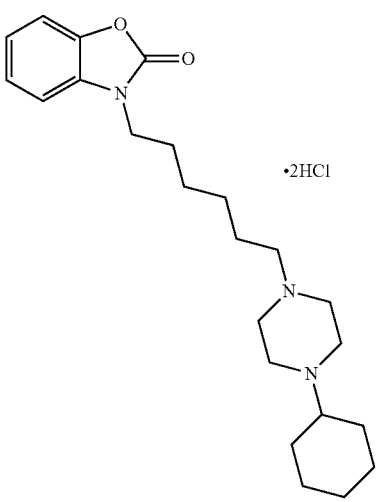 [SMILES: O=c1oc2ccccc2n1CCCCCCN1CCN(C2CCCCC2)CC1] | $\sigma 1 = 4.60 \pm 1.08$ $\sigma 2 = 3.06 \pm 0.45$ |

-continued
| Compd. | Structure | Ki (nM) |
|---|---|---|
| SN-55 | 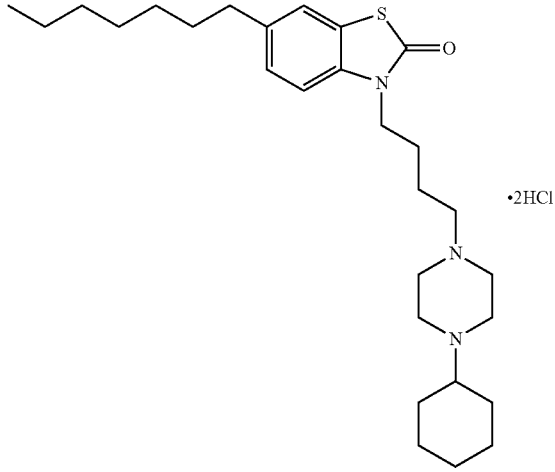 [SMILES: CCCCCCCc1ccc2c(c1)sc(=O)n2CCCCN1CCN(C2CCCCC2)CC1] •2HCl | σ1 = 34.12 ± 8.09<br>σ2 = 31.39 ± 6.87 |
| SN-57 | 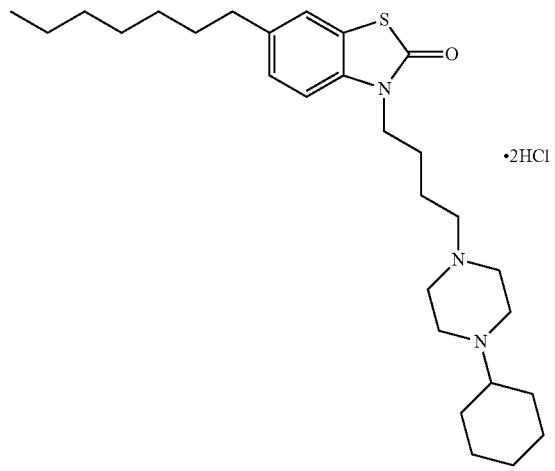 [SMILES: CCCCCCCc1ccc2c(c1)sc(=O)n2CCCCN1CCN(C2CCCCC2)CC1] •2HCl | σ1 = 43.76 ± 6.12<br>σ2 = 29.29 ± 2.83 |
| SN-60 | 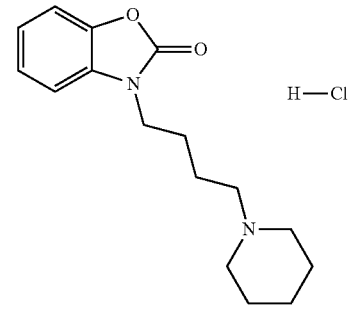 [SMILES: O=c1oc2ccccc2n1CCCCN1CCCCC1 ; Cl] H—Cl | σ1 = 12.06 ± 1.54<br>σ2 = 212.67 ± 11.81 |

-continued
| Compd. | Structure | Ki (nM) |
|---|---|---|
| SN-61 | 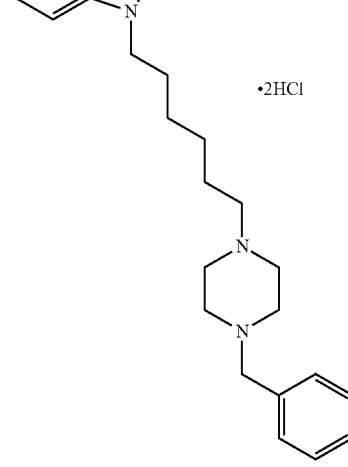 •2HCl | σ1 = 4.68 ± 1.37<br>σ2 = 107.1 ± 32.59 |
| SN-71 | 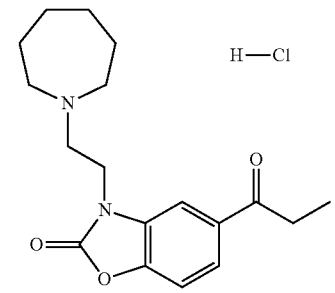 [SMILES: CCC(=O)c1ccc2oc(=O)n(CCN3CCCCCC3)c2c1 ; Cl] H—Cl | σ1 = 114.74 ± 25.91<br>σ2 = 2342 ± 229.80 |
| SN-72 | 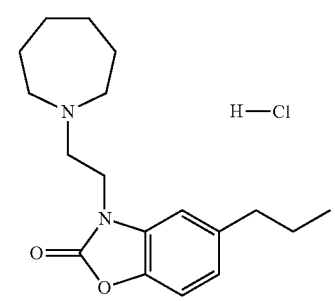 [SMILES: CCCc1ccc2oc(=O)n(CCN3CCCCCC3)c2c1 ; Cl] H—Cl | σ1 = 3.33 ± 0.41<br>σ2 = 1810.66 ± 83.76 |
| SN-78 | 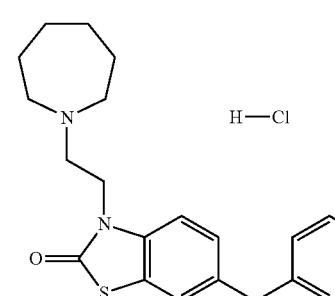 H—Cl | σ1 = 88.31 ± 8.59<br>σ2 = 859.66 ± 86.59 |

-continued

| Compd. | Structure | Ki (nM) |
|---|---|---|
| SN-79 | 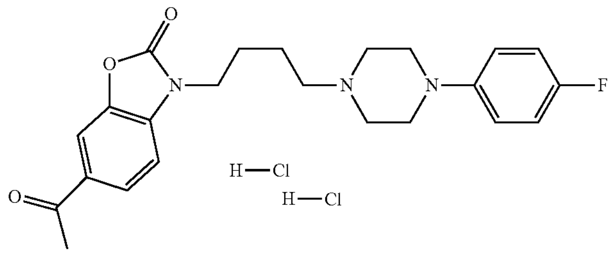 | σ1 = >100,000<br>σ2 = 6.06 ± 0.74 |
| SN-81 | 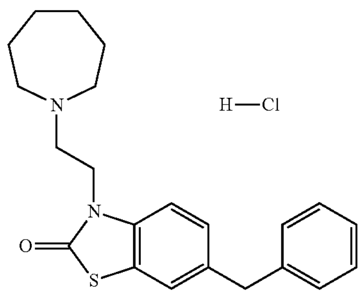 [SMILES: O=c1sc2cc(Cc3ccccc3)ccc2n1CCN1CCCCCC1 ; Cl] | σ1 = 7.42 ± 3.21<br>σ2 = 224.56 ± 46.88 |
| SN-97 | 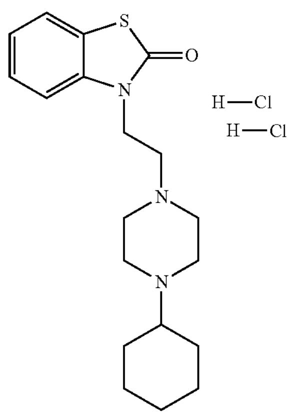 | σ1 = 4.66 ± 0.74<br>σ2 = 2.25 ± 0.37 |
| SN-98 | 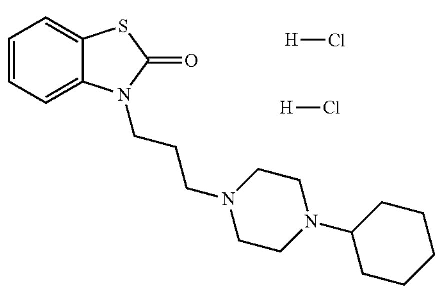 [SMILES: O=c1sc2ccccc2n1CCCN1CCN(C2CCCCC2)CC1 ; Cl ; Cl] | σ1 = 5.61 ± 0.74<br>σ2 = 3.05 ± 0.41 |
| SN-99 | 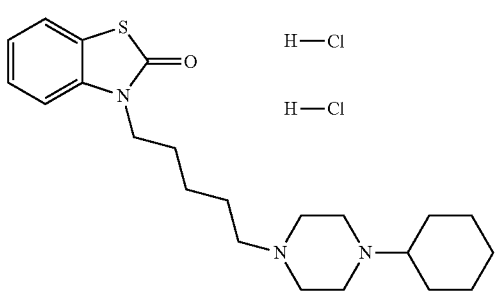 [SMILES: O=c1sc2ccccc2n1CCCCCN1CCN(C2CCCCC2)CC1 ; Cl ; Cl] | σ1 = 4.98 ± 0.42<br>σ2 = 2.44 ± 0.26 |

-continued
| Compd. | Structure | Ki (nM) |
|---|---|---|
| SN-102 | 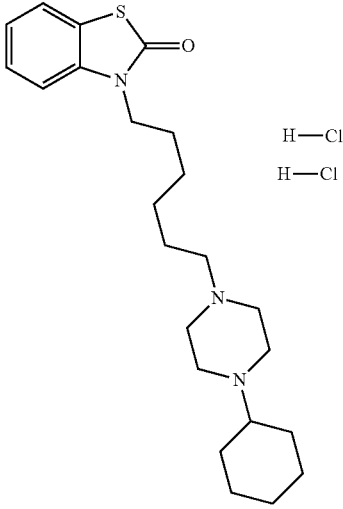 | σ1 = 6.55 ± 0.25<br>σ2 = 1.49 ± 0.18 |
| SN-123 | 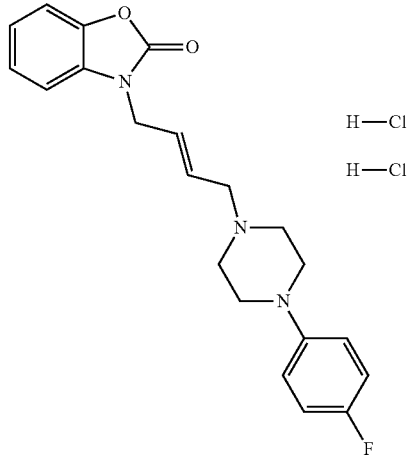 | |
| SN-124 | 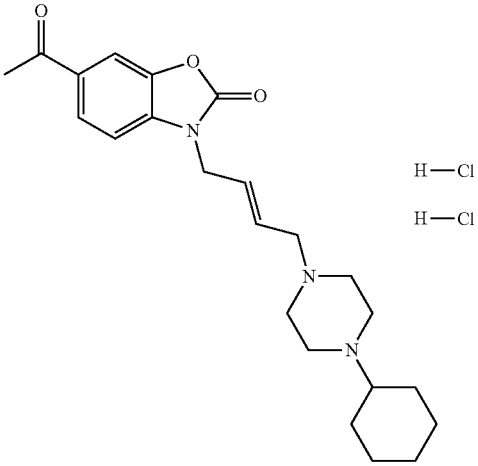 | |

-continued
| Compd. | Structure | Ki (nM) |
|---|---|---|
| SN-125 | 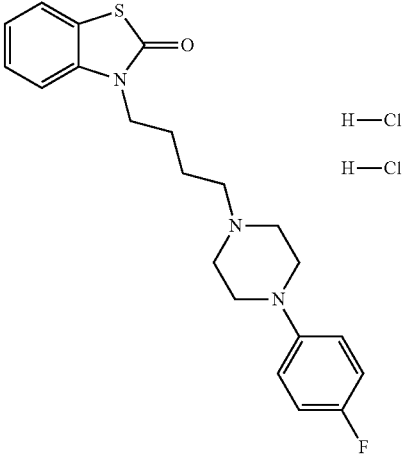 | |
| SN-126 | 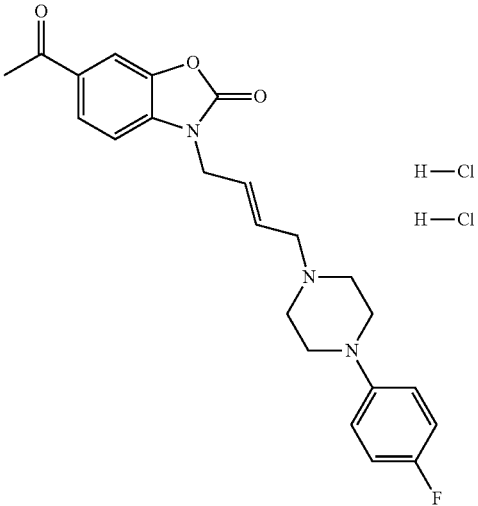 | |
| SN-127 | 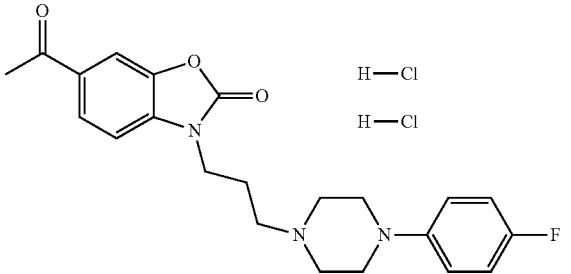 | |

| Compd. | Structure | Ki (nM) |
|---|---|---|
| SN-136 | 6-acetyl-3-[5-(4-(4-fluorophenyl)piperazin-1-yl)pentyl]benzo[d]oxazol-2(3H)-one · 2HCl | |
| SN-137 | 6-acetyl-3-[4-(4-(4-fluorophenyl)piperazin-1-yl)butyl]benzo[d]thiazol-2(3H)-one · 2HCl | |
| SN-138 | 6-acetyl-3-[4-(4-(2-fluorophenyl)piperazin-1-yl)butyl]benzo[d]oxazol-2(3H)-one · 2HCl (not shown as HCl in drawing) | |
| SN-139 | 6-acetyl-3-[6-(4-(4-fluorophenyl)piperazin-1-yl)hexyl]benzo[d]oxazol-2(3H)-one · 2HCl | |
| SN-140 | 3-[(Z)-4-(4-(4-fluorophenyl)piperazin-1-yl)but-2-enyl]benzo[d]oxazol-2(3H)-one · 2HCl | |

-continued
| Compd. | Structure | Ki (nM) |
|---|---|---|
| SN-147 | 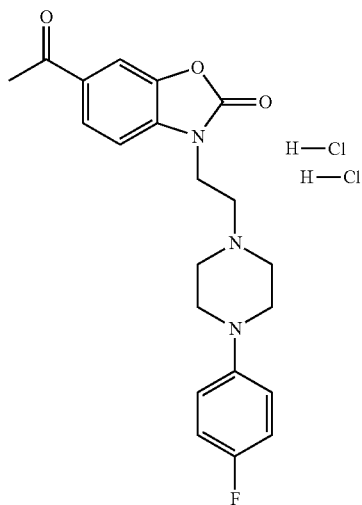 | |
| SN-148 | 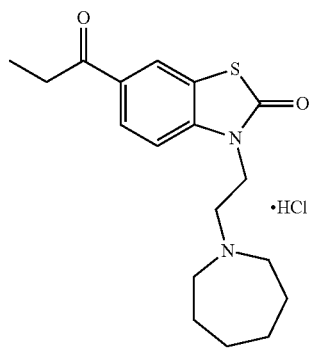 [SMILES: CCC(=O)c1ccc2c(c1)sc(=O)n2CCN1CCCCCC1 ; Cl] | |
| SN-150 | 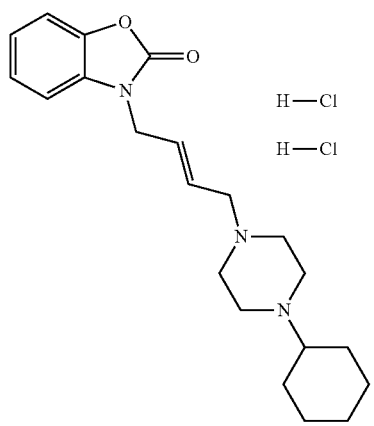 | |

| Compd. | Structure | Ki (nM) |
|---|---|---|
| SN-158 | 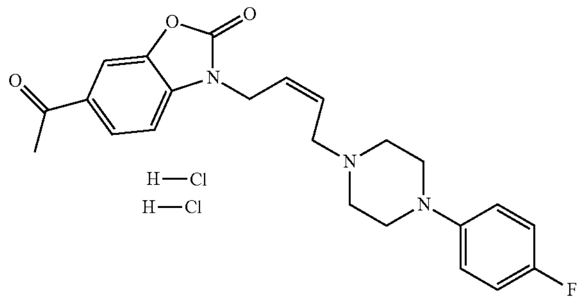 | |
| SN-167 | 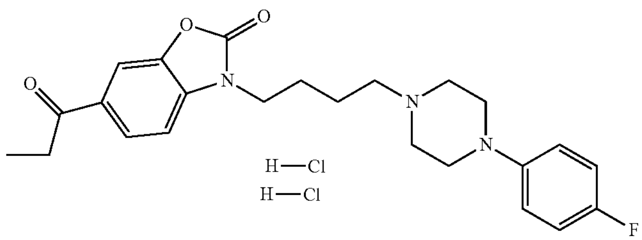 | |
| SN-168 | 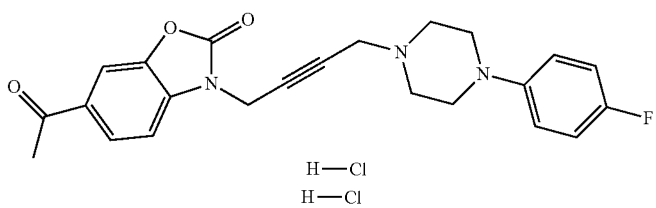 | |
| SN-169 | 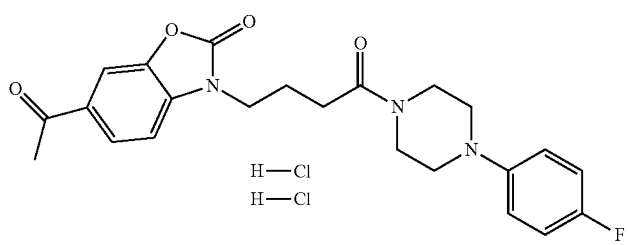 | |
| SN-170 | 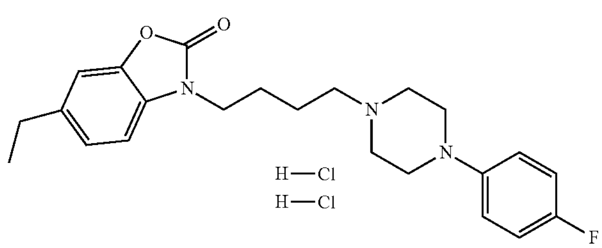 | |
| SN-196 | 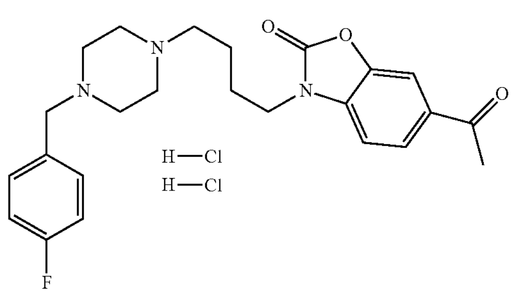 | |

-continued

| Compd. | Structure | Ki (nM) |
|---|---|---|
| SN-197 | 4-chlorophenyl-piperazine-(CH2)4-N(benzoxazol-2-one)-6-acetyl · 2HCl | |
| SN-198 | 4-nitrophenyl-piperazine-(CH2)4-N(benzoxazol-2-one)-6-acetyl · 2HCl | |
| SN-199 | 4-methylphenyl-piperazine-(CH2)4-N(benzoxazol-2-one)-6-acetyl · 2HCl | |
| SN-203 | 4-trifluoromethylphenyl-piperazine-(CH2)4-N(benzoxazol-2-one)-6-acetyl · 2HCl | |
| SN-204 | 4-pyridyl-piperazine-(CH2)4-N(benzoxazol-2-one)-6-acetyl · 2HCl | |
| SN-205 | 2,4-difluorophenyl-piperazine-(CH2)4-N(benzoxazol-2-one)-6-acetyl · 2HCl | |
| SN-212 | phenyl-piperazine-(CH2)4-N(benzoxazol-2-one)-6-acetyl · 2HCl | |
| SN-213 | 4-fluorophenyl-piperazine-(CH2)4-N(benzoxazol-2-one)-6-bromo · 2HCl | |

| Compd. | Structure | Ki (nM) |
|---|---|---|
| SN-214 | (structure: 4-aminophenyl-piperazine-butyl-benzoxazolone with acetyl, 2HCl) | |
| SN-230 | (structure: 4-fluorophenyl-piperazine-butyl-benzoxazolone with benzoyl) | |
| SN-232 | (structure: 4-fluorophenyl-piperazine-butyl-benzoxazolone with phenyl) | |
| SN-231 | (structure: 4-fluorophenyl-piperazine-butyl-benzoxazolone with CH(OH)CH₃) | |

| CMPD | STRUCTURE | Ki (nM) σ₁ | Ki (nM) σ₂ |
|---|---|---|---|
| CM 121 | (cyclohexyl-piperazine-butyl-benzoxazolone) | 11.26 ± 1.25 | 1.83 ± 0.17 |

-continued
| CMPD | STRUCTURE | Ki (nM) $\sigma_1$ | Ki (nM) $\sigma_2$ |
|---|---|---|---|
| CM 124 | 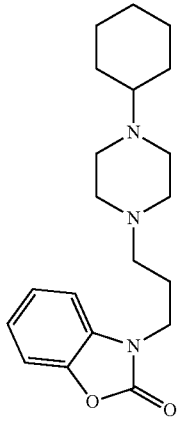 [SMILES: O=c1oc2ccccc2n1CCCN1CCN(C2CCCCC2)CC1] | 5.22 ± 1.11 | 8.74 ± 2.30 |
| CM 126 | 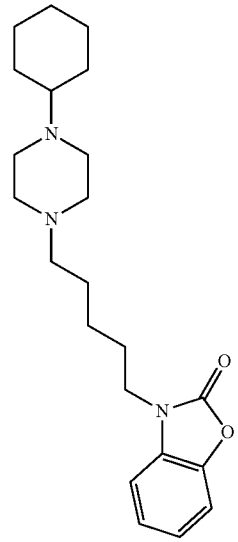 [SMILES: O=c1oc2ccccc2n1CCCCCN1CCN(C2CCCCC2)CC1] | 10.55 ± 2.52 | 5.89 ± 1.31 |
| CM 129 | 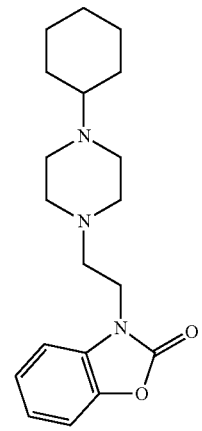 [SMILES: O=c1oc2ccccc2n1CCN1CCN(C2CCCCC2)CC1] | 6.90 ± 0.37 | 5.43 ± 0.78 |

-continued
| CMPD | STRUCTURE | Ki (nM) $\sigma_1$ | Ki (nM) $\sigma_2$ |
|---|---|---|---|
| CM 135 | 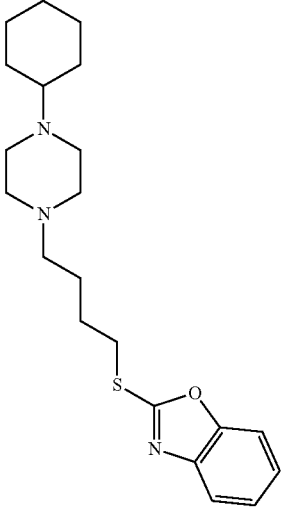 [SMILES: c1ccc2oc(SCCCCN3CCN(C4CCCCC4)CC3)nc2c1] | 3.37 ± 0.28 | 3.77 ± 0.35 |
| CM 138 | 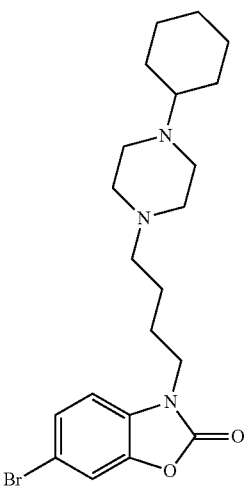 [SMILES: O=c1oc2cc(Br)ccc2n1CCCCN1CCN(C2CCCCC2)CC1] | 7.87 ± 0.19 | 4.47 ± 0.42 |
| CM 142 | 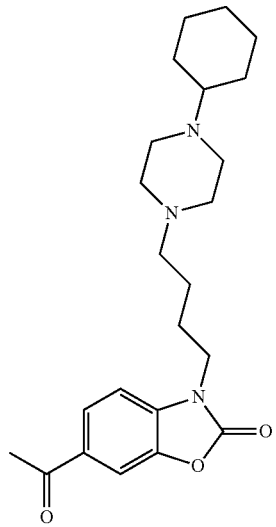 [SMILES: CC(=O)c1ccc2c(c1)oc(=O)n2CCCCN1CCN(C2CCCCC2)CC1] | 46.4 ± 8.06 | 7.04 ± 0.79 |

-continued
| CMPD | STRUCTURE | Ki (nM) $\sigma_1$ | Ki (nM) $\sigma_2$ |
|---|---|---|---|
| CM 145 | 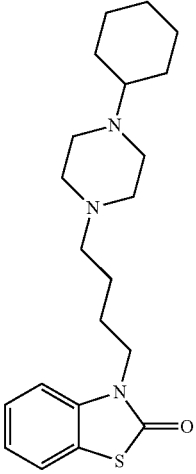 [SMILES: O=c1sc2ccccc2n1CCCCN1CCN(C2CCCCC2)CC1] | 4.17 ± 0.62 | 0.39 ± 0.06 |
| CM 146 | 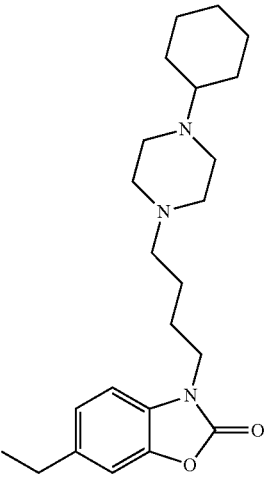 [SMILES: CCc1ccc2c(c1)oc(=O)n2CCCCN1CCN(C2CCCCC2)CC1] | 2.18 ± 0.14 | 2.56 ± 1.22 |
| CM 152 | 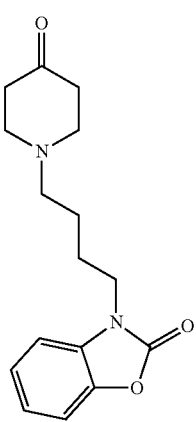 [SMILES: O=C1CCN(CCCCn2c(=O)oc3ccccc32)CC1] | 19.3 ± 0.90 | 78.5 ± 39.6 |

-continued
| CMPD | STRUCTURE | Ki (nM) $\sigma_1$ | Ki (nM) $\sigma_2$ |
|---|---|---|---|
| CM 156 | 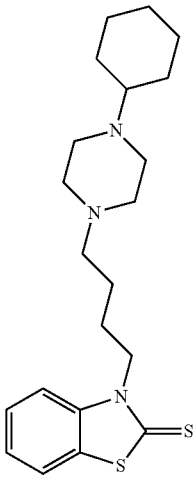 [SMILES: S=c1sc2ccccc2n1CCCCN1CCN(C2CCCCC2)CC1] | 1.28 ± 0.38 | 0.55 ± 0.08 |
| CM 159 | 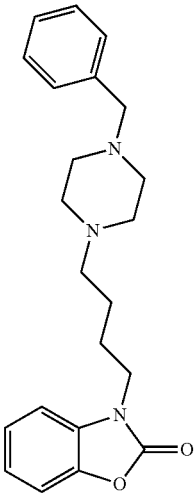 [SMILES: O=c1oc2ccccc2n1CCCCN1CCN(Cc2ccccc2)CC1] | 4.44 ± 0.88 | 46.41 ± 12.61 |
| CM 160 | 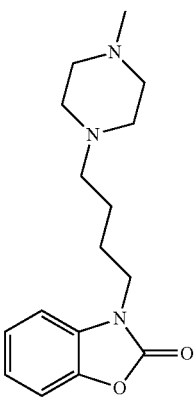 [SMILES: CN1CCN(CCCCn2c(=O)oc3ccccc32)CC1] | 91.69 ± 11.52 | 2382.33 ± 142.94 |

-continued

| CMPD | STRUCTURE | Ki (nM) σ$_1$ | Ki (nM) σ$_2$ |
|---|---|---|---|
| CM 162 | 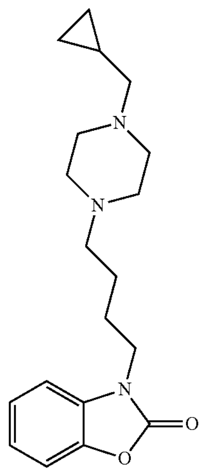 [SMILES: O=c1oc2ccccc2n1CCCCN1CCN(CC2CC2)CC1] | 10.83 ± 1.00 | 46.75 ± 10.18 |
| CM 165 | 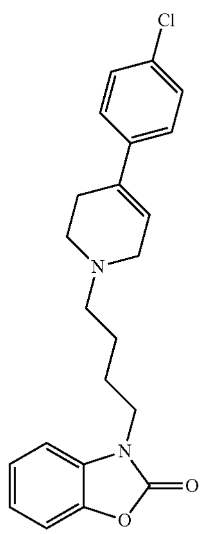 [SMILES: O=c1oc2ccccc2n1CCCCN1CC=C(c2ccc(Cl)cc2)CC1] | 2.40 ± 0.38 | 14.44 ± 3.09 |
| CM 166 | 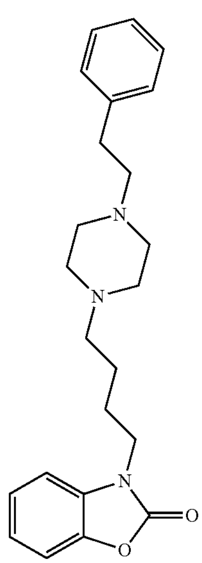 [SMILES: O=c1oc2ccccc2n1CCCCN1CCN(CCc2ccccc2)CC1] | 3.15 ± 0.37 | 92.71 ± 14.14 |

-continued

| CMPD | STRUCTURE | Ki (nM) $\square_1$ | Ki (nM) $\square_2$ |
|---|---|---|---|
| CM 167 | 4-nitrophenyl-piperazine-butyl-benzoxazol-2-one | 259.07 ± 33.45 | 226.00 ± 17.50 |
| CM 168 | 2-pyridyl-piperazine-butyl-benzoxazol-2-one | 311.93 ± 33.22 | 128.10 ± 16.26 |
| CM 169 | 4-chlorophenyl-piperazine-butyl-benzoxazol-2-one | 25.44 ± 4.72 | 241.5 ± 28.98 |

-continued

| CMPD | STRUCTURE | Ki (nM) $\sigma_1$ | Ki (nM) $\sigma_2$ |
|---|---|---|---|
| CM 170 | 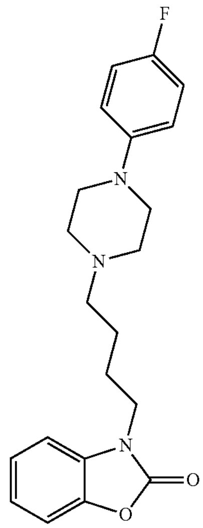 [SMILES: O=c1oc2ccccc2n1CCCCN1CCN(c2ccc(F)cc2)CC1] | 7.59 ± 0.08 | 0.70 ± 0.11 |
| CM 171 | 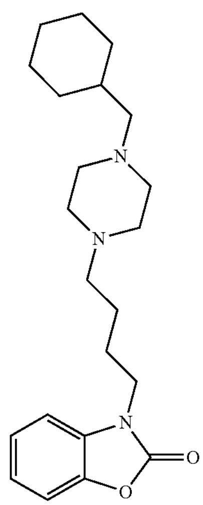 [SMILES: O=c1oc2ccccc2n1CCCCN1CCN(CC2CCCCC2)CC1] | 0.94 ± 0.13 | 13.94 ± 2.86 |
| CM 172 | 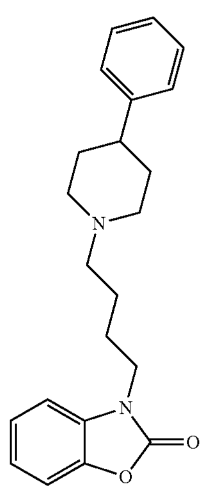 [SMILES: O=c1oc2ccccc2n1CCCCN1CCC(c2ccccc2)CC1] | 0.58 ± 0.22 | 17.22 ± 1.04 |

-continued
| CMPD | STRUCTURE | Ki (nM) $\sigma_1$ | Ki (nM) $\sigma_2$ |
|---|---|---|---|
| CM 174 | 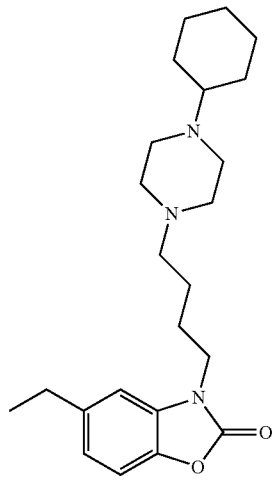 [SMILES: CCc1ccc2oc(=O)n(CCCCN3CCN(C4CCCCC4)CC3)c2c1] | 4.04 ± 0.35 | 58.24 ± 11.48 |
| CM 175 | 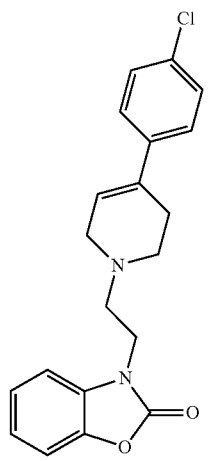 [SMILES: O=c1oc2ccccc2n1CCN1CC=C(c2ccc(Cl)cc2)CC1] | 21.37 ± 3.68 | 616.33 ± 77.47 |
| CM 176 | 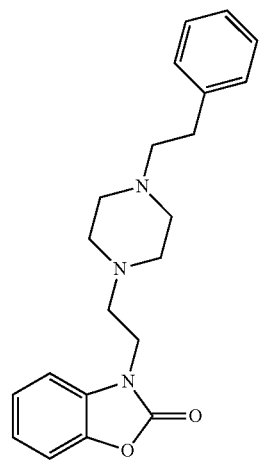 [SMILES: O=c1oc2ccccc2n1CCN1CCN(CCc2ccccc2)CC1] | 1.43 ± 0.26 | 21.73 ± 2.79 |

-continued
| CMPD | STRUCTURE | Ki (nM) $\square_1$ | Ki (nM) $\square_2$ |
|---|---|---|---|
| CM 178 | 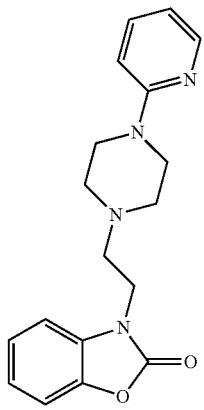 [SMILES: O=c1oc2ccccc2n1CCN1CCN(c2ccccn2)CC1] | >10,000 | >10,000 |
| CM 179 | 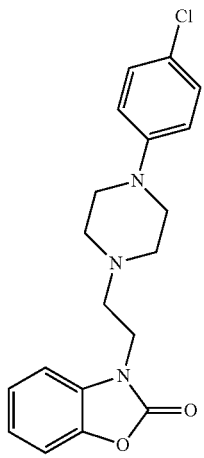 [SMILES: O=c1oc2ccccc2n1CCN1CCN(c2ccc(Cl)cc2)CC1] | 1426.33 ± 185.09 | 2260 ± 96.08 |
| CM 181 | 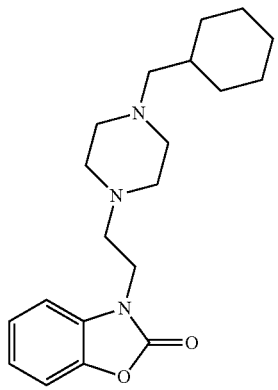 [SMILES: O=c1oc2ccccc2n1CCN1CCN(CC2CCCCC2)CC1] | 2.36 ± 0.38 | 8.83 ± 1.17 |

-continued
| CMPD | STRUCTURE | Ki (nM) $\sigma_1$ | Ki (nM) $\sigma_2$ |
|---|---|---|---|
| CM 182 | 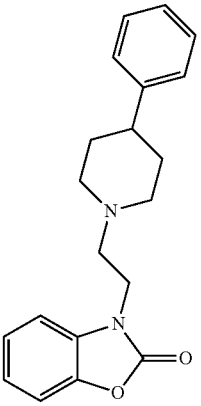 [SMILES: O=c1oc2ccccc2n1CCN1CCC(c2ccccc2)CC1] | 14.08 ± 2.84 | 777.26 ± 72.47 |
| CM 184 | 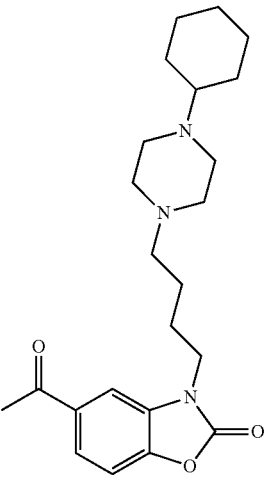 [SMILES: CC(=O)c1ccc2oc(=O)n(CCCCN3CCN(C4CCCCC4)CC3)c2c1] | 40.82 ± 6.21 | 10.41 ± 1.54 |
| CM 188 | 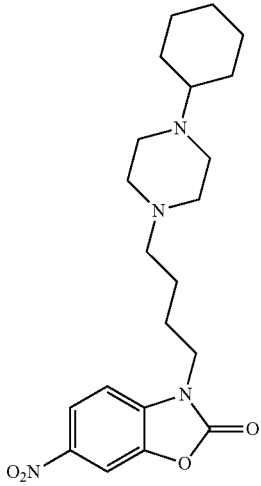 [SMILES: O=c1oc2cc([N+](=O)[O-])ccc2n1CCCCN1CCN(C2CCCCC2)CC1] | 11.11 ± 1.61 | 2.46 ± 0.18 |

-continued
| CMPD | STRUCTURE | Ki (nM) $\sigma_1$ | Ki (nM) $\sigma_2$ |
|---|---|---|---|
| CM 191 | 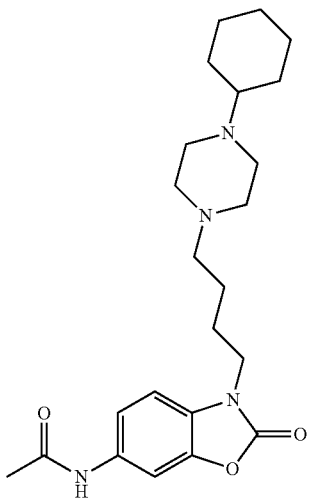 [SMILES: CC(=O)Nc1ccc2c(c1)oc(=O)n2CCCCN1CCN(C2CCCCC2)CC1] | 213.87 ± 55.33 | 77.37 ± 14.22 |
| CM 295 | 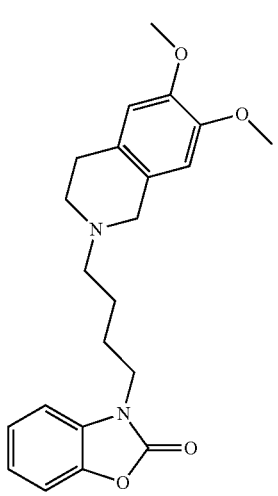 [SMILES: COc1cc2c(cc1OC)CN(CCCCn1c(=O)oc3ccccc31)CC2] | 74.31 ± 3.77 | 1.52 ± 0.64 |
| CM 307 | 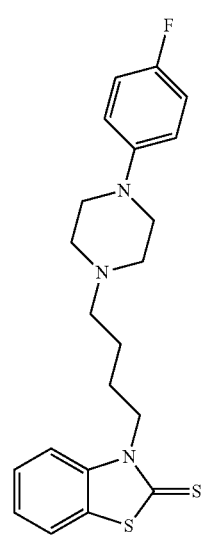 [SMILES: Fc1ccc(N2CCN(CCCCn3c(=S)sc4ccccc43)CC2)cc1] | 6.27 ± 0.78 | 6.61 ± 1.42 |

| CMPD | STRUCTURE | Ki (nM) $\sigma_1$ | Ki (nM) $\sigma_2$ |
|---|---|---|---|
| CM 308 | 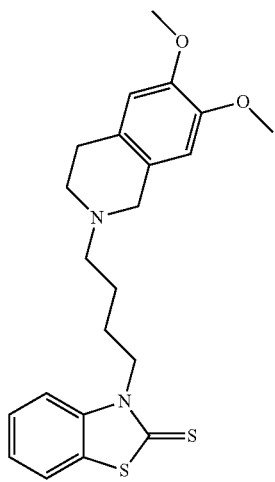 [SMILES: COc1cc2c(cc1OC)CN(CCCCn1c(=S)sc3ccccc31)CC2] | 9.11 ± 1.31 | 0.56 ± 0.12 |
| CM 322 | 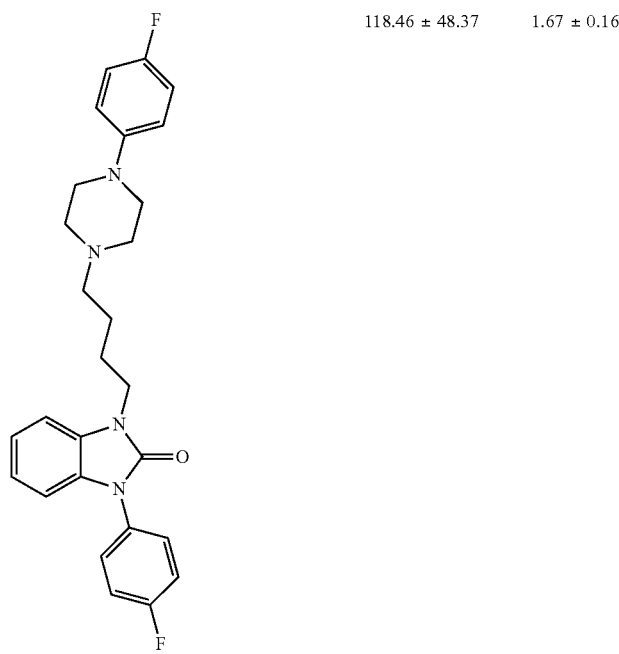 | 118.46 ± 48.37 | 1.67 ± 0.16 |

-continued
| CMPD | STRUCTURE | Ki (nM) $\square_1$ | Ki (nM) $\square_2$ |
|---|---|---|---|
| CM 325 | 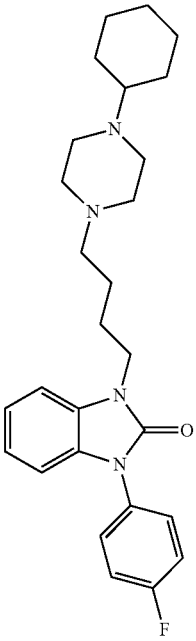 [SMILES: O=c1n(CCCCN2CCN(C3CCCCC3)CC2)c2ccccc2n1-c1ccc(F)cc1] | 5.04 ± 0.66 | 2.12 ± 0.75 |
| CM 328 | 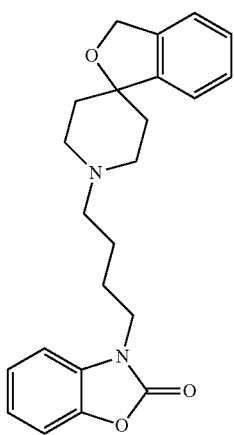 [SMILES: O=c1oc2ccccc2n1CCCCN1CCC2(CC1)OCc1ccccc12] | | |
| CM 329 | 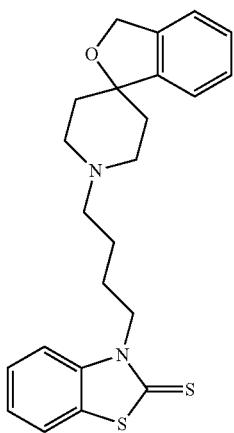 [SMILES: S=c1sc2ccccc2n1CCCCN1CCC2(CC1)OCc1ccccc12] | | |

-continued

| CMPD | STRUCTURE | Ki (nM) □₁ | Ki (nM) □₂ |
|---|---|---|---|
| CM 330 | 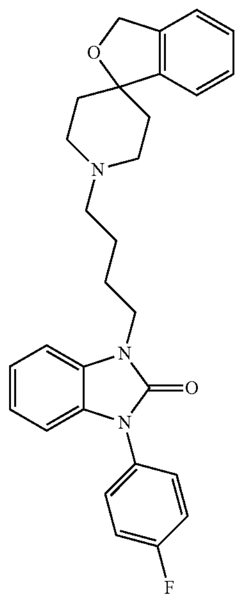 [SMILES: O=c1n(CCCCN2CCC3(CC2)OCc2ccccc23)c2ccccc2n1-c1ccc(F)cc1] | | |
| CM 338 | 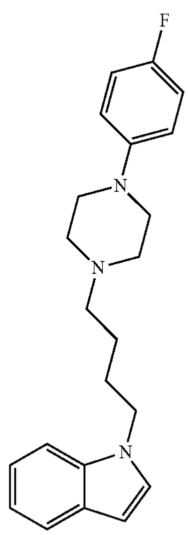 [SMILES: Fc1ccc(N2CCN(CCCCn3ccc4ccccc43)CC2)cc1] | 169.8 ± 5.68 | 1.09 ± 0.03 |
| CM 339 | 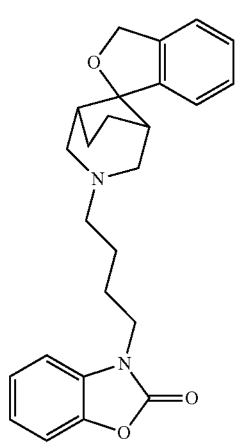 [SMILES: O=c1oc2ccccc2n1CCCCN1CC2CCC(C1)C21OCc2ccccc21] | | |

-continued
| CMPD | STRUCTURE | Ki (nM) $\sigma_1$ | Ki (nM) $\sigma_2$ |
|---|---|---|---|
| CM 341 | 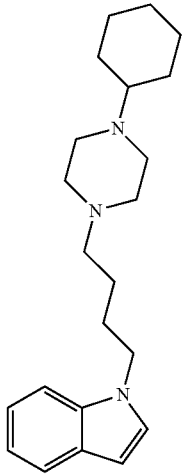 [SMILES: c1ccc2c(c1)ccn2CCCCN1CCN(C2CCCCC2)CC1] | 3.28 ± 0.32 | 1.90 ± 0.16 |
| CM 343 | 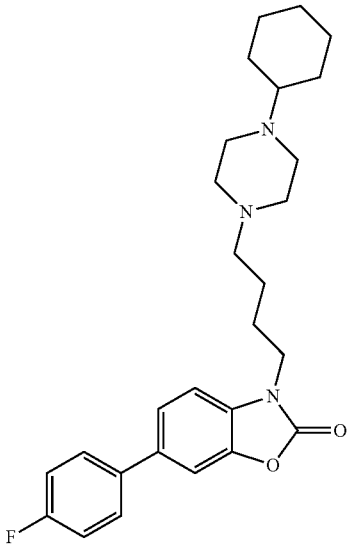 [SMILES: O=c1oc2cc(-c3ccc(F)cc3)ccc2n1CCCCN1CCN(C2CCCCC2)CC1] | 17.6 ± 0.82 | 38.13 ± 1.42 |
| CM 347 | 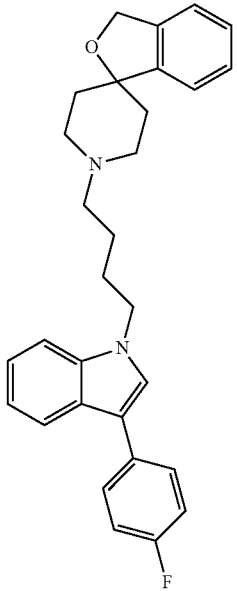 [SMILES: Fc1ccc(-c2cn(CCCCN3CCC4(CC3)OCc3ccccc34)c3ccccc23)cc1] | | |

| CMPD | STRUCTURE | Ki (nM) $\square_1$ | Ki (nM) $\square_2$ |
|---|---|---|---|
| CM 349 | 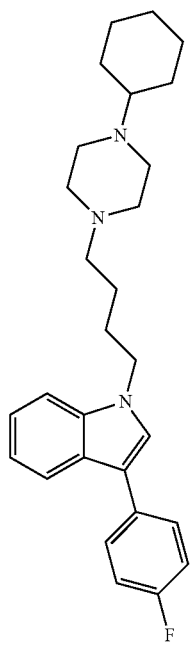 [SMILES: Fc1ccc(-c2cn(CCCCN3CCN(C4CCCCC4)CC3)c3ccccc23)cc1] | 90.87 ± 12.30 | 22.55 ± 1.13 |
| CM 350 | 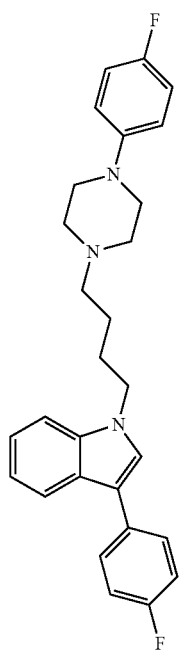 [SMILES: Fc1ccc(-c2cn(CCCCN3CCN(c4ccc(F)cc4)CC3)c3ccccc23)cc1] | 1202 ± 73.89 | 83.33 ± 3.96 |

| CMPD | STRUCTURE | Ki (nM) □₁ | Ki (nM) □₂ |
|---|---|---|---|
| CM 353 | 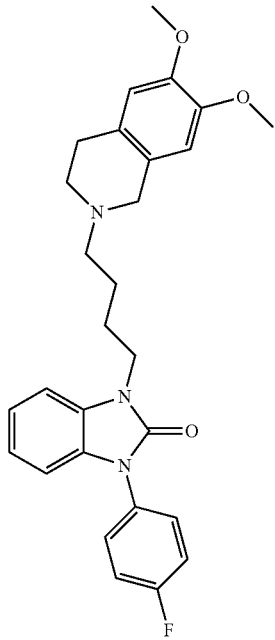 [SMILES: COc1cc2c(cc1OC)CN(CCCCn1c(=O)n(-c3ccc(F)cc3)c3ccccc31)CC2] | | |
| CM 355 | 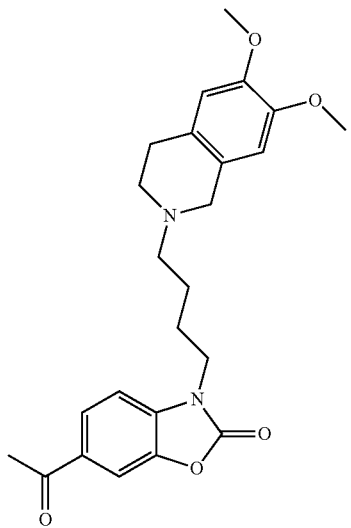 [SMILES: COc1cc2c(cc1OC)CN(CCCCn1c(=O)oc3cc(C(C)=O)ccc31)CC2] | | |

-continued
| CMPD | STRUCTURE | Ki (nM) $\sigma_1$ | Ki (nM) $\sigma_2$ |
|---|---|---|---|
| CM 356 | 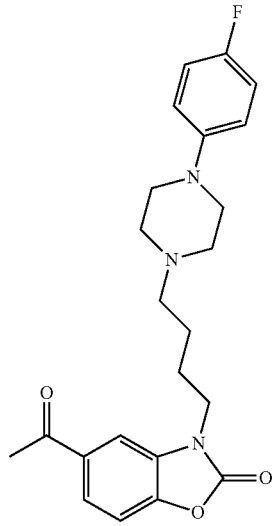 [SMILES: CC(=O)c1ccc2oc(=O)n(CCCCN3CCN(c4ccc(F)cc4)CC3)c2c1] | 27.82 ± 4.14 | 1.21 ± 0.20 |
| CM 357 | 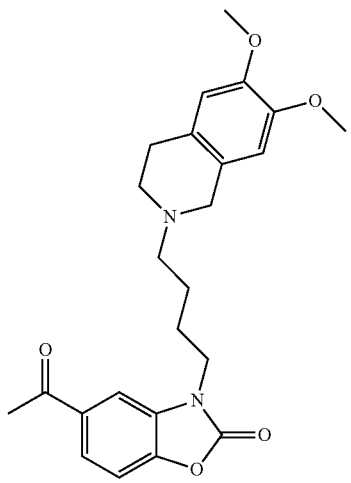 [SMILES: COc1cc2c(cc1OC)CN(CCCCn1c(=O)oc3ccc(C(C)=O)cc31)CC2] | | |
| CM 360 | 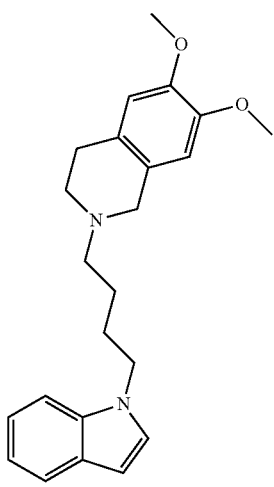 [SMILES: COc1cc2c(cc1OC)CN(CCCCn1ccc3ccccc31)CC2] | 73.25 ± 5.58 | 0.21 ± 0.020 |

-continued
| CMPD | STRUCTURE | Ki (nM) $\square_1$ | Ki (nM) $\square_2$ |
|---|---|---|---|
| CM 361 | 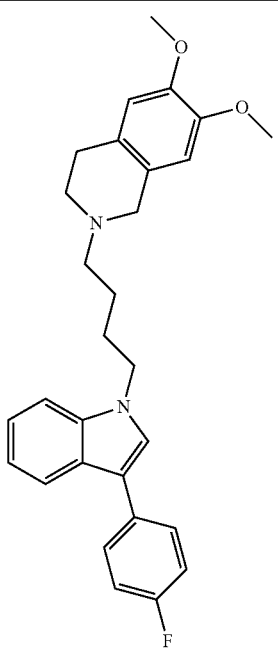 | 4713 ± 449.50 | 4.37 ± 0.33 |
| CM 362 | 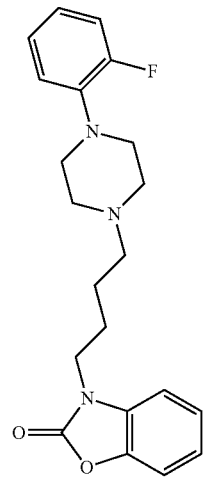 [SMILES: O=c1oc2ccccc2n1CCCCN1CCN(c2ccccc2F)CC1] | 17.64 ± 3.34 | 2.79 ± 0.49 |
| CM 365 | 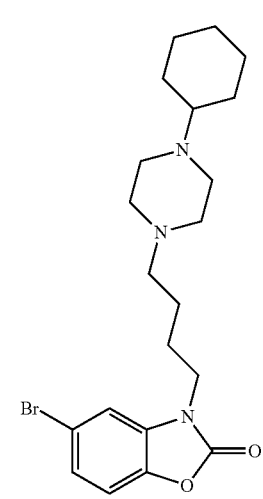 [SMILES: O=c1oc2ccc(Br)cc2n1CCCCN1CCN(C2CCCCC2)CC1] | 5.94 ± 0.35 | 0.055 ± 0.0063 |

-continued
| CMPD | STRUCTURE | Ki (nM) σ₁ | Ki (nM) σ₂ |
|---|---|---|---|
| CM 366 | 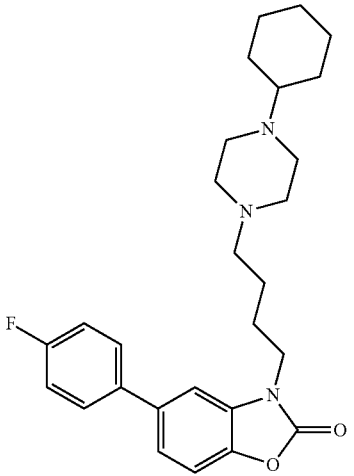 [SMILES: O=c1oc2ccc(-c3ccc(F)cc3)cc2n1CCCCN1CCN(C2CCCCC2)CC1] | 22.55 ± 1.14 | 0.0061 ± 0.00096 |
| CM 372 | 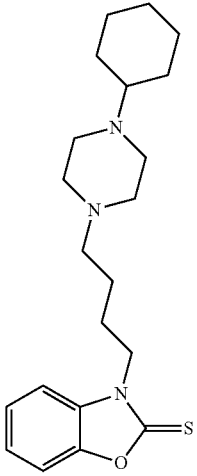 [SMILES: S=c1oc2ccccc2n1CCCCN1CCN(C2CCCCC2)CC1] | 4.90 ± 1.70 | 0.77 ± 0.06 |
| CM 373 | 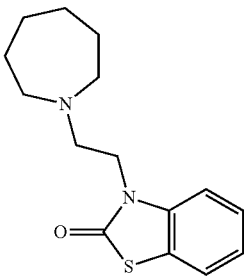 [SMILES: O=c1sc2ccccc2n1CCN1CCCCCC1] | | |
| CM 393 | 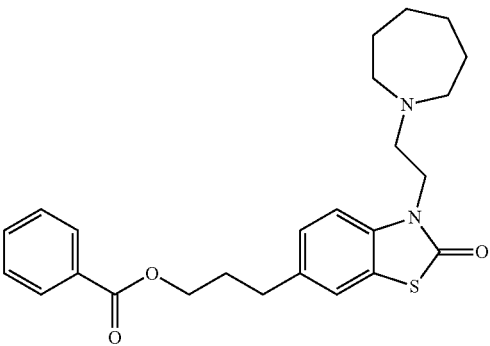 [SMILES: O=C(OCCCc1ccc2c(c1)sc(=O)n2CCN1CCCCCC1)c1ccccc1] | | |

-continued
| CMPD | STRUCTURE | Ki (nM) $\sigma_1$ | Ki (nM) $\sigma_2$ |
|---|---|---|---|
| CM 394 | 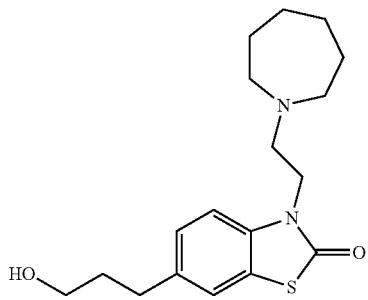 [SMILES: O=c1sc2cc(CCCO)ccc2n1CCN1CCCCCC1] | | |
| CM 396 | 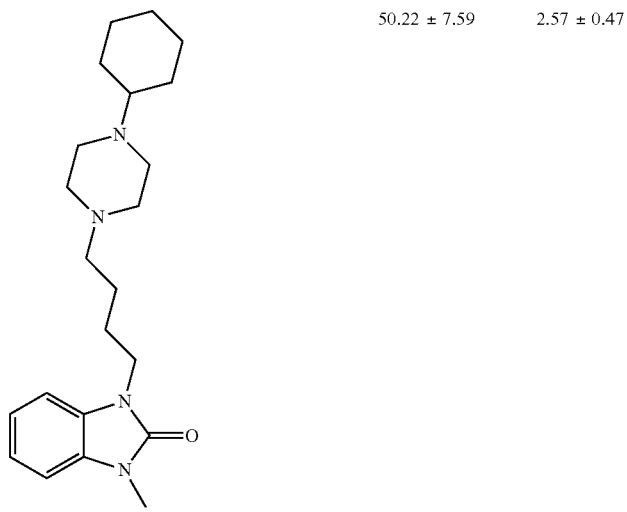 | 50.22 ± 7.59 | 2.57 ± 0.47 |
| CM 397 | 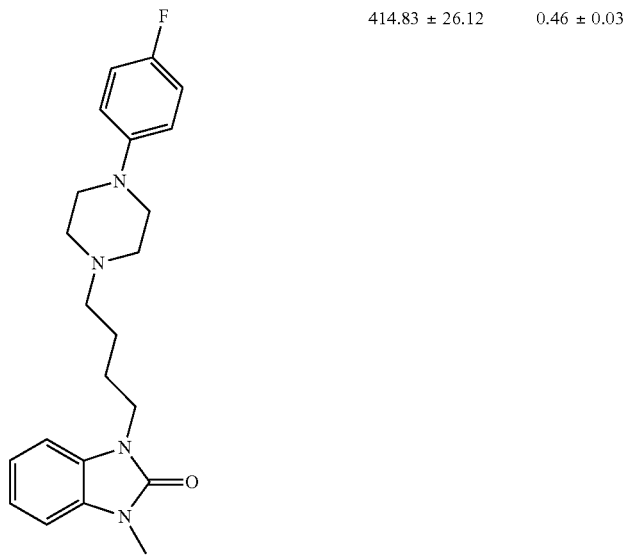 | 414.83 ± 26.12 | 0.46 ± 0.03 |

-continued
| CMPD | STRUCTURE | Ki (nM) $\sigma_1$ | Ki (nM) $\sigma_2$ |
|---|---|---|---|
| CM 398 | 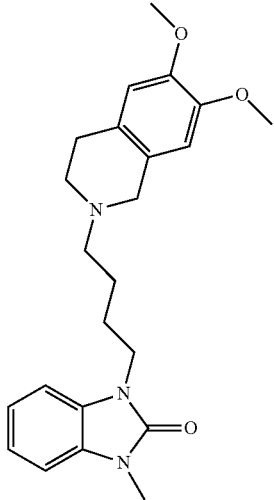 [SMILES: COc1cc2c(cc1OC)CN(CCCCn1c(=O)n(C)c3ccccc31)CC2] | | |
| CM 401 | 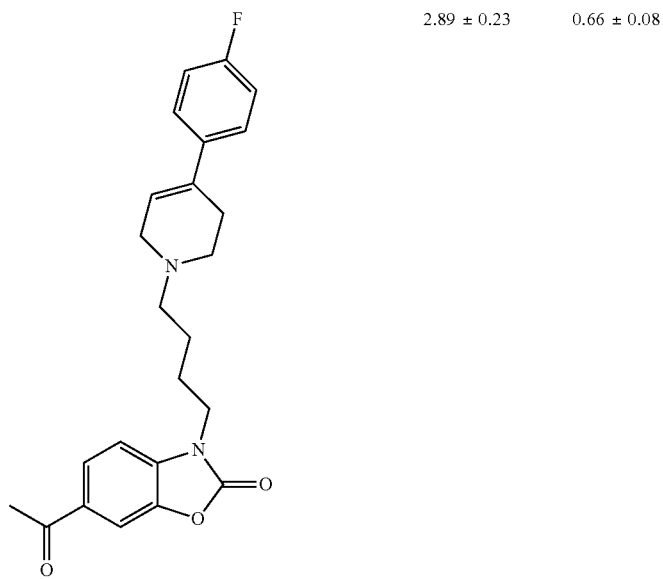 | 2.89 ± 0.23 | 0.66 ± 0.08 |
| CM406 | 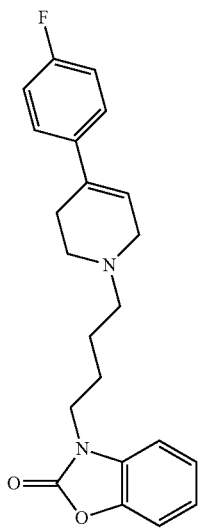 [SMILES: O=c1oc2ccccc2n1CCCCN1CC=C(c2ccc(F)cc2)CC1] | | |

-continued
| CMPD | STRUCTURE | Ki (nM) □₁ | Ki (nM) □₂ |
|---|---|---|---|
| CM407 | 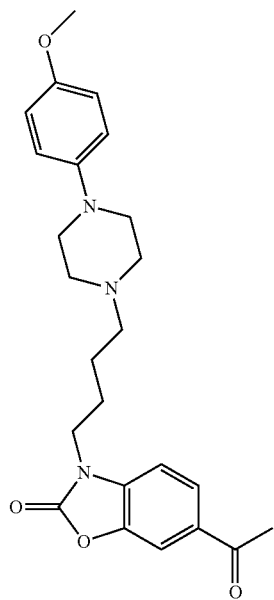 [SMILES: COc1ccc(N2CCN(CCCCn3c(=O)oc4cc(C(C)=O)ccc43)CC2)cc1] | | |
| CM408 | 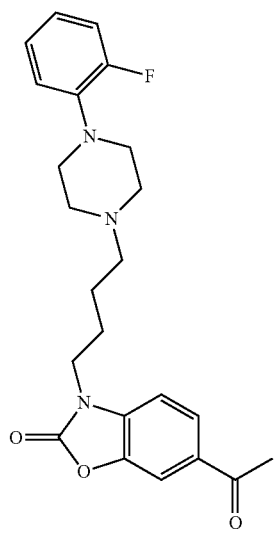 [SMILES: CC(=O)c1ccc2c(c1)oc(=O)n2CCCCN1CCN(c2ccccc2F)CC1] | | |
| CM418 | 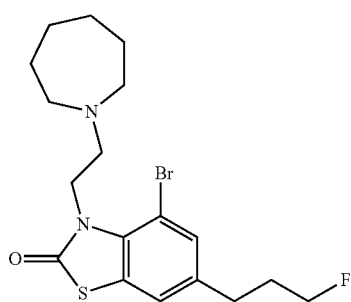 [SMILES: O=c1sc2cc(CCCF)cc(Br)c2n1CCN1CCCCCC1] | | |

-continued
| CMPD | STRUCTURE | Ki (nM) □₁ | Ki (nM) □₂ |
|---|---|---|---|
| CM422 | 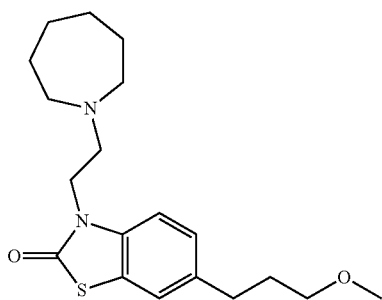 [SMILES: COCCCc1ccc2c(c1)sc(=O)n2CCN1CCCCCC1] | | |
| CM423 | 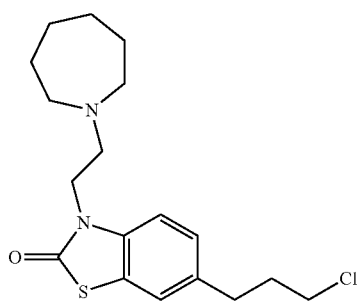 [SMILES: O=c1sc2cc(CCCCl)ccc2n1CCN1CCCCCC1] | | |
| CM433 | 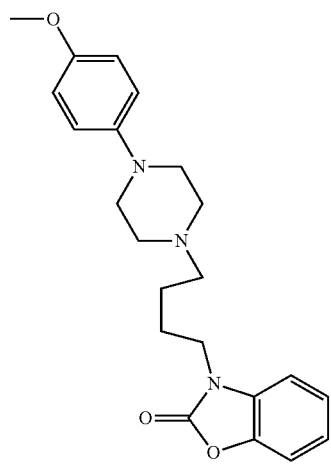 [SMILES: COc1ccc(N2CCN(CCCCn3c(=O)oc4ccccc43)CC2)cc1] | | |
| CM435 | 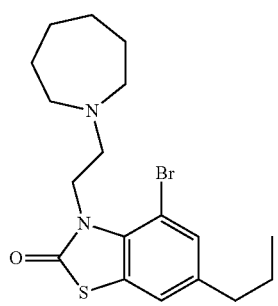 [SMILES: CCCc1cc(Br)c2c(c1)sc(=O)n2CCN1CCCCCC1] | | |

| CMPD | STRUCTURE | Ki (nM) □₁ | Ki (nM) □₂ |
|---|---|---|---|
| CM436 | 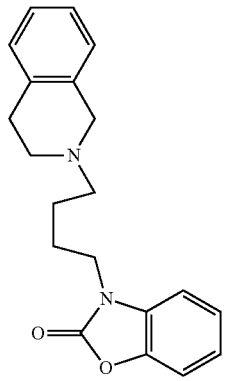 [SMILES: O=c1oc2ccccc2n1CCCCN1CCc2ccccc2C1] | | |
| CM442 | 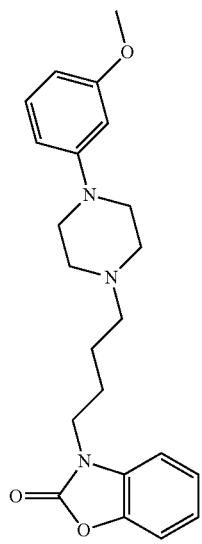 [SMILES: COc1cccc(N2CCN(CCCCn3c(=O)oc4ccccc43)CC2)c1] | | |
| CM444 | 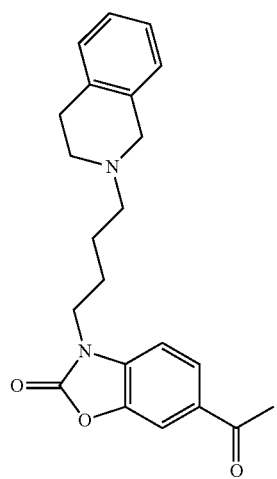 [SMILES: CC(=O)c1ccc2c(c1)oc(=O)n2CCCCN1CCc2ccccc2C1] | | |

-continued
| CMPD | STRUCTURE | Ki (nM) □₁ | Ki (nM) □₂ |
|---|---|---|---|
| CM449 | 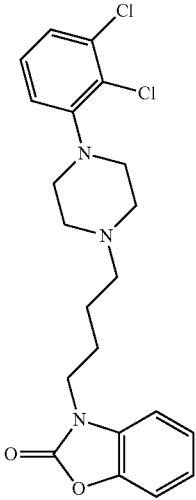 [SMILES: O=c1oc2ccccc2n1CCCCN1CCN(c2cccc(Cl)c2Cl)CC1] | | |
| CM450 | 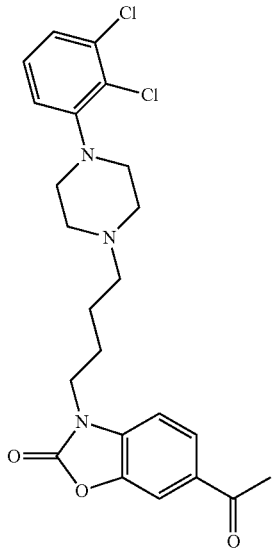 [SMILES: CC(=O)c1ccc2c(c1)oc(=O)n2CCCCN1CCN(c2cccc(Cl)c2Cl)CC1] | | |
| CM454 | 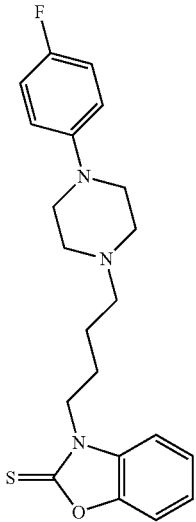 [SMILES: Fc1ccc(N2CCN(CCCCn3c(=S)oc4ccccc43)CC2)cc1] | | |

| CMPD | STRUCTURE | Ki (nM) □₁ | Ki (nM) □₂ |
|---|---|---|---|
| CM458 | 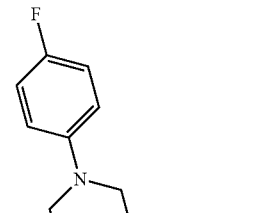 | | |
| CM459 | 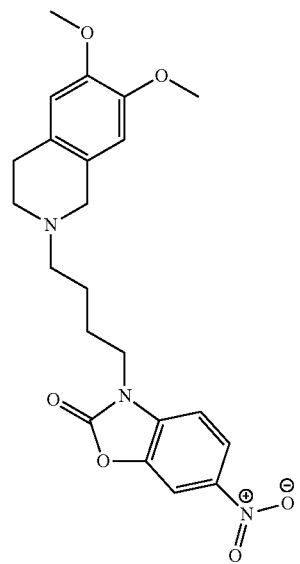 [SMILES: COc1cc2c(cc1OC)CN(CCCCn1c(=O)oc3cc([N+](=O)[O-])ccc31)CC2] | | |

-continued
| CMPD | STRUCTURE | Ki (nM) $\square_1$ | Ki (nM) $\square_2$ |
|---|---|---|---|
| CM461 | 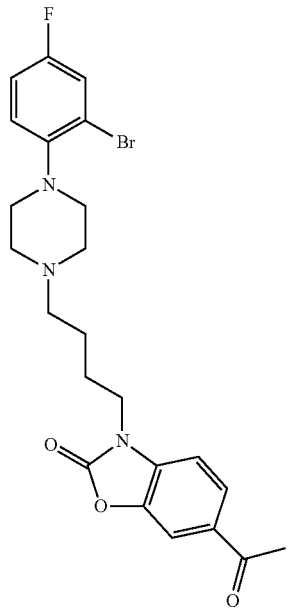 [SMILES: CC(=O)c1ccc2c(c1)oc(=O)n2CCCCN1CCN(c2ccc(F)cc2Br)CC1] | | |
| CM464 | 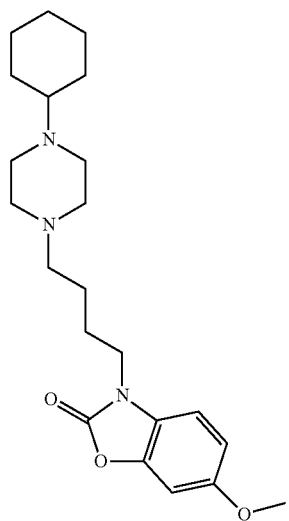 [SMILES: COc1ccc2c(c1)oc(=O)n2CCCCN1CCN(C2CCCCC2)CC1] | | |

-continued
| CMPD | STRUCTURE | Ki (nM) □₁ | Ki (nM) □₂ |
|---|---|---|---|
| CM465 | 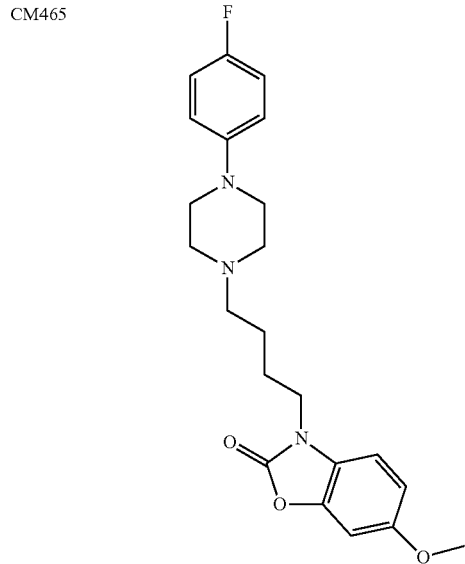 | | |
| CM466 | 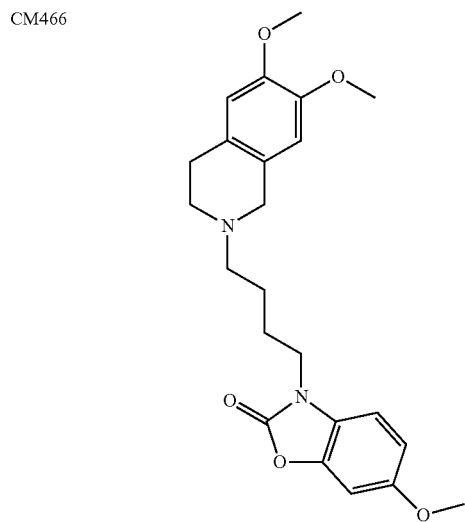 | | |
| CM471 | 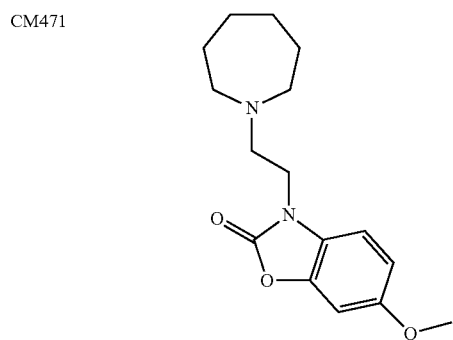 | | |

| CMPD | STRUCTURE | Ki (nM) ☐₁ | Ki (nM) ☐₂ |
|---|---|---|---|
| CM483 | 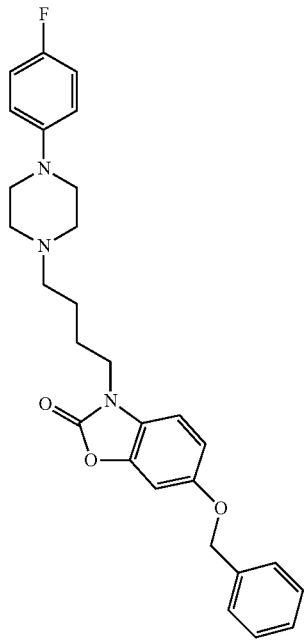 [SMILES: O=c1oc2cc(OCc3ccccc3)ccc2n1CCCCN1CCN(c2ccc(F)cc2)CC1] | | |
| CM484 | 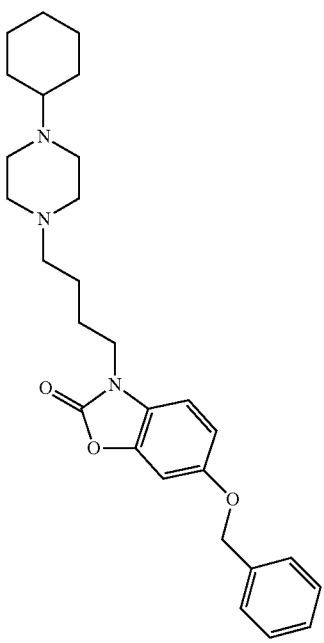 [SMILES: O=c1oc2cc(OCc3ccccc3)ccc2n1CCCCN1CCN(C2CCCCC2)CC1] | | |

-continued
| CMPD | STRUCTURE | Ki (nM) $\square_1$ | Ki (nM) $\square_2$ |
|---|---|---|---|
| CM485 | 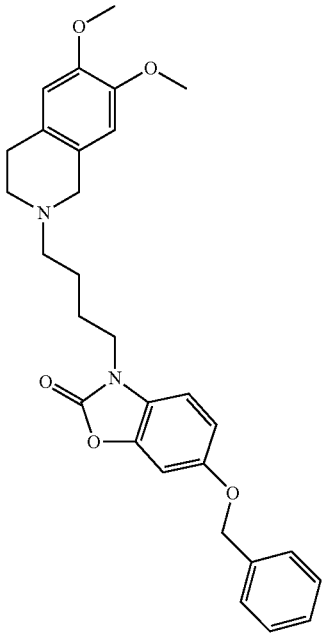 [SMILES: COc1cc2c(cc1OC)CN(CCCCn1c(=O)oc3cc(OCc4ccccc4)ccc31)CC2] | | |
| CM490 | 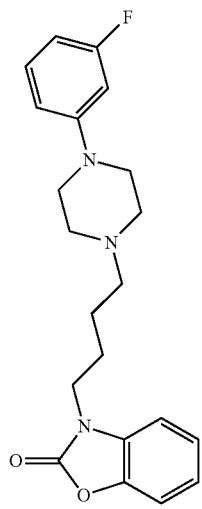 [SMILES: O=c1oc2ccccc2n1CCCCN1CCN(c2cccc(F)c2)CC1] | | |

-continued
| CMPD | STRUCTURE | Ki (nM) $\square_1$ | Ki (nM) $\square_2$ |
|---|---|---|---|
| CM491 | 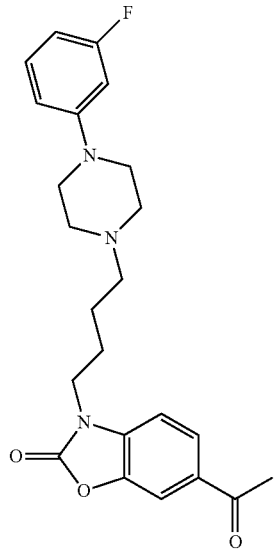 [SMILES: CC(=O)c1ccc2c(c1)oc(=O)n2CCCCN1CCN(c2cccc(F)c2)CC1] | | |
| CM498 | 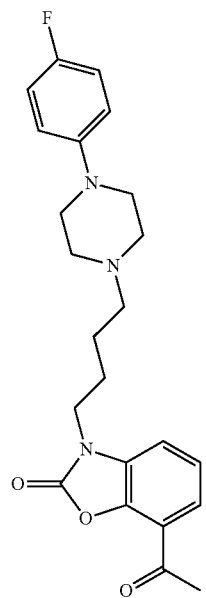 [SMILES: CC(=O)c1cccc2c1oc(=O)n2CCCCN1CCN(c2ccc(F)cc2)CC1] | | |

-continued
| CMPD | STRUCTURE | Ki (nM) □₁ | Ki (nM) □₂ |
|---|---|---|---|
| CM500 | 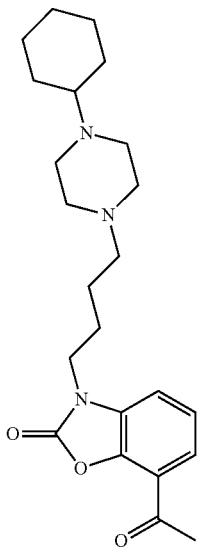 [SMILES: CC(=O)c1cccc2c1oc(=O)n2CCCCN1CCN(C2CCCCC2)CC1] | | |
| CM504 | 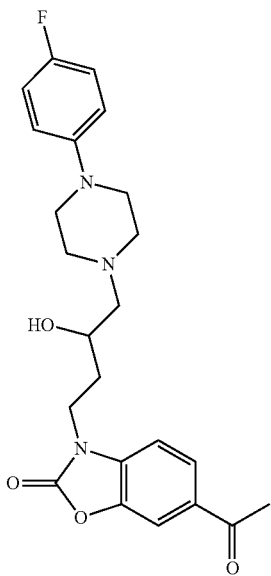 [SMILES: CC(=O)c1ccc2c(c1)oc(=O)n2CCC(O)CN1CCN(c2ccc(F)cc2)CC1] | | |
| CM528 | 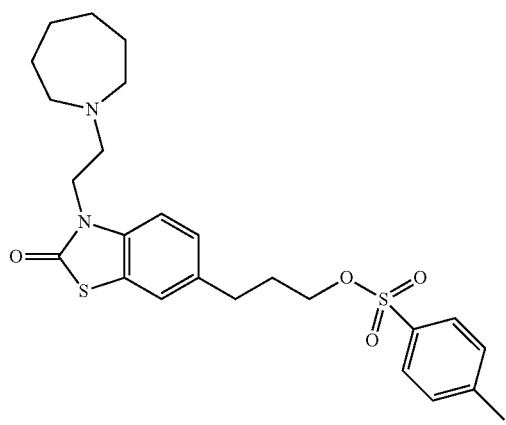 [SMILES: Cc1ccc(S(=O)(=O)OCCCc2ccc3c(c2)sc(=O)n3CCN2CCCCCC2)cc1] | | |

-continued
| CMPD | STRUCTURE | Ki (nM) $\square_1$ | Ki (nM) $\square_2$ |
|---|---|---|---|
| CM538 | 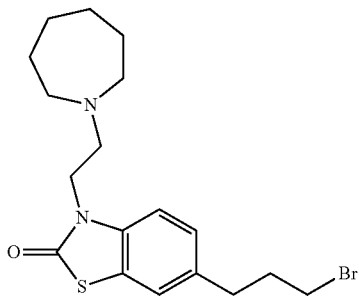 [SMILES: O=c1sc2cc(CCCBr)ccc2n1CCN1CCCCCC1] | | |
| CM539 | 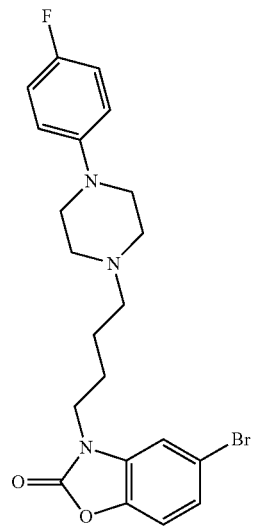 [SMILES: O=c1oc2ccc(Br)cc2n1CCCCN1CCN(c2ccc(F)cc2)CC1] | | |
| CM540 | 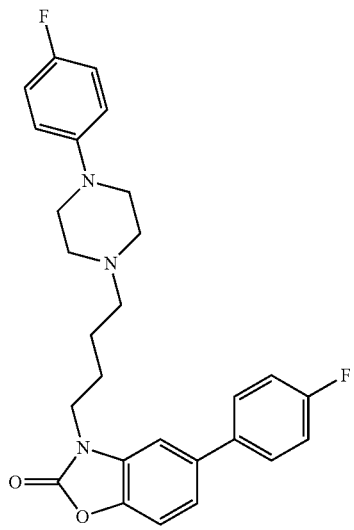 [SMILES: O=c1oc2ccc(-c3ccc(F)cc3)cc2n1CCCCN1CCN(c2ccc(F)cc2)CC1] | | |

| CMPD | STRUCTURE | Ki (nM) □₁ | Ki (nM) □₂ |
|---|---|---|---|
| CM563 | 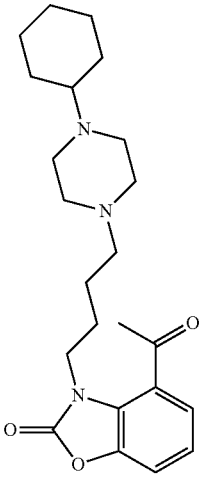 [SMILES: CC(=O)c1cccc2oc(=O)n(CCCCN3CCN(C4CCCCC4)CC3)c12] | | |
| CM564 | 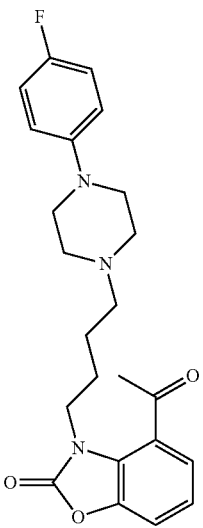 [SMILES: CC(=O)c1cccc2oc(=O)n(CCCCN3CCN(c4ccc(F)cc4)CC3)c12] | | |
| CM566 | 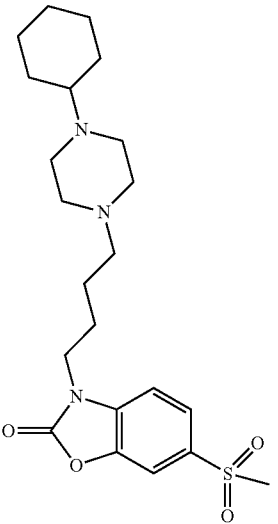 [SMILES: CS(=O)(=O)c1ccc2c(c1)oc(=O)n2CCCCN1CCN(C2CCCCC2)CC1] | | |

-continued
| CMPD | STRUCTURE | Ki (nM) □₁ | Ki (nM) □₂ |
|---|---|---|---|
| CM567 | 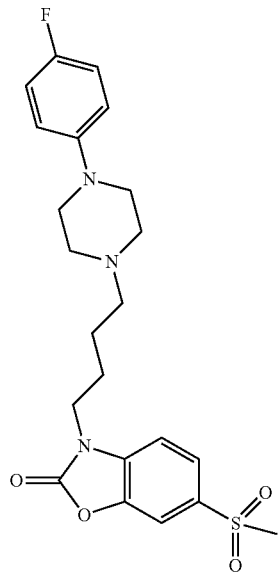 [SMILES: CS(=O)(=O)c1ccc2c(c1)oc(=O)n2CCCCN1CCN(c2ccc(F)cc2)CC1] | | |
| CM569 | 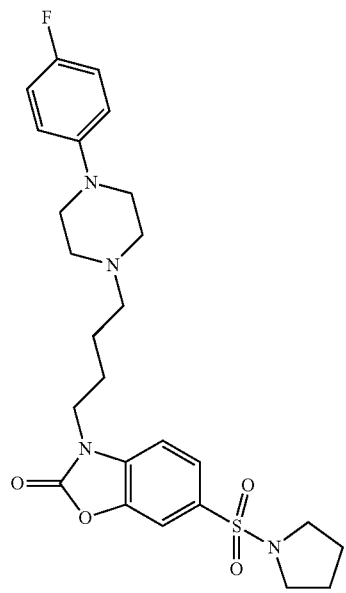 [SMILES: O=c1oc2cc(S(=O)(=O)N3CCCC3)ccc2n1CCCCN1CCN(c2ccc(F)cc2)CC1] | | |

-continued
| CMPD | STRUCTURE | Ki (nM) □₁ | Ki (nM) □₂ |
| --- | --- | --- | --- |
| CM571 | 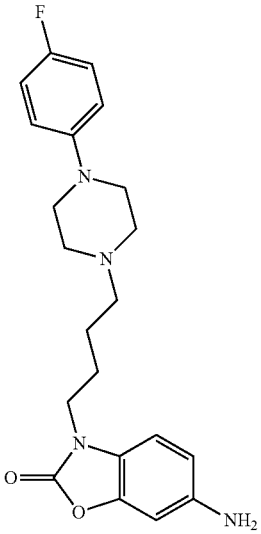 [SMILES: Nc1ccc2c(c1)oc(=O)n2CCCCN1CCN(c2ccc(F)cc2)CC1] | | |
| CM572 | 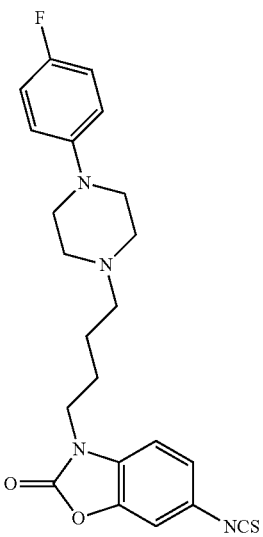 | | |
| CM585 | 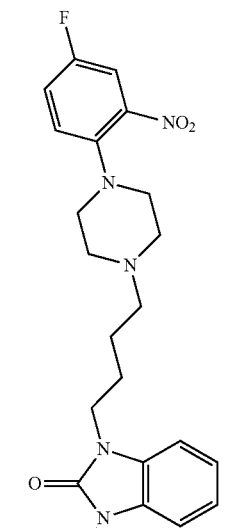 | | |

-continued
| CMPD | STRUCTURE | Ki (nM) $\square_1$ | Ki (nM) $\square_2$ |
|---|---|---|---|
| CM592 | 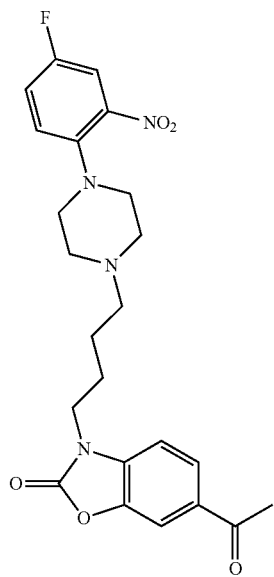 [SMILES: CC(=O)c1ccc2c(c1)oc(=O)n2CCCCN1CCN(c2ccc(F)cc2[N+](=O)[O-])CC1] | 369.1 ± 14.2 | 6.30 ± 0.39 |
| CM599 | 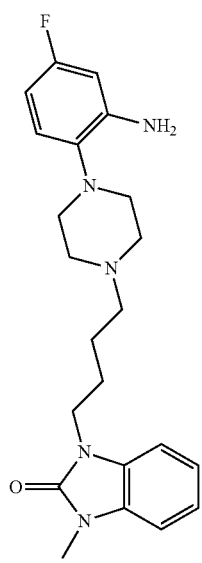 [SMILES: Cn1c(=O)n(CCCCN2CCN(c3ccc(F)cc3N)CC2)c2ccccc21] | 215.7 ± 11.8 | 3.59 ± 0.12 |

-continued
| CMPD | STRUCTURE | Ki (nM) $\sigma_1$ | Ki (nM) $\sigma_2$ |
|---|---|---|---|
| CM600 | 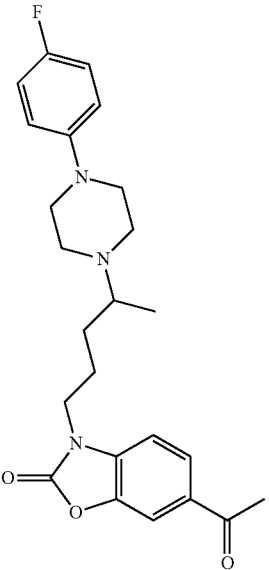 [SMILES: CC(=O)c1ccc2c(c1)oc(=O)n2CCCC(C)N1CCN(c2ccc(F)cc2)CC1] | 27.1 ± 2.32 | 2.15 ± 0.09 |
| CM608 | 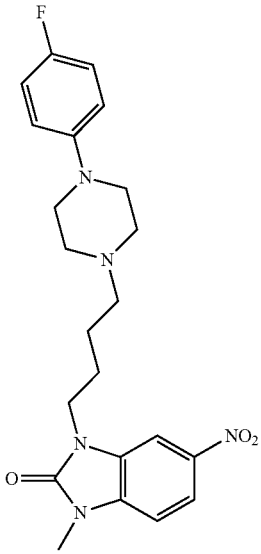 | 15.5 ± 1.75 | 4.72 ± 0.42 |

-continued
| CMPD | STRUCTURE | Ki (nM) $\square_1$ | Ki (nM) $\square_2$ |
|---|---|---|---|
| CM609 | 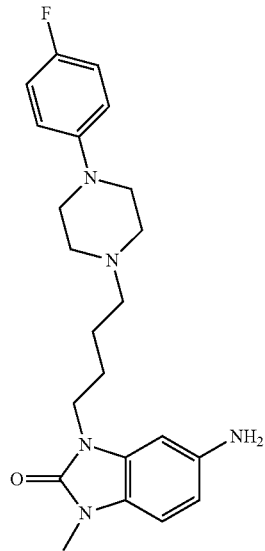 [SMILES: Cn1c(=O)n(CCCCN2CCN(c3ccc(F)cc3)CC2)c2cc([N+](=O)[O-])ccc21] | 23.4 ± 2.63 | 26.6 ± 2.74 |
| CM617 | 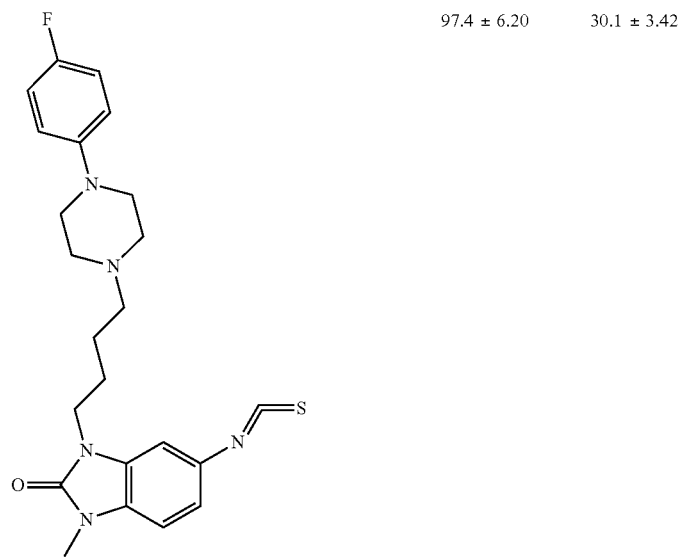 | 97.4 ± 6.20 | 30.1 ± 3.42 |

-continued
| CMPD | STRUCTURE | Ki (nM) $\square_1$ | Ki (nM) $\square_2$ |
|---|---|---|---|
| CM621 | 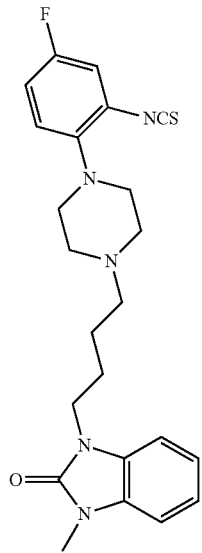 | 96.5 ± 5.80 | 12.60 ± 1.01 |
| CM623 | 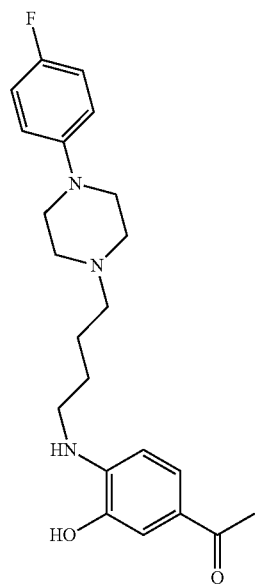 [SMILES: CC(=O)c1ccc(NCCCCN2CCN(c3ccc(F)cc3)CC2)c(O)c1] | 29.4 ± 3.93 | 44.1 ± 3.40 |

-continued
| CMPD | STRUCTURE | Ki (nM) $\sigma_1$ | Ki (nM) $\sigma_2$ |
|---|---|---|---|
| CM624 | 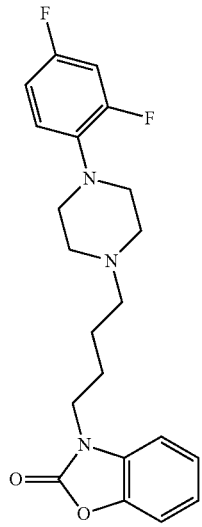 [SMILES: O=c1oc2ccccc2n1CCCCN1CCN(c2ccc(F)cc2F)CC1] | 14.8 ± 0.71 | 1.96 ± 0.11 |
| CM625 | 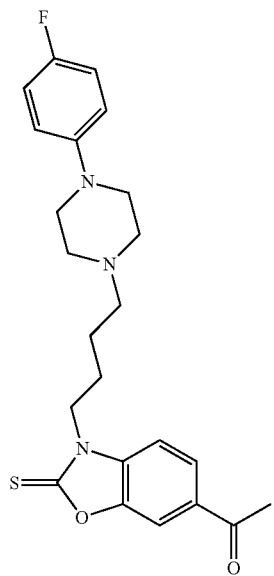 [SMILES: CC(=O)c1ccc2c(c1)oc(=S)n2CCCCN1CCN(c2ccc(F)cc2)CC1] | 10.8 ± 0.78 | 1.88 ± 0.13 |

-continued
| CMPD | STRUCTURE | Ki (nM) $\square_1$ | Ki (nM) $\square_2$ |
|---|---|---|---|
| CM627 | 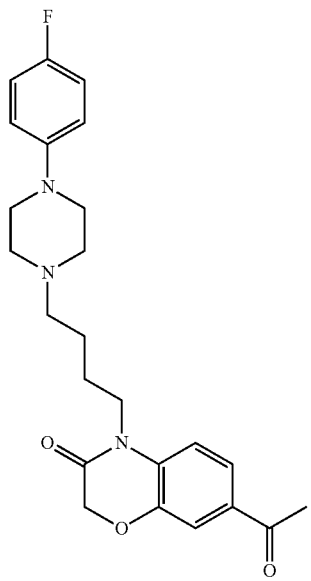 [SMILES: CC(=O)c1ccc2c(c1)OCC(=O)N2CCCCN1CCN(c2ccc(F)cc2)CC1] | 25.5 ± 1.11 | 6.34 ± 0.17 |
| CM657 | 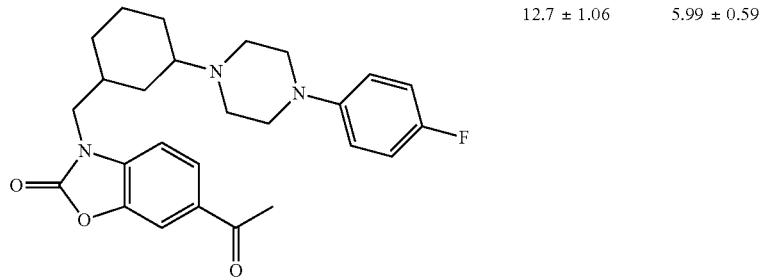 | 12.7 ± 1.06 | 5.99 ± 0.59 |
| CM666 | 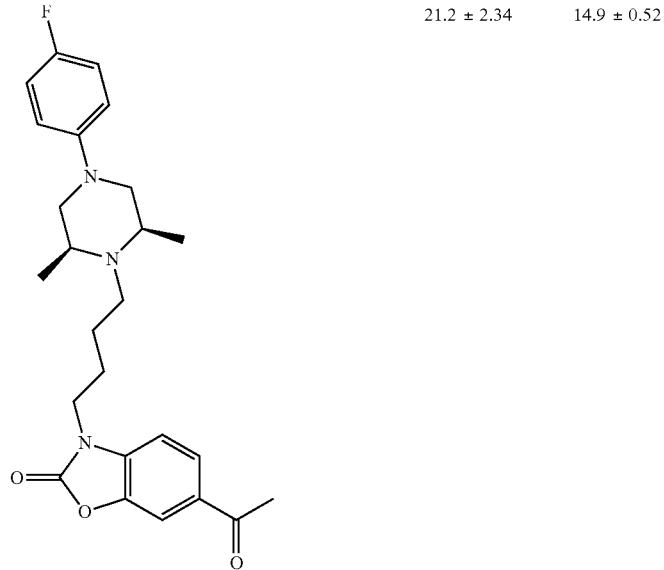 | 21.2 ± 2.34 | 14.9 ± 0.52 |

-continued
| CMPD | STRUCTURE | Ki (nM) $\sigma_1$ | Ki (nM) $\sigma_2$ |
|---|---|---|---|
| CM673 | 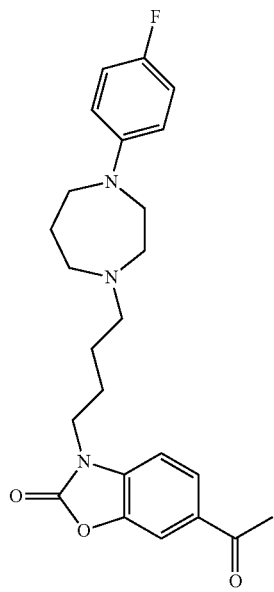 [SMILES: CC(=O)c1ccc2c(c1)oc(=O)n2CCCCN1CCCN(c2ccc(F)cc2)CC1] | 104.1 ± 8.06 | 50.6 ± 4.32 |
| CM697 | 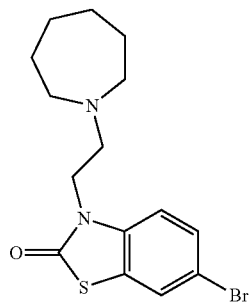 [SMILES: O=c1sc2cc(Br)ccc2n1CCN1CCCCCC1] | | |
| CM699 | 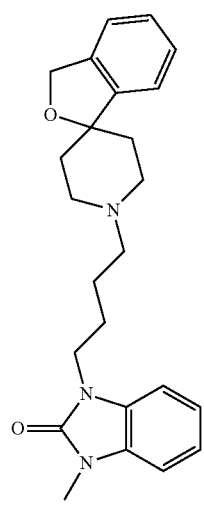 [SMILES: Cn1c(=O)n(CCCCN2CCC3(CC2)OCc2ccccc23)c2ccccc21] | | |

-continued
| CMPD | STRUCTURE | Ki (nM) $\square_1$ | Ki (nM) $\square_2$ |
|---|---|---|---|
| CM711 | 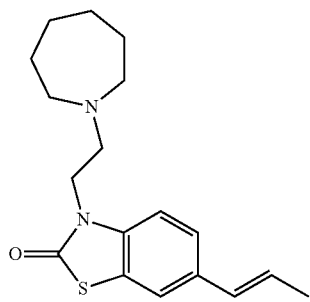 [SMILES: C/C=C/c1ccc2c(c1)sc(=O)n2CCN1CCCCCC1] | | |
| CM728 | 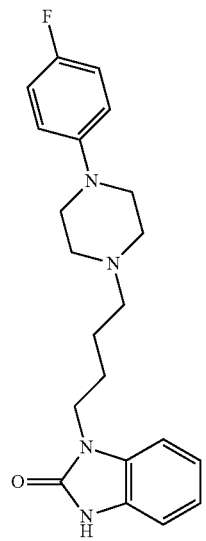 [SMILES: O=c1[nH]c2ccccc2n1CCCCN1CCN(c2ccc(F)cc2)CC1] | 1862 ± 11.8 | 29.6 ± 1.51 |
| CM764 | 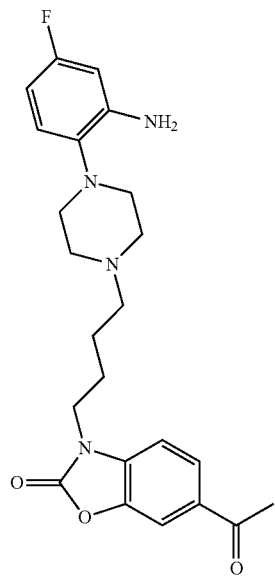 [SMILES: CC(=O)c1ccc2c(c1)oc(=O)n2CCCCN1CCN(c2ccc(F)cc2N)CC1] | | |

-continued
| CMPD | STRUCTURE | Ki (nM) □₁ | Ki (nM) □₂ |
| --- | --- | --- | --- |
| CM768 | 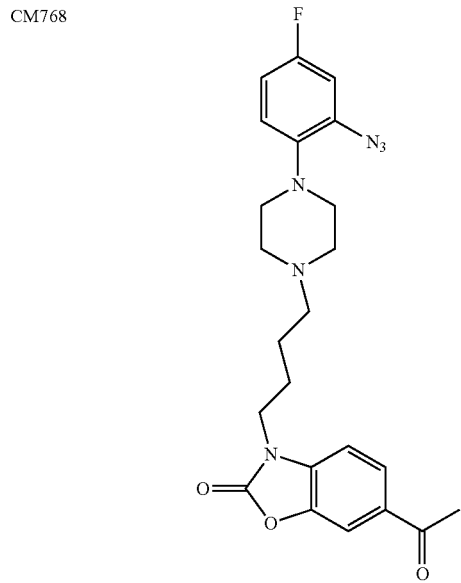 | | |
| CM769 | 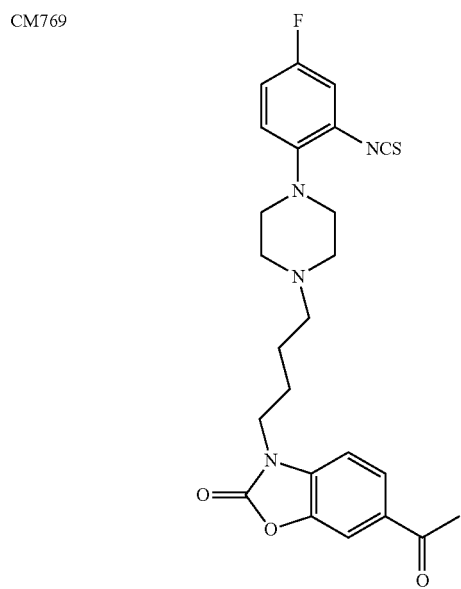 | | |

-continued
| CMPD | STRUCTURE | Ki (nM) □₁ | Ki (nM) □₂ |
|---|---|---|---|
| CM775 | 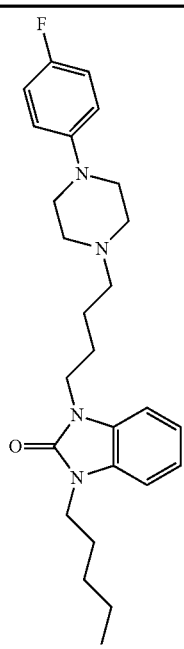 | | |
| CM777 | 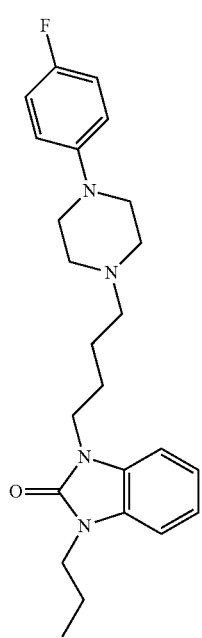 [SMILES: CCCn1c(=O)n(CCCCN2CCN(c3ccc(F)cc3)CC2)c2ccccc21] | | |

-continued
| CMPD | STRUCTURE | Ki (nM) $\square_1$ | Ki (nM) $\square_2$ |
|---|---|---|---|
| CM778 | 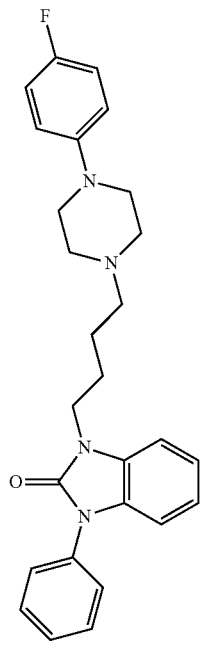 [SMILES: O=c1n(CCCCN2CCN(c3ccc(F)cc3)CC2)c2ccccc2n1-c1ccccc1] | | |
| CM781 | 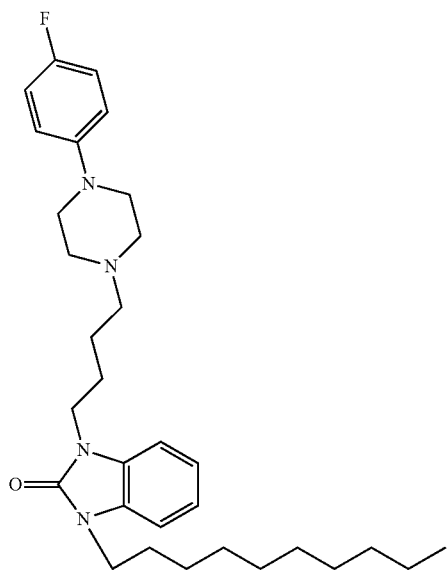 [SMILES: CCCCCCCCCCn1c(=O)n(CCCCN2CCN(c3ccc(F)cc3)CC2)c2ccccc21] | | |

| CMPD | STRUCTURE | Ki (nM) σ₁ | Ki (nM) σ₂ |
|---|---|---|---|
| CM782 | 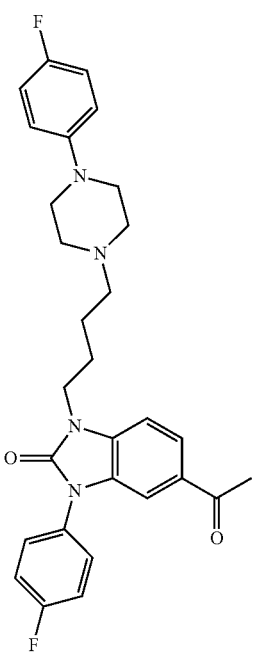 [SMILES: CC(=O)c1ccc2c(c1)n(-c1ccc(F)cc1)c(=O)n2CCCCN1CCN(c2ccc(F)cc2)CC1] | | |
| CMPD | STRUCTURE | Ki (nM) σ₁ | Ki (nM) σ₂ |
|---|---|---|---|
| NF6 | 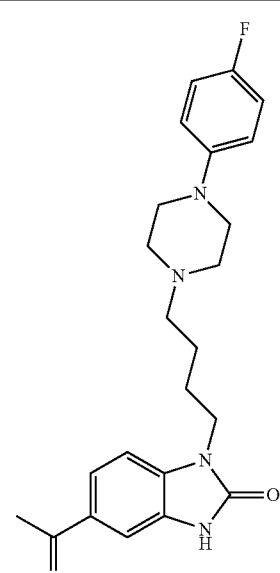 | | |

| CMPD | STRUCTURE | Ki (nM) σ₁ | Ki (nM) σ₂ |
|------|-----------|------------|------------|
| NF7 | 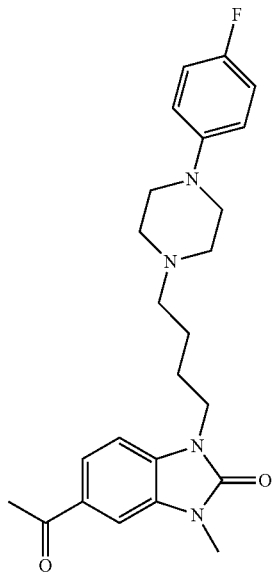 [SMILES: CC(=O)c1ccc2c(c1)n(C)c(=O)n2CCCCN1CCN(c2ccc(F)cc2)CC1] | | |
| NF8 | 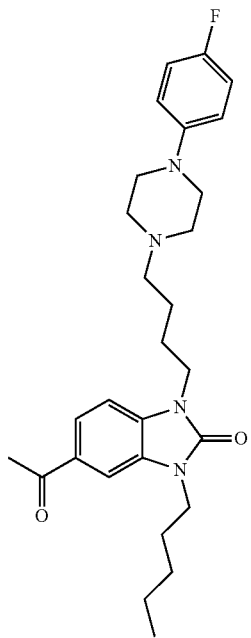 [SMILES: CCCCCn1c(=O)n(CCCCN2CCN(c3ccc(F)cc3)CC2)c2ccc(C(C)=O)cc21] | | |

| CMPD | STRUCTURE | Ki (nM) σ₁ | Ki (nM) σ₂ |
|---|---|---|---|
| NF9 | 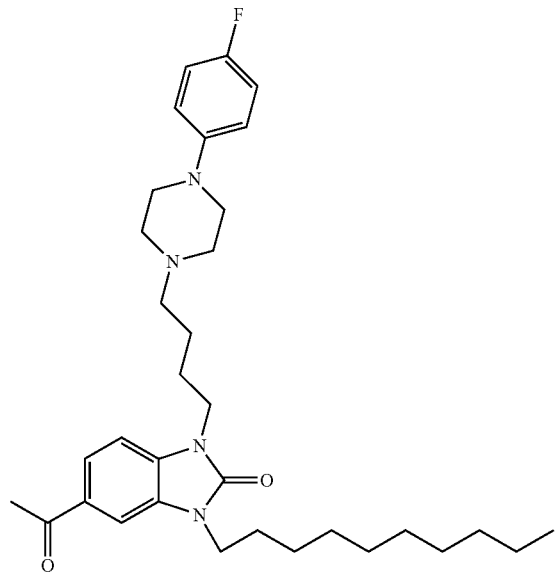 [SMILES: CCCCCCCCCCn1c(=O)n(CCCCN2CCN(c3ccc(F)cc3)CC2)c2ccc(C(C)=O)cc21] | | |
| NF10 | 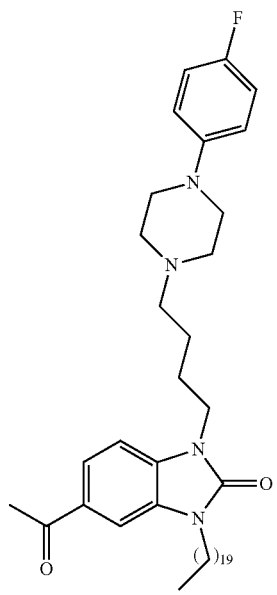 | | |

| CMPD | STRUCTURE | Ki (nM) $\sigma_1$ | Ki (nM) $\sigma_2$ |
|---|---|---|---|
| NF12 | 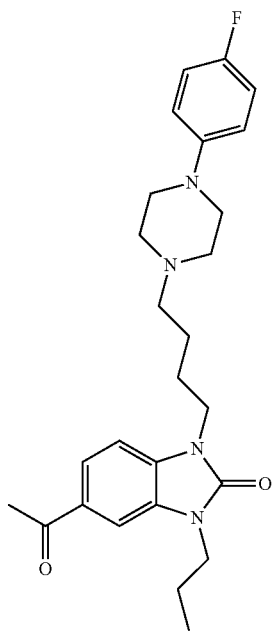 [SMILES: CCCn1c(=O)n(CCCCN2CCN(c3ccc(F)cc3)CC2)c2ccc(C(C)=O)cc21] | | |
| EA2 | 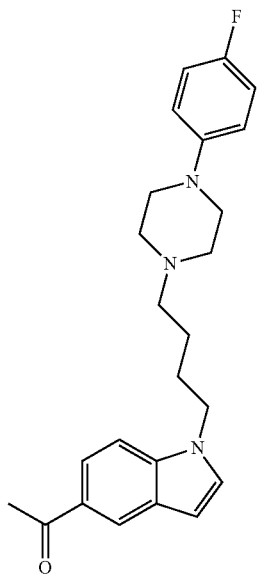 [SMILES: CC(=O)c1ccc2c(ccn2CCCCN2CCN(c3ccc(F)cc3)CC2)c1] | | |

-continued
| CMPD | STRUCTURE | Ki (nM) σ$_1$ | Ki (nM) σ$_2$ |
|---|---|---|---|
| EA6 | 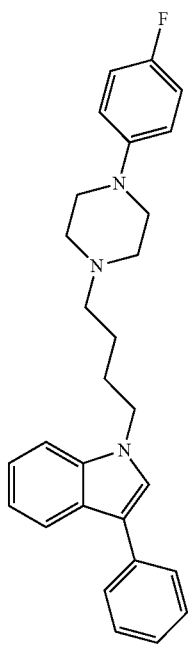 [SMILES: Fc1ccc(N2CCN(CCCCn3cc(-c4ccccc4)c4ccccc43)CC2)cc1] | | |
| EA7 | 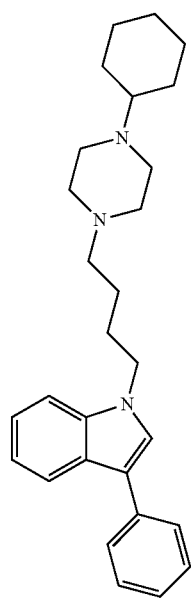 [SMILES: c1ccc(-c2cn(CCCCN3CCN(C4CCCCC4)CC3)c3ccccc23)cc1] | | |

| CMPD | STRUCTURE | Ki (nM) σ$_1$ | Ki (nM) σ$_2$ |
|---|---|---|---|
| EA8 | 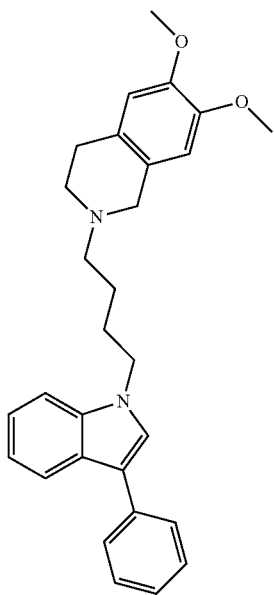 [SMILES: COc1cc2c(cc1OC)CN(CCCCn1cc(-c3ccccc3)c3ccccc31)CC2] | | |
| EA12 | 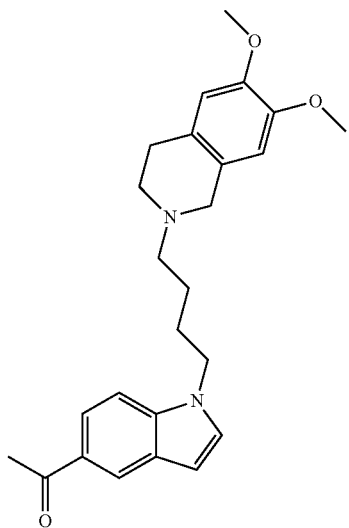 [SMILES: COc1cc2c(cc1OC)CN(CCCCn1ccc3cc(C(C)=O)ccc31)CC2] | | |

| CMPD | STRUCTURE | Ki (nM) $\sigma_1$ | Ki (nM) $\sigma_2$ |
|---|---|---|---|
| EA13 | 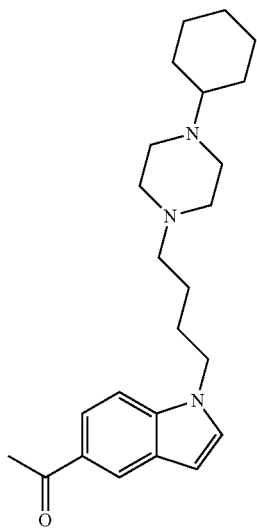 [SMILES: CC(=O)c1ccc2c(ccn2CCCCN2CCN(C3CCCCC3)CC2)c1] | | |
| EA14 | 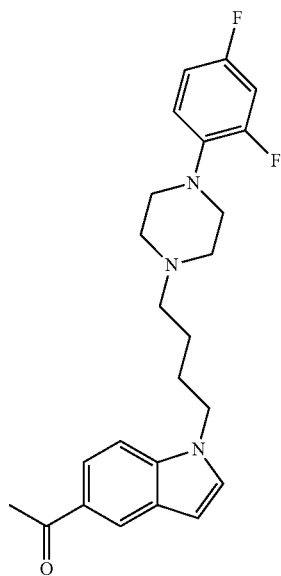 [SMILES: CC(=O)c1ccc2c(ccn2CCCCN2CCN(c3ccc(F)cc3F)CC2)c1] | | |

-continued

| CMPD | STRUCTURE | Ki (nM) σ₁ | Ki (nM) σ₂ |
|---|---|---|---|
| EA18 | 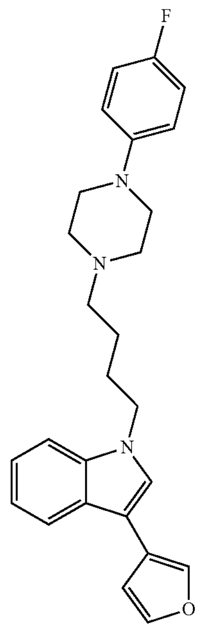 [SMILES: Fc1ccc(N2CCN(CCCCn3cc(-c4ccoc4)c4ccccc43)CC2)cc1] | | |
| EA21 | 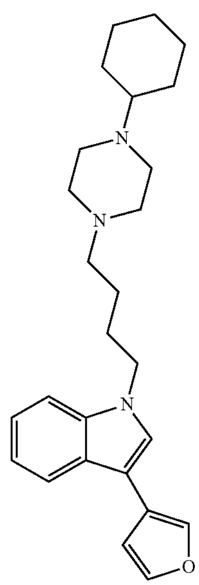 [SMILES: c1ccc2c(c1)c(-c1ccoc1)cn2CCCCN1CCN(C2CCCCC2)CC1] | | |
| SN-228 | 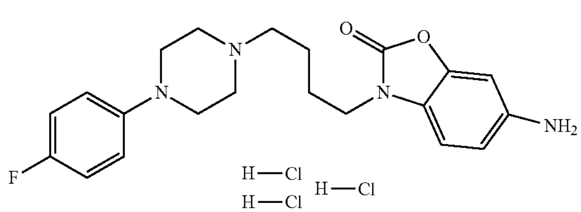 | >10000 | 177.47 ± 10.16 |
| SN-248 | 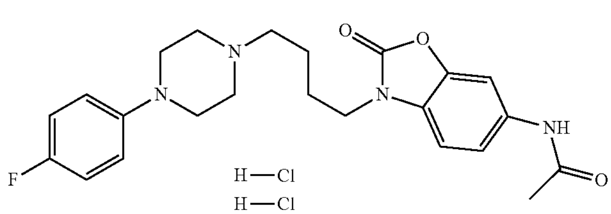 | 88.43 ± 12.72 | 48.13 ± 5.68 |

-continued

| CMPD | STRUCTURE | Ki (nM) σ$_1$ | Ki (nM) σ$_2$ |
|---|---|---|---|
| SN-249 | 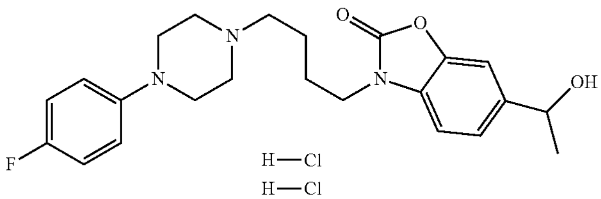 | 608.9 ± 39.75 | 8.68 ± 0.57 |
| SN-250 | 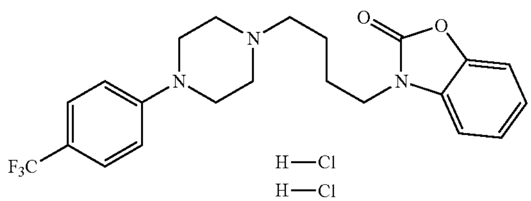 | 87.58 ± 8.77 | 98.81 ± 1.08 |
| SN-251 | 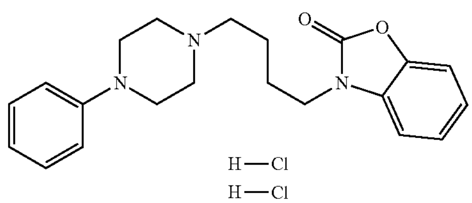 | 18.35 ± 1.46 | 11.44 ± 1.15 |
| SN-252 | 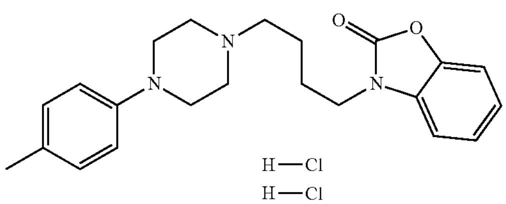 | 212.8 ± 22.24 | 107.02 ± 8.21 |
| SN-253 | 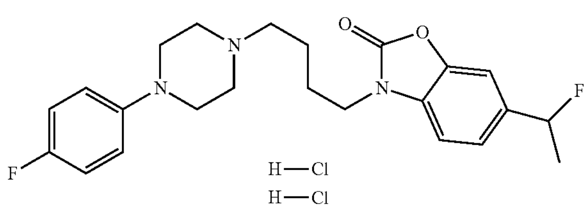 | 162.3 ± 11.45 | 6.12 ± 0.37 |
| SC-5 | 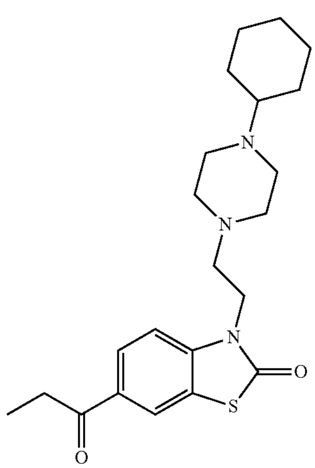 [SMILES: CCC(=O)c1ccc2c(c1)sc(=O)n2CCN1CCN(C2CCCCC2)CC1] | 6.75 ± 0.6 | 3.73 ± 0.43 |

-continued
| CMPD | STRUCTURE | Ki (nM) $\sigma_1$ | Ki (nM) $\sigma_2$ |
|---|---|---|---|
| SC-6 | 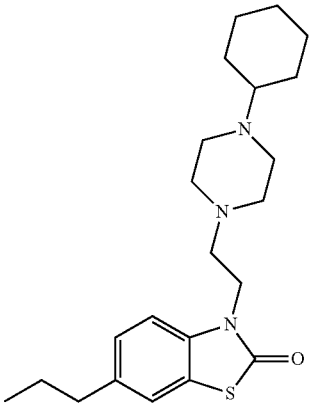 [SMILES: CCCc1ccc2c(c1)sc(=O)n2CCN1CCN(C2CCCCC2)CC1] | 2.15 ± 0.25 | 2.43 ± 0.09 |
| SC-10 | 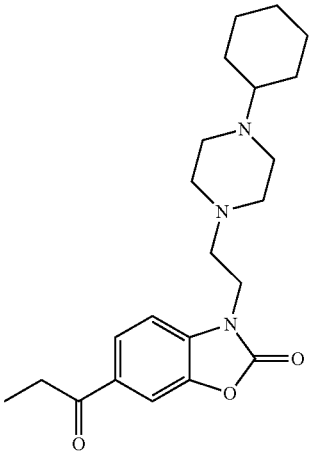 [SMILES: CCC(=O)c1ccc2c(c1)oc(=O)n2CCN1CCN(C2CCCCC2)CC1] | 14.3 ± 0.34 | 4.85 ± 0.31 |
| SC-12 | 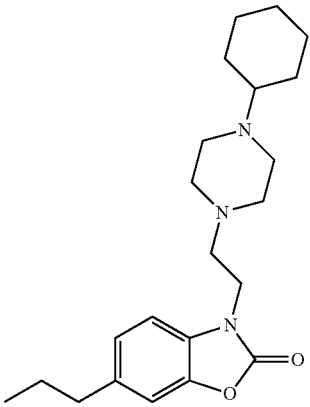 [SMILES: CCCc1ccc2c(c1)oc(=O)n2CCN1CCN(C2CCCCC2)CC1] | 7.50 ± 0.59 | 4.02 ± 0.23 |
| AZ-57 | 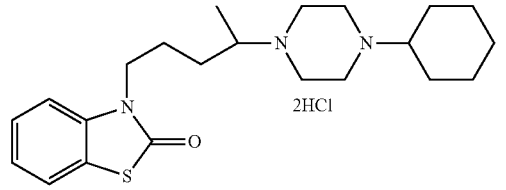<br>Chemical Formula: $C_{22}H_{35}Cl_2N_3OS$<br>Exact Mass: 459.19 | 8.73 ± 1.32 | 3.15 ± 0.19 |

-continued

| CMPD | STRUCTURE | Ki (nM) $\sigma_1$ | Ki (nM) $\sigma_2$ |
|---|---|---|---|
| AZ-59 | 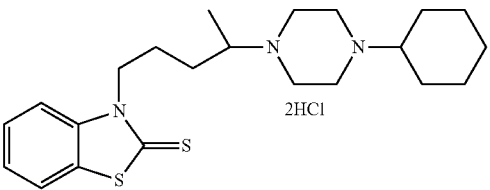<br>2HCl<br>Chemical Formula: $C_{22}H_{35}Cl_2N_3S_2$<br>Exact Mass: 475.16 | 8.94 ± 1.64 | 0.99 ± 0.178 |
| AZ-60 | 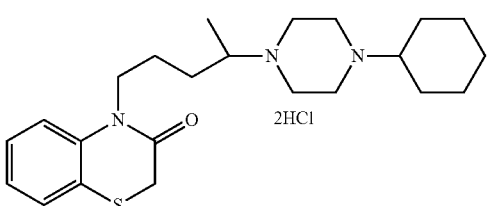<br>2HCl<br>Chemical Formula: $C_{23}H_{37}Cl_2N_3OS$<br>Exact Mass: 473.20 | 92.36 ± 9.76 | 5.49 ± 1.10 |
| AZ-66 | 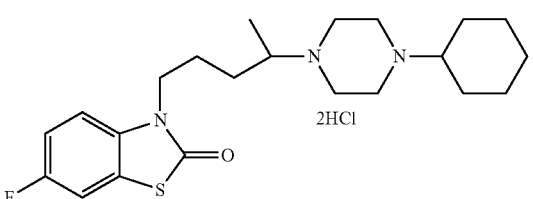<br>2HCl<br>Chemical Formula: $C_{22}H_{34}Cl_2FN_3OS$<br>Exact Mass: 477.18 | 0.31 ± 0.09 | 1.76 ± 0.34 |
| AZ-68 | 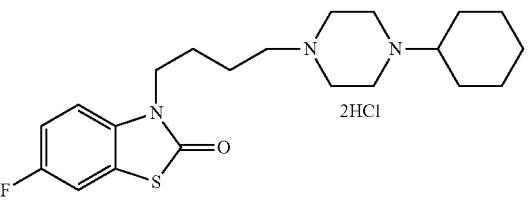<br>2HCl<br>Chemical Formula: $C_{21}H_{32}Cl_2FN_3OS$<br>Exact Mass: 463.16 | 2.01 ± 0.44 | 0.22 ± 0.09 |
| AZ-70 | 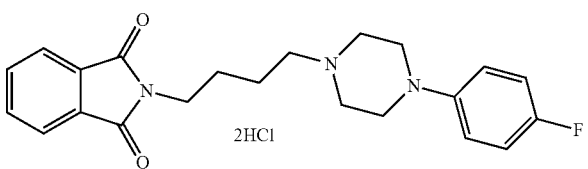<br>2HCl<br>Chemical Formula: $C_{22}H_{26}Cl_2FN_3O_2$<br>Exact Mass: 453.14 | | |
| AZ-71 | 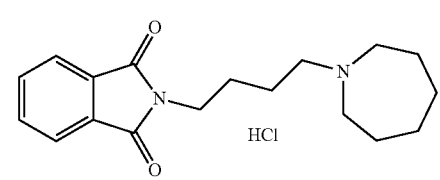<br>HCl<br>Chemical Formula: $C_{18}H_{25}ClN_2O_2$<br>Exact Mass: 336.16 | | |

| CMPD | STRUCTURE | Ki (nM) $\sigma_1$ | Ki (nM) $\sigma_2$ |
|---|---|---|---|
| AZ-72 | 2HCl<br>Chemical Formula: $C_{22}H_{33}Cl_2N_3O_2$<br>Exact Mass: 441.19 | | |
| AZ-73 | HCl<br>Chemical Formula: $C_{16}H_{21}ClN_2O_2$<br>Exact Mass: 308.13 | | |
| AZ-74 | HCl<br>Chemical Formula: $C_{23}H_{27}ClN_2O_4$<br>Exact Mass: 430.17 | | |
| AZ-77 | 2HCl<br>Chemical Formula: $C_{22}H_{34}Cl_2FN_3S_2$<br>Exact Mass: 493.16 | | |
| AZ-78 | 2HCl<br>Chemical Formula: $C_{21}H_{32}Cl_2FN_3S_2$<br>Exact Mass: 479.14 | 7.21 ± 1.20 | 0.50 ± 0.30 |
| AZ-81 | 2HCl<br>Chemical Formula: $C_{21}H_{32}Cl_2FN_3S_2$<br>Exact Mass: 479.14 | 14.3 ± 1.35 | 13.8 ± 1.34 |

| CMPD | STRUCTURE | Ki (nM) σ₁ | Ki (nM) σ₂ |
|---|---|---|---|
| AZ-87 | 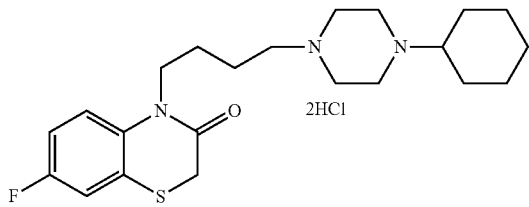<br>Chemical Formula: $C_{22}H_{34}Cl_2FN_3OS$<br>Exact Mass: 477.18 | 6.24 ± 1.97 | 6.45 ± 0.94 |
| AZ-93 | 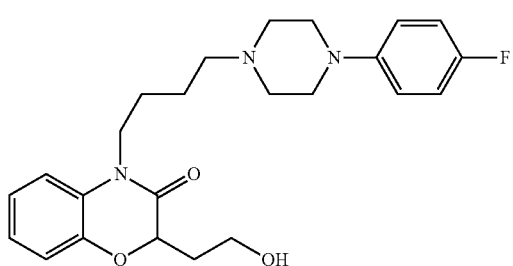<br>Chemical Formula: $C_{24}H_{30}FN_3O_3$<br>Exact Mass: 427.23 | | |
| AZ-94 | 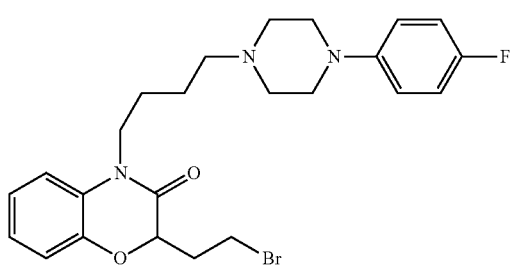<br>Chemical Formula: $C_{24}H_{29}BrFN_3O_2$<br>Exact Mass: 489.14 | | |
| AZ-95 | 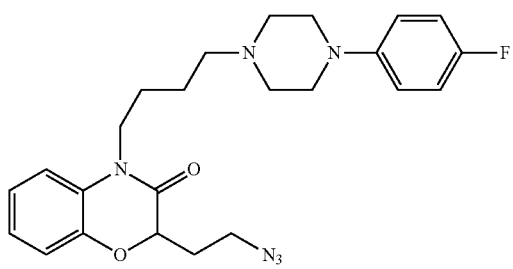<br>Chemical Formula: $C_{24}H_{29}FN_6O_2$<br>Exact Mass: 452.23 | | |

| CMPD | STRUCTURE | Ki (nM) σ₁ | Ki (nM) σ₂ |
|---|---|---|---|
| AZ-96 | 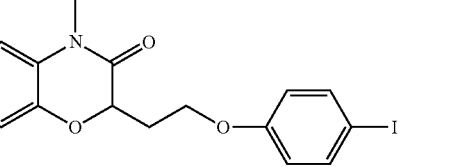<br>Chemical Formula: $C_{30}H_{33}FIN_3O_3$<br>Exact Mass: 629.16 | | |
| AZ-97 | 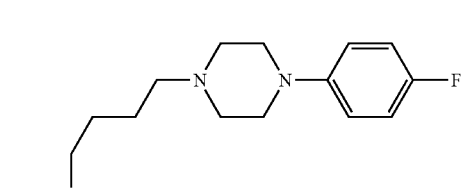<br>Chemical Formula: $C_{26}H_{32}FN_3O_4$<br>Exact Mass: 459.24 | | |
| AZ-98 | 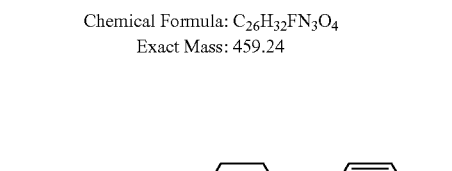<br>Chemical Formula: $C_{30}H_{33}FN_4O_5$<br>Exact Mass: 548.24 | | |
| AZ-99 | 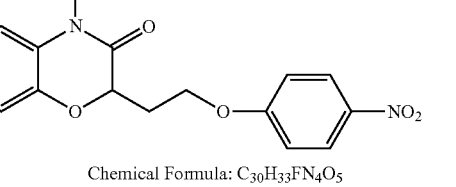<br>Chemical Formula: $C_{30}H_{34}FN_3O_3$<br>Exact Mass: 503.26 | | |

| CMPD | STRUCTURE | Ki (nM) σ₁ | Ki (nM) σ₂ |
|---|---|---|---|
| AZ-100 | 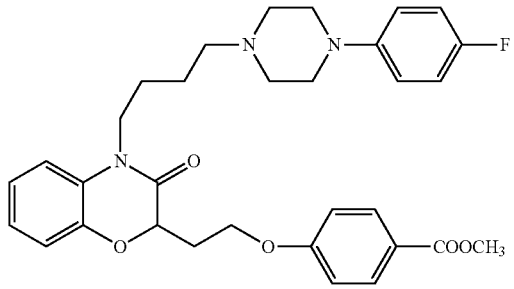<br>Chemical Formula: C₃₂H₃₆FN₃O₅<br>Exact Mass: 561.26 | | |
| AZ-101 | 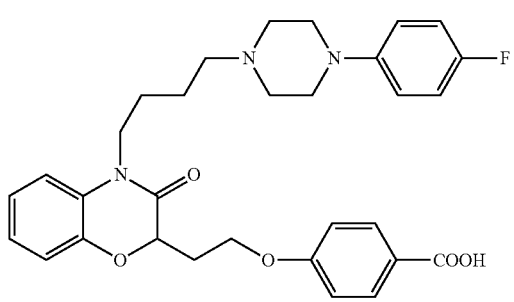<br>Chemical Formula: C₃₁H₃₄FN₃O₅<br>Exact Mass: 547.25 | | |
| AZ-102 | 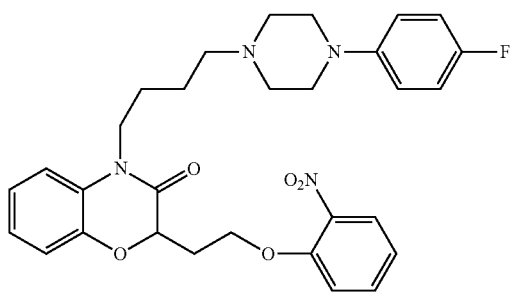<br>Chemical Formula: C₃₀H₃₃FN₄O₅<br>Exact Mass: 548.24 | | |
| AZ-103 | 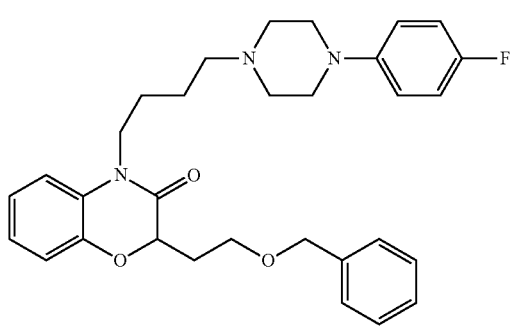<br>Chemical Formula: C₃₁H₃₆FN₃O₃<br>Exact Mass: 517.27 | | |

US 9,724,435 B2
187                                                                                          188
-continued
| CMPD | STRUCTURE | Ki (nM) σ₁ | Ki (nM) σ₂ |
|---|---|---|---|
| AZ-104 | 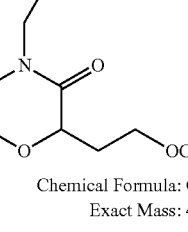<br>Chemical Formula: C₂₅H₃₂FN₃O₃<br>Exact Mass: 441.24 | | |
| AZ-105 | <br>Chemical Formula: C₃₁H₃₄FN₃O₄<br>Exact Mass: 531.25 | | |
| AZ-106 | 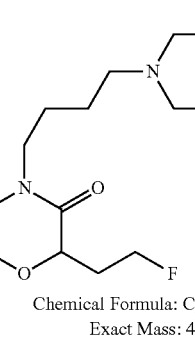<br>Chemical Formula: C₂₄H₂₉F₂N₃O₂<br>Exact Mass: 429.22 | | |
| AZ-107 | 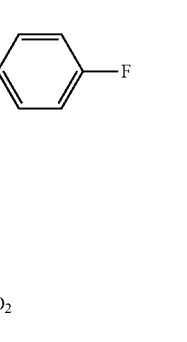<br>Chemical Formula: C₃₄H₄₁F₂N₅O₂<br>Exact Mass: 589.32 | | |

| CMPD | STRUCTURE | Ki (nM) σ₁ | Ki (nM) σ₂ |
|---|---|---|---|
| AZ-108 | 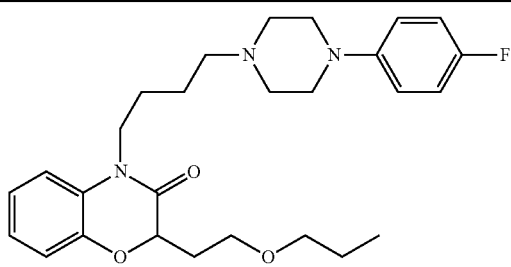<br>Chemical Formula: $C_{27}H_{36}FN_3O_3$<br>Exact Mass: 469.27 | | |
| AZ-109 | 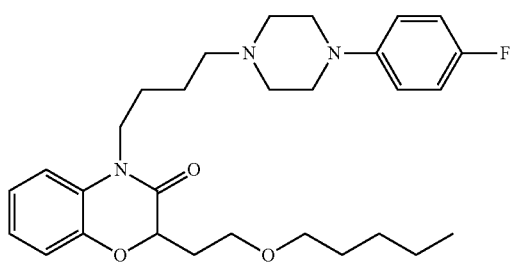<br>Chemical Formula: $C_{29}H_{40}FN_3O_3$<br>Exact Mass: 497.31 | | |
| AZ-110 | 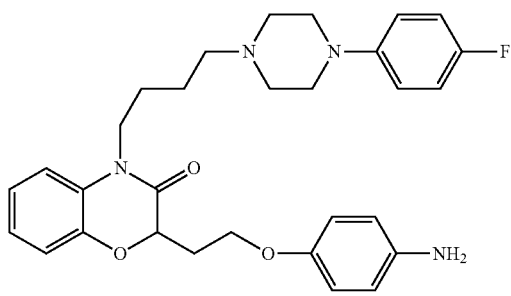<br>Chemical Formula: $C_{30}H_{35}FN_4O_3$<br>Exact Mass: 518.27 | | |
| AZ-112 | 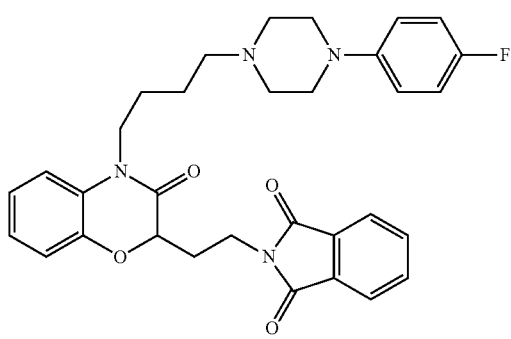<br>Chemical Formula: $C_{32}H_{33}FN_4O_4$<br>Exact Mass: 556.25 | | |

| CMPD | STRUCTURE | Ki (nM) σ₁ | Ki (nM) σ₂ |
|---|---|---|---|
| AZ-113 | 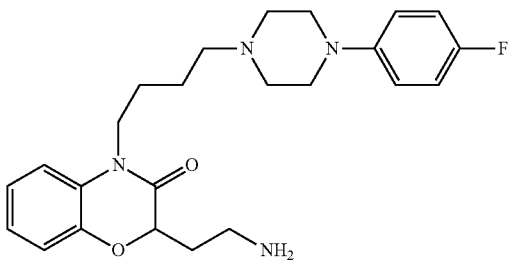<br>Chemical Formula: $C_{24}H_{31}FN_4O_2$<br>Exact Mass: 426.24 | | |
| AZ-114 | 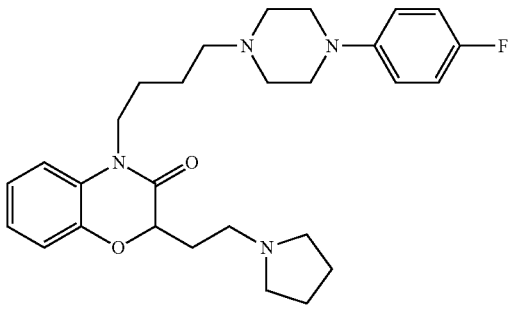<br>Chemical Formula: $C_{28}H_{37}FN_4O_2$<br>Exact Mass: 480.29 | | |
| AZ-115 | 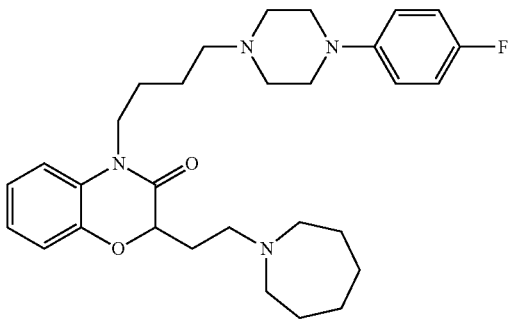<br>Chemical Formula: $C_{30}H_{41}FN_4O_2$<br>Exact Mass: 508.32 | | |
| AZ-116 | 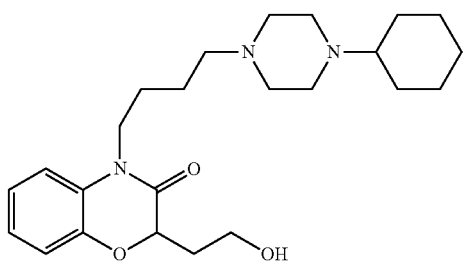<br>Chemical Formula: $C_{24}H_{37}N_3O_3$<br>Exact Mass: 415.28 | | |

| CMPD | STRUCTURE | Ki (nM) σ₁ | Ki (nM) σ₂ |
|---|---|---|---|
| AZ-117 | 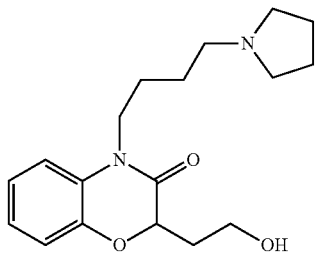<br>Chemical Formula: $C_{18}H_{26}N_2O_3$<br>Exact Mass: 318.19 | | |
| AZ-118 | 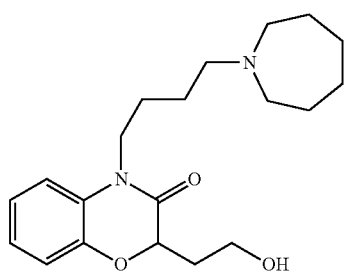<br>Chemical Formula: $C_{20}H_{30}N_2O_3$<br>Exact Mass: 346.23 | | |
| AZ-119 | 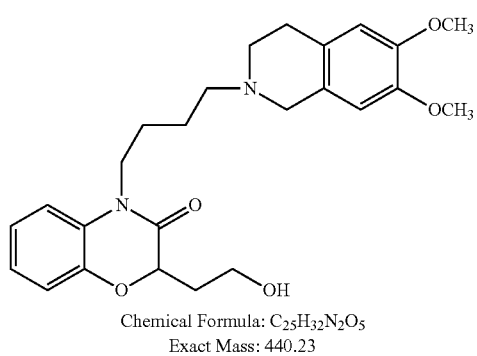 [SMILES: COc1cc2c(cc1OC)CN(CCCCN1C(=O)C(CCO)Oc3ccccc31)CC2]<br>Chemical Formula: $C_{25}H_{32}N_2O_5$<br>Exact Mass: 440.23 | | |
| AZ-120 | 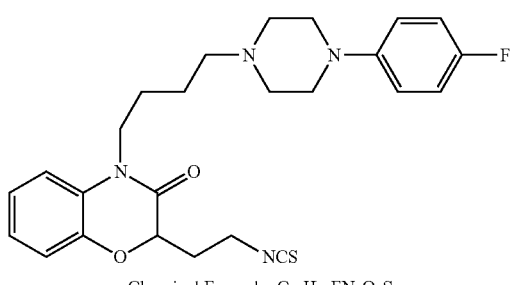<br>Chemical Formula: $C_{25}H_{29}FN_4O_2S$<br>Exact Mass: 468.20 | | |

| CMPD | STRUCTURE | Ki (nM) σ₁ | Ki (nM) σ₂ |
|------|-----------|------------|------------|
| AZ-121 | Chemical Formula: $C_{26}H_{33}FN_4O_3$<br>Exact Mass: 468.25 | | |
| AZ-122 | Chemical Formula: $C_{24}H_{29}F_2N_3O_3$<br>Exact Mass: 445.22 | | |
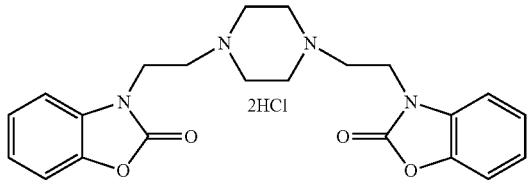
| CMPD | STRUCTURE |
|------|-----------|
| AZ-9 | Chemical Formula: $C_{22}H_{26}Cl_2N_4O_4$<br>Exact Mass: 480.13 |
| AZ-8 | Chemical Formula: $C_{30}H_{42}Cl_2N_4O_4$<br>Exact Mass: 592.26 |
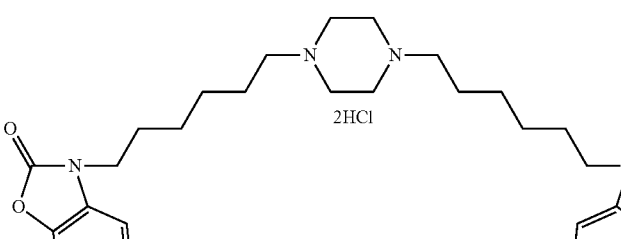

-continued
| CMPD | STRUCTURE |
|---|---|
| AZ-10 | 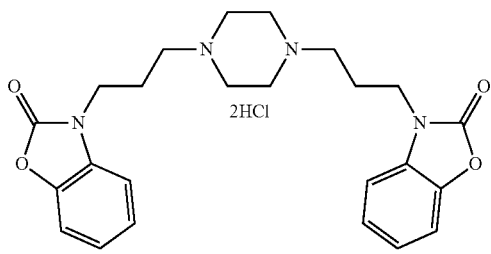
Chemical Formula: $C_{24}H_{30}Cl_2N_4O_4$
Exact Mass: 508.16 |
| AZ-16 | 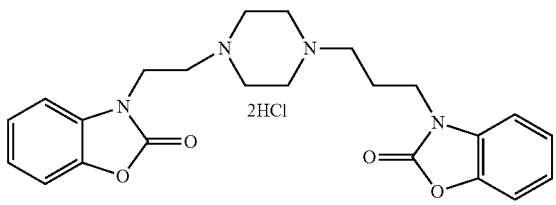
Chemical Formula: $C_{23}H_{28}Cl_2N_4O_4$
Exact Mass: 494.15 |
| AZ-2 | 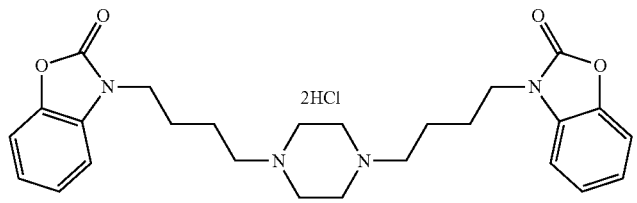
Chemical Formula: $C_{26}H_{34}Cl_2N_4O_4$
Exact Mass: 536.20 |
| AZ-17 | 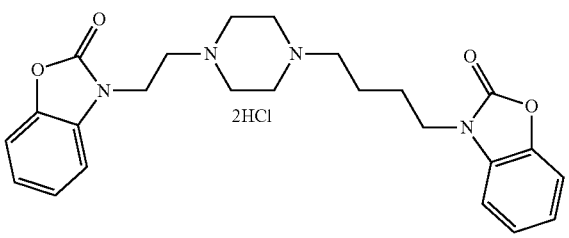
Chemical Formula: $C_{24}H_{30}Cl_2N_4O_4$
Exact Mass: 508.16 |
| AZ-7 | 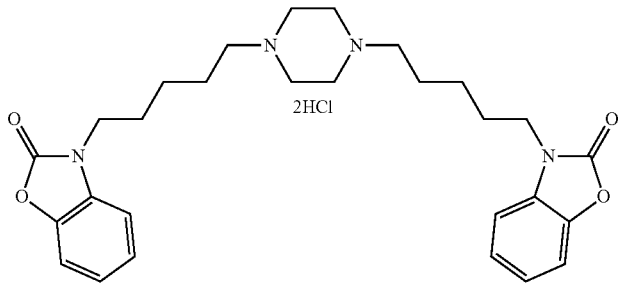
Chemical Formula: $C_{28}H_{38}Cl_2N_4O_4$
Exact Mass: 564.23 |

| CMPD | STRUCTURE |
|---|---|
| AZ-18 | 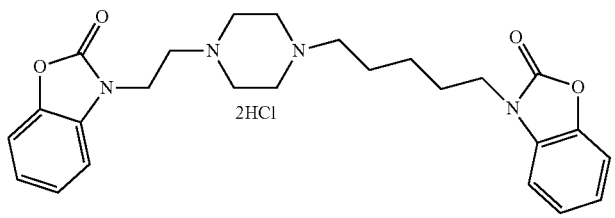<br>Chemical Formula: $C_{25}H_{32}Cl_2N_4O_4$<br>Exact Mass: 522.18 |

The present invention comprises a method of treating a subject for alleviation of the effects on the subject resulting from drug intake or drug abuse by the subject comprising administering to the subject a therapeutically effective amount of at least one compound according to the invention.

The drug abuse or drug intake can result from methamphetamine intake or methamphetamine abuse by the subject or from cocaine abuse or cocaine intake by the subject.

The present invention further comprises a method of treating a subject having a need for therapy involving sigma receptors comprising administering to the subject an effective amount of at least one compound of the present invention and additionally comprises treating a subject to prevent neurotoxic effects resulting from drug abuse or drug intake by the subject comprising administering to the subject a therapeutically effective amount of at least one compound according to the invention.

The invention further comprises radioligand compositions comprising at least one compound according to the invention wherein at least one compound contains a radioactive element.

Pharmaceutical compositions according to the invention are those which are suitable for enteral, such as oral, administration and for parenteral, such as subcutaneous, administration to warm-blooded animals, especially humans, and which contain the pharmacologically active substance on its own or together with a pharmaceutically acceptable carrier. The dosage of the active substance depends on the species of warm-blooded animal and on the age and individual condition, the illness to be treated and also on the mode of administration. Such dosage can be readily determined by those practicing in the relevant art area.

The novel pharmaceutical preparations contain from approximately 10% to approximately 95%, and preferably from approximately 20% to approximately 90%, of the active substance. Pharmaceutical compositions according to the invention can, for example, be in unit dose form, such as dragees, tablets, capsules, suppositories or ampoules.

The pharmaceutical compositions of the present invention are manufactured in a manner known per se, for example, by means of conventional mixing, granulating, confectioning, dissolving or lyophilizing processes. Pharmaceutical compositions for oral use can be obtained by combining the active substance with one or more solid carriers, if desired, granulating a resulting mixture and processing the mixture or granulate, if desired or necessary after the addition of suitable adjuncts, to form tablets or dragee cores. In so doing, they can also be incorporated into plastics carriers which release the active substances or allow them to diffuse in controlled amounts.

Suitable carriers are especially fillers such as sugars, for example, lactose, saccharose, mannitol or sorbitol, cellulose preparations and/or calcium phosphates, for example, tricalcium phosphate or calcium hydrogen phosphate, also binders such as starches, for example, corn, wheat, rice or potato starch, gelatine, tragacanth, methylcellulose, hydroxypropylmethylcellulose, sodium carboxymethylcellulose and/or polyvinylpyrrolidone, and/or, if desired, disintegrators such as the above-mentioned starches, also carboxymethyl starch, cross-linked polyvinylpyrrolidone, agar, alginic acid or a salt thereof such as sodium alginate. Adjuncts are especially flow-regulating and lubricating agents, for example, silica, talc, stearic acid or salts thereof such as magnesium or calcium stearate, and/or polyethylene glycol. Dragee cores are provided with suitable coatings that are, if desired, resistant to gastric juice, there being used, inter alia, concentrated sugar solutions which optionally contain gum arabic, talc, polyvinylpyrrolidone, polyethylene glycol and/or titanium dioxide, lacquer solutions in suitable organic solvents or solvent mixtures or, for the manufacture of coatings that are resistant to gastric juice, solutions of suitable cellulose preparations such as acetylcellulose phthalate or hydroxypropylmethylcellulose phthalate. Coloring substances or pigments can be added to the tablets or dragee coatings, for example for the purpose of identification or for indicating different doses of active substance.

Other orally administrable pharmaceutical compositions are dry-filled capsules made of gelatin and also soft, sealed capsules made of gelatin and a plasticizer such as glycerol or sorbitol. The dry-filled capsules may contain the active ingredient in the form of a granulate, for example, in admixture with fillers such as corn starch, binders and/or glidants such as talc or magnesium stearate and optionally stabilizers. In soft capsules, the active ingredient is preferably dissolved or suspended in suitable liquids or wax-like substances such as fatty oils, paraffin oil or polyethylene glycols, it is possible also for stabilizers to be added.

Other forms of oral administration are, for example, syrups prepared in a customary manner that contain the active ingredient in, for example, suspended form in a concentration that provides a suitable single dose when administered.

Further suitable dosage forms for parenteral administration are sterile aqueous solutions of an active ingredient in water-soluble form, for example, a water-soluble salt, or sterile aqueous injection suspensions which contain substances increasing the viscosity, for example, sodium, carboxymethyl cellulose, sorbitol and/or dextran, and optionally stabilizers. In addition, the active ingredient, with or without adjuvants, can also be in lyophilized form and brought into solution prior to parenteral administration by the addition of suitable solvents.

The invention also relates to a method of treatment of pathological conditions in a mammal, especially human, which as has been described hereinabove, which method comprises administering, a therapeutically effective amount of a compound of the formula I or of a pharmaceutically acceptable salt thereof.

DETAILED DESCRIPTION OF THE RADIOLIGAND INVENTION

The present invention relates to radioligands selective for sigma-1 receptors (σ-1 receptors) compounds useful as sigma receptors of the following formula III':

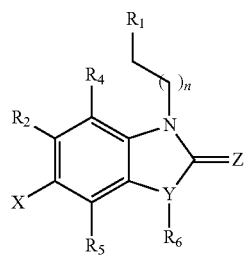

III'

$R_1$ can be an optionally substituted nitrogen-containing heterocycle radical, such as, for example, radicals of optionally substituted piperidines, optionally substituted piperazines, optionally substituted tetrahydropyridines, optionally substituted azepanes, tertiary amines (cyclic or acyclic), isoindoline-1,3-dione, or optionally substituted tetrahydroisoquinolones (aromatically substituted): $R_{2,4,5,6}$ can each independently be any one or combinations of the following moieties, such as, for example, hydrogen, cyano, nitro, acyl, alkyl, amido, azido, isothiocyanate, isocyanate anilino (unsubstituted or substituted), halogens (such as fluorine, chlorine, bromine and iodine), ethers, sulfonamides, thioacyl, nitro, aromatic, heterocyclic, olefinic, acetylenic, deuterium, or tritium; Y can be S, Z can be either H, O, S, S—or NR. R groups can be either H, aryls, alkyls, or cycloalkyls, "n" can be 1 to 5 carbons in length and stereoisomers, analogs, and pharmaceutically acceptable salts thereof as well as compositions comprising said compounds. The moiety bridging $R_1$ and N in the formula II can be a substituted $C_1$-$C_6$ alkylene, $C_1$-$C_6$ alkenylene wherein the alkylene group can have inserted into its chain a $C_3$-$C_5$ cycloalkyl group, aromatic, and heterocyclic group and wherein X is $C_1$-$C_4$ radiohaloalkyl.

The present invention relates to a still yet further series of compounds useful as sigma receptors of the following formula IV':

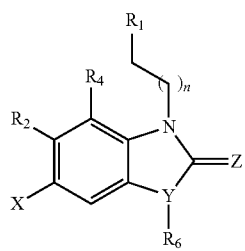

IV'

$R_1$ can be an optionally substituted nitrogen-containing heterocycle radical such as for example, radicals of optionally substituted piperidines, optionally substituted piperazines, optionally substituted tetrahydropyridines, optionally substituted azepanes, tertiary amines (cyclic or acyclic), isoindoline-1,3-dione, or optionally substituted tetrahydroisoquinolones (aromatically substituted): $R_{2,4,6}$ can each independently be any one or combinations of the following moieties, such as, for example, hydrogen, cyano, nitro, acyl, alkyl, amido, azido, isothiocyanate, isocyanate anilino (unsubstituted or substituted), halogens (such as fluorine, chlorine, bromine and iodine), ethers, sulfonamides, thioacyl, nitro, aromatic, heterocyclic, olefinic, acetylenic, deuterium, or tritium; Y is S. Z can be either H, O, S, S—or NR. R groups can be either H, aryls, alkyls, or cycloalkyls. "n" can be 1 to 5 carbons in length and stereoisomers, analogs, and pharmaceutically acceptable salts thereof as well as compositions comprising said compounds. The moiety bridging $R_1$ and N in the formula IV can be a substituted $C_1$-$C_6$ alkylene having the formula —(CHRx-($CH_2$)—$CH_2$)— wherein the —CHRx- moiety is attached to $R_1$ and the alkylene group can have inserted into its chain a $C_3$-$C_5$ cycloalkyl group, aromatic, and heterocyclic group and wherein the Rx is a $C_1$-$C_5$ straight chain or branched chain alkyl or a $C_1$-$C_4$ straight chain or branched chain haloalkyl; X is $C_1$-$C_4$ radiohaloalkyl.

Additionally the present invention further comprises a method of preparing a compound according to formulas III', IV', V', VI', VII', XII' or XIII' comprising radio-halogenating a compound according to formulas III', IV', V', VI', VII', XII' or XIII' wherein X is an alkyl tosylate in the presence of a polar aprotic solvent.

The present invention further relates to compounds useful as sigma receptors of the following formula V':

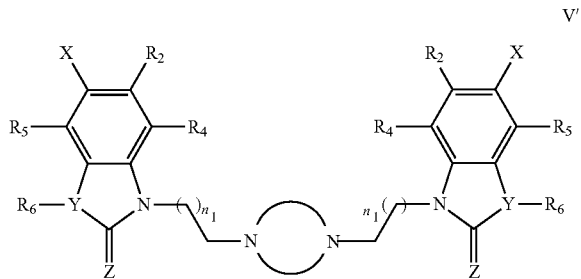

V'

$R_{2,4,5,6}$ can each independently be any one or combinations of the following moieties, such as, for example, hydrogen, cyano, nitro, acyl, alkyl, amido, azido, isothiocyanate, isocyanate anilino (unsubstituted or substituted), halogens (such as fluorine, chlorine, bromine and iodine), ethers, sulfonamides, thioacyl, nitro, aromatic, heterocyclic, olefinic, acetylenic, deuterium, or tritium; Y is S. Z can be either H, O, S, S—or NR. R groups can be either H, aryls, alkyls, or cycloalkyls. "n" can be 1 to 5 carbons in length and stereoisomers, analogs, and pharmaceutically acceptable salts thereof as well as compositions comprising said compounds. The $R_1$ bridging moiety in the formula V can be an optionally substituted $C_1$-$C_6$ alkylene, $C_1$-$C_6$ alkenylene or $C_1$-$C_6$ alkynylene group wherein the alkylene group can have inserted into its chain a $C_3$-$C_5$ cycloalkyl group, aromatic, and heterocyclic group. X is $C_1$-$C_4$ radiohaloalkyl.

DETAILED DESCRIPTION

Synthesis and In Vitro Binding of CM304

The cold ligand was prepared according to Scheme 6. Compounds 10 and 11 were synthesized using known procedures.[50] The fluoro compound was then successfully prepared from 11 via a halogen exchange using t-butylammonium fluoride and potassium fluoride. The fluorinated intermediate 12 was finally alkylated with 2-(hexamethyleneimino)ethylchloride in the presence of potassium carbonate in DMF to give 3-(2-(azepan-1-yl)ethyl)-6-(3-fluoropropyl)benzo[d]thiazol-2(3H)-one (13, CM304).

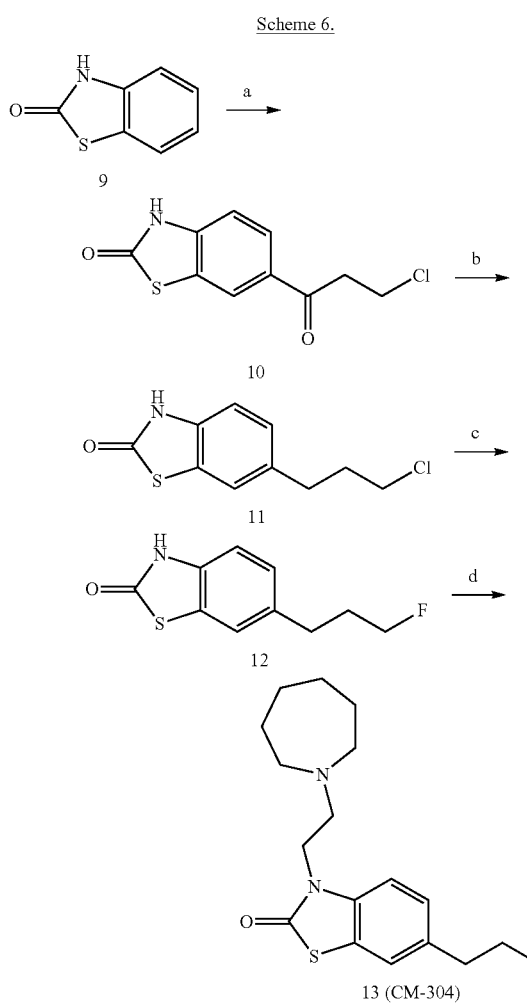

Reagents and conditions: (a) 3-Chloropropionyl chloride, AlCl$_3$, DMF, 85° C.; (b) Et$_3$SiH, CF$_3$COOH, rt; (c) KF, TBAF, reflux; (d) 2-(hexamethyleneimino)ethylchloride, K$_2$CO$_3$, DMF, 55° C.

The experimental pKa (10.4) of CM304 was determined to be slightly higher than the calculated pKa value (9.36) while the experimental Log P O/W±SD−0.15±0.05 was significantly lower than the calculated Log P value (5.02). The experimental Log D PBS, pH 7.4±SD was measured to be 1.45±0.04 (n=6). CM304 was subjected to radioligand binding assays, as previously described,[50] and found to demonstrate high affinity (Ki=2.5 pM) and superior selectivity for σ-1 receptors (>145,000-fold selectivity for sigma-1 compared to sigma-2 receptors). Moreover, in a NovaScreen and in-house profile of 59 targets, CM304 displayed >100,000-fold selectivity for σ-1 receptor compared to other tested targets. CM304 exhibited >50% displacement of the radioligand at a 10,000 nM screening concentration and <20% displacement at a 100 nM screening concentration for nine targets, including: α2-adrenoceptors; histamine H2 receptors; muscarinic M2 receptors; peripheral muscarinic receptors; neuronal (α-bungarotoxin insensitive) nicotinic receptors; norepinephrine transporters; calcium L type channels; sodium, site 2 channels; acetylcholine esterase, suggesting it had 10,000-fold greater selectivity for sigma-1 compared to these targets.

Radiochemistry

The design strategy for generating [$^{18}$F] FTC-146 involved the preparation of a tosylate precursor 17 and its subsequent radiolabeling with fluorine-18 (Scheme 2). Compound II was reacted with benzoic acid to give 14 which was then alkylated with 2-(hexamethyleneimino) ethylchloride. Hydrolysis of the intermediate 15 yielded the corresponding alcohol 16. The tosylate precursor was then prepared by reacting the alcohol with p-toluenesulfonyl chloride in the presence of triethylamine. [$^{18}$F]FTC-146 was successfully synthesized via nucleophilic substitution using an automated GE TRACERlab FX-FN radiosynthesis module. Fluorine-18 (half life=109.8 min) radiolabeling was accomplished by reaction of tosylate precursor (17) with cyclotron-produced $^{18}$F-fluoride as an $^{18}$F-labeled Kryptofix-222/K+/[$^{18}$F]F-complex in dimethylsulfoxide at 150° C. for 15 min. Semi-preparative reverse-phase HPLC of the crude reaction mixture afforded [$^{18}$F]FTC-146 in 3.7±1.9% yield (n=13) at end of bombardment (EOB), in >99% radiochemical purity (RCP), with a specific activity (SA) of 3.9±1.9 Ci/μmol (EOB) in a total synthesis time of 75 min. The formulated version of [$^{18}$F]FTC-146 in saline/ethanol (9:1, total 10 mL) was shown to be stable for at least 5.5 hours via analytical reverse-phase HPLC.

Cell Uptake Studies

Figure 16:
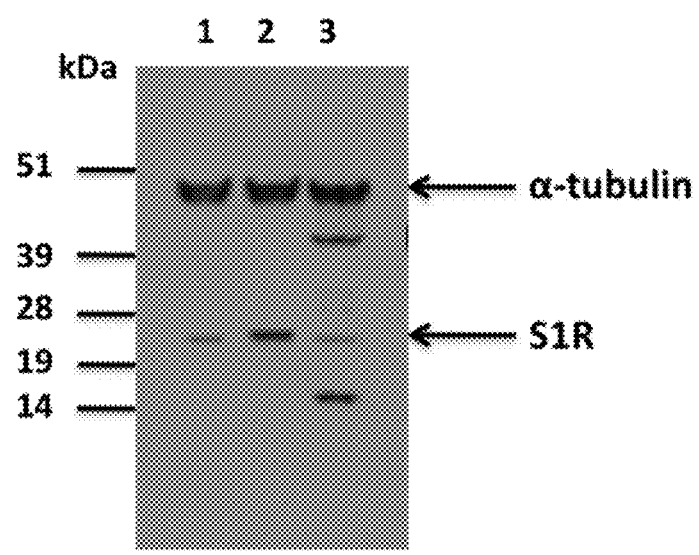
FIG. 16—Western blot analysis of σ-1 receptor expression in CHO cells. Western blot analysis of Sigma-1 receptor (σ-1 receptor) expression in control CHO cells, CHO cells transfected with σ-1 receptor cDNA, and a positive control cell line (JAR cells) known to contain σ-1 receptor protein. Cell lysates (50 ug of protein) were subjected to gel electrophoresis followed by immunoblot analysis with σ-1 receptor specific antibody S-18 (400:1). Lane 1: control CHO cells (transfected with empty σ-1 receptor vector); lane 2: CHO cells over-expressing σ-1 receptor (transfected with vector containing σ-1 receptor cDNA); and lane 3.

Uptake of [$^{18}$F]FTC-146 in Chinese hamster ovarian (CHO) cells was compared to the uptake of the known σ-1 receptor ligand (+)-[$^3$H] pentazocine. Control CHO cells (transfected with a vector not containing the σ-1 receptor gene—to serve as a negative control) and CHO cells transfected with a vector containing σ-1 receptor cDNA (to serve as a positive control for σ-1 receptor expression in cells) were used for the uptake assays. Cells were exposed to [$^{18}$F]FTC-146 or (+)-[$^3$H] pentazocine for 30 and 120 min (triplicate for each time point). The incubated cells were subsequently washed, lysed and counted for radioactivity. All collected data were normalized for amount of protein present in each well. Data for both uptake assays (FIG. 15) showed there was a small increase in uptake for both radioligands between 30 and 120 min in control CHO cells. This increase was more pronounced in CHO cells transfected with σ-1 receptor cDNA, and numerically higher at both 30 and 120 min compared with negative control CHO cells. The uptake of [$^{18}$F]FTC-146 in cells transfected with σ-1 receptor cDNA was 4-fold higher than uptake in control CHO cells at 120 min. This difference was 3.6-fold for (+)-[$^3$H] pentazocine uptake studies (FIG. 16).

Western Blot

Figure 2:
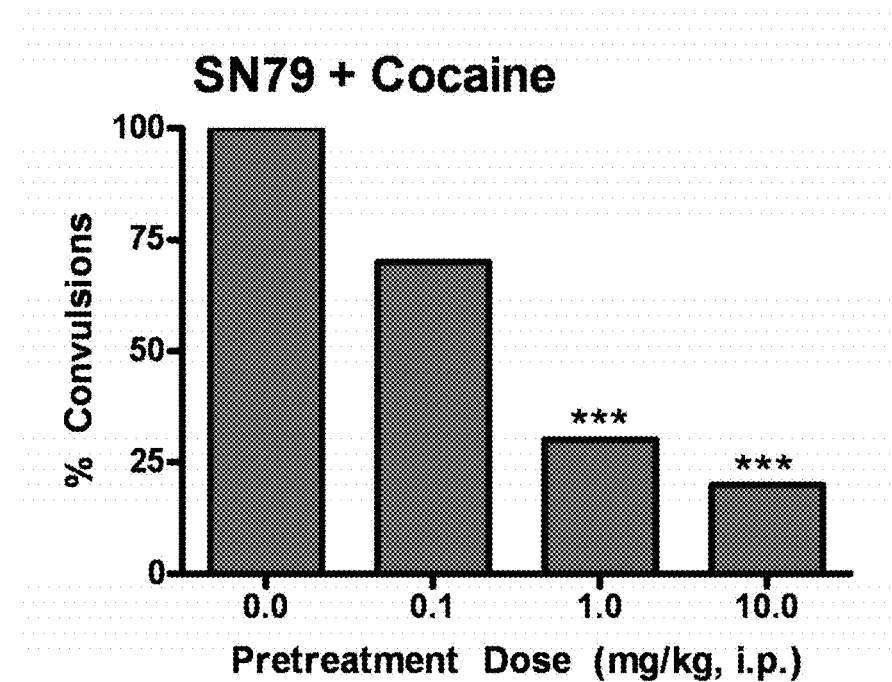
FIG. 2—SN79 attenuates the convulsive effects of cocaine (***P<0.005)
Figure 3:
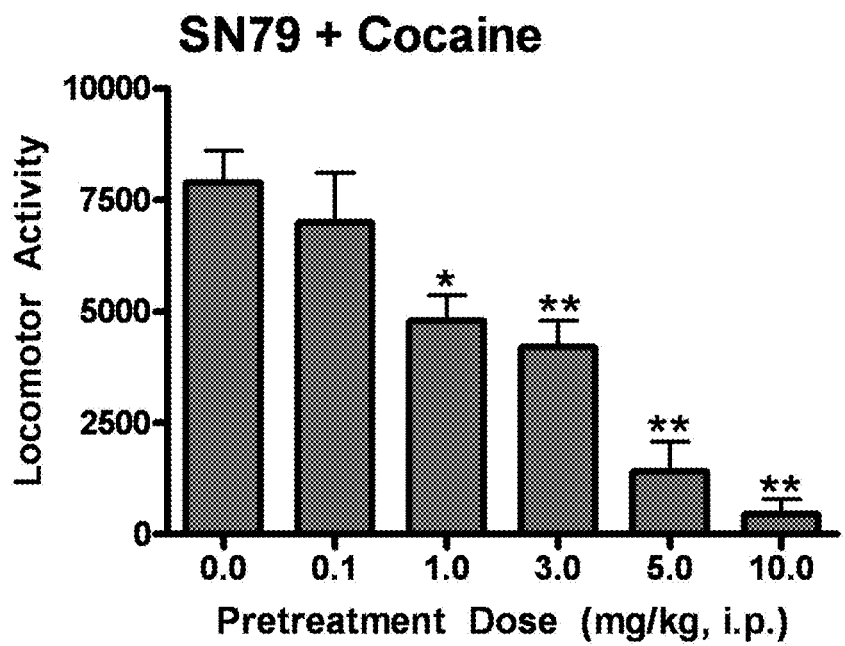
FIG. 3—SN79 pretreatment attenuates cocaine-induced locomotor activity (*P<0.05, **P<0.01)
Figure 4:
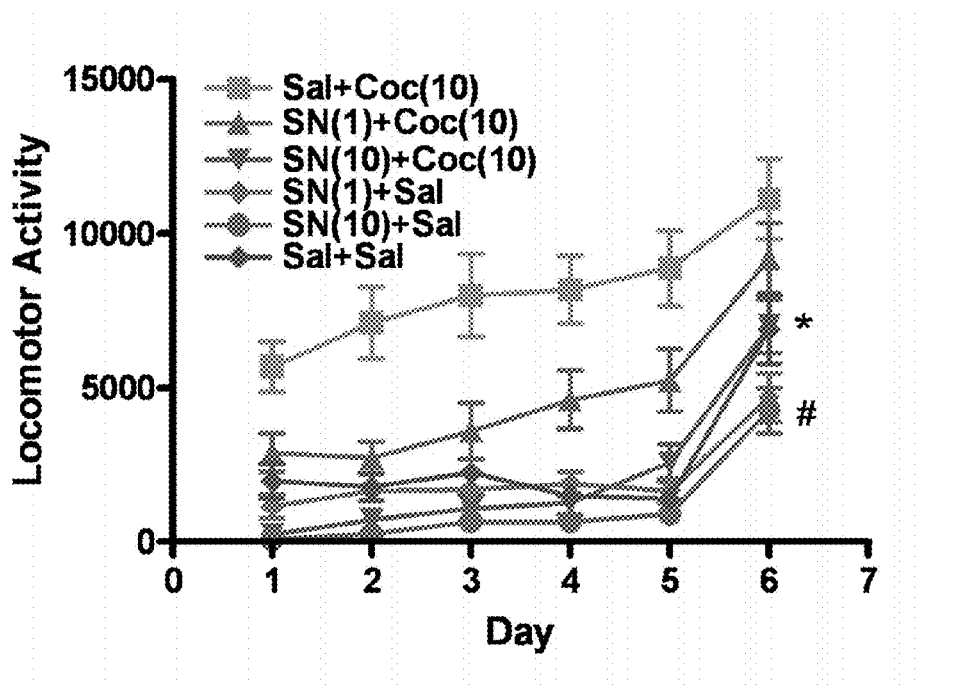
FIG. 4—SN79 pretreatment attenuates the development of cocaine-induced sensitization (*P<0.05, #P<0.05)

Western blot analysis was performed using the computer program Image J (image processing and analysis software in Java) and showed that the level of σ-1 receptor expression in the CHO cells transfected with the σ-1 receptor cDNA was approximately 4.3 times greater than that found in the control CHO cells that had been transfected with an empty vector (FIG. 3).

In Vitro Metabolite Studies in Mouse Serum

The percentage of intact [$^{18}$F] FTC-146 in mouse serum was assessed over time via HPLC. It was found that the percentage of intact [$^{18}$F]FTC-146 remained at 100% throughout the entire time course of the study (5-120 min).

PET Imaging in Mice

The in vivo kinetics of [$^{18}$F] FTC-146 in normal mice were assessed using small animal PET. Dynamic brain PET scanning was commenced one minute prior to administration of [$^{18}$F] FTC-146 and terminated 62 minutes later. FIG. 17 shows the same coronal and sagittal PET slices from one of the baseline mouse studies summed over 0-5 minutes, 20-25 minutes and 52-62 minutes. These images provide visual evidence that [$^{18}$F] FTC-146 rapidly crossed the blood brain barrier and began to slowly wash out over the course of the imaging study. There was also accumulation in the snout and spine that increased over time.

Figure 5:
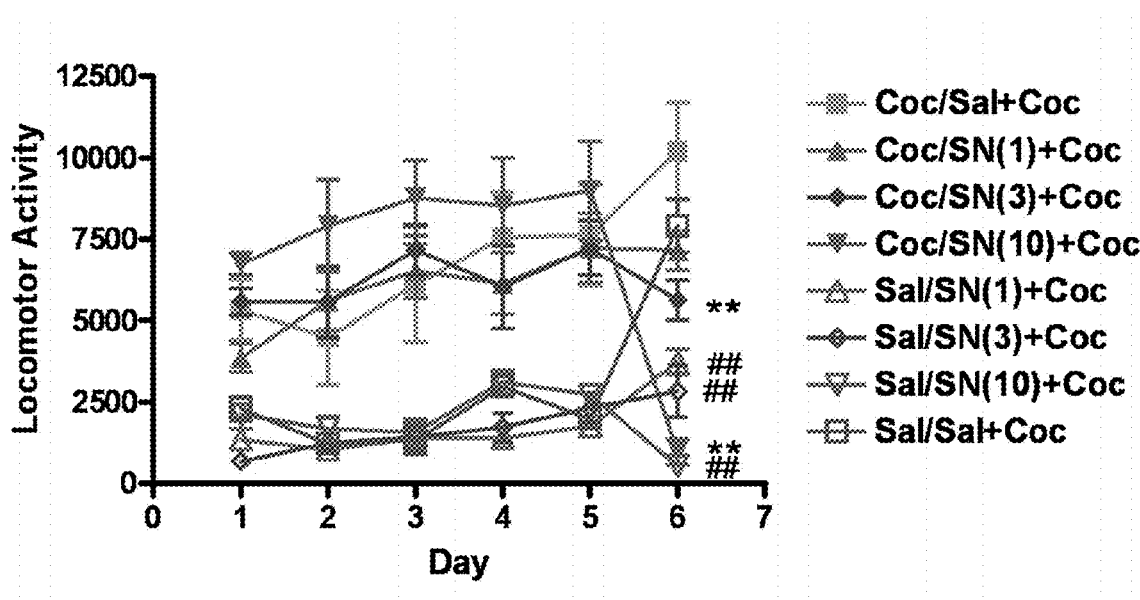
FIG. 5—SN79 pretreatment attenuates the expression of cocaine-induced sensitization (**P<0.05 vs sensitized, ##P<0.05 vs acute cocaine)

Graphs depicting uptake of [$^{18}$F] FTC-146 in the whole mouse brain as a function of time for baseline and blocking studies are displayed in FIG. 5. The baseline time activity curve (TAC) (FIG. 18) demonstrated that [$^{18}$F] FTC-146 entered the brain rapidly, peaked within the first few minutes and then gradually decreased over the remaining time of the scan; however, it did not completely wash out of the brain over the duration of scanning. Pre-treatment with CM304 (1 mg/kg) 10 minutes prior to radioligand administration reduced the binding of [$^{18}$F]FTC-146 in the brain at 60 min by 83% (FIG. 18).

In Vitro Half-Life Studies in Mouse and Rat Liver Microsomes

The metabolic stability of CM304 was evaluated in mouse and rat liver microsomes. First, CM304 was incubated in the presence of an NADPH-generating system at 37° C. for 60 min in test tubes. The reaction was initiated by adding cofactors and quenched at designated time points (0, 5, 10, 15, 30, 45, 60 min) by the addition of an equal volume of ice-cold acetonitrile (ACN). CM304 was found to have a half-life of 4.2 min. with a clearance of 0.55 mL/min./g in mouse and a half-life of 12.6 minutes with a clearance of 0.18 mL/min/g in rat.

Pharmacological Challenge in Mice

CM304 was evaluated for its ability to inhibit/attenuate cocaine-induced convulsions (associated with cocaine overdose) by pre-treating normal mice with either saline or CM304 (0.001, 0.01, 0.1, 1.0 or 10 mg/kg i.p.) 15 minutes prior to administering cocaine (70 mg/kg, i.p.). Subjects were continuously monitored for the onset of convulsions up to 30 min following administration of cocaine. Fisher's exact tests indicated that the following doses of CM304 significantly attenuated cocaine-induced convulsions: 0.001 mg/kg (p<0.005), 0.01 mg/kg (p<0.005), 0.1 mg/kg (p<0.05), 1 mg/kg (p<0.05), 10 mg/kg (p<0.005).

The present invention further comprises a method of differentiating between sigma-1 and sigma-2 receptors in a subject comprising using PET and an imaging agent wherein the imaging agent comprises at least one sigma 1 receptor ligand according to formulas III', IV', V', VI', VII', XII' or XIII'.

Since σ-1 receptors are intimately associated with numerous human cancers, neurodegenerative diseases, and psychiatric conditions, 10 radioligands specific for σ-1 receptors have the potential to serve as novel diagnostic tools and may be useful in assessing treatment effectiveness. The present study describes the synthesis and radiolabeling of a new σ-1 receptor PET radioligand together with its preliminary in vitro and in vivo characterization using cell uptake studies, metabolic stability tests and PET imaging of mice.

CM304 (13) was successfully synthesized (Scheme 6) and found to demonstrate high affinity (Ki=2.5 pM) and superior selectivity for σ-1 receptors (>145,000-fold selectivity for σ-1 receptors compared to σ-2 receptors) when compared to its parent, SN56. These results demonstrated that the small structural modification made to SN56 in order to form CM304 led to an improvement in affinity and selectivity for σ-1 receptors. In fact, both the affinity and selectivity of CM304 are higher than the values reported for other known σ-1 receptor ligands reported in. The results from the NovaScreen profile further confirm the ultra selective nature of CM304.

Radiosynthesis of [$^{18}$F] FTC-146 was achieved by nucleophilic aliphatic radiofluorination of compound 17 (Scheme 7). In this type of reaction the use of a polar aprotic solvent is mandatory in order to take advantage of the nucleophilicity of the $^{18}$F anion. In addition, factors such as precursor concentration, reaction temperature and time can be crucial in influencing the final radiochemical yield (RCY), and thus need to be considered. In the present study, DMSO (a commonly used solvent in this type of labeling reactions) was chosen as the polar aprotic solvent. Since heating the reaction (precursor concentration 1 mg/mL) at 150° C. for 15 minutes afforded high purity product in sufficient yields/quantities (2-5%, 1-5 mCi/mL) for preliminary in vitro and in vivo investigations no further optimizations were pursued at this stage.

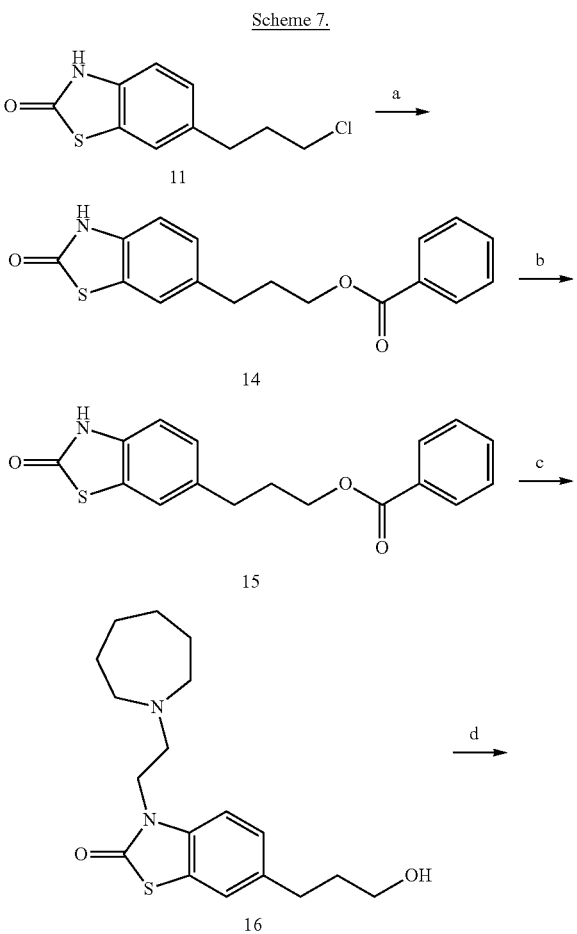

Scheme 7.

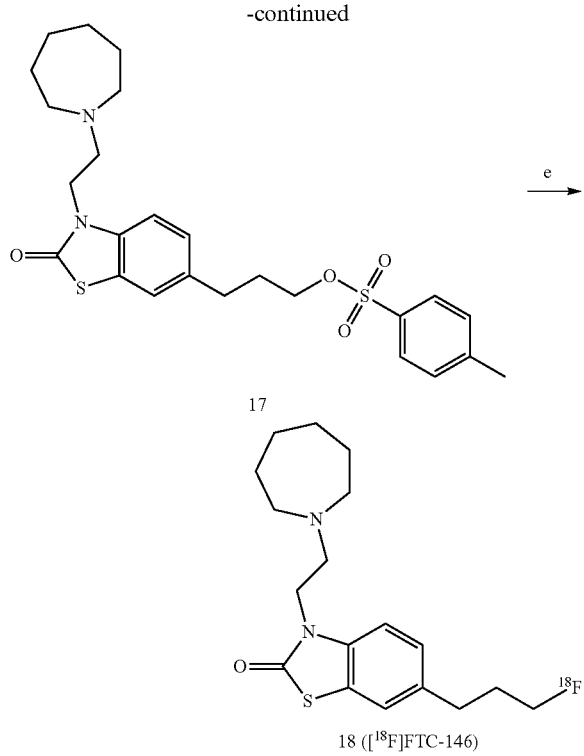

18 ([¹⁸F]FTC-146)

Reagents and conditions: (a) Benzoic acid, K₂CO₃, DMF, 110° C.; (b) (2-hexamethyleneimino)ethylchloride, K₂CO₃, DMF, 65° C.; (c) NaOH, H₂O, MeOH, reflux; (d) p-toluenesulfonyl chloride, Et₃N, DCM, rt; (e) Kryptofix-222/K⁺/[¹⁸F]F⁻, DMSO, 150° C.

It is typical to differentiate between sigma-1 and sigma-2 receptors using benzomorphan-type opiates such as the well known selective σ-1 receptor ligand [³H](+)-pentazocine.[51] For this reason applicant selected [³H](+)-pentazocine as the "gold standard" σ-1 receptor ligand to compare with our new σ-1 receptor ligand [¹⁸F]FTC-146 in cell uptake studies using transfected CHO cells. Results obtained from our cell uptake studies demonstrated the ability of [¹⁸F]FTC-146 to bind σ-1 receptors in CHO cells in a comparable fashion to that of [³H] (+)-pentazocine. The small increase in [¹⁸F] FTC-146 and [³H](+)-pentazocine uptake in control CHO cells between 30 and 120 minutes (FIG. 15) is supported by the Western blot results (FIG. 16) which confirmed the presence of low levels of σ-1 receptor in CHO cells prior to introducing σ-1 receptor cDNA. Uptake of [¹⁸F]FTC-146 in CHO cells transfected with σ-1 receptor cDNA compared to control CHO cells at 120 min (FIG. 15) was 4-fold higher. This was comparable to the 3.6 fold greater uptake of [³H](+)-pentazocine in CHO cells transfected with σ-1 receptor cDNA compared to control CHO cells at 120 min, indicating that [¹⁸F]FTC-146 behaves similarly to [³H](+)-pentazocine and that it may be a more sensitive marker of σ-1 receptor levels. Western blot results verified the level of [¹⁸F]FTC-146 uptake in cell assays (at 120 min) correlated to the level of σ-1 receptor protein levels and therefore highlight its potential as a radioligand for accurately identifying and visualizing σ-1 receptors.

Through stability studies in mouse serum applicant found that [¹⁸F]FTC-146 remained 100% intact over a 120 minute period. This demonstrated that [¹⁸F]FTC-146 was stable in mouse serum in vitro, and although did not account for the possibility of liver metabolism, implied that it should be stable in mice in vivo.

Following these encouraging in vitro cell uptake and serum stability results, the in vivo kinetics and binding of this radio fluorinated ligand were evaluated in living, normal mice using small animal PET. The brain of each mouse was positioned in the center field of view (FOV) for each study as σ-1 receptors are known to be abundantly present in various parts of the brain[7] (predominantly in cortical regions, thalamus, striatum and cerebellum),[43] and thus was thought to be a suitable region of interest for evaluating the kinetics and binding profile of our new radioligand.

PET images of [¹⁸F] FTC-146 in anesthetized mice show high uptake of the radioligand in the brain and also spine (FIG. 17). Baseline TACs (FIG. 18) showed that [¹⁸F]FTC-146 rapidly crossed the blood brain barrier (BBB), reaching a maximum uptake of ~17% ID/g within the first few minutes, followed by a slow decline in uptake levels throughout the remainder of the scan to a level of 6% ID/g at 60 min. Pre-treating mice with CM304 (1 mg/kg) 10 minutes prior to radioligand administration led to a marked reduction of [¹⁸F] FTC-146 binding in the brain (83% reduction at 60 min) (FIG. 5). These results indicated that [¹⁸F]FTC-146 accumulation in mouse brain most likely represents specific σ-1 receptor binding. The initial spike in radioligand uptake shown in the blocking TAC data is typical of blocking studies and is due to the unlabeled compound (in this case CM304) occupying the peripheral σ-1 receptor sites thus creating a situation whereby an additional bolus of the radioligand from the periphery is available to cross the BBB, only to discover it has no free receptors to bind to, and subsequently washes out of the brain in a rapid manner.

Although [¹⁸F]FTC-146 is yet to be evaluated alongside other fluorinated σ-1 receptor radioligands, its initial kinetics (i.e., rapid uptake in mouse brain within the first few minutes) appear similar to that reported in [¹⁸F] FM-SA4503 and [¹⁸F]fluspidine in normal mice.[44,49] However the binding profile of [¹⁸F] FTC-146 in mouse brain at later time points is quite different from the reported uptake levels for other known σ-1 receptor radioligands at corresponding times. For example [¹⁸F] FTC-146 reached its maximum uptake in mouse brain within the first few minutes of imaging and then gradually began to wash out of the brain to a level 65% of its maximum at 60 minutes post injection, whereas [¹⁸F]FM-SA4503 and reached its maximum uptake in the brain at 30 minutes post injection and did not experience significant washout over the remainder of the study (120 minutes post injection). Biodistribution studies with [¹⁸F] fluspidine demonstrated that it reached maximum uptake in the mouse brain at 30 minutes post injection and then washed out to a level 81% of its maximum at 60 minutes post injection. Uptake levels of [¹⁸F] SFE and [¹⁸F] FPS in living mice have not been reported in the literature and thus applicant was unable to visually compare the kinetics of [¹⁸F] FTC-146 with them at present, however the fact that [¹⁸F]FTC-146 displayed relatively fast in vivo binding kinetics suggests it might not have the same irreversible binding problems as [¹⁸F]FM-SA4503 and [¹⁸F] SFE.

Although there was some observed bone uptake in the mouse [¹⁸F]CM304 PET studies (likely due to defluorination), bone uptake has also been reported in studies using [¹⁸F]FM-SA4503[44] and [¹⁸F] fluspidine,[49] the former of which was postulated to be due to high levels of σ-1 receptors in highly proliferative tissues (e.g. bone marrow), and the latter of which was shown through biodistribution studies to be present in both mouse bone and bone marrow.

Currently there are no suitable treatments for cocaine overdose and none of the routinely used anti-convulsants are capable of attenuating cocaine-induced seizures. Since it has been shown that σ-1 receptor antagonists can block the affects of cocaine,[33] applicant evaluated our non-radioactive compound, CM304, for its ability to prevent cocaine-induced convulsions. In vivo cocaine studies were pursued with male, Swiss Webster mice. The pretreated animals were cocaine-challenged (70 mg/kg, i.p.) 15 min after intraperotineal administration of saline or CM304 (0.001 mg/kg-10 mg/kg). The subjects were continuously monitored for the next 30 min for the onset of convulsions. Similar to other putative σ-1 receptors antagonists, CM304 significantly attenuated cocaine-induced convulsions at all doses examined ($P<0.05$, data not shown). This data is consistent with other reported sigma-1 antagonists.

In conclusion, applicant successfully prepared a new, ultra selective $^{18}$F-labeled σ-1 receptor ligand, [$^{18}$F] FTC-146 that demonstrates specific binding to σ-1 receptors in cells and mice making it a promising new candidate for visualizing σ-1 receptors in living subjects. The unlabeled compound, CM304 might also be useful in treating cocaine overdose.

EXPERIMENTAL SECTION

General

For the reported radiochemistry, semi-preparative HPLC separations were performed on Dionex 680 pump with KANUR UV detector K-2001 (for purification of [$^{18}$F]FTC-146). Analytical HPLC was performed on Lab Alliance with Model 500 UV detector. Radioactivity in HPLC eluates was detected with a model 105S single-channel radiation detector (Carroll & Ramsey Associates). (+)-[$^{3}$H] Pentazocine was purchased from NEN Life Science Products (Boston, Mass.). If not otherwise stated, chemicals were purchased from commercial sources and were used without further purification. All PET imaging was performed on a microPET R4 model scanner (Siemens) fitted with a computer-controlled bed, 10.8 cm transaxial and 8 cm axial field of view (FOV), no septa and operated exclusively in 3-dimensional list mode. MicroPET images were reconstructed with 2-dimensional OSEM (Ordered Subsets Expectation Maximization) and analyzed using AMIDE (A Medical Image Data Examiner) software.[52] For metabolite studies an Agilent 1200 HPLC system with Autosampler and Gabi radioactivity detector (Raytest) was used.

The UPLC system, consisted of Water's Acquity UPLC (Milford, Mass., USA) equipped with a binary solvent manager, vacuum degasser, thermostatted column compartment, and an Autosampler. Chromatographic separations were performed on a Waters Acquity UPLC™ BEH C18 column (1.7 μm, 2.1×50 mm). For the metabolism studies an isocratic method was developed using the mobile phase consisted of 0.1% formic acid in water:0.1% formic acid in methanol (50:50, v/v). For the metabolite separation, a linear gradient method was developed with a mobile phase containing 0.1% formic acid in water (A) and 0.1% formic acid in ACN (B). The linear gradient elution program was as follows: 0-80% B over 6 min, followed by an isocratic hold at 80% B for another 4 min. At 10 min, B was returned to 0% in 2 min and the column was equilibrated for 3 min before the next injection. The total run time for each injection was 15 min. The flow rate was 0.2 mL/min. The column temperature was maintained at 25° C. and the injection volume was 10 μL.

The mass spectrophotometer consisted of a Waters Micromass Quattro Micro™ triple-quadrupole system (Manchester, UK). The system was controlled by MassLynx software version 4.0. Ionization was performed in the positive electrospray mode. The MS/MS parameters for the analysis were as follows: capillary voltage 4.95 kV, cone voltage 31 V, extractor voltage 5V, RF lens voltage 0.5V. The source and desolvation temperatures were 110° C. and 400° C., respectively, and the desolvation and cone gas flows were 252 and 76 L/hr, respectively. The selected mass-to-charge (m/z) ratio transition of CM304 ion [M+H]+ used in the single ion recording (SIR) was m/z 337.03 The dwell time was set at 500 ms.

Animals

All experimental procedures involving animals were performed under humane conditions following approval from the Stanford University or University of Mississippi animal research internal review board. Animals had access to food and H$_2$O ad libitum and were kept under a 12 h light/dark cycle.

Materials. Reagents and starting materials were obtained from commercial suppliers and were used without purification. Pre-coated silica gel GF Uniplates from Analtech were used for thin-layer chromatography (TLC). Column chromatography was performed on silica gel 60 (Sorb ent Technologies). $^1$H and $^{13}$C NMR spectra were obtained on a Bruker APX400 at 400 and 100 MHz, respectively. The high resolution mass spectra (HRMS) were recorded on a Waters Micromass Q-Tof Micro mass spectrometer with a lock spray source. The mass spectra (MS) were recorded on a WATERS ACQUITY Ultra Performance LC with ZQ detector in ESI mode. Chemical names were generated using ChemDraw Ultra (CambridgeSoft, version 10.0). The calculated pKa and log P were determined using PALLAS 3.1.2.4 Software from CompuDrug Chemistry, Ltd (Sedona, Ariz. USA).

6-(3-chloropropanoyl)benzo[d]thiazol-2(3H)-one (10). Dimethylformamide (8.6 mL, 115 mmol) was slowly added to aluminum chloride (53.3 g, 400 mmol) under vigorous stirring. After 15 min. of stirring, 2-hydroxybenzothiazole (6.04 g, 40 mmol) was added, and the mixture was brought to 45° C. After 15 min, 3-chloropropionyl chloride (5.8 mL, 60 mmol) was added and the reaction mixture was heated at 85° C. for 3 h. The hot mixture was then carefully poured onto ice, and the crude product was collected by filtration. The solid was dissolved in ethyl acetate and water was added. The layers were then separated and, the organic layer was washed with brine and dried. The solvent was removed in vacuo, and the residue was recrystallized from toluene/dioxane to give 5.15 g (54%) of 6-(3-chloropropanoyl)benzo[d]thiazol-2(3H)-one as a orange solid. $^1$H NMR (DMSO-d6): δ 12.26 (br s, 1H), 8.24 (d, J=1.4 Hz, 1H), 7.90 (dd, J=8.4, 1.7 Hz, 1H), 7.19 (d, J=8.4 Hz, 1H), 3.91 (t, J=6.4 Hz, 2H), 3.50 (d, J=6.3 Hz, 2H). $^{13}$C NMR (DMSO-d6): δ 195.07, 170.37, 140.49, 130.94, 126.89, 123.77, 123.25, 111.19, 40.38, 39.52. MS (EI) m/z 242 (M+−1).

6-(3-chloropropyl)benzo[d]thiazol-2(3H)-one (11). Triethylsilane (4.2 mL, 26 mmol) was added to a stirred solution of 10 (2.73 g, 11.3 mmol) in trifluoroacetic acid (15 mL) and the reaction mixture was stirred for 4 h at room temperature. The solvent was removed in vacuo, and the residue was purified by chromatography on a silica gel column using a gradient of petroleum ether/ether (7:3 to 5:5) as the eluent and recrystallized from toluene/hexanes to give 3 g (72%) of 6-(3-chloropropyl)benzo[d]thiazol-2(3H)-one as a white solid. $^1$H NMR (DMSO-d6): δ 11.76 (br s, 1H), 7.38 (s, 1H), 7.10 (d, J=8.0 Hz, 1H), 7.03 (d, J=8.0 Hz, 1H), 3.59 (t, J=6.4 Hz, 2H), 2.68 (t, J=7.4 Hz, 2H), 1.99 (qu, J=7.2 Hz, 2H). $^{13}$C NMR (DMSO-d6): δ 169.89, 135.12, 134.45, 126.53, 123.40, 122.13, 111.31, 44.52, 33.75, 31.79. MS (EI) m/z 226 (M+−1).

6-(3-fluoropropyl)benzo[d]thiazol-2(3H)-one (12). A mixture of 11 (0.3 g, 1.32 mmoles), KF (0.23 g, 3.95 mmoles) and TBAF (1M in THF, 3.95 mL, 3.95 mmoles) in THF (10 mL) was heated at reflux for 4 h. After completion of the reaction, the reaction mixture was partitioned between ethyl acetate and water, and the organic layer was washed with brine and dried. The solvent was removed in vacuo, and the residue was purified by chromatography on a silica gel column using petroleum ether/ether (8:2) as the eluent to give 0.096 g (35%) of 6-(3-fluoropropyl)benzo[d]thiazol-2 (3H)-one as a white solid. $^{1}$H NMR (CDCl$_{3}$): δ 10.33 (br s, 1H), 7.23 (s, 1H), 7.10 (s, 2H), 4.45 (dt, J=47.2, 5.8 Hz, 2H), 2.76 (t, J=7.6 Hz, 2H), 2.00 (dquint, J=25.2, 6.8 Hz, 2H). $^{13}$C NMR (CDCl$_{3}$): δ 173.26, 136.39, 133.69, 126.83, 124.09, 122.13, 111.79, 82.77 (d, J=164.2 Hz), 32.13 (d, J=19.7 Hz), 31.01 (d, J=5.2 Hz). MS (EI) m/z 210 (M+−1).

3-(2-(azepan-1-yl)ethyl)-6-(3-fluoropropyl)benzo[d]thiazol-2(3H)-one hydrochloride (13, CM304). K$_{2}$CO$_{3}$ (0.18 g, 1.28 mmol) and 2-(hexamethyleneimino)ethylchloride hydrochloride (0.08 g, 0.40 mmol) were added, under mechanical stirring, to a solution of 12 (0.09 g, 0.42 mmol) in anhydrous DMF (2 mL). The reaction mixture was heated at 55° C. for 2 h. After cooling, the mixture was poured into 10 mL of water, extracted with ethyl acetate (3×20 mL), washed with saturated aqueous NaCl and dried. The solvent was removed in vacuo, and the residue was purified by chromatography on a silica gel column using methylene chloride/methanol (9.5:0.5) as the eluent. 3-(2-(azepan-1-yl)ethyl)-6-(3-fluoropropyl)benzo[d]thiazol-2(3H)-one was isolated as a hydrochloride salt (white solid, 0.12 g, 80%) by addition of HCl/dioxane. $^{1}$H NMR (D$_{2}$O): δ 7.34 (br s, 1H), 7.26-7.24 (m, 1H), 7.16-7.14 (m, 1H), 4.46 (dt, J=47.2, 4.5 Hz, 1H), 4.28 (t, J=4.8 Hz, 2H), 3.49-3.37 (m, 6H), 2.70-2.66 (m, 2H), 1.97-1.66 (m, 11H). $^{13}$C NMR (D$_{2}$O): δ 173.02 (C=O), 137.92 (Cq), 133.68 (Cq), 127.31 (CHar), 122.67 (CHar), 122.09 (Cq), 110.90 (CHar), 84.33 (d, J=157.6 Hz, CH2), 55.23 (CH2), 53.46 (CH2), 37.47 (CH2), 31.34 (d, J=18.8 Hz, CH2), 30.30 (d, J=5.5 Hz, CH2), 25.61 (CH2), 23.37 (CH2). HRMS (EI) calcd for C$_{18}$H$_{26}$N$_{2}$OFS [M+H]+ 337.1750, found 337.1764.

3-(2-oxo-2,3-dihydrobenzo[d]thiazol-6-yl)propyl benzoate (14). K$_{2}$CO$_{3}$ (5.31 g, 38.4 mmol) and benzoic acid (9.38 g, 76.8 mmol) were added, under mechanical stirring, to a solution of 11 (3.5 g, 15.4 mmol) in anhydrous DMF (250 mL). The reaction mixture was heated at 110° C. for 6 h. After cooling, the mixture was poured into 100 mL of a 2.5 N HCl solution in water, extracted with ethyl acetate (3×70 mL), and the organic phase was washed with brine. The solvent was dried and removed in vacuo and the residue was chromatographed on a silica gel column using a gradient of petroleum ether/ethyl ether (4:6 to 6:4) as the eluent. The product was then recrystallized in toluene to give 2.97 g (62%) of 3-(2-oxo-2,3-dihydrobenzo[d]thiazol-6-yl)propyl benzoate as a white solid. $^{1}$H NMR (DMSO-d6): δ 11.70 (br s, 1H), 7.91 (d, J=7.6 Hz, 2H), 7.63 (t, J=7.5 Hz, 1H), 7.49 (t, J=7.6 Hz, 2H), 7.41 (s, 1H), 7.12 (d, J=8.1 Hz, 1H), 7.02 (d, J=8.1 Hz, 1H), 4.25 J=6.3 Hz, 2H), 2.71 (t, J=7.4 Hz, 2H), 2.03-1.97 (m, 2H). $^{13}$C NMR (DMSO-d6): δ 170.00, 165.70, 135.77, 134.42, 133.22, 129.76, 129.10, 128.64, 126.58, 123.44, 122.18, 111.34, 64.02, 31.34, 29.93. MS (EI) m/z 312 (M+−1).

3-(3-(2-(azepan-1-yl)ethyl)-2-oxo-2,3-dihydrobenzo[d]thiazol-6-yl)propyl benzoate (15). K$_{2}$CO$_{3}$ (0.75 g, 5.47 mmol) and 2-(hexamethyleneimino)ethylchloride hydrochloride (0.47 g, 2.37 mmol) were added, under mechanical stirring, to a solution of 14 (0.57 g, 1.82 mmol) in anhydrous DMF (10 mL). The reaction mixture was heated at 65° C. for 2 h. After cooling, the mixture was poured into 80 mL of water, extracted with ethyl acetate (3×60 mL), and the combined organic layers were washed with brine and dried. The solvent was removed in vacuo, and the residue was chromatographed on a silica gel column using diethyl ether as the eluent to give 0.72 g (90%) of 3-(3-(2-(azepan-1-yl)ethyl)-2-oxo-2,3-dihydrobenzo[d]thiazol-6-yl)propyl benzoate as a colorless oil. A sample was isolated as a hydrochloride salt for analysis. $^{1}$H NMR (DMSO-d6): δ 11.29 (br s, 1H), 7.92 (d, J=8.4 Hz, 2H), 7.66-7.57 (m, 3H), 7.50 (t, J=7.6 Hz, 2H), 7.28 (d, J=8.0 Hz, 1H), 4.43-4.40 (m, 2H), 4.27 (t, J=6.0 Hz, 2H), 3.44-3.18 (m, 6H), 2.77 (t, J=7.2 Hz, 2H), 2.06-1.56 (m, 10H). $^{13}$C NMR (DMSO-d6): δ 168.74 (CO), 165.52 (CO), 136.68 (Cq), 134.23 (Cq), 133.07 (CHar), 129.59 (Cq), 128.92 (CHar), 128.50 (CHar), 126.78 (CHar), 122.45 (CHar), 121.44 (Cq), 111.36 (CHar), 63.83 (CH2), 53.62 (CH2), 52.05 (CH2), 37.02 (CH2), 31.10 (CH2), 29.72 (CH2), 25.58 (CH2), 22.88 (CH2). HRMS (EI) calcd for C$_{25}$H$_{31}$N$_{2}$O$_{3}$S [M+H]+ 439.2055, found 439.2056.

3-(2-(azepan-1-yl)ethyl)-6-(3-hydroxypropyl)benzo[d]thiazol-2(3H)-one (16). To a solution of 15 (0.67 g, 1.53 mmol) in methanol (10 mL) was added a solution of sodium hydroxide (0.15 g, 3.84 mmol) in water (10 mL). The mixture was heated at 90° C. for 1 h, concentrated in vacuo, poured into 1N HCl (20 mL) and extracted with ethyl acetate (10 mL). The pH of the aqueous layer was adjusted to 10 with potassium carbonate and the mixture was extracted with ethyl acetate (3×20 mL). The combined organic layers were washed with brine, dried and evaporated. The residue was chromatographed on a silica gel column using methylene chloride/methanol (9.7:0.3) as the eluent to give 0.47 g (92%) of 3-(2-(azepan-1-yl)ethyl)-6-(3-hydroxypropyl)benzo[d]thiazol-2(3H)-one as a white solid. A sample was isolated as a hydrochloride salt for analysis. $^{1}$H NMR (DMSO-d6): δ 11.35 (br s, 1H), 7.46 (d, J=1.2 Hz, 1H), 7.36 (d, J=8.4 Hz, 1H), 7.50 (dd, J=8.0, 1.2 Hz, 1H), 4.31 (t, J=6.8 Hz, 2H), 3.80 (br s, 2H), 3.53 (s, 1H), 3.39-3.29 (m, 6H), 2.60 (t, J=7.6 Hz, 2H), 1.79 (br s, 4H), 1.68 (qu, J=8.0 Hz, 2H), 1.58 (br s, 4H). $^{13}$C NMR (DMSO-d6): δ 170.04 (CO), 138.34 (Cq), 134.45 (Cq), 127.41 (CHar), 122.92 (CHar), 121.91 (Cq), 111.58 (CHar), 60.26 (CH2), 54.60 (CH2), 53.07 (CH2), 37.70 (CH2), 34.50 (CH2), 31.47 (CH2), 25.99 (CH2), 23.58 (CH2). HRMS (EI) calcd for C$_{28}$H$_{27}$N$_{2}$O$_{2}$S [M+H]+ 335.1793, found 335.1786.

3-(3-(2-(azepan-1-yl)ethyl)-2-oxo-2,3-dihydrobenzo[d]thiazol-6-yl)propyl 4-methyl benzenesulfonate (17). A solution of p-toluenesulfonyl chloride (0.24 g, 1.26 mmol) in methylene chloride (10 mL) was slowly added to a solution of 16 (0.38 g, 1.15 mmol) and triethylamine (0.16 mL, 2.42 mmol) in methylene chloride (20 mL). The mixture was stirred for 3 days at room temperature and the solvent was evaporated. The residue was purified by chromatography on a silica gel column using a gradient of methylene chloride/methanol (10:0 to 9.7:0.3) as the eluent to give 0.5 g (89%) of 3-(3-(2-(azepan-1-yl)ethyl)-2-oxo-2,3-dihydrobenzo[d]thiazol-6-yl)propyl 4-methyl benzenesulfonate as a pale yellow oil. $^{1}$H NMR (DMSO-d6): δ 7.78 (d, J=8.4 Hz, 2H), 7.46 (d, J=8.4 Hz, 2H), 7.30 (s, 1H), 7.20 (d, J=8.4 Hz, 1H), 7.08 (d, J=8.0 Hz, 1H), 4.00-3.93 (m, 4H), 2.71 (t, J=6.8 Hz, 2H), 2.59-2.55 (m, 6H), 2.41 (s, 3H), 1.88-1.85 (m, 2H), 1.45 (br s, 8H). $^{13}$C NMR (DMSO-d6): δ 168.36, 144.68, 135.24, 135.11, 132.32, 129.98, 127.41, 126.45, 122.10, 121.25, 111.11, 69.77, 54.84, 54.21, 40.64, 30.13, 29.80, 27.93, 26.27, 20.95. MS (EI) m/z 489 (M++1).

Radiosynthesis of [$^{18}$F]FTC-146 (18). No carrier added-aqueous [$^{18}$F]fluoride ion was produced on a PETtrace cyclotron (GE Healthcare, Sweden) by irradiation of a 1.6 mL water target using a 16 MeV proton beam on 95% enriched [$^{18}$O]H$_2$O by the [$^{18}$O(p,n)18F] nuclear reaction. [$^{18}$F]Fluoride in [$^{18}$O]H$_2$O was transferred to a GE TRAC-ERIab FX-FN synthesizer and passed through an anion exchange resin (QMA cartridge in carbonate form, prepared by washing with 1 mL EtOH and 1 mL of water) under vacuum. Trapped [$^{18}$F]fluoride ions were then eluted from the QMA cartridge and transferred to the reactor using an eluent solution containing 3.5 mg of K$_2$CO$_3$ and 15 mg of Kryptofix 222 (K222: 4,7,13,16,21,24-hexaoxa-1,10-diazabicyclo [8.8.8] hexacosan) in acetonitrile (0.9 mL) and water (0.1 mL) mixture. The solution was then evaporated at 65° C. under helium flow and vacuum, followed by heating at 88° C. under vacuum. Tosylate precursor 8, 3-(2-oxo-3-(2-(piperidin-1-yl)ethyl)-2,3-dihydrobenzo[d]thiazol-6-yl) propyl 4-methylbenzenesulfonate (1 mg) was dissolved in dimethylsulfoxide (0.5 mL) and added to the dry Kryptofix-222/K$^+$[$^{18}$F]F$^-$ complex. The mixture was allowed to react at 150° C. for 15 minutes. Upon completion, the reaction mixture was diluted with sterile water (8 mL) and passed through a C18 Sep-Pak cartridge. The C18-trapped-radiolabelled-product was then eluted from the C18 Sep-Pak with ACN (1.5 mL) and sterile water (1.5 mL). The resulting crude mixture was then injected onto two serial HPLC Phenomenex Gemini C-18, 5 µm (10×250 mm) semi-preparative reversed-phase column. Using a mobile phase of H$_2$O (0.1% TEA): ACN (0.1% TEA), (pH=8): (20/80, v:v), and with a flow rate of 5.0 mL/min, the retention time (tR) of [$^{18}$F]FTC-146 was 13 min. The radioactive fraction corresponding to [$^{18}$F]FTC-146 was collected in a round bottom flask containing sterile water (15 mL) and then passed through a C18 Sep-Pak. A further 10 mL of sterile water was passed through the C18 Sep-Pak. The trapped, purified radiolabelled product was eluted from the C18 Sep-Pak using ethanol (1 mL) and saline (9 mL) The formulated solution was then filtered through a sterile 13 mm Millipore GV 0.22 µm filter into a sterile pyrogen free evacuated 30 mL vial. Solutions in saline containing no more than 10% ethanol by volume were used for the studies described in this article.

Quality Control of [$^{18}$F]FTC-146

For determination of specific activity and radiochemical and chemical purity, an aliquot of the final solution of known volume and radioactivity was injected onto an analytical reversed-phase HPLC column (Phenomenex Gemini C18 5 µm (4.6×250 mm). A mobile phase of H$_2$O (0.1% TEA): ACN (0.1% TEA): (20:80; v:v) at a flow rate of 1.0 mL/min was used to elute [$^{18}$F]FTC-146 with a retention time (tR) of 8.33 min. The area of the UV absorbance peak measured at 254 nm. corresponding to the carrier product was measured (integrated) on the HPLC chromatogram and compared to a standard curve relating mass to UV absorbance.

Determination of pKA for CM304

The pKa of CM304 was determined using the potentiometric titration method. A solution of 0.01 M sodium hydroxide was prepared and the pH measured as 11.9. Similarly, 0.01 M hydrochloric acid solution was prepared and the pH measured as 2.07. To 50 mL of a 1 mM CM304 solution, 0.1 mL volumes of sodium hydroxide were added and pH recorded (Mettler Toledo SevenEasy™ pH meter S20) until the pH of the solution became constant. To the same sample, 0.1 mL portions of hydrochloric acid were added and pH recorded until it became constant. A titration curve was then plotted as pH versus the volume of base/acid added. The intersection point of these two curves was noted as the pKa value of CM304.

Determination of Partition Coefficient (Log P) for CM304

Using the Shake-flask method, 47 n-Octanol and water/PBS, pH 7.4 (equal quantity) were added to a glass vial (25 ml). The contents were sealed and stirred continuously for 24 h at 25° C. to achieve mutual saturation of the phases. Water/PBS, pH 7.4 phase was brought into a vessel together with a Teflon-coated magnetic stirring bar. The n-octanol phase containing the known quantity of test substance was poured very carefully on top of the aqueous phase in order to avoid emulsion formation as far as possible. The vessel was not shaken; instead the system was stirred for an extended period of time (at least 36 h) allowing equilibrium to be reached. The contents were allowed to separate on standing and then centrifuged. An aliquot of the aqueous layer was taken and diluted (1000 times) for quantitative analysis by UPLC/MS/MS.

In Vitro Radioligand Binding Assays

Competition binding assays were performed as previously described. Briefly, radioligands were used to tag the targeted sites under standard conditions. CM304 was evaluated at a screening concentration of 10,000 nM. If <50% displacement was observed, then the results are reported as Ki>10,000 nM. For assays run by NovaScreen, a single additional screening concentration of CM304 was tested at 100 nM. For full competition binding assays which were run in-house, 10 concentrations of CM304 were tested to generate IC50 values, which were converted to Ki values using the Cheng Prusoff equation.

Cell Uptake Studies Using Transfected

Cells CHO cells were grown in Ham's F-12 medium. For uptake studies CHO cells were transfected using Lipofectamine 2000 (Invitrogen, Carlsbad, Calif., USA) and either pcDNA (empty vector, negative control) or σ-1 receptor gene (OPRS1, accession number NM_005866.2, origin, Rockville, Md., USA) following manufacturer's directions. The cells were harvested and 2×10$^5$ cells were seeded per well in 24 well plates. Twenty-four hours later, CHO cells were transfected with either 0.8 µg pcDNA (empty vector, control), or 0.8 µg sigma-1 DNA. Media was refreshed 12 hours later. Twenty-four hours after the initial transaction, Ham's F-12 medium was prepared containing enough [$^{18}$F]FTC-146 for 2 µCi per well. After 30 and 120 minutes uptake, medium from each of the triplicate wells was aspirated and cells were washed twice with cold PBS (500 µL). Following this, cells were lysed with 1 N NaOH (500 µL). A portion of each lysate (250 µL) was transferred to a glass tube and activity was measured with a Cobra II γ counter (Packard-Perkin Elmer, Waltham, Mass., USA). Protein content from each well was measured by Bradford assay. The same protocol was followed for (+)-[$^3$H]pentazocine, except the activity was measured with a liquid scintillation counter (Beckman Coulter LS 6500, Brea, Calif., USA).

Western Blot

Cell lysates from 1×10$^6$ cells were prepared by scraping cells into ice-cold harvesting buffer (Lysis Buffer). The lysates were boiled for 5 min and supernatants were collected after centrifugation in an Eppendorf microcentrifuge (14,000 rpm, 5 min) at 4° C. The protein concentration of the supernatant was determined by Bradford assay. Equal amounts of protein (50 µg) were loaded onto 10% SDS-polyacrylamide mini-gels and after gel electrophoresis proteins were transferred to a nitrocellulose membrane and blocked at room temperature using 5% non-fat milk blocking buffer (15 ml 1×TBST, 0.01% Tween 20 and 0.75 g milk powder). Following this, the membrane was incubated overnight at 4° C. with goat polyclonal anti-σ-1 receptor ((S-18): sc-22948, Santa Cruz Biotechnology, Inc., Santa Cruz, Calif.) primary antibody. The primary antibody was diluted 1:400 in a 5% non-fat milk blocking buffer. After washing three times with TBST (TBS with 0.01% Tween 20), bovine anti-goat-IgG horseradish peroxidase-conjugated antibody (Santa Cruz Biotechnology, Inc., Santa Cruz, Calif.) diluted 1:5000 in TBST, was added and incubated for 1 h at room temperature. After washing three times with TBST, σ-1 receptor protein was visualized using ECL reagent (Pierce, Rockford, Ill., USA) and images were obtained using film. The blot was also stained for alpha-tubulin as a protein loading control. Image J (image processing and analysis software in Java) was used for western blot analysis.

In Vitro Metabolite Studies in Mouse Serum

Stability of [$^{18}$F]FTC-146 in mouse serum was assessed using a similar technique to that described by Kronauge and colleagues in 1992.[53] To 1 ml mouse serum (previously equilibrated in a 37° C. water bath) applicant added 100 μL of [$^{18}$F]FTC-146 (from a 3-5 mCi/ml formulated solution), vortexed the mixture, and then incubated at 37° C. Aliquots (100 μL) of the radioactive serum mixtures were removed at 5, 15, 30, 60 and 120 minutes and treated with ice cold ACN (200 μL) to stop enzymatic hydrolysis. The samples were cooled on ice and then centrifuged at 2,500 g for 10 min. The supernatant from each sample was separated from the pelleted cells and 100 μL was assessed via analytical HPLC. The percentage ratio of [$^{18}$F]FTC-146 (tR=6.7 min) to the total radioactivity (corrected for decay) on the HPLC chromatogram was calculated as %=(peak area for [$^{18}$F]FTC-146/total peak area)×100. A small volume (50 μl) from each supernatant was removed for activity measurement in a gamma-counter. Pelleted cells were washed once with 0.5 ml ACN and then counted, and the activity in the supernatant was compared to that in the pellet to afford the percentage of the tracer bound to serum proteins.

Small-Animal PET Imaging in Mice

Normal Balb C mice (25-35 g) were anesthetized using isoflurane gas (3% for induction and 2% for maintenance). Acquisition of the PET data in list mode was commenced just prior to i.v. administration of [$^{18}$F]FTC-146 (95-125 μCi in 100 μL 0.9% saline) via the tail vein, and was continued for a period of 62 min. Following dynamic scanning, two subsequent 5 minutes static scans were performed. Blocking studies involved pre-treatment of mice with different doses of CM304 (0.1 mg/kg, 1 mg/kg, 2 mg/kg) ten minutes prior to tracer administration.

In Vitro Half-Life Studies in Mouse and Rat Liver Microsomes

CM304 was incubated in the presence of an NADPH-generating system at 37° C. for 60 min in test tubes. The basic incubation mixture consisted of 5 mM substrate, 1 mg/mL microsomal protein, 3 mM $MgCl_2$, 1 mM NADP, 5 mM glucose-6-phosphate, 1 IU/mL glucose-6-phosphate dehydrogenase, 100 mM Tris HCl buffer (pH 7.4) in a final volume of 1 mL. The reaction was initiated by adding cofactors and quenched at designated time points (0, 5, 10, 15, 30, 45, 60 min) by addition of an equal volume of ice-cold ACN. The mixture was centrifuged at 3000 rpm for 10 min, and the supernatant was analyzed by UPLC/MS/MS.

In Vivo Cocaine Studies

Male Swiss Webster mice were pretreated (i.p.) with saline or CM304 (0.001, 0.01, 0.1, 1.0, or 10 mg/kg) and challenged 15 min later with a convulsive dose of cocaine (70 mg/kg, i.p.). The mice were continuously monitored for the next 30 min for the onset of convulsions, which were operationally defined as the loss of righting reflexes for at least 5 sec. combined with the presence of clonic or tonic limb movements. Fisher's exact tests were used to determine whether there was a significant difference between the ratios of mice exhibiting convulsions and not, at each tested dose.

The examples provided in the present application serve to illustrate the invention, but should not be construed as a limitation thereof.

The present radioligands can be used for radioligand binding assays and PET imaging. The present sigma-1 receptors and radioligands can be applied to both imaging and therapeutics in the following areas related to sigma-1 receptors:

1) Drug addiction (e.g., Cocaine & Methamphetamine) & therapy;[54,55]
2) Sigma-1R as a molecular chaperone to direct specificity of Sigma-1R-related pharmacotherapy;[56]
3) Chronic pain;[57, 58, 59, 60]
4) Cancer;[61,62]
5) Neuroinflammation (especially in cocaine-HIV-related CNS inflammation or pain);
6) Alzheimer's;[63, 64]
7) Parkinson's;[65]
8) Schizophrenia;[66, 67, 68, 69]
9) Major Depression & Anxiety;[70, 71, 72]
10) Multiple Sclerosis;[73] and
11) Obsessive Compulsive Disorder.[74, 75, 76]

The radioligands can be used in an injectable form and can be formulated using sterile injectable formulating media such as, for example, saline or ethanolic saline. Such formulation and the dosage used for imaging can be readily determined by those skilled in the art. The present invention has developed a sigma-1 receptor selective PET imaging agents that can be utilized to visualize peripheral nerve damage (peripheral neuropathy). This can pin-point the exact location of nerve damage to better direct treatment.

An imaging probe was prepared and tested to localize and quantify S1Rs in order to study their implicated role in nociceptive processing and to guide new analgesic therapies to target S1Rs. Here is described the use of [18F]FTC-146, a highly S1R-selective radioligand, for PET-MRI imaging and autoradiography (ARG). Immunohistochemistry (IHC) was also performed to correlate imaging data with S1R levels.

Methods: [18F]FTC-146 was made as disclosed in this application. Sciatic neuropathic pain model was created by left Spared-Nerve Injury (SNI) in adult male rats. Pain behavior was confirmed by performing Von-Frey filament tests at 4 weeks after operation (p<0.03). PETMRI scans of each rat were obtained following administration of [18F]FTC-146 (~500 Ci). Blocking studies involved Haldol pre-block (16 mg/kg IV) 20 min before tracer administration. After PET-MRI, the sciatic nerves were harvested for ARG and IHC analyses. Results: [18F]FTC-146 was made in 5±2% (dc-RCY to EOB) with SR of 6.73.8 Ci/mol (n=27). Higher PET signal (left vs. right nerve) was observed in the SNI group (4.40.9 vs. 1.70.1) but not in the Sham (2.00.3 vs. 1.70.3) or control groups (2.00.4 vs. 1.90.5). Haldol pre-block abolishes the higher signal seen in SNI group. ARG shows 50% higher uptake in the neuroma formed at the site of SNI vs. uninjured right nerve. PET-MRI and ARG results (FIGS. 19A & 19B) correlate well with the S1R localization displayed by IHC studies. Blocking studies suggest that increased uptake in the SNI is due to S1R-specific binding.

Semiquantitative analysis also shows increase in immunostaining in the neuroma vs. uninjured right nerve (FIG. 19C).

Conclusions: PET-MRI and ARG studies showed increased accumulation of [18F]FTC-146 in the SNI vs. sham and control groups. These results correlated well with the levels and localization of S1Rs demonstrated via IHC studies. Thus, [18F]FTC-146 is a promising PET probe for in vivo studies to understand the S1R-mechanism related to pain.

A further aspect of the present invention relates to peripheral nerve injury as a consequence of trauma, surgery, inflammation, and a variety of other causes. Peripheral nerve injury is a major clinical problem resulting in significant morbidity such as chronic pain, weakness, and sensorimotor dysfunction. The accurate identification of sites of nerve injury and ensuing neuroinflammation has tremendous clinical value in the management of nerve injury and regeneration. The sigma-1 receptor (S1R), a molecular chaperone known to play an important role in signaling and neurotransmitter systems, is a potential biomarker of neuroinflammation. In this study, applicant aims to evaluate the utility of a S1R-selective radioligand [$^{18}$F]FTC-146 for detecting increased S1R density in a rat model of nerve injury via positron emission tomography-magnetic resonance imaging (PET-MRI) and ex vivo autoradiography. PET-MR images demonstrated elevated accumulation of [$^{18}$F]FTC-146 in injured nerve (normalized radioligand uptake: 3.64±1.38; n=4) compared to uninjured control nerve (1.44±0.33; n=4; p<0.001). Similarly, high resolution digital autoradiography results of excised nerves and nerve sections show S1R-specific, increased [$^{18}$F]FTC-146 uptake in the neuroma (pixel intensity value: 36.21×10$^3$±3.36×10$^3$; n=2), compared to uninjured nerve (17.37×10$^3$±3.08×10$^3$; n=2; p<0.01). Both PET-MRI and ex vivo autoradiography results correlated with immunostaining of rat nerve/muscle sections, which showed elevated S1R immunoreactivity in the neuroma, but only low levels in the uninjured nerve and adjacent muscle. These results suggest that the S1R can serve as biomarker for detecting nerve injury, and that PET-MRI with [$^{18}$F]FTC-146 enables non-invasive imaging and quantitation of neural S1R levels. To the best of applicant's knowledge, this is the first report of a technique that enables visualization of S1R levels in nerve injury in a living subject. This novel application of S1R-PET-MRI may provide an accurate means of detecting sites of nerve injury, and could therefore ultimately improve the way we manage and treat numerous nerve injury-related conditions.

Peripheral nerve injuries result in sensorimotor dysfunction and lack of autonomic control of the affected body areas, which could lead to chronic pain. Following injury, the microenvironment of the injured nerve is highly regulated by Schwann cells that can rapidly respond to and orchestrate changes within the nerve (102). Schwann cells undergo phenotypic modulation, acquiring the capacity to proliferate, migrate, and secrete soluble mediators that control Wallerian degeneration and regeneration (103). In the SNI rat model, applicant was able to visualize Schwann cell proliferation and increased S1R density at the site of the neuroma. Co-localization of S1Rs with Schwann cells was observed using double immunofluorescence staining, supporting the conclusion that increased S1R expression is associated with peripheral nerve injury and could play an important role in Schwann cell's response. While others have demonstrated the importance of S1R expression in central sensitization in sciatic nerve injury (60), the results of this study is the first demonstration of enhanced S1R expression at the peripheral nerve injury site.

The chemical structure of novel positron emission tomography (PET) radioligand [$^{18}$F] FTC-146 and its affinity for sigma-1 receptor (S1R) versus sigma-2 receptor (S2R), as measured in rat brain in vitro is shown below:

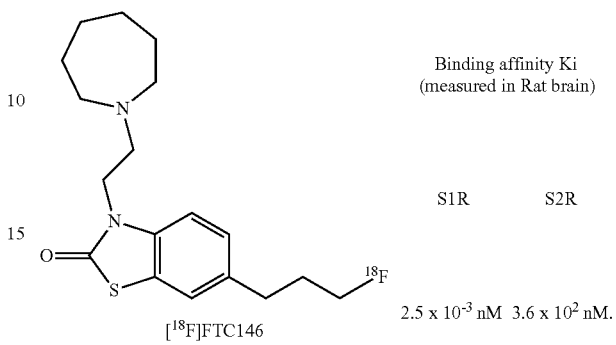

Further, the applicant has been able to show increased S1R density changes in vivo using [$^{18}$F]FTC-146 PET-MRI in a rat nerve injury model. As described previously, [$^{18}$F] FTC-146 binds to S1R with high affinity ($K_i$=2.5×10$^{-3}$ nM, in vitro rat brain) and shows high selectivity (>145,000-fold) for S1R compared to sigma 2 receptor (52R). Moreover, this radioligand has been also evaluated in different species (including rats) for mapping baseline S1R density (James et al, J Nucl Med, submitted). In order to investigate whether [$^{18}$F]FTC-146 accumulation, as shown in autoradiography images of sectioned nerve, corresponds with S1R levels and distribution, S1R-IHC staining was performed. IHC results demonstrated that S1R-immunoreactivity corresponded with radioligand uptake in autoradiography images. [$^{18}$F]FTC-146 uptake in the injured nerves could be blocked to the level of that seen in the uninjured nerves when the SNI animals were pretreated with S1R antagonist, haldoperidol, confirming the specificity of the radiotracer in this disease model. In addition, the radiotracer uptake detected with PET-MRI correlated well with the level of uptake seen in autoradiography of the whole excised nerve. Increased uptake in autoradiography and PET-MRI images at the site of injury also seemed to be directly related to escalated pain sensitivity as observed by Von Frey testing. These collective results indicate specific [$^{18}$F]FTC-146 binding to S1Rs in the nerve injury model and suggest that increased S1R expression is associated with pain generators.

Given the relationship between nerve injury and pain, as well as the connection between S1R antagonism and analgesia, it is possible to further define the role between S1R and pain. [$^{18}$F] FTC-146 PET-MRI, therefore potentially allowing the better understanding of the role and spatiotemporal connection between nerve injury and S1R expression, especially since S1Rs have been known to modulate pain and nociception (92). Absence or antagonism of functional S1Rs results in a marked attenuation of pain behaviors in S1R knockout or animal neuropathic or inflammatory pain models (94, 96, 98). The results of this study have enabled the applicant to identify sites of nerve injury and neuro inflammation that could be responsible for pain generation. Given the fact that there are approximately 116 million Americans suffering from pain costing society on the order of $560 to $635 billion dollars a year (104), there is an obvious clinical need for more accurate and informative medical imaging methods that can reliably assess and localize chronic pain generators. Additionally, by combining the sensitivity of PET with the anatomic localization obtained from co-registering MRI images of the same tissue, this synergistic imaging strategy may be able to detect the subtle changes in molecular targets that could not be previously appreciated using either modality independently.

In conclusion, the applicant has demonstrated that one can detect increased S1R density at the site of nerve injury in a neuropathic pain model via the use of, for example, a novel S1R radioligand ([$^{18}$F] FTC-146) and small animal PET-MRI. This study is, to the best of applicant's knowledge, the first to: 1) evaluate S1R levels in an injured peripheral nerve, 2) demonstrate the feasibility of imaging S1Rs in an animal model of nerve injury, and 3) highlight the potential of S1R-PET imaging as a non-invasive biomarker of nerve injury and inflammation. The powerful synergy of high sensitivity PET, using S1R-specific [$^{18}$F] FTC-146, with the excellent tissue contrast of MRI could provide a more informative means to non-invasively localize peripheral pain generators. The present invention further comprises the use of S1 specific compounds such as disclosed herein, such as for example, [$^{18}$F] FTC-146, for the use of said S1R specific compounds in guiding peripheral treatment of nerve regeneration and neuropathic pain in animal models for clinical use.

Materials and Methods

Radiochemistry

[$^{18}$F]FTC-146 was synthesized via aliphatic nucleophilic substitution ($^{18}$F/Tosylate exchange) using TRACERlab FX FN (GE Healthcare) as previously described (101). Briefly, tosylate precursor solution (2 mg in 1 mL anhydrous DMSO) was added into azeotropically dried $^{18}$F/K$_{222}$/K$_2$CO$_3$ complex, it was heated to 150° C. for 15 min, then the crude product was purified on semi-prep HPLC. The [$^{18}$F]FTC-146 HPLC fraction was formulated in saline containing no more than 10% ethanol.

Animal Model of Neuropathic Pain

Animal experiments were approved by Stanford IACUC. Animals had access to food and water ad libitum and were kept under a 12 h light/dark cycle. Experiments were carried out using adult male Sprague-Dawley rats weighing 200-250 g. Three groups of animals were used with n=7 in each group.

1. Spared Nerve Injury (SNI): Applicant utilized the SNI model as it is a well-characterized model of nerve injury, the extent and duration of which can be measured with standard behavioral tests. Animals underwent a left SNI procedure, which creates a well-characterized rat nerve injury and neuropathic pain model showing chronic mechanical and thermal hypersensitivity with onset of symptoms occurring 24 h post-surgery and lasting several months (105). Briefly, animals were anesthetized with inhalational 2-3% isoflurane and placed on a warming bed. Hair was removed from the posterolateral aspect of the left thigh. Following a longitudinal skin incision, the left sciatic nerve was identified, exposed and followed distally until its trifurcation into the tibial, common peroneal and sural nerves. An axotomy and ligation of the tibial and common peroneal nerves were performed with cautious sparing of the sural nerve. The muscle layer was closed with absorbable interrupted sutures (4-0, plain gut; Ethicon) and the skin was apposed with staples. After recovery from anesthesia, animals were returned to their cages and allowed free access to food and water. The staples were removed five days after the surgery. The right hind limb was used as control. Animals were permitted to heal four weeks after the surgery.
2. Sham: Animals underwent a surgery similar to SNI animals until the trifurcation of the sciatic nerve was identified, then the wound was closed similarly without any axotomy or ligation. Post-surgical care was similar to SNI animals.
3. Control: Animals did not undergo any surgical procedure prior to imaging. Animals were in similar in age and weight to the animals in the SNI and Sham-operated groups.

Assessment of Pain (Allodynia)

Development of allodynia in the animals was evaluated by assessing mechanical allodynia using von Frey Hair filaments. A pre-surgery baseline test was performed and then on the day before imaging. Sensitivity to mechanical stimulation was measured by recording the paw withdrawal response to serially increasing filament stiffness. For the test, the animals were placed on a raised platform with a wire mesh floor. They were acclimatized to the platform for two hours each for four days prior to testing and an hour just before testing. The filament was applied to the lateral portion of the plantar aspect of both hind paws through the mesh floor and pressed until it bent, and then kept in place for eight seconds. A positive response was recorded if the animal withdrew the paw briskly off the floor in response to the application, which was confirmed by repeating the test with the same filament at a minimum interval of 60 seconds. Testing of the paw was terminated if it showed 3 consecutive positive responses for the same filament or if the filament lifted the paw off the floor. The data thus collected was fitted on to a normalized sigmoid curve to calculate the 50% withdrawal threshold value (in log filament stiffness units) using the Psychofit program (http://psych.colorado.edu/~lharvey/html/software.html). The threshold is defined as the stimulus intensity at which the withdrawal is detected 50% of the time (106).

PET-MRI

For PET-MRI, all animals were anesthetized with humidified, oxygen-enriched 2-3% isoflurane (inhalation (IH)). The animal was secured in a transportable holder with fixed firm padding to eliminate motion between PET and MRI scans, while allowing it to breathe 2-3% isoflurane via a nose cone fixed to the animal holder. Fiducial markers made with diluted [$^{18}$F]FTC-146 solution (30 μCi/mL) in longitudinal plastic tubes placed across the bottom of the animal holder were utilized for assistance in PET and MRI image co-registration. The animals underwent sequential PET (micro-PET R4; Siemens Medical Solutions) and MRI (a self-shielded 30-cm-bore 7-T magnet [Varian] with a 9-cm-bore gradient insert [Resonance Research Inc.] using EXCITE2 electronics and the supporting LX11 platform [GE Healthcare]) using dedicated small animal imaging instruments. For PET scan, 1000 μCi (37 MBq) [$^{18}$F] FTC-146 was injected via tail vein and a 10 min static scan of the thighs was obtained 30 min post-injection. For MRI, T1 Fast Spin Echo images (TR 800 ms; TE 7.7 ms; slice thickness 1 mm; in-plane resolution 234 μm$^2$) were obtained of the rat thighs. Haloperidol (1.6 mg/kg), a widely used S1R blocker, was given intravenously 30 min prior to tracer administration for the blocking studies.+

Image Analysis

PET and MRI images were co-registered using Inveon Research Workplace (IRW) image analysis software (Siemens Healthcare). MR images were used to define the anatomic location of the sciatic nerves and regions of interest (ROIs) were placed around the injured nerves, proximal to the site of injury, on 5 consecutive transaxial slices covering the neuroma. For uninjured nerves, ROIs were similarly placed around the corresponding location on 5 slices. Radioactivity counts were then recorded from within the ROIs in the fused PET-MRI images. The maximum signals from the ROIs on each nerve were averaged and then normalized to the average signal from adjacent muscle.

Autoradiography (Excised Whole Nerve)

Immediately after PET-MR imaging, rats from SNI, Sham and Control groups (unblocked n=2 and blocked n=2), were sacrificed 60 min post injection and sciatic nerves were harvested. The nerves were exposed on a phosphor screen (medium MultiSensitive Phosphor Screen; PerkinElmer) for 12 h. The screen was imaged using a Typhoon 9410 Variable Mode Imager (Amersham Biosciences) and images were analyzed by Image J (Image Processing and Analysis in Java, version 1.46; http://imagej.nih.gov/ij/index.html). ROIs were drawn on the neuroma within each injured nerve and compared with similar sized ROIs in the same region of intact nerves.

Autoradiography (Nerve/Muscle Sections)

After PET-MRI imaging, tissue containing sciatic nerve and adjacent muscle was rapidly dissected from both hind limbs of rats from each group (i.e., SNI, sham and control; n=2 for each group). Tissue blocks were quickly frozen in optimal cutting temperature (O.C.T.) compound (Tissue-Tek, Sakura, USA). Subsequently, 6 µm-thick sections were cut using a cryostat microtome HM500 (Microm) and mounted on microscope slides (Fisherbrand Superfrost® Plus Microscope Slides). The mounted sections were air-dried for 10 min, and then exposed to $^{18}$F-sensitive storage phosphor screens (Perkin Elmer) for 12 h. The image plates were scanned using a Typhoon 9410 Variable Mode Imager (Amersham Biosciences) and the images were analyzed using Image J software.

Immunohistochemistry (Sciatic Rat Nerve)

Staining was performed on sections of sciatic rat nerves and adjacent muscle tissue. Serial frozen longitudinal sections (6 µm thick) from sciatic nerve/muscle tissue blocks embedded in OCT were cut in a cryostat (Leica CM1950) and collected onto plus-plus slides (Fisherbrand Superfrost Plus Microscope Slides). The sections were then washed (3×5 min) in a solution of tris-buffered saline (TBS). Following washing, the sections were then incubated in a 1% $H_2O_2$, 50% TBS/MeOH solution for 30 min to quench the endogenous peroxidase activity. After subsequently washing (3×5 min) in TBS, the sections were then placed in a 10% normal goat serum (NGS, Vector Laboratories), TBST (1% Triton X-100) for 1 h in order to block unspecific staining and permeabilize the cells.

Finally, without further washing, the sections were then incubated with the S1R specific primary antibody 1:200 (35) containing 5% NGS and TBST (0.1% Triton X-100) for 24 h at room temperature. The sections were then washed (3×5 min) in TBST (0.1% Triton X-100) and incubated with biotinylated anti-rabbit secondary antibody 1:400 (Vector Laboratories) in 5% NGS and TBST (0.1% Triton X-100) for 1 h at room temperature. The sections were then washed again in the Triton-TBS solution (3×5 min), and an avidin-biotin complex was applied (diluted 1:1000 in TBS, Vector Laboratories) for 90 min at room temperature. The sections were then washed (3×5 min) in TBS again, before being incubated with 3,3'-Diaminobenzidine (DAB) for 15 min. Finally, the sections were washed (3×5 min) with ice-cold TBS to stop the reaction. The immunohistochemical stained sections were dehydrated and cover-slipped with Permount (Sigma Aldrich) for microscopic observation.

Omission of the primary antibody abolished the staining. To confirm the specificity of the primary antibody, 50 µm slices from a S1R knockout-mouse were processed immunohistochemically and no staining was seen.

Double Fluorescence Staining

Double immunofluorescent staining of S1R and S100 was performed using adjacent sections of rat sciatic nerve/muscle to those stained with S1R antibody and DAB. In brief, 6 µm frozen sections were air dried for 30 min, washed once in TBS, placed in ice-cold acetone for 5 min, and then air-dried at room temperature for 1 hour. After sections were washed once more in TBS, they were incubated in TBST (1% Triton X-100) containing 10% normal goat serum for 1 h at room temperature to permeabilize tissue and block nonspecific binding. Without further washing, sections were incubated for 20 h at 4° C. with primary antibodies (1:200 rabbit anti-S1R 19Ab, 1:100 mouse anti-S100 Ab—Sigma Aldrich) in TBST (1% Triton X-100) and 10% normal goat serum. Sections were then washed in TBST (0.1% Triton X-100) and incubated in the dark for 1 h at room temperature with secondary antibodies 1:1000 (Alexa 488-conjugated goat anti-mouse IgG and Alexa 594-conjugated goat anti-rabbit IgG—both from Jackson ImmunoResearch) in TBST (1% Triton X-100) containing 10% normal goat serum, and then washed again (3×8 min) in TBST (0.1% Triton X-100). Sections were coverslipped using Vectashield+DAPI mounting medium (Vector Laboratories). Sections were visualized with a Zeiss AxioImager M1 fluorescence microscope using 10×, 20×, and 40× objectives. Secondary only staining was performed to determine specific signal for both primary antibodies.

Statistics

Statistical analysis was done using IBM SPSS Statistical Analysis Software (version 19) using one-way between subjects Analysis of Variance (ANOVA) to compare multiple means, followed by Tukey's post hoc analysis if significance was achieved. $\alpha=0.05$ was considered significant. All values in text represent mean±standard deviation with p values representing Tukey's post hoc comparison with a mean value of injured nerves. The error bars in figures represent standard errors of the means. Mean PET and autoradiography signals were tested for linear correlation.

Radiochemistry

[$^{18}$F]FTC-146 was synthesized as previously reported (29) and was obtained with radiochemical yield of 5.06±1.91% and specific radioactivity of 6.90±3.73 Ci/µmol (255.30±138.01 GBq/µmol) (Scheme 1). Both radiochemical and chemical purities were >99%. All radiochemical yields and specific radioactivities were decay corrected to end of bombardment (n=45).

Animals with Spared-Nerve Injury (SNI) Exhibit Allodynia

Von Frey filament tests indicated the development of allodynia observed in the left hind paws of SNI animals. The SNI group also exhibited decreased paw withdrawal thresholds in the injured hind limb (in log filament stiffness units, 4.92±0.07) relative to levels within the same animals in the contralateral uninjured side (5.85±0.15; p<0.001), Sham (5.72±0.27; p<0.001), and the control groups (5.77±0.17; p<0.001) (FIG. 20).

Injured Sciatic Nerves Show Increased [$^{28}$F] FTC-146 Uptake on PET-MRI

PET-MRI images demonstrated increased [$^{18}$F] FTC-146 uptake (normalized to adjacent muscle) in the injured left sciatic nerve (3.64±1.38; n=4) compared to the uninjured right sciatic nerve (1.44±0.33; n=4; p<0.001) in the (SNI) group as well as the nerves of the Sham group (1.25±0.19; n=4; p<0.001), and Control groups (1.40±0.12; n=4; p<0.001) (FIG. 21C). When blocked with haloperidol, the injured left sciatic nerves show significantly reduced [$^{18}$F] FTC-146 uptake in the blocking studies (1.53±0.25; n=2; p<0.01) relative to baseline. Pre-blocking with haloperidol did not appear to cause a similar decrease in [$^{18}$F] FTC-146 uptake in sciatic nerves on either side for the sham or control groups. (FIGS. 21A-C)

Injured Sciatic Nerves Show Increased [$^{18}$F] FTC-146 Uptake on Autoradiography Autoradiography showed higher maximum signal in the left injured nerves (especially in the neuroma at the site of transection) in SNI animals (pixel intensity value: 36.22×10$^3$±3.36×10$^3$; n=2) compared to the right uninjured nerves (17.37×10$^3$±3.08×10$^3$; n=2; p<0.01) as well as those in Sham (16.94×10$^3$±1.4×10$^3$; n=2; p<0.01) and Control groups (14.22×10$^3$±2.63×10$^3$; n=2; p<0.01) (FIG. 2D). Consistent with PET-MRI data, pre-blocking with haloperidol significantly reduced [$^{18}$F] FTC-146 accumulation in the injured nerves (15.78×10$^3$±0.5×10$^3$; n=2; p<0.01). The average maximum pixel signal intensities on autoradiography correlate with average maximum voxel tracer uptake in PET images (r (10)=0.75; p<0.01). Autoradiography of nerve sections also showed increased signal in the neuroma at the site of transection of injured sciatic nerves compared to the uninjured nerves (FIG. 22).

Increased S1R Expression in the Injured Nerve is Confirmed with Immunostaining

Immunohistochemical (IHC) staining of sections adjacent to those used for autoradiography (above), with a specific S1R antibody, showed elevated levels of S1Rs in injured nerves (SNI left injured nerve n=2) compared to uninjured control nerves (uninjured right nerve from SNI n=2, Sham-operated rat nerve n=2, control rat nerve n=2) (FIG. 3). Within each injured nerve, the neuroma itself was shown to contain the highest levels of S1R staining (FIG. 22). Double immunofluorescent staining with S1R and S100 (Schwann cells) revealed high levels of both S1R and S100 immunoreactivity in injured nerves compared to uninjured nerves (FIG. 23 A, B, E, F), and that the highest levels of S1R/S100 staining were found in the neuroma. Additionally, double immunofluorescent staining revealed that S1R staining co-localized with S100 staining (FIG. 23 D, H), and that there were much higher levels of DAPI staining in injured nerves compared to uninjured nerves (FIG. 23 C, G).

A further aspect of the present invention relates to Alzheimer's disease (AD). AD is a major public health problem that impacts millions of Americans and their families every year. Although promising targets for early detection and therapy including beta amyloid and tau protein have been investigated, new targets remain critically important in order to understand the early onset and progression of AD before cognitive decline begins. Sigma-1 receptors have recently been implicated in AD but initial studies have not been able to clearly understand its biological role. In 2005, it was reported that sigma-1 receptor ligands demonstrated some neuroprotective activity against amyloid toxicity and that a sigma-1 antagonist could block this neuroprotection. Early attempts to utilize positron emission tomography (PET) with [$^{11}$C] SA4503 to examine sigma-1 receptors in AD demonstrated a link between a lower receptor density in early AD patients compared to age-matched controls. Although several other PET compounds have been made to image S1Rs, [$^{11}$C] SA4503 is currently the only radiotracer being used for imaging S1R in the clinic, despite its moderate selectivity for the sigma-2 receptor, the vesicular acetylcholine transporter (VAChT), and the emopamil binding protein (EBP). It is an object of this invention to investigate the 1R ligands disclosed herein as new highly S1R-specific ligands to reliably image and elucidate the function(s) of S1R in AD without having any significant binding to other brain targets.

The binding profile of [$^{18}$F] FTC-146 in mouse brain at later time points is quite different from the reported uptake levels for other known S1R radioligands at corresponding times. For example, [$^{18}$F] FTC-146 reached its maximum uptake in mouse brain within the first few minutes of imaging and then gradually began to wash out of the brain to a level 65% of its maximum at 60 min post injection, whereas [$^{18}$F] FM-SA4503 reached its maximum uptake in the brain at 30 min post injection and did not experience significant washout over the remainder of the study (120 min post injection). Uptake levels of [$^{18}$F] SFE and [$^{18}$F] FPS in living mice have not been reported in the literature and thus applicant was unable to visually compare the kinetics of [$^{18}$F] FTC-146 with them at present, however the fact that [$^{18}$F] FTC-146 displayed relatively fast in vivo binding kinetics suggests it might not have the same irreversible binding problems as [$^{18}$F] FM-SA4503 and [$^{18}$F] SFE. Since [$^{18}$F]FTC-146 may exhibit the best known kinetics (e.g., fast uptake and irreversible binding) for imaging S1Rs in living subjects and these new lead candidates including [$^{18}$F]FTC-146 may be even better imaging agents for future clinical translation.

Established nontransgenic models of AD have been characterized in rodents infused with the amyloid β1-40 protein or in mice injected centrally with amyloid β25-35 peptide (Aβ25-35). A nontransgenic AD mouse model can be chosen to test the effectiveness of our best radioligand to monitor AD therapy. Prior results suggest that sigma-1 receptor agonists might be useful agents in treating AD because they could not only alleviate the cognitive deficits observed in AD patients, but may also reduce neuronal damage.

REFERENCES CITED (1) Matsumoto, R. R.; McCracken, K. A.; Pouw, B.; Miller, J.; Bowen, W. D.; Williams, W.; De Costa, B. R. N-alkyl substitute analogs of the σ receptor ligand BD1008 and traditional σ receptor ligands affect cocaine-induced convulsions and lethality in mice. *Eur. J. Pharmacol.* 2001, 411, 261-273.

(2) Maurice, T.; Lockhart, B. P. Neuroprotective and anti-amnesic potentials of sigma (σ) receptor ligands. *Prog. Neuropsychopharmacol. Biol. Psychiatry* 1997, 21, 69-102.

(3) Matsumoto, R. R.; Bowen, W. D.; Su, T. P., eds. *Sigma receptors: chemistry, cell biology and clinical implications*. New York: Springer, 2007.

(4) Hanner, M.; Moebus, F. F.; Flandorfer, A.; Knaus, H-G.; Striessing, J.; Kempner, E.; Glossmann, H. Purification, molecular cloning, and expression of the mammalian sigma$_1$-binding site. *Proc. Natl. Acad. Sci. USA*, 1996, 93, 8072-8077.

(5) Kekuda, R.; Prasad, P. D.; Fei, Y-J.; Leibach, F. H.; Ganaphthy, V. Cloning and functional expression of the human type 1 sigma receptor (hSigmaR1). *Biochem. Biophys. Res. Commun.* 1996, 229, 553-558.

(6) Seth, P.; Leibach, F. H.; Ganaphthy, V. Cloning and structural analysis of the cDNA and the gene encoding the murine type 1 sigma receptor. *Biochem. Biophys. Res. Commun.* 1997, 241, 535-540.

(7) Seth, P.; Fei, Y-J.; Li, H. W.; Huang, W.; Leibach, F. H.; Ganaphthy, V. Cloning and functional characterization of a σ receptor from rat brain. *J. Neurochem.* 1998, 70, 922-931.

(8) Mei, J.; Pasternak, G. W. Molecular cloning and pharmaceutical characterization of the rat sigma$_1$ receptor. *Biochem. Pharmacol.* 2001, 62, 349-355.

(9) Perrine, D. M. *The Chemistry of Mind-Altering Drugs.* Washington, D.C.: American Chemical Society, 1996.

(10) Wohler, V. Fortsetzung der Untersuchungen uber die Coca and das Cocain. *Justus Liebigs Annalen der Chemie* 1862, 121, 372, 372.

(11) National Survey on Drug Use and Health—http://www.samhsa.gov

(12) Carroll, F. I.; Howell, L. L.; Kuhar, M. J. Pharmacotherapies for treatment of cocaine abuse: preclinical aspects. *J. Med. Chem.* 1999, 42, 2721-2736.

(13) Sharkey, J.; Glen, K. A.; Wolfe, S.; Kuhar, M. J. Cocaine binding at sigma receptors. *Eur. J. Pharmacol.* 1988, 149, 171-174.

(14) Mittleman, R.; Wetli, C. V. Death caused by recreational cocaine use: an update. *JAMA* 1984, 252, 1889-1893.

(15) Martin, W. R.; Eades, C. G.; Thompson, J. A.; Huppler, R. E.; Gilbert, P. E. The effects of morphine- and nalorphine-like drugs in the nondependent and morphine-dependent chronic spinal dog. *J Pharmacol Exp Ther.* 1976, 197, 517-32.

(16) Martin, W. R. A steric theory of opioid agonists, antagonists, agonist-antagonists, and partial agonists. *NIDA Res Monogr.* 1984, 49, 16-23.

(17) Hellewell, S. B.; Bruce, A.; Feinstein, G.; Orringer, J.; Williams, W.; Bowen, W. D. Rat liver and kidney contain high densities of sigma 1 and sigma 2 receptors: characterization by ligand binding and photoaffinity labeling. *Eur J Pharmacol.* 1994, 268, 9-18.

(18) Maurice, T.; Su, T. P. The pharmacology of sigma-1 receptors. *Pharmacol Ther.* 2009, 124, 195-206.

(19) Quirion, R.; Bowen, W. D.; Itzhak, Y.; Junien, J. L.; Musacchio, J. M.; Rothman, R. B.; Su, T. P.; Tam, S. W.; Taylor, D. P. A proposal for the classification of sigma binding sites. *Trends Pharmacol Sci.* 1992, 13, 85-6.

(20) Guitart, X.; Codony, X.; Monroy, X. Sigma receptors: biology and therapeutic potential. *Psychopharmacology (Berl).* 2004, 174, 301-19.

(21) Walker, J. M.; Bowen, W. D.; Walker, F. O.; Matsumoto, R. R.; De Costa, B.; Rice, K. C. Sigma receptors: biology and function. *Pharmacol Rev.* 1990, 42, 355-402.

(22) Maurice, T.; Phan, V. L.; Privat, A. The anti-amnesic effects of sigma1 (sigma1) receptor agonists confirmed by in vivo antisense strategy in the mouse. *Brain Res.* 2001, 898, 113-21.

(23) Su, T. P. Delineating biochemical and functional properties of sigma receptors: emerging concepts. *Crit Rev Neurobiol.* 1993, 7, 187-203.

(24) Vilner, B. J.; John, C. S.; Bowen, W. D. Sigma-1 and sigma-2 receptors are expressed in a wide variety of human and rodent tumor cell lines. *Cancer Res.* 1995, 55, 408-13.

(25) Wang, B.; Rouzier, R.; Albarracin, C. T.; Sahin, A.; Wagner, P.; Yang, Y.; Smith, T. L.; Meric-Bemstam, F.; Marcelo Aldaz, C.; Hortobagyi, G. N.; Pusztai, L. Expression of sigma 1 receptor in human breast cancer. *Breast Cancer Res Treat.* 2004, 87, 205-14.

(26) Gonzalez, G. M.; Werling, L. L. Release of [3H] dopamine from guinea pig striatal slices is modulated by signal receptor agonists. *Naunyn Schmiedebergs Arch Pharmacol.* 1997, 356, 455-61.

(27) Kobayashi, T.; Matsuno, K.; Nakata, K.; Mita, S. Enhancement of acetylcholine release by SA4503, a novel sigma 1 receptor agonist, in the rat brain. *J Pharmacol Exp Ther.* 1996, 279, 106-13.

(28) Collier, T. L.; Waterhouse, R. N.; Kassiou, M. Imaging sigma receptors: applications in drug development. *Curr Pharm Des.* 2007, 13, 51-72.

(29) Maurice, T. Improving Alzheimer's Disease-Related Cognitive Deficits with sigma1 Receptor Agonists. *Drug News Perspect.* 2002, 15, 617-625.

(30) Senda, T.; Matsuno, K.; Kobayashi, T.; Nakazawa, M.; Nakata, K.; Mita, S. Ameliorative effect of SA4503, a novel cognitive enhancer, on the basal forebrain lesion-induced impairment of the spatial learning performance in rats. *Pharmacol Biochem Behav.* 1998, 59, 129-34.

(31) Harukuni, I.; Bhardwaj, A.; Shaivitz, A. B.; DeVries, A. C.; London, E. D.; Hum, P. D.; Traystman, R. J.; Kirsch, J. R.; Faraci, F. M. sigma(1)-receptor ligand 4-phenyl-1-(4-phenylbutyl)-piperidine affords neuroprotection from focal ischemia with prolonged reperfusion. *Stroke.* 2000, 31, 976-82.

(32) Volz, H. P.; Stoll, K. D. Clinical trials with sigma ligands. *Pharmacopsychiatry.* 2004, 37 Suppl 3, S214-20.

(33) Xu, Y. T.; Kaushal, N.; Shaikh, J.; Wilson, L. L.; Mesangeau, C.; McCurdy, C. R.; Matsumoto, R. R. A novel substituted piperazine, CM156, attenuates the stimulant and toxic effects of cocaine in mice. *J Pharmacol Exp Ther.* 2010, 333, 491-500.

(34) Ucar, H.; Cacciaguerra, S.; Spampinato, S.; Van der poorten, K.; Isa, M.; Kanyonyo, M.; Poupaert, J. H. 2(3H)-benzoxazolone and 2(3H)-benzothiazolone derivatives: novel, potent and selective signal receptor ligands. *Eur J Pharmacol.* 1997, 335, 267-73.

(35) Berardi, F.; Ferorelli, S.; Abate, C.; Pedone, M. P.; Colabufo, N. A.; Contino, M.; Perrone, R. Methyl substitution on the piperidine ring of N-[omega-(6-methoxynaphthalen-1-yl)alkyl] derivatives as a probe for selective binding and activity at the sigma(1) receptor. *J Med Chem.* 2005, 48, 8237-44.

(36) Hudkins, R. L.; Mailman, R. B.; DeHaven-Hudkins, D. L. RLH-033, a novel, potent and selective ligand for the sigma 1 recognition site. *Eur J Pharmacol.* 1994, 271, 235-6.

(37) Maestrup, E. G.; Fischer, S.; Wiese, C.; Schepmann, D.; Hiller, A.; Deuther-Conrad, W.; Steinbach, J.; Wunsch, B.; Brust, P. Evaluation of spirocyclic 3-(3-fluoropropyl)-2-benzofurans as signal receptor ligands for neuroimaging with positron emission tomography. *J Med Chem.* 2009, 52, 6062-72.

(38) Matsuno, K.; Nakazawa, M.; Okamoto, K.; Kawashima, Y.; Mita, S. Binding properties of SA4503, a novel and selective sigma 1 receptor agonist. *Eur J Pharmacol.* 1996, 306, 271-9.

(39) Moussa, I. A.; Banister, S. D.; Beingt, C.; Giboureau, N.; Reynolds, A. J.; Kassiou, M. Design, synthesis, and structure-affinity relationships of regioisomeric N-benzyl alkyl ether piperazine derivatives as sigma-1 receptor ligands. *J Med Chem.* 2010, 53, 6228-39.

(40) Piergentili, A.; Amantini, C.; Del Bello, F.; Giannella, M.; Mattioli, L.; Palmery, M.; Perfumi, M.; Pigini, M.; Santoni, G.; Tucci, P.; Zotti, M.; Quaglia, W. Novel highly potent and selective sigma 1 receptor antagonists related to spipethiane. *J Med Chem.* 2010, 53, 1261-9.

(41) Quaglia, W.; Giannella, M.; Piergentili, A.; Pigini, M.; Brasili, L.; Di Toro, R.; Rossetti, L.; Spampinato, S.;

Melchiorre, C. 1'-Benzyl-3,4-dihydrospiro[2H-1-benzothiopyran-2,4'-piperidine] (spipethiane), a potent and highly selective sigma1 ligand. *J Med Chem.* 1998, 41, 1557-60.

(42) Yous, S.; Wallez, V.; Belloir, M.; Caignard, D. H.; McCurdy, C. R. Novel 2(3H)-Benzothiazolones as Highly Potent and Selective Sigma-1 Receptor Ligands. *Med Chem Res.* 2005, 14, 158-168.

(43) Kawamura, K.; Ishiwata, K.; Tajima, H.; Ishii, S.; Matsuno, K.; Homma, Y.; Senda, M. In vivo evaluation of [$^{11}$C] SA4503 as a PET ligand for mapping CNS sigma (1) receptors. *Nucl Med Biol.* 2000, 27, 255-61.

(44) Kawamura, K.; Tsukada, H.; Shiba, K.; Tsuji, C.; Harada, N.; Kimura, Y.; Ishiwata, K. Synthesis and evaluation of fluorine-18-labeled SA4503 as a selective sigma1 receptor ligand for positron emission tomography. *Nucl Med Biol.* 2007, 34, 571-7.

(45) Waterhouse, R. N.; Collier, T. L. In vivo evaluation of [$^{18}$F] 1-(3-fluoropropyl)-4-(4-cyanophenoxymethyl)piperidine: a selective sigma-1 receptor radioligand for PET. *Nucl Med Biol.* 1997, 24, 127-34.

(46) Waterhouse, R. N.; Chang, R. C.; Zhao, J.; Carambot, P. E. In vivo evaluation in rats of [$^{18}$F] 1-(2-fluoroethyl)-4-[(4-cyanophenoxy)methyl]piperidine as a potential radiotracer for PET assessment of CNS sigma-1 receptors. *Nucl Med Biol.* 2006, 33, 211-5.

(47) Waterhouse, R. N.; Zhao, J.; Stabin, M. G.; Ng, H.; Schindler-Horvat, J.; Chang, R. C.; Mirsalis, J. C. Preclinical acute toxicity studies and dosimetry estimates of the novel sigma-1 receptor radiotracer, [$^{18}$F]SFE. *Mol Imaging Biol.* 2006, 8, 284-91.

(48) Mach, R. H.; Gage, H. D.; Buchheimer, N.; Huang, Y.; Kuhner, R.; Wu, L.; Morton, T. E.; Ehrenkaufer, R. L. N—[$^{18}$F]-4'-fluorobenzylpiperidin-4yl-(2-fluorophenyl) acetamide ([18F]FBFPA): a potential fluorine-18 labeled PET radiotracer for imaging sigma-1 receptors in the CNS. *Synapse.* 2005, 58, 267-74.

(49) Fischer, S.; Wiese, C.; Grosse Maestrup, E.; Hiller, A.; Deuther-Conrad, W.; Scheunemann, M.; Schepmann, D.; Steinbach, J.; Wunsch, B.; Brust, P. Molecular imaging of sigma receptors: synthesis and evaluation of the potent sigma(1) selective radioligand [$^{18}$F]fluspidine. *Eur J Nucl Med Mol Imaging.* 2010.

(50) Fishback, J. A.; Mesangeau, C.; Poupaert, J. H.; McCurdy, C. R.; Matsumoto, R. R. Synthesis and characterization of [$^{3}$H]-SN56, a novel radioligand for the σ1 receptor. *European Journal of Pharmacology.* In Press.

(51) Bowen, W. D.; Tolentino, P. J.; Kirschner, B. N.; Varghese, P.; de Costa, B. R.; Rice, K. C. Sigma receptors and signal transduction: negative modulation of signaling through phosphoinositide-linked receptor systems. *NIDA Res Monogr.* 1993, 133, 69-93.

(52) Loening, A. M.; Gambhir, S. S. AMIDE: a free software tool for multimodality medical image analysis. *Mol Imaging.* 2003, 2, 131-7.

(53) Kronauge, J. F.; Noska, M. A.; Davison, A.; Holman, B. L.; Jones, A. G. Interspecies variation in biodistribution of technetium (2-carbomethoxy-2-isocyanopropane)6+. *J Nucl Med.* 1992, 33, 1357-65.

(54) Rodvelt, K. R.; Lever, S. Z.; Lever, J. R.; Blount, L. R.; Fan, K.-H.; Miller, D. K. SA 4503 attenuates cocaine-induced hyperactivity and enhances methamphetamine substitution for a cocaine discriminative stimulus. *Pharmacology, Biochemistry and Behavior.* 2011, 97, 676-682.

(55) Matsumoto, R. R.; Liu, Y.; Lerner, M.; Howard, E. W.; Brackett, D. J. Sigma receptors: potential medications development target for anti-cocaine agents. *Eur. J. Phamracol.,* 2003, 469, 1-12.

(56) Su, T.-P.; Hayashi, T.; Maurice, T.; Buch, S.; Ruoho, A. E. The sigma-1 receptor chaperone as an inter-organelle signaling modulator. *Trends in Pharmacological Sciences.* 2010, 31, 557-566

(57) Roh, D.-H.; Kim, H.-W.; Yoon, S.-Y.; Seo, H.-S.; Kwon, Y.-B.; Kim, K.-W.; Han, H.-J.; Beitz, A. J.; Lee, J.-H. Intrathecal Administration of Sigma-1 Receptor Agonists Facilitates Nociception: Involvement of a Protein Kinase C-development Pathway. *Journal of Neuroscience Research.* 2008, 86, 3644-3654.

(58) Roh, D.-H.; Kim, H.-W.; Yoon, S.-Y.; Seo, H.-S.; Kwon, Y.-B.; Kim, K.-W.; Han, H.-J.; Beitz, A. J.; Na, H.-S.; Lee, J.-H. Intrathecal injection of the σ1 receptor antagonist BD1047 blocks both mechanical allodynia and increases in spinal NR1 expression during the induction phase of rodent neuropathic pain. *Anesthesiology.* 2008, 109, 879-889.

(59) Kibaly, C.; Meyer, L.; Patte-Mensah, C.; Mensah-Nyagan, A. G. Biochemical and functional evidence for the control of pain mechanisms by dehydroepiandrosterone endogenously synthesized in the spinal cord. *The FASEB Journal.* 2008, 22, 93-104.

(60) de la Puente, B.; Nadal, X.; Portillo-Salido, E.; Sanchez-Arroyos, R.; Ovalle, S.; Palacios, G.; Nuro, A.; Romero, L.; Entrena, J. M.; Baeyens, J. M.; Lopez-Garcia, J. A.; Maldonado, R.; Zamanillo, D.; Vela, J. M. Sigma-1 receptors regulate activity-induced spinal sensitization and neuropathic pain after peripheral nerve injury. *Pain.* 2009, 145, 294-303.

(61) Rybczynska, A. A.; Elising a, P. H.; Sijbesma, J. W.; Ishiwata, K.; de Jong, J. R.; de Vries, E. F.; Dierckx, R. A.; van Waarde, A. Steroid hormones affect binding of the sigma ligand $^{11}$C-SA4503 in tumour cells and tumour-bearing rats. *Eur. J. Nucl Mol Imaging.* 2009, 36, 1167-1175.

(62) van Waarde, A.; Rybczynska, A. A.; Ramakrishnan, N.; Ishiwata, K.; Elsing a, P. H.; Dierckx, R. A. Sigma receptors in oncology: therapeutic and diagnostic applications of sigma ligands. *Curr Pharm Des.* 2010, 16, 3519-1537.

(63) Jansen, K. L. R.; Faull, R. L. M.; Storey, P.; Leslie, R. A. Loss of sigma binding sites in the CA1 area of the anterior hippocampus in Alzheimer's disease correlates with CA1 pyramidal cell loss. *Brain Research.* 1993, 623, 299-302.

(64) Mishina, M.; Ohyama, M.; Ishii, K.; Kitamura, S.; Kimura, Y.; Oda, K.-i.; Kawamura, K.; Sasaki, T.; Kobayashi, S.; Katayama, Y.; Ishiwata, K. Low density of $sigma_1$ receptors in early Alzheimer's disease. *Ann. Nucl. Med.* 2008, 22, 151-156.

(65) Mishina, M.; Ishiwata, K.; Ishii, K.; Kitamura, S.; Kimura, Y.; Kawamura, K.; Oda, K.; Sasaki, T.; Sakayori, O.; Hamamoto, M.; Kobayashi, S.; Katayama, Y. Function of $sigma_1$ receptors in Parkinsons's disease. *Acta Neural Scand.* 2005, 112, 103-107.

(66) Weissman, A. D.; Casanova, M. F.; Kleinman, J. E.; London, E. D.; de Souza, E. B. Selective loss of cerebral cortical Sigma, but not PCP binding sites in schizophrenia. *Biol Psychiatry.* 1991, 29, 41-54.

(67) Shibuya, H.; Mori, H.; Toni, M. Sigma receptors in schizophrenic cerebral cortices. *Neurochem Res.* 1992, 17, 983-990.

(68) Silver, H.; Barash, I.; Aharon, N.; Kaplan, A.; Poyurovsky, M. Fluvoxamine augmentation of antipsychotics improves negative symptoms in psychotic chronic schizophrenic patients: a placebo-controlled study. *Int. Clin. Psychopharmacol.* 2000, 15, 257-261.

(69) Iyo, M.; Shirayama, Y.; Watanabe, H.; Fujisaki, M.; Miyatake, R.; Fukami, G.; Shiina, A.; Nakazato, M.; Shiraishi, T. Letter to the Editor (Case Report): Fluvoxamine as a sigma-1 receptor agonist improved cognitive impairments in a patient with schizophrenia. *Prog. Neuropsych. Biol. Psych.* 2008, 32, 1072-1073.

(70) Gatti, F.; Bellini, L.; Gasperini, M.; Perez, J.; Zanardi, R.; Smeraldi, E. Fluvoxamine alone in the treatment of delusional depression. *Am. J. Psychiatry,* 1996, 153, 414-416.

(71) Narita, N.; Hashimoto, K.; Tomitaka, S.-i.; Minabe, Y. Interactions of selective serotonin reuptake inhibitors with subtypes of σ receptors in rat brain. *Eur. J. Pharmacol.* 1996, 307, 117-119.

(72) Zanardi, R.; Franchini, L.; Gasperini, M.; Lucca, A.; Smeraldi, E.; Perez, J. Faster Onset of Action of Fluvoxamine in Combination with Pindolol in the Treatment of Delusional Depression: A controlled study. *J. Clin. Psychopharmacol.* 1998,18, 441-446.

(73) Haiman, G.; Pratt, H.; Miller, A. Effects of dextromethorphan/quinidine on auditory event-related potentials in multiple sclerosis patients with pseudobulbar affect. *J. Clin. Psychopharmacol.* 2009, 29, 444-452.

(74) Cottraux, J.; Mollard, E.; Bouvard, M.; Marks, I. Exposure therapy, fluvoxamine, or combination treatment in obsessive-compulsive disorder: one-year followup. *Psychiatry Research.* 1993, 49, 63-75.

(75) Hohagen, F.; Berger, M. New perspectives in research and treatment of obsessive-compulsive disorder. *Br. J. Psychiatry Suppl.* 1998, 35, 1.

(76) Dell'Osso, B.; Allen, A.; Hollander, E. Fluvoxamine: a selective serotonin re-uptake inhibitor for the treatment of obsessive-compulsive disorder. *Expert Opinion on Pharmacotherapy.* 2005, 6, 2727-2740.

77. Freedman M, et al. (2012) Electrodiagnostic evaluation of compressive nerve injuries of the upper extremities. The Orthopedic clinics of North America 43(4):409-416.

78. Subhawong T K, et al. (2012) High resolution imaging of tunnels by magnetic resonance neurography. Skeletal radiology 41(1):15-31.

79. Jarvik J G, Yuen E, & Kliot M (2004) Diagnosis of carpal tunnel syndrome: electrodiagnostic and MR imaging evaluation. Neuroimag Clin N Am 14(1):93-+.

80. Sartoretti-Schefer S, Brandle P, Wichmann W, & Valavanis A (1996) Intensity of MR contrast enhancement does not correspond to clinical and electroneurographic findings in acute inflammatory facial nerve palsy. AJNR. American journal of neuroradiology 17(7):1229-1236.

81. Mondelli M, Filippou G, Gallo A, & Frediani B (2008) Diagnostic utility of ultrasonography versus nerve conduction studies in mild carpal tunnel syndrome. Arthritis and rheumatism 59(3):357-366.

82. Terzis J K & Novikov M L (2005) Radiological and Electrophysiological Detection of Nerve Roots Avulsion in Patients with Birth-Related Brachial Plexus Paralysis. Seminars in plastic surgery 19(1): 24-41.

15. Martin W R, Eades C G, Thompson J A, Huppler R E, & Gilbert P E (1976) Effects of Morphine-Like and Nalorphine-Like Drugs in Nondependent and Morphine-Dependent Chronic Spinal Dog. Journal of Pharmacology and Experimental Therapeutics 197(3):517-532.

20. Guitart X, Codony X, & Monroy X (2004) Sigma receptors: biology and therapeutic potential. Psychopharmacology 174(3):301-319.

18. Maurice T & Su T P (2009) The pharmacology of sigma-1 receptors. Pharmacol Therapeut 124(2):195-206.

83. Walker J M, et al. (1990) Sigma-Receptors—Biology and Function. Pharmacol Rev 42(4):355-402.

84. Chien C C & Pasternak G W (1995) Sigma antagonists potentiate opioid analgesia in rats. Neuroscience letters 190(2):137-139.

85. Yang C, Chen Y, Tang L, & Wang Z J (2011) Haloperidol Disrupts Opioid-Antinociceptive Tolerance and Physical Dependence. Journal of Pharmacology and Experimental Therapeutics 338(1):164-172.

86. Aydar E, Palmer C P, Klyachko V A, & Jackson M B (2002) The sigma receptor as a ligand-regulated auxiliary potassium channel subunit. Neuron 34(3):399-410.

87. Iyengar S, et al. (1990) Sigma Receptors Modulate Both A9 and A10 Dopaminergic-Neurons in the Rat-Brain—Functional Interaction with Nmda Receptors. Brain research 524(2):322-326.

88. Urani A, Privat A, & Maurice T (1998) The modulation by neurosteroids of the scopolamine-induced learning impairment in mice involves an interaction with sigma(1) (sigma(1)) receptors. Brain research 799(1):64-77.

89. Zhang H L & Cuevas J (2002) Sigma receptors inhibit high-voltage-activated calcium channels in rat sympathetic and parasympathetic neurons. J Neurophysiol 87(6):2867-2879.

90. Mei J F & Pasternak G W (2002) sigma(1) receptor modulation of opioid analgesia in the mouse. Journal of Pharmacology and Experimental Therapeutics 300(3): 1070-1074.

31. Cendan C M, Pujalte J M, Portillo-Salido E, Montoliu L, & Baeyens J M (2005) Formalin-induced pain is reduced in sigma(1) receptor knockout mice. European journal of pharmacology 511(1):73-74.

60. de la Puente B, et al. (2009) Sigma-1 receptors regulate activity-induced spinal sensitization and neuropathic pain after peripheral nerve injury. Pain 145(3):294-303.

92. Drews E & Zimmer A (2009) Central sensitization needs sigma receptors. Pain 145(3):269-270.

93. Cendan C M, Pujalte J M, Portillo-Salido E, & Baeyens J M (2005) Antinociceptive effects of haloperidol and its metabolites in the formalin test in mice. Psychopharmacology 182(4):485-493.

94. Romero L, et al. (2012) Pharmacological properties of S1RA, a new sigma-1 receptor antagonist that inhibits neuropathic pain and activity-induced spinal sensitization. British journal of pharmacology 166(8):2289-2306.

95. Roh D H, et al. (2011) Spinal neuronal NOS activation mediates sigma-1 receptor-induced mechanical and thermal hypersensitivity in mice: involvement of PKC-dependent GluN1 phosphorylation. British journal of pharmacology 163(8):1707-1720.

96. Kim H W, et al. (2008) Activation of the spinal sigma-1 receptor enhances NMDA-induced pain via PKC- and PKA-dependent phosphorylation of the NR1 subunit in mice. British journal of pharmacology 154(5):1125-1134.

97. Yoon S Y, et al. (2010) An increase in spinal dehydroepiandrosterone sulfate (DHEAS) enhances NMDA-induced pain via phosphorylation of the NR1 subunit in mice: Involvement of the sigma-1 receptor. Neuropharmacology 59(6):460-467.

98. Nieto F R, et al. (2012) Role of Sigma-1 Receptors in Paclitaxel-Induced Neuropathic Pain in Mice. J Pain 13(11):1107-1121.

99. Wunsch B (2012) The sigma(1) Receptor Antagonist S1RA Is a Promising Candidate for the Treatment of Neurogenic Pain. J Med Chem 55(19):8209-8210.
100. Kwon Y B, Jeong Y C, Kwon J K, Son J S, & Kim K W (2009) The Antinociceptive Effect of Sigma-1 Receptor Antagonist, BD1047, in a Capsaicin Induced Headache Model in Rats. Korean J Physiol Pha 13(6):425-429.
101. James M L, et al. (2012) New Positron Emission Tomography (PET) Radioligand for Imaging sigma-1 Receptors in Living Subjects. J Med Chem 55(19):8272-8282.
102. Campana W M (2007) Schwann cells: Activated peripheral glia and their role in neuropathic pain. Brain Behavior and Immunity 21(5):522-527.
103. Allodi I, Udina E, & Navarro X (2012) Specificity of peripheral nerve regeneration: Interactions at the axon level. Prog Neurobiol 98(1):16-37.
104. Pizzo P A & Clark N M (2012) Alleviating Suffering 101-Pain Relief in the United States. New Engl J Med 366(3):197-199.
105. Decosterd I & Woolf C J (2000) Spared nerve injury: an animal model of persistent peripheral neuropathic pain. Pain 87(2):149-158.
106. Berquin A D, Lijesevic V, Blond S, & Plaghki L (2010) An Adaptive Procedure for Routine Measurement of Light-Touch Sensitivity Threshold. Muscle & nerve 42(3):328-338.
107. Mavlyutov T A, Epstein M L, Andersen K A, Ziskind-Conhaim L, & Ruoho A E (2010) The Sigma-1 Receptor Is Enriched in Postsynaptic Sites of C-Terminals in Mouse Motoneurons. An Anatomical and Behavioral Study. Neuroscience 167(2):247-255.

We claim:

1. A method of detecting increased S1R density at the site of nerve injury arising from neuropathic pain comprising S1R-PET imaging a tissue with an imaging agent to determine a non-invasive biomarker of nerve injury and inflammation wherein the imaging agent comprises at least one SR1 selective compound or radioligand selected from the general formula III', or IV'

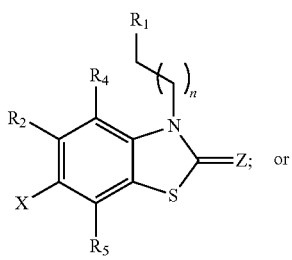

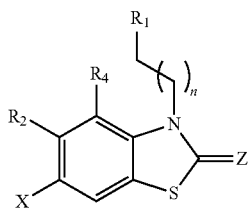

wherein $R_1$ is a radical of an optionally substituted piperazine, an optionally substituted tetrahydropyridine, an optionally substituted azepane or an optionally substituted tetrahydroisoquinoline in which the optional substituents are on the aromatic moiety or isoindoline-1,3-dione; $R_{2,4,5}$ are each independently any one or combinations of the following moieties, hydrogen, cyano, nitro, acyl, alkyl, amido, azido, isothiocyanate, isocyanate, optionally substituted anilino, halogens, ethers, sulfonamides, thioacyl, nitro, aromatic, heterocyclic, olefinic, acetylene, deuterium, or tritium; Z is O, "n" is 1 to 5 carbons in length; wherein the moiety bridging $R_1$ and N is a substituted alkylene; and wherein X is or $C_1$-$C_4$ radiohaloalkyl; and stereoisomers, or pharmaceutically acceptable salts thereof.

2. The method of claim 1, wherein the optionally substituted N-containing heterocyclic radical is an optionally substituted azepane.

3. The method of claim 1, having the formula XII'

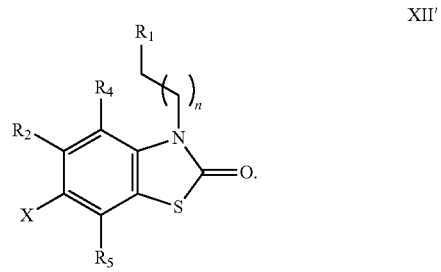

4. The method of claim 1, where R1 is optionally substituted

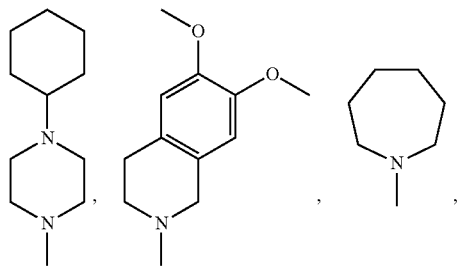

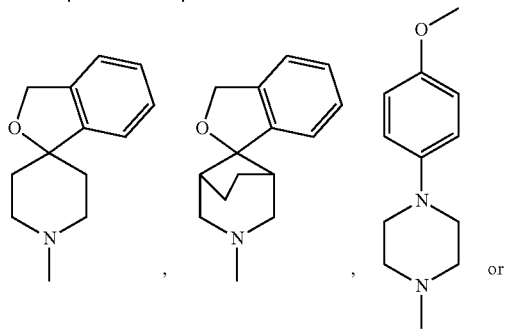

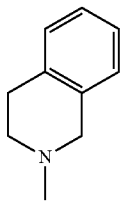

5. The method of claim 1, wherein X is $F^{18}$ $C_1$-$C_4$ alkyl.

* * * * *

UNITED STATES PATENT AND TRADEMARK OFFICE
CERTIFICATE OF CORRECTION

PATENT NO. : 9,724,435 B2
APPLICATION NO. : 14/196483
DATED : August 8, 2017
INVENTOR(S) : Christopher R. McCurdy et al.

Page 1 of 1

It is certified that error appears in the above-identified patent and that said Letters Patent is hereby corrected as shown below:

In the Specification

Column 1, Section Cross-Reference to Related Applications, Line 25, replace second paragraph with: The subject invention was made with government support under a research project supported by the United States Government in NIDA Grant Number NIGMS Grant Number P20 GM104932 and NCI ICMIC P50 CA114747 and the government has certain rights in this invention.

Signed and Sealed this
Thirtieth Day of January, 2018

Joseph Matal
*Performing the Functions and Duties of the*
*Under Secretary of Commerce for Intellectual Property and*
*Director of the United States Patent and Trademark Office*